US011807625B2

(12) United States Patent
Bekerman et al.

(10) Patent No.: US 11,807,625 B2
(45) Date of Patent: Nov. 7, 2023

(54) CAPSID INHIBITORS FOR THE PREVENTION OF HIV

(71) Applicant: Gilead Sciences, Inc., Foster City, CA (US)

(72) Inventors: Elena Bekerman, Castro Valley, CA (US); Wade S. Blair, Poolesville, MD (US); Anna Chiu, Burlingame, CA (US); Tomas Cihlar, Burlingame, CA (US); Dana J. Levine, San Leandro, CA (US); Winston C. Tse, Redwood City, CA (US); Stephen R. Yant, Boulder Creek, CA (US); Jim X. Zheng, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/104,554

(22) Filed: Nov. 25, 2020

(65) Prior Publication Data

US 2021/0188815 A1   Jun. 24, 2021

Related U.S. Application Data

(60) Provisional application No. 63/028,804, filed on May 22, 2020, provisional application No. 62/940,535, filed on Nov. 26, 2019.

(51) Int. Cl.
    C07D 401/14      (2006.01)
    A61P 31/18       (2006.01)
    A61K 45/06       (2006.01)

(52) U.S. Cl.
    CPC ........... C07D 401/14 (2013.01); A61K 45/06 (2013.01); A61P 31/18 (2018.01); *C07B 2200/13* (2013.01)

(58) Field of Classification Search
    None
    See application file for complete search history.

(56) References Cited

U.S. PATENT DOCUMENTS

| 3,845,770 A | 11/1974 | Theeuwes et al. |
| 4,326,525 A | 4/1982 | Swanson et al. |

(Continued)

FOREIGN PATENT DOCUMENTS

| CN | 101910133 A | 12/2010 |
| CN | 107207498 | 9/2017 |

(Continued)

OTHER PUBLICATIONS

Benzaria, S. et al. (Dec. 6, 1996). "Synthesis, In Vitro Antiviral Evaluation, and Stability Studies of Bis( S-Acyl-2-Thioethyl) Ester Derivatives of 9-[2-(Phosphonomethoxy)Ethyl]adenine (PMEA) as Potential PMEA Prodrugs with Improved Oral Bioavailability," J. Med. Chem. 39(25):4958-4965.

(Continued)

*Primary Examiner* — Brian J Davis

(74) *Attorney, Agent, or Firm* — Fish & Richardson P.C.

(57) ABSTRACT

The present disclosure provides methods of preventing HIV in a subject, comprising administering to the subject a therapeutically effective amount of a compounds of Formula (Ia) or (Ib):

(Ia)

(Ib)

or a pharmaceutically acceptable salt thereof, optionally in combination with one or more additional therapeutic agents. Methods of reducing the risk of acquiring HIV (e.g., HIV-1 and/or HIV-2) are also provided.

69 Claims, 7 Drawing Sheets

Specification includes a Sequence Listing.

(56) References Cited

U.S. PATENT DOCUMENTS

| | | |
|---|---|---|
| 4,816,570 A | 3/1989 | Farquhar |
| 4,902,514 A | 2/1990 | Barclay et al. |
| 4,968,788 A | 11/1990 | Farquhar |
| 4,992,445 A | 2/1991 | Lawter et al. |
| 5,001,139 A | 3/1991 | Lawter et al. |
| 5,023,252 A | 6/1991 | Hseih |
| 5,616,345 A | 4/1997 | Geoghegan et al. |
| 5,663,159 A | 9/1997 | Starrett, Jr. et al. |
| 5,792,756 A | 8/1998 | Starrett, Jr. et al. |
| 5,922,695 A | 7/1999 | Arimilli et al. |
| 5,935,946 A | 8/1999 | Munger, Jr. et al. |
| 5,977,089 A | 11/1999 | Arimilli et al. |
| 7,390,791 B2 | 6/2008 | Becker et al. |
| 7,803,788 B2 | 9/2010 | Becker et al. |
| 8,193,225 B2 | 6/2012 | Schneider et al. |
| 8,263,627 B2 | 9/2012 | Barrow et al. |
| 8,435,968 B2 | 5/2013 | Greig et al. |
| 8,748,412 B2 | 6/2014 | Liao et al. |
| 8,754,065 B2 | 6/2014 | Liu et al. |
| 8,835,488 B2 | 9/2014 | Yamashita et al. |
| 9,012,441 B2 | 4/2015 | Bondy et al. |
| 9,050,344 B2 | 6/2015 | Brizgys et al. |
| 9,216,996 B2 | 12/2015 | Jin et al. |
| 9,220,710 B2 | 12/2015 | Bondy et al. |
| 9,540,343 B2 | 1/2017 | Bondy et al. |
| 9,670,205 B2 | 6/2017 | Aktoudianakis et al. |
| 9,730,936 B2 | 8/2017 | Baszcynski et al. |
| 9,789,089 B2 | 10/2017 | Bondy et al. |
| 9,873,680 B2 | 1/2018 | Brizgys et al. |
| 9,944,619 B2 | 4/2018 | Bondy et al. |
| 9,951,043 B2 | 4/2018 | Brizgys et al. |
| 10,071,985 B2 | 9/2018 | Graupe et al. |
| 10,294,234 B2 | 5/2019 | Bacon et al. |
| 10,370,342 B2 | 8/2019 | Chin et al. |
| 10,370,358 B2 | 8/2019 | Bondy et al. |
| 10,640,499 B2 | 5/2020 | Chin et al. |
| 10,654,827 B2 | 5/2020 | Graupe et al. |
| 10,696,657 B2 | 6/2020 | Vandehey |
| 10,836,746 B2 | 11/2020 | Brizgys et al. |
| 10,849,892 B2 | 12/2020 | Houston et al. |
| 11,078,208 B1 | 8/2021 | Bacon et al. |
| 11,117,886 B2 | 9/2021 | Vandehey et al. |
| 2005/0282805 A1 | 12/2005 | Hangeland et al. |
| 2007/0083045 A1 | 4/2007 | Di Francesco et al. |
| 2008/0234251 A1 | 9/2008 | Doherty et al. |
| 2008/0306050 A1 | 12/2008 | Doherty et al. |
| 2010/0029585 A1 | 2/2010 | Dietsch et al. |
| 2010/0129306 A1 | 5/2010 | Julien et al. |
| 2010/0143301 A1 | 6/2010 | Desai et al. |
| 2010/0249176 A1 | 9/2010 | Barrow et al. |
| 2011/0092485 A1 | 4/2011 | Burgess et al. |
| 2011/0118235 A1 | 5/2011 | Burgess et al. |
| 2012/0045761 A1 | 2/2012 | Jagannath et al. |
| 2012/0082658 A1 | 4/2012 | Hershberg |
| 2012/0219615 A1 | 8/2012 | Coukos et al. |
| 2013/0165489 A1 | 6/2013 | Cocklin et al. |
| 2013/0251673 A1 | 9/2013 | Flores et al. |
| 2014/0045849 A1 | 2/2014 | McGowan et al. |
| 2014/0066432 A1 | 3/2014 | Burgess et al. |
| 2014/0073642 A1 | 3/2014 | Embrechts et al. |
| 2014/0088085 A1 | 3/2014 | Burgess et al. |
| 2014/0142085 A1 | 5/2014 | Bondy et al. |
| 2014/0221346 A1 | 8/2014 | Halcomb et al. |
| 2014/0221347 A1 | 8/2014 | Brizgys et al. |
| 2014/0221356 A1 | 8/2014 | Jin et al. |
| 2014/0221378 A1 | 8/2014 | Miyazaki et al. |
| 2014/0221380 A1 | 8/2014 | Miyazaki et al. |
| 2014/0221417 A1 | 8/2014 | Halcomb et al. |
| 2014/0221421 A1 | 8/2014 | Bondy et al. |
| 2014/0275167 A1 | 9/2014 | Hartman |
| 2014/0296266 A1 | 10/2014 | Hu et al. |
| 2014/0303164 A1 | 10/2014 | Brizgys et al. |
| 2014/0350031 A1 | 11/2014 | McGowan et al. |
| 2016/0067224 A1 | 3/2016 | Bondy et al. |
| 2016/0083368 A1 | 3/2016 | Brizgys et al. |
| 2016/0108030 A1 | 4/2016 | Brizgys et al. |
| 2016/0250215 A1 | 9/2016 | Baszcynski et al. |
| 2016/0289229 A1 | 10/2016 | Aktoudianakis et al. |
| 2016/0368881 A1 | 12/2016 | Bondy et al. |
| 2017/0137405 A1 | 5/2017 | Bondy et al. |
| 2018/0051005 A1 | 2/2018 | Graupe et al. |
| 2018/0194746 A1 | 7/2018 | Bondy et al. |
| 2018/0258097 A1 | 9/2018 | Bacon et al. |
| 2018/0273508 A1 | 9/2018 | Brizgys et al. |
| 2018/0370950 A1 | 12/2018 | Graupe et al. |
| 2019/0083478 A1 | 3/2019 | Houston et al. |
| 2019/0084963 A1 | 3/2019 | Shi |
| 2019/0300505 A1 | 10/2019 | Allan et al. |
| 2019/0345136 A1 | 11/2019 | Brizgys et al. |
| 2019/0375726 A1 | 12/2019 | Bondy et al. |
| 2020/0038389 A1 | 2/2020 | Bauer |
| 2020/0262815 A1 | 8/2020 | Graupe et al. |
| 2020/0369647 A1 | 11/2020 | Allan et al. |
| 2020/0397772 A1 | 12/2020 | Houston et al. |
| 2021/0009555 A1 | 1/2021 | Brizgys et al. |
| 2022/0009904 A1 | 1/2022 | Allan et al. |
| 2022/0249460 A1 | 8/2022 | Houston et al. |
| 2022/0251069 A1 | 8/2022 | Shi |
| 2023/0012449 A1 | 1/2023 | Bondy et al. |

FOREIGN PATENT DOCUMENTS

| | | |
|---|---|---|
| WO | WO 1991/19721 | 12/1991 |
| WO | WO 2003/002530 | 1/2003 |
| WO | WO 2003/002553 | 1/2003 |
| WO | WO 2004/050643 | 6/2004 |
| WO | WO 2004/071448 | 8/2004 |
| WO | WO 2004/096286 | 11/2004 |
| WO | WO 2005/087725 | 9/2005 |
| WO | WO 2005/123680 | 12/2005 |
| WO | WO 2006/015261 | 2/2006 |
| WO | WO 2006/110157 | 10/2006 |
| WO | WO 2007/070826 | 8/2007 |
| WO | WO 2008/013622 | 1/2008 |
| WO | WO 2009/005677 | 1/2009 |
| WO | WO 2009/010804 | 1/2009 |
| WO | WO 2009/062285 | 5/2009 |
| WO | WO 2009/114677 | 9/2009 |
| WO | WO 2010/130034 | 11/2010 |
| WO | WO 2011/059887 | 5/2011 |
| WO | WO 2011/143772 | 11/2011 |
| WO | WO 2012/003497 | 1/2012 |
| WO | WO 2012/003498 | 1/2012 |
| WO | WO 2012/065062 | 5/2012 |
| WO | WO 2012/145728 | 10/2012 |
| WO | WO 2013/006738 | 1/2013 |
| WO | WO 2013/006792 | 1/2013 |
| WO | WO 2013/091096 | 6/2013 |
| WO | WO 2013/159064 | 10/2013 |
| WO | WO 2014/016358 | 1/2014 |
| WO | WO 2014/023813 | 2/2014 |
| WO | WO 2014/028931 | 2/2014 |
| WO | WO 2014/056953 | 4/2014 |
| WO | WO 2014/076221 | 5/2014 |
| WO | WO 2014/100323 | 6/2014 |
| WO | WO 2014/110297 | 7/2014 |
| WO | WO 2014/110298 | 7/2014 |
| WO | WO 2014/110323 | 7/2014 |
| WO | WO 2014/128189 | 8/2014 |
| WO | WO 2014/134566 | 9/2014 |
| WO | WO 2015/008097 | 1/2015 |
| WO | WO 2015/061518 | 4/2015 |
| WO | WO 2015/130966 | 9/2015 |
| WO | WO 2016/033243 | 3/2016 |
| WO | WO 2016/040084 | 3/2016 |
| WO | WO 2016/172424 | 10/2016 |
| WO | WO 2016/172425 | 10/2016 |
| WO | WO 2017/007689 | 1/2017 |
| WO | WO 2018/035359 | 2/2018 |
| WO | WO 2018/145021 | 8/2018 |
| WO | WO 2018/203235 | 11/2018 |
| WO | WO 2019/035904 | 2/2019 |

(56) References Cited

FOREIGN PATENT DOCUMENTS

| WO | WO 2019/035973 | 2/2019 |
|---|---|---|
| WO | WO 2020/018459 | 1/2020 |

OTHER PUBLICATIONS

Berge et al., (1977) "Pharmaceutical Salts," J. Pharma. Sci., 66(1): 1-19.
Bhattacharya et al. (2014) Structural Basis of HIV-1 Capsid Recognition by PF74 and CPSF6, PNAS; 111 (52):18625-18630.
Blair et al., (2010) "HIV Capsid is a Tractable Target for Small Molecule Therapeutic Intervention," PLoS Pathog. 6(12): e1001220, 10 pages.
Briggs et al., (2003) "Structural Organization of Authentic, Mature HIV-1 Virions and Cores," The EMBO Journal; vol. 22 No. 7 pp. 1707-1715.
Brittain, "Polymorphism in pharmaceutical solids," Marcel Dekker, Inc., 1999, 235-238.
Brown, M.K. et al. (2005) "Highly Enantioselective Cu-Catalyzed Conjugate Additions of Dialkylzinc Reagents to Unsaturated Furanones and Pyranones: Preparation of Air-Stable and Catalytically Active Cu-Peptide," Angew. Chem. Int. Ed. Engl. 44(33):5306-5310.
Bundgaard, H. (1991). "Design and Application of Prodrugs," Chapter 5 in a Textbook of Drug Design and Development, Krogsgaard-Larsen, P. et al. eds., Harwood Academic Publishers, Chur, Switzerland, pp. 113-191.
Campbell et al., (2015) "HIV-1 Capsid: The Multifaceted Key Player in HIV-1 Infection," Nat Rev Microbial.; 13(8): 471-483.
Carnes et al., "Inhibitors of the HIV-1 Capsid, A Target of Opportunity," Curr. Opin. HIV AIDS, 2018, 13(4):359-365.
Chin et al. (2015) "Direct Visualization of HIV-1 Replication Intermediates Shows That Capsid and CPSF6 Modulate HIV-1 Intra-Nuclear Invasion and Integration", Cell Reports 13:1717-1731.
Cos, P. et al. (1998) "Structure-Activity Relationship and Classification of Flavonoids as Inhibitors of Xanthine Oxidase and Superoxide Scavengers," J. Natl. Prod. 61:71-76.
Cossy, J. et al. (Oct. 23, 1995). "Ring Opening of Cyclopropylketones Induced by Photochemical Electron Transfer," Tetrahedron 51 (43):11751-11764.
Curreli et al., (2011) "Virtual Screening Based Identification of Novel Small-molecule Inhibitors Targeted to the HIV-1 Capsid," Bioorganic & Medicinal Chemistry 19:77-90.
De Lombaert, S. et al. (Feb. 18, 1994). "N-Phosphonomethyl Dipeptides and Their Phosphonate Prodrugs, A New Generation of Neutral Endopeptidase (NEP, EC 3.4.24.11) Inhibitors," J. Med. Chem. 37(4):498-511.
Fader et al., (2013) Optimization of a 1,5 dihydrobenzo[b][1,4]diazepine-2,4-dione Series of HIV Capsid Assembly Inhibitors 2: Structure-Activity Relationships (SAR) of the C3-Phenyl Moiety, Bioorganic & Medicinal Chemistiy Letters, 23(11):3396-3400.
Farquhar, D. et al. (Mar. 1983). "Biologically Reversible Phosphate-Protective Groups," J. Pharm. Sci. 72(3):324-325.
Fields, G. B. (1994) "Methods for Removing the Fmoc Group," Methods in Molecular Biology, 35: 17-27.
Forshey et al., (2002) "Formation of a Human Immunodeficiency Virus Type 1 Core of Optimal Stability Is Crucial for Viral Replication," J. Virology, 76(11) p. 5667-5677.
Foster, A. B. (1984) "Deuterium Isotope Effects in Studies of Drug Metabolism," Trends Pharmacol. Sci., 5(12):524-527.
Ganser et al. (1999) "Assembly and Analysis of Conical Models for the HIV-1 Core," Science 283, 80-82.
Ganser-Pornillos et al., (2007) "Structure of Full-Length HIV-1 CA: A Model for the Mature Capsid Lattice," Cell., 131(1):70-9, 29 pages.
Hagmann, W. K. (2008) "The many roles for fluorine in medicinal chemistry," J. Med. Chem., 51(15):4359-4369.
Hammer, S. et al. (Aug. 6, 2008). "Antiretroviral Treatment of Adult HIV Infection. 2008 Recommendations of the International AIDS Society: USA Panel," JAMA 300(5):555-570.
Hanack, M. et al., (1964) "cis-und trans bicyclo [3.1.0] hexano-(2)," Chemische Berichte, 97(6):1669-1672, XP055573746 (with English translation).
Hodgson, D.M. et al. (2004). "Intramolecular Cyclopropanation of Unsaturated Terminal Epoxides," J. Am. Chem. Soc. 126(28):8664-8665.
Hodgson, D.M. et al. (2007) "Intramolecular Cyclopropanation of Unsaturated Terminal Epoxides and Chlorohydrins," J. Am. Chem. Soc., 129(14):4456-4462.
Hung et al. (2013) "Large-Scale Functional Purification of Recombinant HIV-1 Capsid" PLOS One, vol. 8, Issue 3, e58035, 11 pages.
Ishiyama, T. et al., (1995) "Palladium(0)-Catalyzed Cross-Coupling Reaction of Alkoxydiboron with Haloarenes: A Direct Procedure for Arylboronic Esters," J. Org. Chem., 60(23):7508-7510.
Jeong, .J.U. (2010) "Synthesis of Tetrasubstituted Pyrazones and Pyrazone N-Oxides," Tetrahedron Letters 51 (6):974-976.
Jin et al., (2010) "SAR and Molecular Mechanism Study of Novel Acylhydrazone Compounds Targeting HIV-1 CA," Bioorganic & Medicinal Chemistry, 18: 2135-2140.
Jouvenet et al., (2006) "Plasma Membrane Is the Site of Productive HIV-1 Particle Assembly," PLoS Biol. 4(12):e435, 15 pages.
Kashima, C. et al. (1991). "New Peptide Synthesis Using the Ozonolysate of 2-(1-Phthalimido)alkyl-5-Phenyloxazoles," J. Heterocyclic Chem. 28: 1241-1244.
Kelly, B. N., et al., (2007) "Structure of the Antiviral Assembly Inhibitor CAP-1 Complex with the HIV-1 CA Protein," Journal of Molecular Biology 373(2):355-66.
Khamnei, S. et al. (1996). "Neighboring Group Catalysis in the Design of Nucleotide Prodrugs," J. Med. Chem. 39(20):4109-4115.
Kim, S. et al., (2013) "Discovery of a New HIV-1 Inhibitor Scaffold and Synthesis of Potential Prodrugs of Indazoles," Bioorganic & Medicinal Chemistry Letters, 23(10): 2888-2892.
Kocienski, P.J. (May 1994). "Carbonyl Protecting Groups," Chapter 5 in Protecting Groups, Thieme Publishing Group: New York, NY, pp. 155-184.
Kocienski, P.J. (May 1994). "Carboxyl Protecting Groups," Chapter 4 in Protecting Groups, Thieme Publishing Group: New York, NY, pp. 118-154.
Kocienski, P.J. (May 1994). "Diol Protecting Groups," Chapter 3 in Protecting Groups, Thieme Publishing Group: New York, NY, pp. 95-117.
Kocienski, P.J. (May 1994). "Hydroxyl Protecting Groups," Chapter 2 in Protecting Groups, Thieme Publishing Group: New York, NY, pp. 21-94.
Kocienski, P.J. (May 1994). "Protecting Groups: An Overview," Chapter 1 in Protecting Groups, Thieme Publishing Group: New York, NY, pp. 1-20.
Lad et al., (2015) "Functional Label-Free Assays for Characterizing the in Vitro Mechanism of Action of Small Molecule Modulators of Capsid Assembly" Biochemistry, 54: 2240-2248.
Lamorte et al. (2015) "Discovery of Novel Small-Molecule HIV-1 Replication Inhibitors That Stabilize Capsid Complexes" Antimicrobial Agents and Chemotherapy, 57(10): 4622-4631.
Lazerwith et al., (2017) "New Antiretrovirals for HIV and Antivirals for HBV," in Comprehensive Medicinal Chemistry, 3rd Edition, 1-36.
Lee et al., (2010) "Flexible Use of Nuclear Import Pathways by HIV-1," Cell Host & Microbe 7: 221-233.
Lemke, C.T. et al. (Jun. 2012). "Distinct Effects of Two HIV-1 Capsid Assembly Inhibitor Families That Bind the Same Site Within the N-Terminal Domain of the Viral CA Protein," J. Virol. 86(12):6643-6655.
MacMillan, D. S. et al., (2013) "Evaluation of alternative solvent in common amide coupling reactions: replacement of dicloromethane and N,N-dimethlformamide," Green Chem, 15: 596-600.
Matreyek et al., (2013) "Nucleoporin NUP153 Phenylalanine-Glycine Motifs Engage a Common Binding Pocket within the HIV-1 Capsid Protein to Mediate Lentiviral infectivity," PLOS Pathogens vol. 9, Issue 10, e1003693. 21 pages.

(56) References Cited

OTHER PUBLICATIONS

Mitchell, A.G. et al. (1992). "Bioreversible Protection for the Phospho Group: Bioactivation of the Di(4-Acyloxybenzyl) and Mono(4-acyloxybenzyl) Phosphoesters of Methylphosphonate and Phosphonoacetate," J. Chem. Soc. Perkin Trans. 1, pp. 2345-2353.

Miyaura, N. and Suzuki, A. (1995) "Palladium-Catalyzed Cross-Coupling Reactions of Oganoboron Compounds," Chem Rev, 95:2457-2483.

Molina et al., "On-Demand Preexposure Prophylaxis in Men at High Risk for HIV-1 Infection," N Engl. J Med. 2015, 353:2237-2246.

Montalbetti, C. A. G. N. and Falque, V. (2005) "Amide bond formation and peptide coupling," Tetrahedon, 61:10827-10852.

Nicolaou, K. C. et al. (2005) "Palladium-Catalyzed Cross-Coupling Reactions in Total Synthesis," Angew Chem Int Ed, 44:4442-4489.

Ovais, S. et al. (2013) "Synthesis, antiproliferative and anti-inflammatory activities of some novel 6-aryl-2-(p-(methanesulfonyl)phenyl)-4,5-dihydropyridazi-3(2H)-ones," European Journal of Medicinal Chemistry, 67:352-358.

Owen, A. et al. (2016) "Strengths, weaknesses, opportunities and challenges for long acting injectable therapies: Insights for applications in HIV therapy," Advances Drug Delivery Reviews 103:144-156.

Palella, F. J. et al. (1998) "Declining morbidity and mortality among patients with advanced human immunodeficiency virus infection," N Engl. J Med., 338:853-860.

Patel, H. R. et al., (2009) "Poloxamers: a pharmaceutical excipients with therapeutic behaviors," International Journal of PharmTech Research, 1(2):299-303.

Pornillos et al., (2009) "X-ray Structures of the Hexameric Building Block of the HIV Capsid" Cell 137(7): 1282-92.

Pornillos et al., (2009) Supplemental Data for "X-ray Structures of the Hexameric Building Block of the HIV Capsid" Cell, 137(7):1282-92.

Powers, J. J. et al. (2009) "Synthesis of Methyl-, Fluoro-, and Chloro-substituted 6-Hydroxyisoindolin-1-1-Ones" Tetrahedron Letters 50(12):1267-1269.

Price et al. (2012) "CPSF6 Defines a Conserved Capsid Interface That Modulates HIV-1 Replication" PLOS Pathogens, 8(8):e1002896, 14 pages.

Puech, F. et al. (Oct. 1993). "Intracellular Delivery of Nucleoside Monophosphates Through a Reductase-Mediated Activation Process," Antiviral Res. 22(2-3):155-174.

Registry (STN) [online], Mar. 22, 2010 [date of retrieval: Nov. 12, 2018], CAS registry No. 1213065-84-9.

Registry (STN) [online], Mar. 23, 2010 [date of retrieval: Nov. 12, 2018], CAS registry No. 1213495-28-3.

Rihn et al., (2013) "Extreme Genetic Fragility of the HIV-1 Capsid" PLOS One, vol. 9 Issue 6 e1003461, 25 pages.

Shi et al. (2011) "Small-Molecule Inhibition of Human Immunodeficiency Virus Type 1 Capsid Destabilization" Journal of Virology 85(1): 542-549.

Siddiqui, A. et al. (1999) "The Presence of Substituents on the Aryl Moiety of the Aryl Phosphoramidate Derivative of d4T Enhances Anti-HIV Efficacy in Cell Culture: A Structure-Activity Relationship" J. Med. Chem. 42:393-399.

Smith, R.J. et al. (2010) "Evolutionary Dynamics of Complex Networks of HIV Drug-Resistant Strains: The Case of San Francisco," Science 327(5966):697-701.

Sticht et al., (2005) "A peptide inhibitor of HIV-1 assembly in vitro" Nature Structural & Molecular Biology, 12(8): 671-677.

Sublocade Product Label, issued: Nov. 2017, 43 pages.

Taiwo, B. (2009). "Understanding Transmitted HIV Resistance Through the Experience in the USA," Int'l J. of Infectious Diseases 13(5):552-559.

Talele, "The 'Cyclopropyl Fragment' is a Versatile Player that Frequently Appears in Preclinical/Clinical Drug Molecules," Journal of Medicinal Chemistry, 2016, 59(19):8712-8756.

Tanaka, R. et al. (2005) "One-Pot Synthesis of Metalated Pyridines from Two Acetylenes, a Nitrile, and a Titanium(II) Alkoxide," J. Am. Chem. Soc. 127(21):7774-7780.

Tang et al., (2003) "Antiviral Inhibition of the HIV-1 Capsid Protein," J. Mol. Biol., 327: 1013-1020.

Thenin-Houssier et al., "HIV-1 capsid inhibitors as antiretroviral agents," Curr. HIV Res., 2016, 14(3):270-282.

Tse et al., "Discovery of Novel Potent HIV Capsid Inhibitors with Long-Acting Potential," Presentation at the Conference on Retroviruses and Opportunistic Infections (CROI), Seattle, WA, Feb. 14, 2017, 18 pages.

Tsiang et al., (2012) "A Trimer of Dimers Is the Basic Building Block for Human Immunodeficiency Virus-1 Capsid Assembly" Biochemistry, 51: 4416-4428.

Wong et al., (2014) "SPR Assay Development to Characterize Capsid Inhibitors Binding & MOA," Poster Presented at the Developments in Protein Interaction (DiPIA), La Jolla, CA, 1 page.

Wu et al., "Selective Inhibitors of Tumor Progression Loci-2(Tpl2) Kinase with Potent Inhibition of TNF-Alpha Production in Human Whole Blood," Bioorg. Med. Chem. Lett., 2009, 19(13):3485-3488.

Xianghui et al., "In Silico Virtual Screening," Biotechnology in the Post-Genome Era, 2003, 16 pages.

Yadav et al., "Co-crystals: a novel approach to modify physicochemical properties of active pharmaceutical ingredients" Indian J. Pharm. Sci., 2009, 71(4):359-370.

Yale, H. L. (1958) "The trifluoromethyl group in medicinal chemistry," J. Med. Chem., 1(2):121-133.

Yant et al., (2014) "An Improved PF74 Analog Inhibits Multiple HIV Capsid Functions Independently of Host Cyclophilin A and CPSF6" Poster Presented at the Conference on Retroviruses and Opportunistic Infections (CROI), Boston, Massachusetts, 1 page.

Yant et al., (2014) "PF74 Inhibits Multiple HIV Capsid Functions Independently of Host Cyclophilin A and CPSF6" Abstract for Poster Presented at the Conference on Retroviruses and Opportunistic Infections (CROI), Boston, Massachusetts, 1 page.

Zheng, J. et al. (2018) "GS-6207: A Novel, Potent and Selective First-In-Class Inhibitor of HIV-1 Capsid Function Displays Nonclinical Pharmacokinetics Supporting Long-Acting Potential," Poster Presented at ID Week 2018, San Francisco, CA, 1 page.

Zhou et al. (2015) "HIV-1 Resistance to the Capsid-Targeting Inhibitor PF74 Results in Altered Dependence on Host Factors Required for Virus Nuclear Entry" Journal of Virology, 89(17): 9068-9079.

[No Author Listed], "2-[9-(Difluoromethyl)-5,5-difluoro-7,8 diazatricylo[4.4.0.02,4]nona-1(6),8-dien-7-yl]acetic acid," PubChem CID 71186949, Mar. 21, 2013, retrieved on Jul. 15, 2020, retrieved from URL https://pubchem.ncbi.nlm.nih.gov/compound/71186949, 18 pages.

[No Author Listed], "3-Methyl-3-methylsulfonylbut-1-yne," PubChem CID 14241469, Feb. 9, 2002, retrieved on Jul. 15, 2020, retrieved from URL https://pubchem.ncbi.nlm.nih.gov/compound/142469, 16 pages.

[No Author Listed], CAS Registry No. 1620056-83-8, "1H-Cyclopropa[3,4]cyclopenta[1,2-c]pyrazole-1-acetic acid, 5,5-difluoro-3b,4,4a,5-tetrahydro-3-(trifluoromethyl)-, (3bS, 4aR)—(CA Index Name)," Aug. 6, 2014, retrieved on Jul. 16, 2020, retrieved from URL https://www.stn.org/stn/#/, 1 page.

Bastin et al., "Salt Selection and Optimisation Procedures for Pharmaceutical New Chemical Entities," Organic Process Research & Development, Jul. 2000, 4(5): 427-435.

Fontes Ferreira da Cunha et al., "4D-QSAR Models of HOE/BAY-793 Analogues as HIV-1 Protease Inhibitors," QSAR & Combinatorial Science, 2005, 24(2): 240-253.

Jarvis et al., "Conquering HIV's capsid", C&EN Chicago, Jul. 2017, 95(31): 23-25.

Morissette et al., "High-throughput crystallization: polymorphs, salts, co-crystals and solvates of pharmaceutical solids," Advanced Drug Delivery Reviews, Feb. 2004, 56(3):275-300.

Pornillos et al., "Atomic level modeling of the HIV capsid," Nature, Jan. 2011, 469(7330):424-427.

(56) References Cited

OTHER PUBLICATIONS

Pungpo et al., "Computer-aided molecular design of highly potent HIV-1 RT inhibitors: 3D QSAR and molecular docking studies of efavirenz derivatives," SAR and QSAR in Environmental Research, 2006, 17(4):353-370.
Registry (STN)[online], STN Registry No. 137349-29-2, "2H-Isoindole-2-acetamide, 1,3-dihydro-1, 3-dioxo-N-[2-phenyl-1-(5-phenyl-2-oxazolyl) etyl]-, (S)-(9CI)," Nov. 15, 1991, 1 page.
Silverman, "The Organic Chemistry of Drug Design and Drug Action," Elsevier, 2004, pp. 121-169.
Silvestri et al., "Novel Indolyl Aryl Sulfones Active against HIV-1 Carrying NNRTI Resistance Mutations: Synthesis and SAR Studies," Journal of Medical Chemistry, 2003, 46(12): 2482-2493.
Yang et al., "Design, synthesis and anti-HIV-1 evaluation of hydrazide-based peptidomimetics as selective gelatinase inhibitors," Bioorganic & Medicinal Chemistry, May 2016, 24(9):2125-2136.
PCT International Preliminary Report on Patentability in International Application No. PCT/US2020/062221, dated Jun. 9, 2022, 9 pages.
PCT International Search Report and Written Opinion in International Application No. PCT/US2020/062221, dated Mar. 15, 2021, 12 pages.
Taiwanese Office Action in Patent Application No. 109141436, dated Nov. 4, 2021, 8 pages (with English translation).
Choy et al., "Synthesis of irreversible HIV-1 protease inhibitors containing sulfonamide and sulfone as amide bond isosteres," Bioorganic & Medicinal Chemistry Letters, Oct. 1997, 7(20):2635-38.
Taiwanese Office Action in Patent Application No. 109141436, dated Aug. 26, 2022, 7 pages (with English translation).
Japanese Office Action in JP Appln. No. 2022-530736, dated Jun. 5, 2023, 9 pages (with English translation).
Australian Office Action in AU Appln. No. 2020391466, dated Jun. 23, 2023, 4 pages.
Canadian Office Action in CA Appln. No. 3,157,275, dated Jun. 29, 2023, 4 pages.

A. Vehicle only

B. Compound (Ib), 300 mg/kg (4 × 0.25 mL/kg @ 300 mg/mL)

C. Compound (Ib), 150 mg/kg (2 × 0.25 mL/kg @ 300 mg/mL)

Time (weeks)

CAPSID INHIBITORS FOR THE PREVENTION OF HIV

FIELD

The present disclosure provides methods of preventing HIV in a subject comprising administering to the subject a therapeutically effective amount of an HIV capsid inhibitor, or a pharmaceutically acceptable salt thereof, optionally in combination with one or more additional therapeutic agents.

SEQUENCE LISTING

This disclosure contains a Sequence Listing which has been submitted electronically in ASCII format and is hereby incorporated by reference in its entirety. Said ASCII copy, created on Nov. 16, 2020, is named 1329.P2PC_PF Sequence Listing.txt and is 854 bytes in size.

BACKGROUND

The HIV/AIDS pandemic has claimed the lives of millions of people, and millions more are currently infected. Antiretroviral therapy has turned HIV infection into a chronic, manageable disease; however, no cure yet exists for HIV. Reduction in the number of new HIV infections is a global goal. To this end, prevention regimens relating to both pre-exposure prophylaxis (PrEP) and post-exposure prophylaxis (PEP) are being explored. Truvada (emtricitabine-tenofovir disoproxil fumarate) and Descovy (emtricitabine-tenofovir alafenamide) are currently the only medications approved for PrEP. Accordingly, new and effective means for preventing HIV infection are needed and the methods described herein are developed to help meet this need.

SUMMARY

The present disclosure provides a method of preventing an HIV infection in a subject, or a method of reducing the risk of acquiring HIV in a subject, comprising administering to the subject a therapeutically effective amount of an HIV capsid inhibitor, or a pharmaceutically acceptable salt thereof, optionally in combination with one or more additional therapeutic agents.

The present disclosure further provides an HIV capsid inhibitor, or a pharmaceutically acceptable salt thereof, for use in any of the methods described herein.

The present disclosure further provides use of an HIV capsid inhibitor, or a pharmaceutically acceptable salt thereof, for the preparation of a medicament for use in any of the methods described herein.

DETAILED DESCRIPTION

Figure 1:
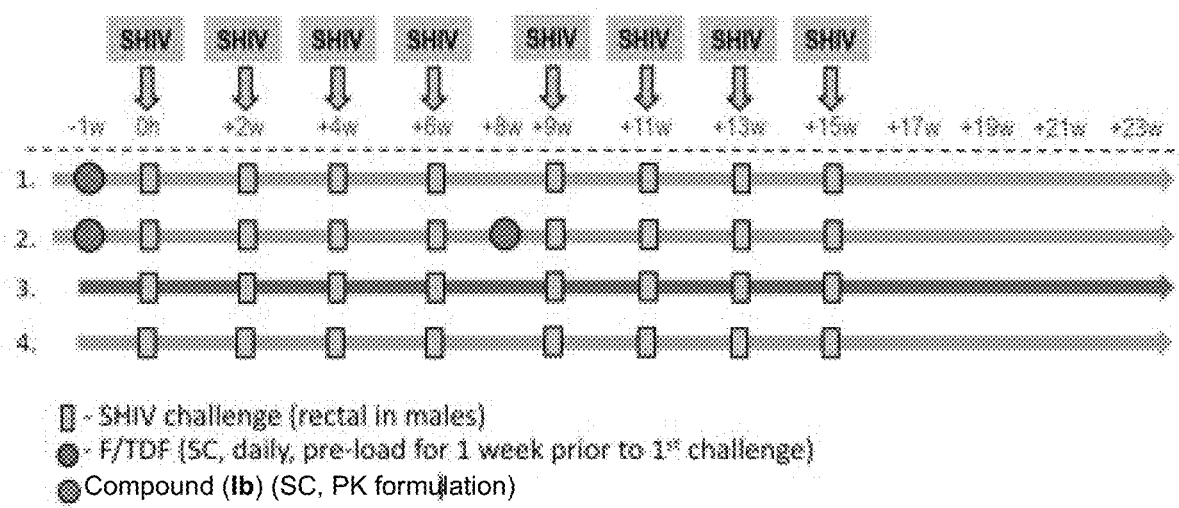
FIG. 1 shows a representative scheme illustrating the PrEP study design of Example 1.

The present disclosure relates to a method of preventing an HIV infection (e.g., HIV-1 and/or HIV-2) in a subject (e.g., a human) by administering to the subject a therapeutically effective amount of an HIV capsid inhibitor, or a pharmaceutically acceptable salt thereof.

In some embodiments, the HIV capsid inhibitor (e.g., a compound of Formula (Ia) or (Ib)), or a pharmaceutically acceptable salt thereof, is administered as a monotherapy (i.e., in the absence of an additional therapeutic agent). In some embodiments, the HIV capsid inhibitor (e.g., a compound of Formula (Ia) or (Ib)), or a pharmaceutically acceptable salt thereof, is administered in combination with one or more additional therapeutic agents, such as anti-HIV agents.

In some embodiments, the HIV capsid inhibitor is a compound of Formula (Ia) or Formula (Ib):

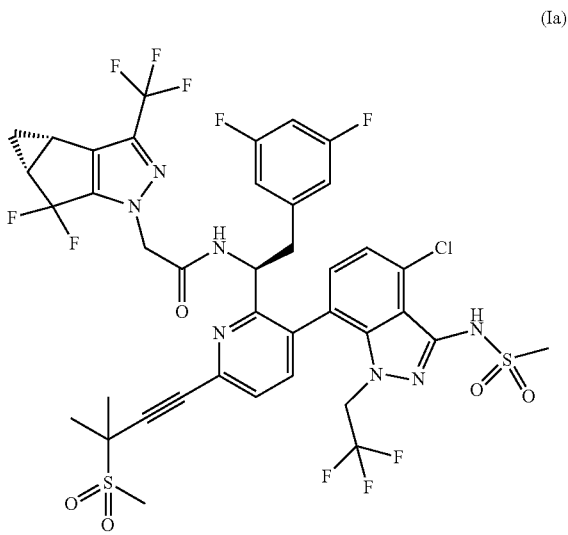 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

(Ia)

-continued

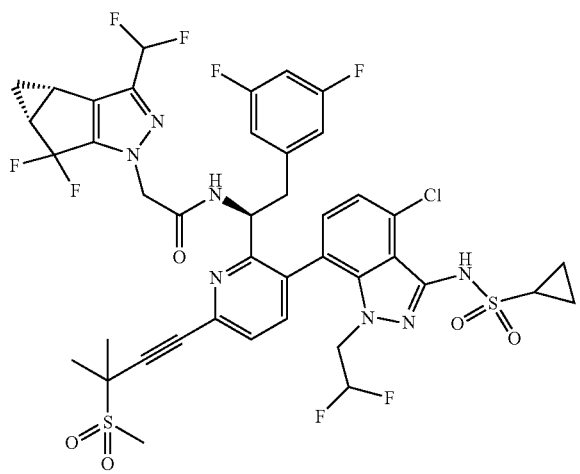

(Ib)

or a pharmaceutically acceptable salt thereof.

In some embodiments, the method comprises administering the compound of Formula (Ia), or a pharmaceutically acceptable salt thereof. In some embodiments, the method comprises administering the compound of Formula (Ib), or a pharmaceutically acceptable salt thereof.

The present disclosure includes methods of using a compound of Formula (Ia), N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl) 43bS,4aR)-5,5-difluoro-3-(trifluoromethyl)-3b,4,4a,5-tetrahydro-1H-cyclopropa[3,4] cyclopenta[1,2-c]pyrazol-1-yl)acetamide, having the following structure:

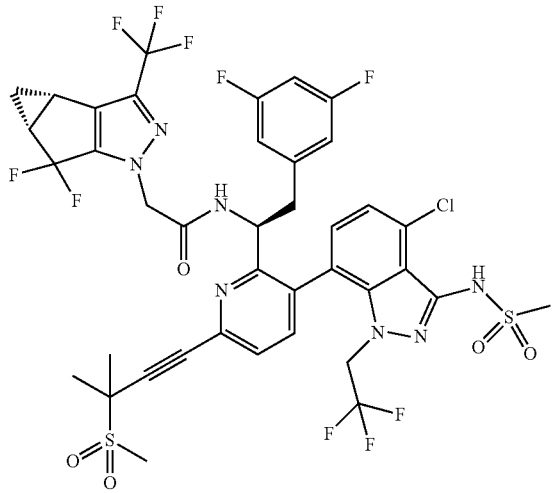

(Ia)

or a pharmaceutically acceptable salt thereof, for the prevention of an HIV infection.

The present disclosure also includes methods of using a compound of Formula (Ib), N—((S)-1-(3-(4-chloro-3-(cyclopropanesulfonamido)-1-(2,2-difluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3b S,4aR)-3-(difluoromethyl)-5,5-difluoro-3b,4,4a,5-tetrahy dro-1H-cyclopropa[3,4] cyclopenta[1,2-c]pyrazol-1-yl)acetamide, having the following structure:

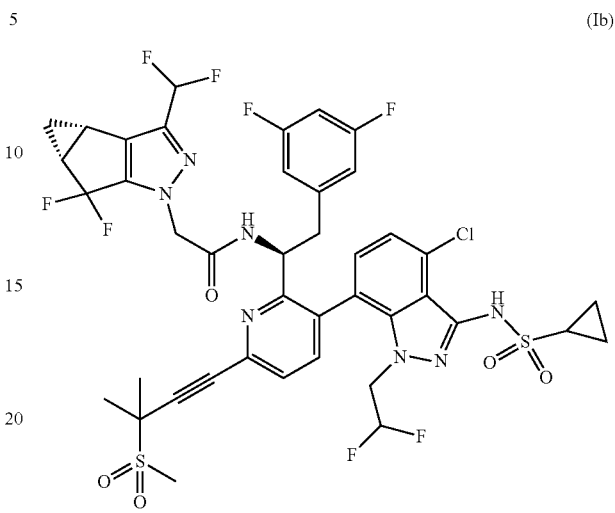

(Ib)

or a pharmaceutically acceptable salt thereof, for the prevention of an HIV infection.

Synthesis and characterization of the compounds of Formula (Ia) and Formula (Ib), and salts thereof are described in WO 2018/035359 (see also US 20180051005) and WO 2019/161280, the contents of which are hereby incorporated by reference in their entirety. Various forms of the compounds of Formula (Ia) are disclosed in WO 2019/035973 (see also US 20190083478) and WO/2019/035904 (see also US 20190084963), the contents of which are hereby incorporated by reference in their entirety.

In some embodiments, the HIV capsid inhibitor is a pharmaceutically acceptable salt of the compound of Formula (Ia) or Formula (Ib). Non-limiting examples of pharmaceutically acceptable salts of the compound of Formula (Ia) and Formula (Ib) include sodium salts. In some embodiments, the compound of Formula (Ia) is a sodium salt.

In the absence of a specific reference to a particular pharmaceutically acceptable salt and/or solvate of the above provided compound of Formula (Ia) or Formula (Ib), any dosages, whether expressed in milligrams or as % by weight, should be understood as referring to the amount of the free acid, i.e., the compound of Formula (Ia) or Formula (Ib). For example, a reference to "50 mg" of Formula (Ia), or a pharmaceutically acceptable salt thereof, refers to an amount of the compound of Formula (Ia), or a pharmaceutically acceptable salt thereof, which provides the same amount of the compound of Formula (Ia) as 50 mg of the compound of Formula (Ia) free acid. In some embodiments, a dosage referring to 50 mg of Formula (Ia) contains about 51.1 mg of Formula (Ia) monosodium salt.

In some embodiments of the methods disclosed herein, the compound of Formula (Ia) or Formula (Ib), or a pharmaceutically acceptable salt thereof, is administered in a dosage of from about 10 mg to about 2000 mg. In some embodiments of the methods disclosed herein, the compound of Formula (Ia) or Formula (Ib), or a pharmaceutically acceptable salt thereof, is administered in a dosage of from about 10 mg to about 3000 mg. In some embodiments, the compound of Formula (Ia) or Formula (Ib), or a pharmaceutically acceptable salt thereof, is administered in a dosage of about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg. In some embodiments, the compound of Formula (Ia) or Formula (Ib), or a pharmaceutically acceptable salt thereof, is administered in a dosage of about 2050 mg, about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 mg, about 2700 mg, about 2750 mg, about 2800 mg, about 2850 mg, about 2900 mg, about 2950 mg, or about 3000 mg. In some embodiments, the compound of Formula (Ia) or Formula (Ib), or a pharmaceutically acceptable salt thereof, is administered in a dosage of about 900 mg. In some embodiments, the compound of Formula (Ia) or Formula (Ib), or a pharmaceutically acceptable salt thereof, is administered in a dosage of about 500 mg. In some embodiments, the compound of Formula (Ia) or Formula (Ib), or a pharmaceutically acceptable salt thereof, is administered in a dosage of about 300 mg. In some embodiments, the compound of Formula (Ia) or Formula (Ib), or a pharmaceutically acceptable salt thereof, is administered in a dosage of about 100 mg. In some embodiments, the compound of Formula (Ia) or Formula (Ib), or a pharmaceutically acceptable salt thereof, is administered in a dosage of about 50 mg.

In some embodiments, the subject may have or be at risk of contracting an HIV infection. In some embodiments, the subject has been identified as an individual who is at risk of sexual transmission of HIV. In some embodiments, the individual has been identified as a man (e.g., who has sexual intercourse with a man or a woman), transgender man, transgender woman, a woman (e.g., who has sexual intercourse with a man or a woman), and/or a sex worker. In some embodiments, the individual has been identified as:
  having anal sex with at least two different sexual partners and no consistent condom use over the last 6 months; and/or
  having history of sexually transmitted diseases (STDs) during the last 12 months (e.g., syphilis, gonorrhea, chlamydiae, HBV or HCV infection); and/or
  using psycho-active drugs during sexual intercourses (e.g., cocaine, gammahydroxybutyric acid (GHB), methylenedioxymethamphetamine (MDMA), mephedrone); and/or
  having sexual intercourse with one or more partners originating from a region with high prevalence of HIV infection (>1%) (e.g., South America, Sub-Saharan Africa, South-East Asia, Eastern Europe, French Guyana) and no consistent condom use; and/or
  a sex worker; and/or
  having a sexual partner who is an intravenous drug user sharing injection material; and/or
  having an HIV-infected sexual partner with a detectable plasma viral load (e.g., >50 copies (cp)/milliliter (mL)).

In some embodiments, the subject is HIV-negative. In some embodiments, the HIV is HIV-1. In some embodiments, the HIV is HIV-2. In some embodiments, the HIV is HIV-1 and HIV-2.

As used herein, the terms "prevention" or "preventing" refers to the administration of a compound, pharmaceutically acceptable salt thereof, or composition comprising the compound or the pharmaceutically acceptable salt thereof according to the present disclosure pre- or post-exposure of the subject to the virus but before the appearance of symptoms of the disease, and/or prior to the detection of the virus in the blood. The terms also refer to prevention of the appearance of symptoms of the disease and/or to prevent the virus from reaching detectable levels in the blood. The terms include both pre-exposure prophylaxis (PrEP), as well as post-exposure prophylaxis (PEP) and event driven or "on demand" prophylaxis. The terms also refer to prevention of perinatal transmission of HIV from mother to baby by administration of a compound, pharmaceutically acceptable salt thereof, or composition comprising the compound or the pharmaceutically acceptable salt thereof according to the present disclosure to the mother before giving birth and to the child within the first days of life. The term also refers to prevention of transmission of HIV through blood transfusion.

As used herein, the term "period of exposure" refers to a period of time, ranging from a single event or to multiple events over an extended period of time, in which a subject is exposed to HIV. For example, a subject who engages in one sexual intercourse event with a partner who is HIV-positive has a period of exposure that is limited to the time and duration of that one sexual intercourse event with that partner. As another example, a subject who has sexual intercourse with a partner who is HIV-positive on multiple occasions over an extended period of time (e.g., days, weeks, months, or years) has a period of exposure that ranges from the first instance to the last instance of sexual intercourse with that partner.

As used herein, the term "inhibitory quotient" (IQ) refers to the $EC_{95}$ value of a compound of Formula (Ia) or Formula (Ib), or a pharmaceutically acceptable salt thereof, that is adjusted for serum protein binding.

In some embodiments, the compound of Formula (Ia) or Formula (Ib) as disclosed herein, or a pharmaceutically acceptable salt thereof, is administered daily. In some embodiments, the methods disclosed herein involve repeated administrations at intervals less than once daily. For example, in certain embodiments, the methods disclosed herein involve administration of the compound of Formula (Ia) or Formula (Ib), or a pharmaceutically acceptable salt thereof, every other day, five times per week, four times per week, three times per week, two times per week, one time per week, one time every two weeks, one time every three weeks, one time every four weeks, one time every five weeks, one time every six weeks, one time every seven weeks, or one time every eight weeks. In some embodiments of the methods disclosed herein, the methods involve administration of the compound of Formula (Ia) or Formula (Ib), or a pharmaceutically acceptable salt thereof, once every month, once every two months, once every three months, once every four months, once every five months, once every six months, or once every year.

In some embodiments, the methods disclosed herein comprise event driven administration of the compound of Formula (Ia) or Formula (Ib), or a pharmaceutically acceptable salt thereof, to the subject. As used herein, the terms "event driven" or "event driven administration" refer to administration of the compound of Formula (Ia) or Formula (Ib), or a pharmaceutically acceptable salt thereof, (1) prior to an event (e.g., 2 hours, 1 day, 2 days, 5 days, 7 days, 10 days, 14 days, 28 days (i.e., one month), or more days prior to the event) that would expose the subject to HIV (or that would otherwise increase the subject's risk of acquiring HIV); and/or (2) during an event (or more than one recurring event) that would expose the subject to HIV (or that would otherwise increase the subject's risk of acquiring HIV); and/or (3) after an event (or after the final event in a series of recurring events) that would expose the subject to HIV (or that would otherwise increase the subject's risk of acquiring HIV). In some embodiments, the event driven administration is performed pre-exposure of the subject to the HIV. In some embodiments, the event driven administration is performed during exposure of the subject to the HIV. In some embodiments, the event driven administration is performed post-exposure of the subject to the HIV.

In some embodiments, the event driven administration is performed pre-exposure of the subject to the HIV and during exposure of the subject to the HIV In some embodiments, the event driven administration is performed pre-exposure of the subject to the HIV and post-exposure of the subject to the HIV.

In some embodiments, the event driven administration is performed during exposure of the subject to the HIV and post-exposure of the subject to the HIV.

In certain embodiments, the methods disclosed herein involve administration prior to and/or after an event that would expose the subject to HIV or that would otherwise increase the subject's risk of acquiring HIV, e.g., as pre-exposure prophylaxis (PrEP) and/or as post-exposure prophylaxis (PEP). Examples of events that could increase a subject's risk of acquiring HIV include, without limitation, no condom use during anal intercourse with an HIV positive partner or a partner of unknown HIV status; anal intercourse with more than 3 sex partners; exchange of money, gifts, shelter or drugs for anal sex; sex with male partner and diagnosis of sexually transmitted infection; and no consistent use of condoms with sex partner known to be HIV positive. In some embodiments, the methods disclosed herein comprise pre-exposure prophylaxis (PrEP). In some embodiments, methods disclosed herein comprise post-exposure prophylaxis (PEP). In some embodiments, the methods disclosed herein comprise pre-exposure prophylaxis (PrEP) and post-exposure prophylaxis (PEP).

In some embodiments, the compound of Formula (Ia) or Formula (Ib), or a pharmaceutically acceptable salt thereof, is administered before exposure of the subject to the HIV.

In some embodiments, the compound of Formula (Ia) or Formula (Ib), or a pharmaceutically acceptable salt thereof, is administered during exposure of the subject to the HIV.

In some embodiments, the compound of Formula (Ia) or Formula (Ib), or a pharmaceutically acceptable salt thereof, is administered after exposure of the subject to the HIV.

In some embodiments, the compound of Formula (Ia) or Formula (Ib), or a pharmaceutically acceptable salt thereof, is administered before and during exposure of the subject to the HIV.

In some embodiments, the compound of Formula (Ia) or Formula (Ib), or a pharmaceutically acceptable salt thereof, is administered before and after exposure of the subject to the HIV.

In some embodiments, the compound of Formula (Ia) or Formula (Ib), or a pharmaceutically acceptable salt thereof, is administered during and after exposure of the subject to the HIV.

In some embodiments, the compound of Formula (Ia) or Formula (Ib), or a pharmaceutically acceptable salt thereof, is administered before, during, and after exposure of the subject to the HIV.

In some embodiments, the dose of the compound of Formula (Ia) or Formula (Ib), or a pharmaceutically acceptable salt thereof, administered during each period (i.e., before, during, and after exposure) may be different, i.e., independently selected from any of the doses disclosed herein.

An example of event driven dosing regimen includes administration of the compound of Formula (Ia) or Formula (Ib), or a pharmaceutically acceptable salt thereof, at or within 5 to 10 days (e.g., about 7 days or one week) prior to HIV exposure (e.g., first sexual activity with sex partner known to be HIV positive, including sexual intercourse), followed by administration of the compound of Formula (Ia) or Formula (Ib), or a pharmaceutically acceptable salt, once every 1 to 12 weeks during the period of exposure (e.g., sexual activity with sex partner known to be HIV positive). Such a dosing regimen can be followed by a further administration of the compound of Formula (Ia) or Formula (Ib), or a pharmaceutically acceptable salt thereof, after the last exposure (e.g., sexual activity with sex partner known to be HIV positive).

In certain embodiments, e.g., when administered as PrEP, the compound of Formula (Ia) or Formula (Ib), or a pharmaceutically acceptable salt thereof, is administered 1 hour to 240 hours (i.e., within 10 days), 1 hour to 216 hours, 1 hour to 192 hours, 1 hour to 168 hours, 1 hour to 144 hours, 1 hour to 120 hours, 1 hour to 96 hours, 1 hour to 72 hours, 1 hour to 48 hours, 1 hour to 24 hours, or 1 hour to 12 hours prior to an event that would increase the subject's risk of acquiring HIV (e.g., prior to sexual activity) prior to an event that would increase the subject's risk of acquiring HIV (e.g., prior to sexual intercourse or other exposure to the HIV). In some embodiments, the compound of Formula (Ia) or Formula (Ib), or a pharmaceutically acceptable salt thereof, is administered within 14 days, 13 days, 12 days, 11 days, 10 days, 9 days, 8 days, 7 days, 6 days, 5 days, 4 days, 3 days, 2 days, or 1 day prior to an event that would increase the subject's risk of acquiring HIV (e.g., prior to sexual intercourse or other exposure to the HIV). In some embodiments, the compound of Formula (Ia) or Formula (Ib), or a pharmaceutically acceptable salt thereof, is administered within 72 hours, 60 hours, 48 hours, 24 hours, 12 hours, 9 hours, 6 hours, 4 hours, 3 hours, 2 hours, or 1 hour prior to an event that would increase the subject's risk of acquiring HIV (e.g., prior to sexual intercourse or other exposure to the HIV). In certain embodiments, when the compound of Formula (Ia) or Formula (Ib), or a pharmaceutically acceptable salt thereof, is administered prior to an event that would increase the subject' risk of acquiring HIV, it is administered daily prior to the event (e.g., sexual activity). In certain embodiments, when the compound of Formula (Ia) or Formula (Ib), or a pharmaceutically acceptable salt thereof, is administered prior to an event that would increase the subject's risk of acquiring HIV, it is administered one to three times prior to the event. In certain embodiments, when the compound of Formula (Ia) or Formula (Ib), or a pharmaceutically acceptable salt thereof, is administered prior to an event that would increase the subject's risk of acquiring HIV, it is administered one time (i.e., once) prior to the event.

In some embodiments, the compound of Formula (Ia) or Formula (Ib), or a pharmaceutically acceptable salt thereof, is administered from about 14 days to about one day before exposure of the subject to the HIV. In some embodiments, the compound of Formula (Ia) or Formula (Ib), or a pharmaceutically acceptable salt thereof, is administered once from about 14 days to about one day before exposure of the subject to the HIV.

In some embodiments, the compound of Formula (Ia) or Formula (Ib), or a pharmaceutically acceptable salt thereof, is administered from about 10 days to about 5 days before exposure of the subject to the HIV. In some embodiments, the compound of Formula (Ia) or Formula (Ib), or a pharmaceutically acceptable salt thereof, is administered once from about 10 days to about 5 days before exposure of the subject to the HIV.

In some embodiments, the compound of Formula (Ia) or Formula (Ib), or a pharmaceutically acceptable salt thereof, is administered from about 8 days to about 6 days before exposure of the subject to the HIV. In some embodiments, the compound of Formula (Ia) or Formula (Ib), or a pharmaceutically acceptable salt thereof, is administered once from about 8 days to about 6 days before exposure of the subject to the HIV.

In some embodiments, the compound of Formula (Ia) or Formula (Ib), or a pharmaceutically acceptable salt thereof, is administered about 7 days before exposure of the subject to the HIV. In some embodiments, the compound of Formula (Ia) or Formula (Ib), or a pharmaceutically acceptable salt thereof, is administered once about 7 days before exposure of the subject to the HIV.

In some embodiments, the compound of Formula (Ia) or Formula (Ib), or a pharmaceutically acceptable salt thereof, is administered from about 72 hours to about 1 hour before exposure of the subject to the HIV. In some embodiments, the compound of Formula (Ia) or Formula (Ib), or a pharmaceutically acceptable salt thereof, is administered once from about 72 hours to about 1 hour before exposure of the subject to the HIV.

In some embodiments of the methods provided herein, the pre-exposure prophylaxis (PrEP) comprises continuous PrEP. In some embodiments, the continuous PrEP comprises daily administration of the compound of Formula (Ia) or Formula (Ib), or a pharmaceutically acceptable salt thereof, from about 14 days to about 1 hour before the exposure of the subject to the HIV.

In certain embodiments where the compound of Formula (Ia) or Formula (Ib), or a pharmaceutically acceptable salt thereof, is administered before exposure of the subject to the HIV, the methods disclosed herein further comprise administering one or more additional doses of the compound of Formula (Ia) or Formula (Ib), or a pharmaceutically acceptable salt thereof, during, and/or after exposure of the subject to the HIV.

In some embodiments, e.g., when administered as part of a PrEP regimen or as part of a PEP regimen, the compound of Formula (Ia) or Formula (Ib), or a pharmaceutically acceptable salt thereof, is administered during the period of exposure of the subject to the HIV. In certain embodiments wherein the compound of Formula (Ia) or Formula (Ib), or a pharmaceutically acceptable salt thereof, is administered before HIV exposure, the compound of Formula (Ia) or Formula (Ib), or a pharmaceutically acceptable salt thereof, is administered about every 7 days, about every 14 days, about every 21 days, about every 28 days, about every 35 days, or about every 42 days (e.g., as a single dose) during the time of HIV exposure (e.g., during the time period of sexual activity with sex partner known to be HIV positive). In some embodiments, the compound of Formula (Ia) or Formula (Ib), or a pharmaceutically acceptable salt thereof, is administered once about every 7 days, about every 14 days, about every 21 days, about every 28 days, about every 35 days, or about every 42 days during the period of exposure of the subject to the HIV.

In some embodiments, the compound of Formula (Ia) or Formula (Ib), or a pharmaceutically acceptable salt thereof, is administered once (e.g., at about 7 days, 14 days, 21 days, or 28 days) after final exposure to the HIV (e.g., after a period of sexual activity with sex partner known to be HIV positive).

In some embodiments, the compound of Formula (Ia) or Formula (Ib), or a pharmaceutically acceptable salt thereof, administered prior to exposure to the HIV is at a different dose than the compound of Formula (Ia) or Formula (Ib), or a pharmaceutically acceptable salt thereof, administered during and/or after exposure to the HIV. For example, in some embodiments, the dose of the compound of Formula (Ia) or Formula (Ib), or a pharmaceutically acceptable salt thereof, is increased, e.g., as a double dose, as a triple dose, and the like as compared to an earlier administered dose (e.g., a dose prior to exposure to the HIV). In some embodiments, the increased dose of the compound of Formula (Ia) or Formula (Ib), or a pharmaceutically acceptable salt thereof, is a double dose. In some embodiments, the dose of the compound of Formula (Ia) or Formula (Ib), or a pharmaceutically acceptable salt thereof, is decreased, e.g., a half dose as compared to an earlier administered dose (e.g., a dose prior to exposure to the HIV).

In some embodiments, the compound of Formula (Ia) or Formula (Ib), or a pharmaceutically acceptable salt thereof, is administered as a single dose from about 1 hour to about 10 days before exposure of the subject to the HIV.

Additional examples of PrEP and/or PEP can be found, for example, at the clinical trial summary titled "On Demand Antiretroviral Pre-exposure Prophylaxis for HIV Infection in Men Who Have Sex With Men" (Clinical Trial #NCT01473472); the clinical trial summary titled "Prevention of HIV in Ile-de-France" (Clinical Trials #NCT03113123), and at Molina et al, N Engl. J. Med. 2015, 353:2237-2246, the disclosure of each of which is incorporated herein by reference in its entirety.

In some embodiments, e.g., when administered as part of a PrEP regimen or as part of a PEP regimen, the compound of Formula (Ia) or Formula (Ib), or a pharmaceutically acceptable salt thereof, is administered 1 hour to 10 days, 1 hour to 7 days, 1 hour to 5 days, 1 to 72 hours, 1 to 48 hours, 1 to 36 hours, 1 to 24 hours, or 1 to 12 hours following an event that would increase the subject's risk of acquiring HIV (e.g., following sexual intercourse or other exposure to the HIV).

In certain embodiments, e.g., when administered as PEP, the compound of Formula (Ia) or Formula (Ib), or a pharmaceutically acceptable salt thereof, is administered for 7 days, 14 days, 21 days, 28 days, 30 days, or 45 days following an event that would increase the subject's risk of acquiring HIV (e.g., following sexual intercourse or other exposure to the HIV). In certain embodiments, e.g., when administered as PEP, the compound of Formula (Ia) or Formula (Ib), or a pharmaceutically acceptable salt thereof, is administered for 30 days following an event that would increase the subject's risk of acquiring HIV (e.g., following sexual intercourse or other exposure to the HIV). In certain embodiments, the compound of Formula (Ia) or Formula (Ib), or a pharmaceutically acceptable salt thereof, is administered less than 1 hour, 2 hours, 3 hours, 4 hours, 5 hours, 6 hours, 7 hours, 8 hours, 9 hours, 12 hours, 18 hours, 24 hours, 36 hours, or 48 hours following an event that would increase the subject's risk of acquiring HIV (e.g., following sexual intercourse or other exposure to the HIV virus). In certain embodiments, the compound of Formula (Ia) or Formula (Ib), or a pharmaceutically acceptable salt thereof, is administered for 1 day, 2 days, 3 days, 4 days, or 5 days following an event that would increase the subject's risk of acquiring HIV (e.g., following sexual intercourse or other exposure to the HIV). In certain embodiments, when the compound of Formula (Ia) or Formula (Ib), or a pharmaceutically acceptable salt thereof, is administered following an event that would increase the subject's risk of acquiring HIV, it is administered daily following the event. In certain embodiments, when the compound of Formula (Ia) or Formula (Ib), or a pharmaceutically acceptable salt thereof, is administered following an event that would increase the subject's risk of acquiring HIV, it is administered one to three times following the event. In certain embodiments, when the compound of Formula (Ia) or Formula (Ib), or a pharmaceutically acceptable salt thereof, is administered following an event that would increase the subject's risk of acquiring HIV, it is administered once following the event.

In certain embodiments, e.g., when administered as PEP, the compound of Formula (Ia) or Formula (Ib), or a pharmaceutically acceptable salt thereof, is administered once about every month, once about every 2 months, once about every 3 months, once about every 4 months, once about every 5 months, once about every 6 months, or once about every 12 months following an event that would increase the subject's risk of acquiring HIV (e.g., following sexual intercourse or other exposure to the HIV). In certain embodiments, e.g., when administered as PEP, the compound of Formula (Ia) or Formula (Ib), or a pharmaceutically acceptable salt thereof, is administered once about every month following an event that would increase the subject's risk of acquiring HIV (e.g., following sexual intercourse or other exposure to the HIV). In certain embodiments, e.g., when administered as PEP, the compound of Formula (Ia) or Formula (Ib), or a pharmaceutically acceptable salt thereof, is administered once about every 2 months following an event that would increase the subject's risk of acquiring HIV (e.g., following sexual intercourse or other exposure to the HIV). In certain embodiments, e.g., when administered as PEP, the compound of Formula (Ia) or Formula (Ib), or a pharmaceutically acceptable salt thereof, is administered once about every 3 months following an event that would increase the subject's risk of acquiring HIV (e.g., following sexual intercourse or other exposure to the HIV). In certain embodiments, e.g., when administered as PEP, the compound of Formula (Ia) or Formula (Ib), or a pharmaceutically acceptable salt thereof, is administered once about every 4 months following an event that would increase the subject's risk of acquiring HIV (e.g., following sexual intercourse or other exposure to the HIV). In certain embodiments, e.g., when administered as PEP, the compound of Formula (Ia) or Formula (Ib), or a pharmaceutically acceptable salt thereof, is administered once about every 5 months following an event that would increase the subject's risk of acquiring HIV (e.g., following sexual intercourse or other exposure to the HIV). In certain embodiments, e.g., when administered as PEP, the compound of Formula (Ia) or Formula (Ib), or a pharmaceutically acceptable salt thereof, is administered once about every 6 months following an event that would increase the subject's risk of acquiring HIV (e.g., following sexual intercourse or other exposure to the HIV). In certain embodiments, e.g., when administered as PEP, the compound of Formula (Ia) or Formula (Ib), or a pharmaceutically acceptable salt thereof, is administered once about every 12 months following an event that would increase the subject's risk of acquiring HIV (e.g., following sexual intercourse or other exposure to the HIV).

In certain embodiments, e.g., when administered as PEP, the compound of Formula (Ia) or Formula (Ib), or a pharmaceutically acceptable salt thereof, is administered for one month, two months, three months, four months, five months, six months, or twelve months following an event that would increase the subject's risk of acquiring HIV (e.g., following sexual intercourse or other exposure to the HIV).

In certain embodiments, when the compound of Formula (Ia) or Formula (Ib), or a pharmaceutically acceptable salt thereof, is administered following an event that would increase the subject's risk of acquiring HIV, it is administered one to fifty times following the event. In certain embodiments, when the compound of Formula (Ia) or Formula (Ib), or a pharmaceutically acceptable salt thereof, is administered following an event that would increase the subject's risk of acquiring HIV, it is administered one to forty times following the event. In certain embodiments, when the compound of Formula (Ia) or Formula (Ib), or a pharmaceutically acceptable salt thereof, is administered following an event that would increase the subject's risk of acquiring HIV, it is administered one to thirty times following the event. In certain embodiments, when the compound of Formula (Ia) or Formula (Ib), or a pharmaceutically acceptable salt thereof, is administered following an event that would increase the subject's risk of acquiring HIV, it is administered one to twenty times following the event. In certain embodiments, when the compound of Formula (Ia) or Formula (Ib), or a pharmaceutically acceptable salt thereof, is administered following an event that would increase the subject's risk of acquiring HIV, it is administered one to fifteen times following the event. In certain embodiments, when the compound of Formula (Ia) or Formula (Ib), or a pharmaceutically acceptable salt thereof, is administered following an event that would increase the subject's risk of acquiring HIV, it is administered one to ten times following the event. In certain embodiments, when the compound of Formula (Ia) or Formula (Ib), or a pharmaceutically acceptable salt thereof, is administered following an event that would increase the subject's risk of acquiring HIV, it is administered one to five times following the event.

In certain embodiments, when the compound of Formula (Ia) or Formula (Ib), or a pharmaceutically acceptable salt thereof, is administered following an event that would increase the subject's risk of acquiring HIV, it is administered two times following the event. In certain embodiments, when the compound of Formula (Ia) or Formula (Ib), or a pharmaceutically acceptable salt thereof, is administered following an event that would increase the subject's risk of acquiring HIV, it is administered three times following the event. In certain embodiments, when the compound of Formula (Ia) or Formula (Ib), or a pharmaceutically acceptable salt thereof, is administered following an event that would increase the subject's risk of acquiring HIV, it is administered four times following the event. In certain embodiments, when the compound of Formula (Ia) or Formula (Ib), or a pharmaceutically acceptable salt thereof, is administered following an event that would increase the subject's risk of acquiring HIV, it is administered five times following the event. In certain embodiments, when the compound of Formula (Ia) or Formula (Ib), or a pharmaceutically acceptable salt thereof, is administered following an event that would increase the subject's risk of acquiring HIV, it is administered six times following the event. In certain embodiments, when the compound of Formula (Ia) or Formula (Ib), or a pharmaceutically acceptable salt thereof, is administered following an event that would increase the subject's risk of acquiring HIV, it is administered seven times following the event. In certain embodiments, when the compound of Formula (Ia) or Formula (Ib), or a pharmaceutically acceptable salt thereof, is administered following an event that would increase the subject's risk of acquiring HIV, it is administered eight times following the event. In certain embodiments, when the compound of Formula (Ia) or Formula (Ib), or a pharmaceutically acceptable salt thereof, is administered following an event that would increase the subject's risk of acquiring HIV, it is administered nine times following the event. In certain embodiments, when the compound of Formula (Ia) or Formula (Ib), or a pharmaceutically acceptable salt thereof, is administered following an event that would increase the subject's risk of acquiring HIV, it is administered ten times following the event.

In certain embodiments, when the compound of Formula (Ia) or Formula (Ib), or a pharmaceutically acceptable salt thereof, is administered following an event that would increase the subject's risk of acquiring HIV, it is administered twice following the event.

In some embodiments, the compound of Formula (Ia) or Formula (Ib), or a pharmaceutically acceptable salt thereof, is administered during exposure of the subject to the HIV (e.g., during a period of sexual activity with sex partner known to be HIV positive).

In some embodiments, the compound of Formula (Ia) or Formula (Ib), or a pharmaceutically acceptable salt thereof, is administered after exposure (e.g., after final exposure) of the subject to the HIV (e.g., after a period of sexual activity with sex partner known to be HIV positive). In some embodiments, the compound of Formula (Ia) or Formula (Ib), or a pharmaceutically acceptable salt thereof, is administered from about 1 hour to about 14 days after exposure (e.g., after final exposure) of the subject to the HIV. In some embodiments, the compound of Formula (Ia) or Formula (Ib), or a pharmaceutically acceptable salt thereof, is administered once from about 1 hour to about 14 days after exposure (e.g., after final exposure) of the subject to the HIV. In some embodiments, the compound of Formula (Ia) or Formula (Ib), or a pharmaceutically acceptable salt thereof, is administered from about 1 hour to about 7 days after exposure (e.g., after final exposure) of the subject to the HIV. In some embodiments, the compound of Formula (Ia) or Formula (Ib), or a pharmaceutically acceptable salt thereof, is administered once from about 1 hour to about 7 days after exposure (e.g., after final exposure) of the subject to the HIV. In some embodiments, the compound of Formula (Ia) or Formula (Ib), or a pharmaceutically acceptable salt thereof, is administered from about 1 hour to about 72 hours after exposure (e.g., after final exposure) of the subject to the HIV. In some embodiments, the compound of Formula (Ia) or Formula (Ib), or a pharmaceutically acceptable salt thereof, is administered once from about 1 hour to about 72 hours after exposure (e.g., after final exposure) of the subject to the HIV. In some embodiments, the compound of Formula (Ia) or Formula (Ib), or a pharmaceutically acceptable salt thereof, is administered from about 1 hour to about 24 hours after exposure (e.g., after final exposure) of the subject to the HIV. In some embodiments, the compound of Formula (Ia) or Formula (Ib), or a pharmaceutically acceptable salt thereof, is administered once from about 1 hour to about 24 hours after exposure (e.g., after final exposure) of the subject to the HIV. In some embodiments, the compound of Formula (Ia) or Formula (Ib), or a pharmaceutically acceptable salt thereof, is administered from about 24 hours to about 72 hours after exposure (e.g., after final exposure) of the subject to the HIV. In some embodiments, the compound of Formula (Ia) or Formula (Ib), or a pharmaceutically acceptable salt thereof, is administered once from about 24 hours to about 72 hours after exposure (e.g., after final exposure) of the subject to the HIV.

In some embodiments, e.g., when administered as PrEP, the compound of Formula (Ia) or Formula (Ib), or a pharmaceutically acceptable salt thereof, is administered prior to an event that would increase the subject's risk of acquiring HIV (e.g., prior to sexual activity), and following the event. For example, in certain embodiments, when administered as PrEP, the compound of Formula (Ia) or Formula (Ib), or a pharmaceutically acceptable salt thereof, is administered 1 to 240 hours (i.e., within 10 days), 1 hour to 216 hours, 1 hour to 192 hours, 1 hour to 168 hours, 1 hour to 144 hours, 1 hour to 120 hours, 1 hour to 96 hours, 1 hour to 72 hours, 1 hour to 48 hours, 1 hour to 24 hours, or 1 hour to 12 hours prior to an event that would increase the subject's risk of acquiring HIV (e.g., prior to sexual activity) and 1 hour to 240 hours (i.e., within 10 days), 1 hour to 216 hours, 1 hour to 192 hours, 1 hour to 168 hours, 1 hour to 144 hours, 1 hour to 120 hours, 1 hour to 96 hours, 1 hour to 72, 1 hour to 48 hours, 1 hour to 36 hours, 1 hour to 24 hours, or 1 hour to 12 hours following the event. For example, in some embodiments, one or more (e.g., one, two, or three) dosages of the compound of Formula (Ia) or Formula (Ib), or a pharmaceutically acceptable salt thereof, are administered one to ten days (e.g., seven days) prior to an event that would increase the subject's risk of acquiring HIV (e.g., prior to sexual intercourse) and once during a period of one to ten days following the event. In some embodiments, the compound of Formula (Ia) or Formula (Ib), or a pharmaceutically acceptable salt thereof, is administered once per week, twice per week, three times per week, four times per week, or five times per week and one or more times (e.g., one, two, or three times) beginning 1 to 48 hours following an event that would increase the subject's risk of acquiring HIV (e.g., following sexual intercourse).

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically acceptable salt thereof, once every 7 days during the period of exposure to the HIV. In some embodiments, the compound of Formula (Ia) or Formula (Ib), or a pharmaceutically acceptable salt thereof, administered in step (i) is at a different dose than the compound of Formula (Ia) or Formula (Ib), or a pharmaceutically acceptable salt thereof, administered in step (ii).

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 14 days during the period of exposure to the HIV. In some embodiments, the compound of Formula (Ia) or Formula (Ib), or a pharmaceutically acceptable salt thereof, administered in step (i) is at a different dose than the compound of Formula (Ia) or Formula (Ib), or a pharmaceutically acceptable salt thereof, administered in step (ii).

In some embodiments, the methods comprise:
(i) administering the compound of Formula (Ia) or Formula (Ib), or a pharmaceutically acceptable salt thereof, at about 7 days prior to exposure of the subject to the HIV; and (ii) administering the compound of Formula (Ia) or Formula (Ib), or a pharmaceutically salt thereof, once every 21 days during the period of exposure to the HIV. In some embodiments, the compound of Formula (Ia) or Formula (Ib), or a pharmaceutically acceptable salt thereof, administered in step (i) is at a different dose than the compound of Formula (Ia) or Formula (Ib), or a pharmaceutically acceptable salt thereof, administered in step (ii).

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 28 days during the period of exposure to the HIV. In some embodiments, the compound of Formula (Ia) or Formula (Ib), or a pharmaceutically acceptable salt thereof, administered in step (i) is at a different dose than the compound of Formula (Ia) or Formula (Ib), or a pharmaceutically acceptable salt thereof, administered in step (ii).

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 35 days during the period of exposure to the HIV. In some embodiments, the compound of Formula (Ia) or Formula (Ib), or a pharmaceutically acceptable salt thereof, administered in step (i) is at a different dose than the compound of Formula (Ia) or Formula (Ib), or a pharmaceutically acceptable salt thereof, administered in step (ii).

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 42 days during the period of exposure to the HIV. In some embodiments, the compound of Formula (Ia) or Formula (Ib), or a pharmaceutically acceptable salt thereof, administered in step (i) is at a different dose than the compound of Formula (Ia) or Formula (Ib), or a pharmaceutically acceptable salt thereof, administered in step (ii).

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 1 month during the period of exposure to the HIV.

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 2 months during the period of exposure to the HIV.

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 3 months during the period of exposure to the HIV.

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 6 months during the period of exposure to the HIV.

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 12 months during the period of exposure to the HIV.

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 1 month during the period of exposure to the HIV. In some embodiments, the compound of Formula (Ia) or Formula (Ib), or a pharmaceutically acceptable salt thereof, administered in step (i) is at a different dose than the compound of Formula (Ia) or Formula (Ib), or a pharmaceutically acceptable salt thereof, administered in step (ii).

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 2 months during the period of exposure to the HIV. In some embodiments, the compound of Formula (Ia) or Formula (Ib), or a pharmaceutically acceptable salt thereof, administered in step (i) is at a different dose than the compound of Formula (Ia) or Formula (Ib), or a pharmaceutically acceptable salt thereof, administered in step (ii).

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 3 months during the period of exposure to the HIV. In some embodiments, the compound of Formula (Ia) or Formula (Ib), or a pharmaceutically acceptable salt thereof, administered in step (i) is at a different dose than the compound of Formula (Ia) or Formula (Ib), or a pharmaceutically acceptable salt thereof, administered in step (ii).

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 6 months during the period of exposure to the HIV. In some embodiments, the compound of Formula (Ia) or Formula (Ib), or a pharmaceutically acceptable salt thereof, administered in step (i) is at a different dose than the compound of Formula (Ia) or Formula (Ib), or a pharmaceutically acceptable salt thereof, administered in step (ii).

In some embodiments, the methods comprise:
(i) administering the compound of Formula (Ia) or Formula (Ib), or a pharmaceutically acceptable salt thereof, at about 7 days prior to exposure of the subject to the HIV; and
(ii) administering the compound of Formula (Ia) or Formula (Ib), or a pharmaceutically salt thereof, once every 12 months during the period of exposure to the HIV. In some embodiments, the compound of Formula (Ia) or Formula (Ib), or a pharmaceutically acceptable salt thereof, administered in step (i) is at a different dose than the compound of Formula (Ia) or Formula (Ib), or a pharmaceutically acceptable salt thereof, administered in step (ii).

In some embodiments, the administrations of the compound of Formula (Ia) or Formula (Ib), or a pharmaceutically acceptable salt thereof (as in steps (i) or (ii)), further comprise administration of:
(a) bictegravir, or a pharmaceutically acceptable salt thereof;
(b) tenofovir alafenamide, or a pharmaceutically acceptable salt thereof or
(c) bictegravir, or a pharmaceutically acceptable salt thereof and tenofovir alafenamide, or a pharmaceutically acceptable salt thereof.

In some embodiments, the administrations of the compound of Formula (Ia) or Formula (Ib), or a pharmaceutically acceptable salt thereof (as in steps (i) or (ii)), further comprise administration of bictegravir, or a pharmaceutically acceptable salt thereof, in a dosage of from about 10 mg to about 600 mg and tenofovir alafenamide, or a pharmaceutically acceptable salt thereof, in a dosage of from about 10 mg to about 50 mg.

In some embodiments, the administrations of the compound of Formula (Ia) or Formula (Ib), or a pharmaceutically acceptable salt thereof (as in steps (i) or (ii)), further comprise administration of bictegravir, or a pharmaceutically acceptable salt thereof, in a dosage of from about 10 mg to about 200 mg and tenofovir alafenamide, or a pharmaceutically acceptable salt thereof, in a dosage of from about 10 mg to about 50 mg.

Also provided herein is a method of reducing the risk of acquiring HIV in a subject, comprising administering to the subject a compound of Formula (Ia) or Formula (Ib), or a pharmaceutically acceptable salt thereof.

In some embodiments, methods for reducing the risk of acquiring HIV (e.g., HIV-1 and/or HIV-2) comprise administration of the compound of Formula (Ia) or Formula (Ib), or a pharmaceutically acceptable salt thereof, to a subject in combination with safer sexual intercourse practices. In certain embodiments, methods for reducing the risk of acquiring HIV (e.g., HIV-1 and/or HIV-2) comprise administration of the compound of Formula (Ia) or Formula (Ib), or a pharmaceutically acceptable salt thereof, to a subject at risk of acquiring HIV. Examples of subjects at high risk for acquiring HIV include, without limitation, a subject who is at risk of sexual transmission of HIV.

In some embodiments, the reduction in risk of acquiring HIV is at least about 40%, 50%, 60%, 70%, 80%, 90%, or 95% (compared to a subject having not been administered the compound of Formula (Ia) or Formula (Ib), or a pharmaceutically acceptable salt thereof according to any of the methods provided herein). In some embodiments, the reduction in risk of acquiring HIV is about 80%, 85%, or 90%. In some embodiments, the reduction in risk of acquiring HIV is at least about 75%. In some embodiments, the reduction in risk of acquiring HIV is at least about 80%. In some embodiments, the reduction in risk of acquiring HIV is at least about 85%. In some embodiments, the reduction in risk of acquiring HIV is at least about 90%.

Dosing Regimens

In some embodiments, the compound of Formula (Ia) or Formula (Ib), or a pharmaceutically acceptable salt thereof, is administered to a subject (e.g., a human patient) in accordance with an effective dosing regimen for a desired period of time or duration. In some embodiments, the dosing regimen includes administration of the compound of Formula (Ia) or Formula (Ib), or a pharmaceutically acceptable salt thereof, for at least about 1 week, about 2 weeks, about 4 weeks, about 8 weeks, about 12 weeks, about 16 weeks, about 20 weeks, about 24 weeks, about 28 weeks, about 32 weeks, about 36 weeks, about 40 weeks, about 44 weeks, about 48 weeks, about 52 weeks, or longer.

In some embodiments, the dosing regimen includes administration of the compound of Formula (Ia) or Formula (Ib), or a pharmaceutically acceptable salt thereof, for at least about 1 year, 2 years, 3 years, 4 years, 5 years, 10 years, or longer. In some embodiments, the dosing regimen includes continuous administration of the compound of Formula (Ia) or Formula (Ib), or a pharmaceutically acceptable salt thereof, during the life of the subject.

In some embodiments, the compound of Formula (Ia) or Formula (Ib), or a pharmaceutically acceptable salt thereof, is administered on a daily or intermittent schedule. In some embodiments, the compound of Formula (Ia) or Formula (Ib), or a pharmaceutically acceptable salt thereof, is administered once daily. In some embodiments, the compound of Formula (Ia) or Formula (Ib), or a pharmaceutically acceptable salt thereof, is administered on a monthly schedule. In some embodiments, the compound of Formula (Ia) or Formula (Ib), or a pharmaceutically acceptable salt thereof, is administered once about every 1 week, about every 2 weeks, about every 4 weeks, about every 8 weeks, about every 12 weeks, about every 16 weeks, about every 20 weeks, about every 24 weeks, or once about every 48 weeks. In some embodiments, the compound of Formula (Ia) or Formula (Ib), or a pharmaceutically acceptable salt thereof, is administered once every 4 weeks (or monthly). In some embodiments, the compound of Formula (Ia) or Formula (Ib), or a pharmaceutically acceptable salt thereof, is administered once every 8 weeks (or 2 months). In some embodiments, the compound of Formula (Ia) or Formula (Ib), or a pharmaceutically acceptable salt thereof, is administered once every 12 weeks (or three months). In some embodiments, the compound of Formula (Ia) or Formula (Ib), or a pharmaceutically acceptable salt thereof, is administered once every 16 weeks (or four months). In some embodiments, the compound of Formula (Ia) or Formula (Ib), or a pharmaceutically acceptable salt thereof, is administered once every 20 weeks (or five months). In some embodiments, the compound of Formula (Ia) or Formula (Ib), or a pharmaceutically acceptable salt thereof, is administered every 24 weeks (or 6 months). In some embodiments, the compound of Formula (Ia) or Formula (Ib), or a pharmaceutically acceptable salt thereof, is administered every 52 weeks (or yearly).

In some embodiments, the compound of Formula (Ia) or Formula (Ib), or a pharmaceutically acceptable salt thereof, is administered once about every month, about every 2 months, about every 3 months, about every 4 months, about every 5 months, about every 6 months, or about every 12 months during the period of exposure of the subject to the HIV. In some embodiments, the compound of Formula (Ia) or Formula (Ib), or a pharmaceutically acceptable salt thereof, is administered once about every month during the period of exposure of the subject to the HIV. In some embodiments, the compound of Formula (Ia) or Formula (Ib), or a pharmaceutically acceptable salt thereof, is administered once about every 2 months during the period of exposure of the subject to the HIV. In some embodiments, the compound of Formula (Ia) or Formula (Ib), or a pharmaceutically acceptable salt thereof, is administered once about every 3 months during the period of exposure of the subject to the HIV. In some embodiments, the compound of Formula (Ia) or Formula (Ib), or a pharmaceutically acceptable salt thereof, is administered once about every 4 months during the period of exposure of the subject to the HIV. In some embodiments, the compound of Formula (Ia) or Formula (Ib), or a pharmaceutically acceptable salt thereof, is administered once about every 5 months during the period of exposure of the subject to the HIV. In some embodiments, the compound of Formula (Ia) or Formula (Ib), or a pharmaceutically acceptable salt thereof, is administered once about every 6 months during the period of exposure of the subject to the HIV. In some embodiments, the compound of Formula (Ia) or Formula (Ib), or a pharmaceutically acceptable salt thereof, is administered once about every 12 months during the period of exposure of the subject to the HIV.

In some embodiments, the compound of Formula (Ia) or Formula (Ib), or a pharmaceutically acceptable salt thereof, is subcutaneously administered to a subject (e.g., a human patient) for at least about one month. In some embodiments, the compound of Formula (Ia) or Formula (Ib), or a pharmaceutically acceptable salt thereof, is subcutaneously or intramuscularly administered to a subject for at least about 2 months, at least about 3 months, at least about 4 months, or at least about 6 months. In some embodiments, the compound of Formula (Ia) or Formula (Ib), or a pharmaceutically acceptable salt thereof, is subcutaneously administered to a subject once about every month. In some embodiments, the compound of Formula (Ia) or Formula (Ib), or a pharmaceutically acceptable salt thereof, is subcutaneously or intramuscularly administered to a subject once about every 3 months. In some embodiments, the compound of Formula (Ia) or Formula (Ib), or a pharmaceutically acceptable salt thereof, is subcutaneously or intramuscularly administered to a subject once about every 6 months. In some embodiments, the compound of Formula (Ia) or Formula (Ib), or a pharmaceutically acceptable salt thereof, is subcutaneously or intramuscularly administered to a subject once about every 12 months. In some embodiments, the compound of Formula (Ia) or Formula (Ib), or a pharmaceutically acceptable salt thereof, is subcutaneously administered to a subject once about every 12 months. In some embodiments, the compound of Formula (Ia) or Formula (Ib), or a pharmaceutically acceptable salt thereof, is intramuscularly administered to a subject once about every 12 months.

In some embodiments, the compound of Formula (Ia) or Formula (Ib), or a pharmaceutically acceptable salt thereof, is intramuscularly administered to a subject once about every month. In some embodiments, the compound of Formula (Ia) or Formula (Ib), or a pharmaceutically acceptable salt thereof, is subcutaneously administered to a subject once about every 3 months. In some embodiments, the compound of Formula (Ia) or Formula (Ib), or a pharmaceutically acceptable salt thereof, is intramuscularly administered to a subject once about every 3 months. In some embodiments, the compound of Formula (Ia) or Formula (Ib), or a pharmaceutically acceptable salt thereof, is subcutaneously administered to a subject once about every 6 months. In some embodiments, the compound of Formula (Ia) or Formula (Ib), or a pharmaceutically acceptable salt thereof, is intramuscularly administered to a subject once about every 6 months. In some embodiments, the compound of Formula (Ia) or Formula (Ib), or a pharmaceutically acceptable salt thereof, is subcutaneously administered to a subject once about every year. In some embodiments, the compound of Formula (Ia) or Formula (Ib), or a pharmaceutically acceptable salt thereof, is intramuscularly administered to a subject once about every year.

In some embodiments, the compound of Formula (Ia) or Formula (Ib), or a pharmaceutically acceptable salt thereof, is orally administered to a subject once daily. In some embodiments, the compound of Formula (Ia) or Formula (Ib), or a pharmaceutically acceptable salt thereof, is orally administered to a subject once about every 1 week, about every 2 weeks, about every 4 weeks, about every 8 weeks, about every 12 weeks, about every 16 weeks, about every 20 weeks, about every 24 weeks, about every 48 weeks, or about every year. In some embodiments, the compound of Formula (Ia) or Formula (Ib), or a pharmaceutically acceptable salt thereof, is orally administered to a subject once about every 1 week. In some embodiments, the compound of Formula (Ia) or Formula (Ib), or a pharmaceutically acceptable salt thereof, is orally administered to a subject once about every month. In some embodiments, the compound of Formula (Ia) or Formula (Ib), or a pharmaceutically acceptable salt thereof, is orally administered to a subject once about every 3 months. In some embodiments, the compound of Formula (Ia) or Formula (Ib), or a pharmaceutically acceptable salt thereof, is orally administered to a subject once about every 6 months. In some embodiments, the compound of Formula (Ia) or Formula (Ib), or a pharmaceutically acceptable salt thereof, is orally administered to a subject once about every year.

The dosage or dosing frequency of a compound of Formula (Ia) or Formula (Ib), or a pharmaceutically acceptable salt thereof, can be adjusted over the course of the treatment, based on the judgment of the administering physician.

In some embodiments, the compound of Formula (Ia) or Formula (Ib), or a pharmaceutically acceptable salt thereof, is administered to a subject (for example, a human) in a therapeutically effective amount. In some embodiments, the compound of Formula (Ia) or Formula (Ib), or a pharmaceutically acceptable salt thereof, is administered once daily.

In some embodiments, the compound of Formula (Ia) or Formula (Ib), or a pharmaceutically acceptable salt thereof, is administered monthly. In some embodiments, the compound of Formula (Ia) or Formula (Ib), or a pharmaceutically acceptable salt thereof, is administered every two months. In some embodiments, the compound of Formula (Ia) or Formula (Ib), or a pharmaceutically acceptable salt thereof, is administered every three months. In some embodiments, the compound of Formula (Ia) or Formula (Ib), or a pharmaceutically acceptable salt thereof, is administered every four months. In some embodiments, the compound of Formula (Ia) or Formula (Ib), or a pharmaceutically acceptable salt thereof, is administered every six months. In some embodiments, the compound of Formula (Ia) or Formula (Ib), or a pharmaceutically acceptable salt thereof, is administered yearly.

In some embodiments, the compound of Formula (Ia) or Formula (Ib), or a pharmaceutically acceptable salt thereof, is administered in a dosage amount that is effective. In some embodiments, the dosage is from about 1 mg to about 1000 mg of the compound of Formula (Ia) or Formula (Ib), or a pharmaceutically acceptable salt thereof. In certain embodiments, the dosage amount is about 1 mg, about 10 mg, about 20 mg, about 30 mg, about 40 mg, about 50 mg, about 60 mg, about 70 mg, about 80 mg, about 90 mg, about 95 mg, about 100 mg, about 105 mg, about 110 mg, about 120 mg, about 130 mg, about 140 mg, or about 150 mg of the compound of Formula (Ia) or Formula (Ib), or a pharmaceutically acceptable salt thereof. In certain embodiments, the dosage amount is about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg of the compound of Formula (Ia) or Formula (Ib), or a pharmaceutically acceptable salt thereof.

In certain embodiments, the dosage amount is about 1 mg, about 5 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 2000 mg, about 2050 mg, or about 3000 mg of the compound of Formula (Ia) or Formula (Ib), or a pharmaceutically acceptable salt thereof.

In some embodiments, the dosage amount of the compound of Formula (Ia) or Formula (Ib), or a pharmaceutically acceptable salt thereof, is about 1 mg to about 2500 mg. In some embodiments, the dosage amount of the compound of Formula (Ia) or Formula (Ib), or a pharmaceutically acceptable salt thereof, is about 5 mg to about 2400 mg. In some embodiments, the dosage amount of the compound of Formula (Ia) or Formula (Ib), or a pharmaceutically acceptable salt thereof, is about 5 mg to about 2000 mg. In some embodiments, the dosage amount of the compound of Formula (Ia) or Formula (Ib), or a pharmaceutically acceptable salt thereof, is about 5 mg to about 1500 mg. In some embodiments, the dosage amount of the compound of Formula (Ia) or Formula (Ib), or a pharmaceutically acceptable salt thereof, is about 5 mg to about 1200 mg. In some embodiments, the dosage amount of the compound of Formula (Ia) or Formula (Ib), or a pharmaceutically acceptable salt thereof, is about 5 mg to about 1000 mg. In some embodiments, the dosage amount of the compound of Formula (Ia) or Formula (Ib), or a pharmaceutically acceptable salt thereof, is about 5 mg to about 500 mg. In some embodiments, the dosage amount of the compound of Formula (Ia) or Formula (Ib), or a pharmaceutically acceptable salt thereof, is about 5 mg to about 300 mg. In some embodiments, the dosage amount of the compound of Formula (Ia) or Formula (Ib), or a pharmaceutically acceptable salt thereof, is about 5 mg to about 200 mg. In some embodiments, the dosage amount of the compound of Formula (Ia) or Formula (Ib), or a pharmaceutically acceptable salt thereof, is about 5 mg to about 100 mg. In some embodiments, the dosage amount of the compound of Formula (Ia) or Formula (Ib), or a pharmaceutically acceptable salt thereof, is about 5 mg to about 50 mg.

In some embodiments, the compound of Formula (Ia) or Formula (Ib), or a pharmaceutically acceptable salt thereof, is administered in a once daily dose of about 1 mg to about 1500 mg. In some embodiments, the compound of Formula (Ia) or Formula (Ib), or a pharmaceutically acceptable salt thereof, is administered in a once daily dose of about 5 mg to about 1200 mg. In some embodiments, the compound of Formula (Ia) or Formula (Ib), or a pharmaceutically acceptable salt thereof, is administered in a once daily dose of about 100 mg to about 1200 mg. In some embodiments, the compound of Formula (Ia) or Formula (Ib), or a pharmaceutically acceptable salt thereof, is administered in a once daily dose of about 200 mg to about 1200 mg. In some embodiments, the compound of Formula (Ia) or Formula (Ib), or a pharmaceutically acceptable salt thereof, is administered in a once daily dose of about 300 mg to about 1200 mg. In some embodiments, the compound of Formula (Ia) or Formula (Ib), or a pharmaceutically acceptable salt thereof, is administered in a once daily dose of about 500 mg to about 1200 mg.

In some embodiments, the compound of Formula (Ia) or Formula (Ib), or a pharmaceutically acceptable salt thereof, is administered in a once daily dose of about 1 mg to about 200 mg. In some embodiments, the compound of Formula (Ia) or Formula (Ib), or a pharmaceutically acceptable salt thereof, is administered in a once daily dose of about 5 mg to about 200 mg. In some embodiments, the compound of Formula (Ia) or Formula (Ib), or a pharmaceutically acceptable salt thereof, is administered in a once daily dose of about 10 mg to about 200 mg. In some embodiments, the compound of Formula (Ia) or Formula (Ib), or a pharmaceutically acceptable salt thereof, is administered in a once daily dose of about 50 mg to about 200 mg. In some embodiments, the compound of Formula (Ia) or Formula (Ib), or a pharmaceutically acceptable salt thereof, is administered in a once daily dose of about 100 mg to about 200 mg.

In some embodiments, the compound of Formula (Ia) or Formula (Ib), or a pharmaceutically acceptable salt thereof, is administered in a once daily dose of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg.

In some embodiments, the compound of Formula (Ia) or Formula (Ib), or a pharmaceutically acceptable salt thereof, is administered in a once daily dose of about 1 mg.

In some embodiments, the compound of Formula (Ia) or Formula (Ib), or a pharmaceutically acceptable salt thereof, is administered in a once daily dose of about 5 mg. In some embodiments, the compound of Formula (Ia) or Formula (Ib), or a pharmaceutically acceptable salt thereof, is administered in a once daily dose of about 10 mg. In some embodiments, the compound of Formula (Ia) or Formula (Ib), or a pharmaceutically acceptable salt thereof, is administered in a once daily dose of about 15 mg. In some embodiments, the compound of Formula (Ia) or Formula (Ib), or a pharmaceutically acceptable salt thereof, is administered in a once daily dose of about 20 mg. In some embodiments, the compound of Formula (Ia) or Formula (Ib), or a pharmaceutically acceptable salt thereof, is administered in a once daily dose of about 25 mg. In some embodiments, the compound of Formula (Ia) or Formula (Ib), or a pharmaceutically acceptable salt thereof, is administered in a once daily dose of about 50 mg. In some embodiments, the compound of Formula (Ia) or Formula (Ib), or a pharmaceutically acceptable salt thereof, is administered in a once daily dose of about 75 mg. In some embodiments, the compound of Formula (Ia) or Formula (Ib), or a pharmaceutically acceptable salt thereof, is administered in a once daily dose of about 100 mg. In some embodiments, the compound of Formula (Ia) or Formula (Ib), or a pharmaceutically acceptable salt thereof, is administered in a once daily dose of about 125 mg. In some embodiments, the compound of Formula (Ia) or Formula (Ib), or a pharmaceutically acceptable salt thereof, is administered in a once daily dose of about 150 mg. In some embodiments, the compound of Formula (Ia) or Formula (Ib), or a pharmaceutically acceptable salt thereof, is administered in a once daily dose of about 175 mg. In some embodiments, the compound of Formula (Ia) or Formula (Ib), or a pharmaceutically acceptable salt thereof, is administered in a once daily dose of about 200 mg. In some embodiments, the compound of Formula (Ia) or Formula (Ib), or a pharmaceutically acceptable salt thereof, is administered in a once daily dose of about 300 mg. In some embodiments, the compound of Formula (Ia) or Formula (Ib), or a pharmaceutically acceptable salt thereof, is administered in a once daily dose of about 400 mg. In some embodiments, the compound of Formula (Ia) or Formula (Ib), or a pharmaceutically acceptable salt thereof, is administered in a once daily dose of about 500 mg. In some embodiments, the compound of Formula (Ia) or Formula (Ib), or a pharmaceutically acceptable salt thereof, is administered in a once daily dose of about 600 mg. In some embodiments, the compound of Formula (Ia) or Formula (Ib), or a pharmaceutically acceptable salt thereof, is administered in a once daily dose of about 700 mg. In some embodiments, the compound of Formula (Ia) or Formula (Ib), or a pharmaceutically acceptable salt thereof, is administered in a once daily dose of about 800 mg. In some embodiments, the compound of Formula (Ia) or Formula (Ib), or a pharmaceutically acceptable salt thereof, is administered in a once daily dose of about 900 mg. In some embodiments, the compound of Formula (Ia) or Formula (Ib), or a pharmaceutically acceptable salt thereof, is administered in a once daily dose of about 1000 mg. In some embodiments, the compound of Formula (Ia) or Formula (Ib), or a pharmaceutically acceptable salt thereof, is administered in a once daily dose of about 1100 mg. In some embodiments, the compound of Formula (Ia) or Formula (Ib), or a pharmaceutically acceptable salt thereof, is administered in a once daily dose of about 1200 mg. In some embodiments, the compound of Formula (Ia) or Formula (Ib), or a pharmaceutically acceptable salt thereof, is administered in a once daily dose of about 1300 mg. In some embodiments, the compound of Formula (Ia) or Formula (Ib), or a pharmaceutically acceptable salt thereof, is administered in a once daily dose of about 1400 mg. In some embodiments, the compound of Formula (Ia) or Formula (Ib), or a pharmaceutically acceptable salt thereof, is administered in a once daily dose of about 1500 mg.

In some embodiments, the compound of Formula (Ia) or Formula (Ib), or a pharmaceutically acceptable salt thereof, is administered weekly at a dose of about 100 mg to about 2500 mg. In some embodiments, the compound of Formula (Ia) or Formula (Ib), or a pharmaceutically acceptable salt thereof, is administered weekly at a dose of about 100 mg to about 2400 mg. In some embodiments, the compound of Formula (Ia) or Formula (Ib), or a pharmaceutically acceptable salt thereof, is administered weekly at a dose of about 100 mg to about 2000 mg. In some embodiments, the compound of Formula (Ia) or Formula (Ib), or a pharmaceutically acceptable salt thereof, is administered weekly at a dose of about 300 mg to about 2500 mg. In some embodiments, the compound of Formula (Ia) or Formula (Ib), or a pharmaceutically acceptable salt thereof, is administered weekly at a dose of about 500 mg to about 2500 mg. In some embodiments, the compound of Formula (Ia) or Formula (Ib), or a pharmaceutically acceptable salt thereof, is administered weekly at a dose of about 800 mg to about 2500 mg. In some embodiments, the compound of Formula (Ia) or Formula (Ib), or a pharmaceutically acceptable salt thereof, is administered weekly at a dose of about 1000 mg to about 2500 mg. In some embodiments, the compound of Formula (Ia) or Formula (Ib), or a pharmaceutically acceptable salt thereof, is administered weekly at a dose of about 100 mg to about 1200 mg. In some embodiments, the compound of Formula (Ia) or Formula (Ib), or a pharmaceutically acceptable salt thereof, is administered weekly at a dose of about 150 mg to about 1200 mg. In some embodiments, the compound of Formula (Ia) or Formula (Ib), or a pharmaceutically acceptable salt thereof, is administered weekly at a dose of about 200 mg to about 1200 mg. In some embodiments, the compound of Formula (Ia) or Formula (Ib), or a pharmaceutically acceptable salt thereof, is administered weekly at a dose of about 300 mg to about 1200 mg. In some embodiments, the compound of Formula (Ia) or Formula (Ib), or a pharmaceutically acceptable salt thereof, is administered weekly at a dose of about 500 mg to about 1200 mg. In some embodiments, the compound of Formula (Ia) or Formula (Ib), or a pharmaceutically acceptable salt thereof, is administered weekly at a dose of about 600 mg to about 1200 mg. In some embodiments, the compound of Formula (Ia) or Formula (Ib), or a pharmaceutically acceptable salt thereof, is administered weekly at a dose of about 800 mg to about 1200 mg. In some embodiments, the compound of Formula (Ia) or Formula (Ib), or a pharmaceutically acceptable salt thereof, is administered weekly at a dose of about 1000 mg to about 1200 mg. In some embodiments, the compound of Formula (Ia) or Formula (Ib), or a pharmaceutically acceptable salt thereof, is administered weekly at a dose of about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, or about 2500 mg.

In some embodiments, the compound of Formula (Ia) or Formula (Ib), or a pharmaceutically acceptable salt thereof, is administered weekly at a dose of about 100 mg. In some embodiments, the compound of Formula (Ia) or Formula (Ib), or a pharmaceutically acceptable salt thereof, is administered weekly at a dose of about 150 mg. In some embodiments, the compound of Formula (Ia) or Formula (Ib), or a pharmaceutically acceptable salt thereof, is administered weekly at a dose of about 175 mg. In some embodiments, the compound of Formula (Ia) or Formula (Ib), or a pharmaceutically acceptable salt thereof, is administered weekly at a dose of about 200 mg. In some embodiments, the compound of Formula (Ia) or Formula (Ib), or a pharmaceutically acceptable salt thereof, is administered weekly at a dose of about 300 mg.

In some embodiments, the compound of Formula (Ia) or Formula (Ib), or a pharmaceutically acceptable salt thereof, is administered weekly at a dose of about 400 mg. In some embodiments, the compound of Formula (Ia) or Formula (Ib), or a pharmaceutically acceptable salt thereof, is administered weekly at a dose of about 500 mg. In some embodiments, the compound of Formula (Ia) or Formula (Ib), or a pharmaceutically acceptable salt thereof, is administered weekly at a dose of about 600 mg. In some embodiments, the compound of Formula (Ia) or Formula (Ib), or a pharmaceutically acceptable salt thereof, is administered weekly at a dose of about 700 mg. In some embodiments, the compound of Formula (Ia) or Formula (Ib), or a pharmaceutically acceptable salt thereof, is administered weekly at a dose of about 800 mg. In some embodiments, the compound of Formula (Ia) or Formula (Ib), or a pharmaceutically acceptable salt thereof, is administered weekly at a dose of about 900 mg. In some embodiments, the compound of Formula (Ia) or Formula (Ib), or a pharmaceutically acceptable salt thereof, is administered weekly at a dose of about 1000 mg. In some embodiments, the compound of Formula (Ia) or Formula (Ib), or a pharmaceutically acceptable salt thereof, is administered weekly at a dose of about 1100 mg. In some embodiments, the compound of Formula (Ia) or Formula (Ib), or a pharmaceutically acceptable salt thereof, is administered weekly at a dose of about 1200 mg. In some embodiments, the compound of Formula (Ia) or Formula (Ib), or a pharmaceutically acceptable salt thereof, is administered weekly at a dose of about 1300 mg. In some embodiments, the compound of Formula (Ia) or Formula (Ib), or a pharmaceutically acceptable salt thereof, is administered weekly at a dose of about 1400 mg. In some embodiments, the compound of Formula (Ia) or Formula (Ib), or a pharmaceutically acceptable salt thereof, is administered weekly at a dose of about 1500 mg. In some embodiments, the compound of Formula (Ia) or Formula (Ib), or a pharmaceutically acceptable salt thereof, is administered weekly at a dose of about 1600 mg. In some embodiments, the compound of Formula (Ia) or Formula (Ib), or a pharmaceutically acceptable salt thereof, is administered weekly at a dose of about 1700 mg. In some embodiments, the compound of Formula (Ia) or Formula (Ib), or a pharmaceutically acceptable salt thereof, is administered weekly at a dose of about 1800 mg. In some embodiments, the compound of Formula (Ia) or Formula (Ib), or a pharmaceutically acceptable salt thereof, is administered weekly at a dose of about 1900 mg. In some embodiments, the compound of Formula (Ia) or Formula (Ib), or a pharmaceutically acceptable salt thereof, is administered weekly at a dose of about 2000 mg. In some embodiments, the compound of Formula (Ia) or Formula (Ib), or a pharmaceutically acceptable salt thereof, is administered weekly at a dose of about 2100 mg. In some embodiments, the compound of Formula (Ia) or Formula (Ib), or a pharmaceutically acceptable salt thereof, is administered weekly at a dose of about 2200 mg. In some embodiments, the compound of Formula (Ia) or Formula (Ib), or a pharmaceutically acceptable salt thereof, is administered weekly at a dose of about 2300 mg. In some embodiments, the compound of Formula (Ia) or Formula (Ib), or a pharmaceutically acceptable salt thereof, is administered weekly at a dose of about 2400 mg. In some embodiments, the compound of Formula (Ia) or Formula (Ib), or a pharmaceutically acceptable salt thereof, is administered weekly at a dose of about 2500 mg.

In some embodiments, the compound of Formula (Ia) or Formula (Ib), or a pharmaceutically acceptable salt thereof, is administered monthly at a dose of about 100 mg to about 3000 mg. In some embodiments, the compound of Formula (Ia) or Formula (Ib), or a pharmaceutically acceptable salt thereof, is administered monthly at a dose of about 100 mg to about 2500 mg. In some embodiments, the compound of Formula (Ia) or Formula (Ib), or a pharmaceutically acceptable salt thereof, is administered monthly at a dose of about 100 mg to about 2400 mg. In some embodiments, the compound of Formula (Ia) or Formula (Ib), or a pharmaceutically acceptable salt thereof, is administered monthly at a dose of about 100 mg to about 2000 mg. In some embodiments, the compound of Formula (Ia) or Formula (Ib), or a pharmaceutically acceptable salt thereof, is administered monthly at a dose of about 300 mg to about 2500 mg. In some embodiments, the compound of Formula (Ia) or Formula (Ib), or a pharmaceutically acceptable salt thereof, is administered monthly at a dose of about 500 mg to about 2500 mg. In some embodiments, the compound of Formula (Ia) or Formula (Ib), or a pharmaceutically acceptable salt thereof, is administered monthly at a dose of about 800 mg to about 2500 mg. In some embodiments, the compound of Formula (Ia) or Formula (Ib), or a pharmaceutically acceptable salt thereof, is administered monthly at a dose of about 1000 mg to about 2500 mg.

In some embodiments, the compound of Formula (Ia) or Formula (Ib), or a pharmaceutically acceptable salt thereof, is administered monthly at a dose of about 200 mg to about 2000 mg. In some embodiments, the compound of Formula (Ia) or Formula (Ib), or a pharmaceutically acceptable salt thereof, is administered monthly at a dose of about 300 mg to about 2000 mg. In some embodiments, the compound of Formula (Ia) or Formula (Ib), or a pharmaceutically acceptable salt thereof, is administered monthly at a dose of about 400 mg to about 2000 mg. In some embodiments, the compound of Formula (Ia) or Formula (Ib), or a pharmaceutically acceptable salt thereof, is administered monthly at a dose of about 500 mg to about 2000 mg. In some embodiments, the compound of Formula (Ia) or Formula (Ib), or a pharmaceutically acceptable salt thereof, is administered monthly at a dose of about 800 mg to about 2000 mg. In some embodiments, the compound of Formula (Ia) or Formula (Ib), or a pharmaceutically acceptable salt thereof, is administered monthly at a dose of about 1000 mg to about 2000 mg. In some embodiments, the compound of Formula (Ia) or Formula (Ib), or a pharmaceutically acceptable salt thereof, is administered monthly at a dose of about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 mg, about 2700 mg, about 2750 mg, about 2800 mg, about 2850 mg, about 2900 mg, about 2950 mg, or about 3000 mg.

In some embodiments, the compound of Formula (Ia) or Formula (Ib), or a pharmaceutically acceptable salt thereof, is administered monthly at a dose of about 100 mg. In some embodiments, the compound of Formula (Ia) or Formula (Ib), or a pharmaceutically acceptable salt thereof, is administered monthly at a dose of about 150 mg. In some embodiments, the compound of Formula (Ia) or Formula (Ib), or a pharmaceutically acceptable salt thereof, is administered monthly at a dose of about 200 mg. In some embodiments, the compound of Formula (Ia) or Formula (Ib), or a pharmaceutically acceptable salt thereof, is administered monthly at a dose of about 300 mg. In some embodiments, the compound of Formula (Ia) or Formula (Ib), or a pharmaceutically acceptable salt thereof, is administered monthly at a dose of about 400 mg. In some embodiments, the compound of Formula (Ia) or Formula (Ib), or a pharmaceutically acceptable salt thereof, is administered monthly at a dose of about 500 mg. In some embodiments, the compound of Formula (Ia) or Formula (Ib), or a pharmaceutically acceptable salt thereof, is administered monthly at a dose of about 800 mg. In some embodiments, the compound of Formula (Ia) or Formula (Ib), or a pharmaceutically acceptable salt thereof, is administered monthly at a dose of about 1000 mg. In some embodiments, the compound of Formula (Ia) or Formula (Ib), or a pharmaceutically acceptable salt thereof, is administered monthly at a dose of about 1100 mg. In some embodiments, the compound of Formula (Ia) or Formula (Ib), or a pharmaceutically acceptable salt thereof, is administered monthly at a dose of about 1200 mg. In some embodiments, the compound of Formula (Ia) or Formula (Ib), or a pharmaceutically acceptable salt thereof, is administered monthly at a dose of about 1500 mg. In some embodiments, the compound of Formula (Ia) or Formula (Ib), or a pharmaceutically acceptable salt thereof, is administered monthly at a dose of about 1800 mg. In some embodiments, the compound of Formula (Ia) or Formula (Ib), or a pharmaceutically acceptable salt thereof, is administered monthly at a dose of about 2000 mg. In some embodiments, the compound of Formula (Ia) or Formula (Ib), or a pharmaceutically acceptable salt thereof, is administered monthly at a dose of about 2100 mg. In some embodiments, the compound of Formula (Ia) or Formula (Ib), or a pharmaceutically acceptable salt thereof, is administered monthly at a dose of about 2200 mg. In some embodiments, the compound of Formula (Ia) or Formula (Ib), or a pharmaceutically acceptable salt thereof, is administered monthly at a dose of about 2300 mg. In some embodiments, the compound of Formula (Ia) or Formula (Ib), or a pharmaceutically acceptable salt thereof, is administered monthly at a dose of about 2400 mg. In some embodiments, the compound of Formula (Ia) or Formula (Ib), or a pharmaceutically acceptable salt thereof, is administered monthly at a dose of about 2500 mg. In some embodiments, the compound of Formula (Ia) or Formula (Ib), or a pharmaceutically acceptable salt thereof, is administered monthly at a dose of about 2600 mg. In some embodiments, the compound of Formula (Ia) or Formula (Ib), or a pharmaceutically acceptable salt thereof, is administered monthly at a dose of about 2700 mg. In some embodiments, the compound of Formula (Ia) or Formula (Ib), or a pharmaceutically acceptable salt thereof, is administered monthly at a dose of about 2800 mg. In some embodiments, the compound of Formula (Ia) or Formula (Ib), or a pharmaceutically acceptable salt thereof, is administered monthly at a dose of about 2900 mg. In some embodiments, the compound of Formula (Ia) or Formula (Ib), or a pharmaceutically acceptable salt thereof, is administered monthly at a dose of about 3000 mg.

In some embodiments, the compound of Formula (Ia) or Formula (Ib), or a pharmaceutically acceptable salt thereof, is administered every 6 months at a dose of about 600 mg.

Salts and Compositions

The present methods comprise administration of salts of the compound of Formula (Ia) or Formula (Ib), such as pharmaceutically acceptable salts. A salt generally refers to a derivative of a disclosed compound wherein the parent compound is modified by converting an existing acid or base moiety to its salt form. A pharmaceutically acceptable salt is one that, within the scope of sound medical judgment, is suitable for use in contact with the tissues of human beings and animals without excessive toxicity, irritation, allergic response, or other problem or complication, commensurate with a reasonable benefit/risk ratio. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety. In some embodiments, the salt is a sodium salt.

The compound of Formula (Ia) or Formula (Ib), or its salt, can be present in a composition (such as a pharmaceutical composition or formulation) where the composition includes at least one compound other than the compound of Formula (Ia) or Formula (Ib) or salt of the disclosure.

In some embodiments, the composition comprises the compound of Formula (Ia) or Formula (Ib), or a salt thereof, and one or more additional compounds (e.g., one or more additional therapeutic compounds), or salts thereof. In some embodiments, the composition comprises the compound of Formula (Ia) or Formula (Ib), or a salt thereof bictegravir, or a salt thereof and one or more additional compounds (e.g., one or more additional therapeutic compounds such as tenofovir alafenamide, or a pharmaceutically acceptable salt thereof), or salts thereof.

Compositions can include mixtures containing the compound of Formula (Ia) or Formula (Ib), or salt thereof, and one or more solvents, substrates, carriers, etc. In some embodiments, the composition comprises the compound of Formula (Ia) or Formula (Ib), or salt thereof, in an amount greater than about 25% by weight, for example, greater than about 25% by weight, greater than about 50% by weight, greater than about 75% by weight, greater than about 80% by weight, greater than about 90% by weight, or greater than about 95% by weight.

The present disclosure further includes pharmaceutical compositions comprising the compound of Formula (Ia) or Formula (Ib), or pharmaceutically acceptable salt thereof, and at least one pharmaceutically acceptable carrier. As used herein, "pharmaceutically acceptable carrier" is meant to refer to any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Administration of the compound of Formula (Ia) or Formula (Ib), or a pharmaceutically acceptable salt thereof, can be carried out via any of the accepted modes of administration of agents for serving similar utilities. The pharmaceutical compositions of the disclosure can be prepared by combining the compound of Formula (Ia) or Formula (Ib), or a pharmaceutically acceptable salt thereof, with an appropriate pharmaceutically acceptable carrier and, in specific embodiments, are formulated into preparations in solid, semi solid, liquid or gaseous forms, such as tablets, capsules, powders, granules, ointments, solutions, suppositories, injections, inhalants, gels, microspheres, and aerosols. Exemplary routes of administering such pharmaceutical compositions include, without limitation, oral, topical, transdermal, inhalation, parenteral, sublingual, buccal, rectal, vaginal, and intranasal. In some embodiments, pharmaceutical compositions of the disclosure are tablets. In some embodiments, pharmaceutical compositions of the disclosure are injection (e.g., intramuscular (IM) or intraperitoneal (IP)). Pharmaceutical compositions of the disclosure are formulated so as to allow the active ingredients contained therein to be bioavailable upon administration of the composition to a subject. Compositions that will be administered to a subject take the form of one or more dosage units, where for example, a tablet may be a single dosage unit, and a container of the compound of Formula (Ia) or Formula (Ib), or a pharmaceutically acceptable salt thereof, in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of the compound of Formula (Ia) or Formula (Ib), or a pharmaceutically acceptable salt thereof, for prevention of an HIV infection or reducing the risk of acquiring HIV, as described herein.

In some embodiments, the compound of Formula (Ia) or Formula (Ib), or a pharmaceutically acceptable salt thereof, is administered orally, subcutaneously, intramuscularly, or intravenously.

In some embodiments, the compound of Formula (Ia) or Formula (Ib), or a pharmaceutically acceptable salt thereof, is administered orally. In some embodiments, the compound of Formula (Ia) or Formula (Ib), or a pharmaceutically acceptable salt thereof, is administered orally at a concentration of about 20 mg/mL to about 300 mg/mL. In some embodiments, the compound of Formula (Ia) or Formula (Ib), or a pharmaceutically acceptable salt thereof, is administered orally at a concentration of about 300 mg/mL. In some embodiments, the compound of Formula (Ia) or Formula (Ib), or a pharmaceutically acceptable salt thereof, is administered orally at a concentration of about 200 mg/mL. In some embodiments, the compound of Formula (Ia) or Formula (Ib), or a pharmaceutically acceptable salt thereof, is administered orally at a concentration of about 20 mg/mL to about 100 mg/mL. In some embodiments, the compound of Formula (Ia) or Formula (Ib), or a pharmaceutically acceptable salt thereof, is administered orally at a concentration of about 30 mg/mL. In some embodiments, the compound of Formula (Ia) or Formula (Ib), or a pharmaceutically acceptable salt thereof, is administered orally at a concentration of about 50 mg/mL.

In some embodiments, the compound of Formula (Ia) or Formula (Ib), or a pharmaceutically acceptable salt thereof, is formulated as a hard gelatin capsule.

In some embodiments, the compound of Formula (Ia) or Formula (Ib), or a pharmaceutically acceptable salt thereof, is formulated as a soft gelatin capsule.

In some embodiments, the compound of Formula (Ia) or Formula (Ib), or a pharmaceutically acceptable salt thereof, is formulated as a tablet. In some embodiments, the tablet comprises from about 5 mg to about 500 mg of the compound of Formula (Ia) or Formula (Ib), or a pharmaceutically acceptable salt thereof. In some embodiments, the tablet comprises about 50 mg of the compound of Formula (Ia) or Formula (Ib), or a pharmaceutically acceptable salt thereof. In some embodiments, the tablet comprises about 300 mg of the compound of Formula (Ia) or Formula (Ib), or a pharmaceutically acceptable salt thereof.

In some embodiments, the compound of Formula (Ia) or Formula (Ib), or a pharmaceutically acceptable salt thereof, is administered parenterally. Parenteral administration includes, but is not limited to, intravenous, intraarterial, subcutaneous, intraperitoneal, intramuscular, intracranial, transdermal, and vaginal administration. Parenteral administration can be administered, for example, in the form of a single bolus dose or by a continuous perfusion pump. In some embodiments, the compound of Formula (Ia) or Formula (Ib), or a pharmaceutically acceptable salt thereof, is administered to the subject through a medical device. Exemplary medical devices include, but are not limited to, a patch (e.g., a transdermal patch), an implantable device (e.g., an implantable device for metered or sustained release of an active agent; a subdermal device), a syringe, a contraceptive device (e.g., a vaginal ring, an intrauterine device), and the like.

In some embodiments, the compound of Formula (Ia) or Formula (Ib), or a pharmaceutically acceptable salt thereof, is administered subcutaneously. In some embodiments, the compound of Formula (Ia) or Formula (Ib), or a pharmaceutically acceptable salt thereof, is administered subcutaneously at a concentration of about 10 mg/mL to about 500 mg/mL. In some embodiments, the compound of Formula (Ia) or Formula (Ib), or a pharmaceutically acceptable salt thereof, is administered subcutaneously at a concentration of about 50 mg/mL. In some embodiments, the compound of Formula (Ia) or Formula (Ib), or a pharmaceutically acceptable salt thereof, is administered subcutaneously at a concentration of about 100 mg/mL. In some embodiments, the compound of Formula (Ia) or Formula (Ib), or a pharmaceutically acceptable salt thereof, is administered subcutaneously at a concentration of about 150 mg/mL. In some embodiments, the compound of Formula (Ia) or Formula (Ib), or a pharmaceutically acceptable salt thereof, is administered subcutaneously at a concentration of about 300 mg/mL.

In some embodiments, the compound of Formula (Ia) or Formula (Ib), or a pharmaceutically acceptable salt thereof, is administered subcutaneously at a concentration of about 125 mg/mL. In some embodiments, the compound of Formula (Ia) or Formula (Ib), or a pharmaceutically acceptable salt thereof, is administered subcutaneously at a concentration of about 309 mg/mL. In some embodiments, the compound of Formula (Ia) or Formula (Ib), or a pharmaceutically acceptable salt thereof, is administered subcutaneously at a concentration of about 400 mg/mL. In some embodiments, the compound of Formula (Ia) or Formula (Ib), or a pharmaceutically acceptable salt thereof, is administered subcutaneously at a concentration of about 500 mg/mL.

In some embodiments of the methods provided herein, the compound of Formula (Ia) or Formula (Ib) is administered to the subject as a solution (e.g., for subcutaneous administration or for oral administration via, e.g., a capsule). In some embodiments, the solution comprises a compound of Formula (Ia) or Formula (Ib), or a pharmaceutically acceptable salt thereof, PEG 300, and water. In some embodiments, the solution comprises a compound of Formula (Ia) or a pharmaceutically acceptable salt thereof, PEG 300, and water. In some embodiments, the solution comprises a compound of Formula (Ib), or a pharmaceutically acceptable salt thereof, PEG 300, and water. In some embodiments, the solution comprises a sodium salt of the compound of Formula (Ia), PEG 300, and water. In some embodiments, the solution comprises a compound of Formula (Ib), PEG 300, and water.

In some embodiments, the solution comprises a compound of Formula (Ia), PEG 300, and water. In some embodiments, the concentration of the compound of Formula (Ia) in the solution comprising a compound of Formula (Ia), PEG 300, and water is about 50 mg/ml to about 500 mg/ml. In some embodiments, the concentration of the compound of Formula (Ia) in the solution comprising a compound of Formula (Ia), PEG 300, and water is about 50 mg/ml to about 400 mg/ml. In some embodiments, the concentration of the compound of Formula (Ia) in the solution comprising a compound of Formula (Ia), PEG 300, and water is about 50 mg/ml to about 300 mg/ml. In some embodiments, the concentration of the compound of Formula (Ia) in the solution comprising a compound of Formula (Ia), PEG 300, and water is about 75 mg/ml to about 300 mg/ml. In some embodiments, the concentration of the compound of Formula (Ia) in the solution comprising a compound of Formula (Ia), PEG 300, and water is about 50 mg/ml. In some embodiments, the concentration of the compound of Formula (Ia) in the solution comprising a compound of Formula (Ia), PEG 300, and water is about 75 mg/ml. In some embodiments, the concentration of the compound of Formula (Ia) in the solution comprising a compound of Formula (Ia), PEG 300, and water is about 100 mg/ml. In some embodiments, the concentration of the compound of Formula (Ia) in the solution comprising a compound of Formula (Ia), PEG 300, and water is about 125 mg/ml. In some embodiments, the concentration of the compound of Formula (Ia) in the solution comprising a compound of Formula (Ia), PEG 300, and water is about 150 mg/ml. In some embodiments, the concentration of the compound of Formula (Ia) in the solution comprising a compound of Formula (Ia), PEG 300, and water is about 175 mg/ml. In some embodiments, the concentration of the compound of Formula (Ia) in the solution comprising a compound of Formula (Ia), PEG 300, and water is about 200 mg/ml. In some embodiments, the concentration of the compound of Formula (Ia) in the solution comprising a compound of Formula (Ia), PEG 300, and water is about 225 mg/ml. In some embodiments, the concentration of the compound of Formula (Ia) in the solution comprising a compound of Formula (Ia), PEG 300, and water is about 250 mg/ml. In some embodiments, the concentration of the compound of Formula (Ia) in the solution comprising a compound of Formula (Ia), PEG 300, and water is about 275 mg/ml. In some embodiments, the concentration of the compound of Formula (Ia) in the solution comprising a compound of Formula (Ia), PEG 300, and water is about 300 mg/ml. In some embodiments, the concentration of the compound of Formula (Ia) in the solution comprising a compound of Formula (Ia), PEG 300, and water is about 325 mg/ml. In some embodiments, the concentration of the compound of Formula (Ia) in the solution comprising a compound of Formula (Ia), PEG 300, and water is about 350 mg/ml. In some embodiments, the concentration of the compound of Formula (Ia) in the solution comprising a compound of Formula (Ia), PEG 300, and water is about 375 mg/ml. In some embodiments, the concentration of the compound of Formula (Ia) in the solution comprising a compound of Formula (Ia), PEG 300, and water is about 400 mg/ml. In some embodiments, the concentration of the compound of Formula (Ia) in the solution comprising a compound of Formula (Ia), PEG 300, and water is about 425 mg/ml. In some embodiments, the concentration of the compound of Formula (Ia) in the solution comprising a compound of Formula (Ia), PEG 300, and water is about 450 mg/ml. In some embodiments, the concentration of the compound of Formula (Ia) in the solution comprising a compound of Formula (Ia), PEG 300, and water is about 475 mg/ml. In some embodiments, the concentration of the compound of Formula (Ia) in the solution comprising a compound of Formula (Ia), PEG 300, and water is about 500 mg/ml.

In some embodiments, the amount of water in the solution comprising a compound of Formula (Ia), PEG 300, and water is about 5 w/w % to about 15 w/w %. In some embodiments, the amount of water in the solution comprising a compound of Formula (Ia), PEG 300, and water is about 5 w/w % to about 10 w/w %. In some embodiments, the amount of water in the solution comprising a compound of Formula (Ia), PEG 300, and water is about 8 w/w % to about 12 w/w %. In some embodiments, the amount of water in the solution comprising a compound of Formula (Ia), PEG 300, and water is about 9 w/w % to about 10 w/w %. In some embodiments, the amount of water in the solution comprising a compound of Formula (Ia), PEG 300, and water is about 8.0 w/w %, about 8.1 w/w %, about 8.2 w/w %, about 8.3 w/w %, about 8.4 w/w %, about 8.5 w/w %, about 8.6 w/w %, about 8.7 w/w %, about 8.8 w/w %, about 8.9 w/w %, about 9.0 w/w %, about 9.1 w/w %, about 9.2 w/w %, about 9.3 w/w %, about 9.4 w/w %, about 9.5 w/w %, about 9.6 w/w %, about 9.7 w/w %, about 9.8 w/w %, about 9.9 w/w %, about 10.0 w/w %, about 10.1 w/w %, about 10.2 w/w %, about 10.3 w/w %, about 10.4 w/w %, about 10.5 w/w %, about 10.6 w/w %, about 10.7 w/w %, about 10.8 w/w %, about 10.9 w/w %, about 11.0 w/w %, about 11.1 w/w %, about 11.2 w/w %, about 11.3 w/w %, about 11.4 w/w %, about 11.5 w/w %, about 11.6 w/w %, about 11.7 w/w %, about 11.8 w/w %, about 11.9 w/w %, or about 12.0 w/w %. In some embodiments, the amount of water in the solution comprising a compound of Formula (Ia), PEG 300, and water is about 9.0 w/w %, about 9.1 w/w %, about 9.2 w/w %, about 9.3 w/w %, about 9.4 w/w %, about 9.5 w/w %, about 9.6 w/w %, about 9.7 w/w %, about 9.8 w/w %, about 9.9 w/w %, or about 10.0 w/w %. In some embodiments, the amount of water in the solution comprising a compound of Formula (Ia), PEG 300, and water is about 9.5 w/w %, about 9.6 w/w %, about 9.7 w/w %, about 9.8 w/w %, about 9.9 w/w %, or about 10.0 w/w %. In some embodiments, the amount of water in the solution comprising a compound of Formula (Ia), PEG 300, and water is about 9.8 w/w %. In some embodiments, the amount of water in the solution comprising a compound of Formula (Ia), PEG 300, and water is about 10 w/w %.

In some embodiments, the amount of PEG 300 in the solution comprising a compound of Formula (Ia), PEG 300, and water is about 50 w/w % to about 85 w/w %. In some embodiments, the amount of PEG 300 in the solution comprising a compound of Formula (Ia), PEG 300, and water is about 60 w/w % to about 80 w/w %. In some embodiments, the amount of PEG 300 in the solution comprising a compound of Formula (Ia), PEG 300, and water is about 60 w/w % to about 70 w/w %. In some embodiments, the amount of PEG 300 in the solution comprising a compound of Formula (Ia), PEG 300, and water is about 50 w/w %, about 55 w/w %, about 60 w/w %, about 65 w/w %, about 70 w/w %, about 75 w/w %, about 80 w/w %, or about 85 w/w %. In some embodiments, the amount of PEG 300 in the solution comprising a compound of Formula (Ia), PEG 300, and water is about 65 w/w %. In some embodiments, the amount of PEG 300 in the solution comprising a compound of Formula (Ia), PEG 300, and water is about 65.0 w/w %.

In some embodiments, the amount of the compound of Formula (Ia) in the solution comprising a compound of Formula (Ia), PEG 300, and water is about 15 w/w % to about 35 w/w %. In some embodiments, the amount of the compound of Formula (Ia) in the solution comprising a compound of Formula (Ia), PEG 300, and water is about 20 w/w % to about 35 w/w %. In some embodiments, the amount of the compound of Formula (Ia) in the solution comprising a compound of Formula (Ia), PEG 300, and water is about 24 w/w % to about 26 w/w %. In some embodiments, the amount of the compound of Formula (Ia) in the solution comprising a compound of Formula (Ia), PEG 300, and water is about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, or about 25.5 w/w %. In some embodiments, the amount of the compound of Formula (Ia) in the solution comprising a compound of Formula (Ia), PEG 300, and water is about 25 w/w %. In some embodiments, the amount of the compound of Formula (Ia) in the solution comprising a compound of Formula (Ia), PEG 300, and water is about 25.2 w/w %.

In some embodiments, the solution comprises about 5 w/w % to about 15 w/w % water, about 50 w/w % to about 85 w/w % PEG 300, and about 15 w/w % to about 35 w/w % of a compound of Formula (Ia). In some embodiments, the solution comprises about 5 w/w % to about 10 w/w % water, about 60 w/w % to about 80 w/w % PEG 300, and about 20 w/w % to about 35 w/w % of a compound of Formula (Ia). In some embodiments, the solution comprises about 8 w/w % to about 12 w/w % water, about 60 w/w % to about 70 w/w % PEG 300, and about 15 w/w % to about 35 w/w % of a compound of Formula (Ia). In some embodiments, the solution comprises about 9 w/w % to about 10 w/w % water, about 60 w/w % to about 70 w/w % PEG 300, and about 24 w/w % to about 26 w/w % of a compound of Formula (Ia). In some embodiments, the solution comprises about 9.8 w/w % water, about 65.0 w/w % PEG 300, and about 25.2 w/w % of a compound of Formula (Ia). In some embodiments, the solution comprises about 10 w/w % water, about 65.0 w/w % PEG 300, and about 25 w/w % of a compound of Formula (Ia).

In some embodiments, the solution comprises a sodium salt of the compound of Formula (Ia), PEG 300, and water. In some embodiments, the concentration of the compound of Formula (Ia) in the solution comprising a sodium salt of the compound of Formula (Ia), PEG 300, and water is about 50 mg/ml to about 500 mg/ml. In some embodiments, the concentration of the compound of Formula (Ia) in the solution comprising a sodium salt of the compound of Formula (Ia), PEG 300, and water is about 50 mg/ml to about 300 mg/ml. In some embodiments, the concentration of the compound of Formula (Ia) in the solution comprising a sodium salt of the compound of Formula (Ia), PEG 300, and water is about 75 mg/ml to about 300 mg/ml. In some embodiments, the concentration of the compound of Formula (Ia) in the solution comprising a sodium salt of the compound of Formula (Ia), PEG 300, and water is about 50 mg/ml. In some embodiments, the concentration of the compound of Formula (Ia) in the solution comprising a sodium salt of the compound of Formula (Ia), PEG 300, and water is about 75 mg/ml. In some embodiments, the concentration of the compound of Formula (Ia) in the solution comprising a sodium salt of the compound of Formula (Ia), PEG 300, and water is about 100 mg/ml. In some embodiments, the concentration of the compound of Formula (Ia) in the solution comprising a sodium salt of the compound of Formula (Ia), PEG 300, and water is about 125 mg/ml. In some embodiments, the concentration of the compound of Formula (Ia) in the solution comprising a sodium salt of the compound of Formula (Ia), PEG 300, and water is about 150 mg/ml. In some embodiments, the concentration of the compound of Formula (Ia) in the solution comprising a sodium salt of the compound of Formula (Ia), PEG 300, and water is about 175 mg/ml. In some embodiments, the concentration of the compound of Formula (Ia) in the solution comprising a sodium salt of the compound of Formula (Ia), PEG 300, and water is about 200 mg/ml. In some embodiments, the concentration of the compound of Formula (Ia) in the solution comprising a sodium salt of the compound of Formula (Ia), PEG 300, and water is about 225 mg/ml. In some embodiments, the concentration of the compound of Formula (Ia) in the solution comprising a sodium salt of the compound of Formula (Ia), PEG 300, and water is about 250 mg/ml. In some embodiments, the concentration of the compound of Formula (Ia) in the solution comprising a sodium salt of the compound of Formula (Ia), PEG 300, and water is about 275 mg/ml. In some embodiments, the concentration of the compound of Formula (Ia) in the solution comprising a sodium salt of the compound of Formula (Ia), PEG 300, and water is about 300 mg/ml. In some embodiments, the concentration of the compound of Formula (Ia) in the solution comprising a sodium salt of the compound of Formula (Ia), PEG 300, and water is about 325 mg/ml. In some embodiments, the concentration of the compound of Formula (Ia) in the solution comprising a sodium salt of the compound of Formula (Ia), PEG 300, and water is about 350 mg/ml. In some embodiments, the concentration of the compound of Formula (Ia) in the solution comprising a sodium salt of the compound of Formula (Ia), PEG 300, and water is about 375 mg/ml. In some embodiments, the concentration of the compound of Formula (Ia) in the solution comprising a sodium salt of the compound of Formula (Ia), PEG 300, and water is about 400 mg/ml. In some embodiments, the concentration of the compound of Formula (Ia) in the solution comprising a sodium salt of the compound of Formula (Ia), PEG 300, and water is about 425 mg/ml. In some embodiments, the concentration of the compound of Formula (Ia) in the solution comprising a sodium salt of the compound of Formula (Ia), PEG 300, and water is about 450 mg/ml. In some embodiments, the concentration of the compound of Formula (Ia) in the solution comprising a sodium salt of the compound of Formula (Ia), PEG 300, and water is about 475 mg/ml. In some embodiments, the concentration of the compound of Formula (Ia) in the solution comprising a sodium salt of the compound of Formula (Ia), PEG 300, and water is about 500 mg/ml.

In some embodiments, the concentration of the compound of Formula (Ia) in the solution comprising a sodium salt of the compound of Formula (Ia), PEG 300, and water is about 309 mg/ml.

In some embodiments, the amount of water in the solution comprising a sodium salt of the compound of Formula (Ia), PEG 300, and water is about 10 w/w % to about 40 w/w %. In some embodiments, the amount of water in the solution comprising a sodium salt of the compound of Formula (Ia), PEG 300, and water is about 15 w/w % to about 35 w/w %. In some embodiments, the amount of water in the solution comprising a sodium salt of the compound of Formula (Ia), PEG 300, and water is about 20 w/w % to about 30 w/w %. In some embodiments, the amount of water in the solution comprising a sodium salt of the compound of Formula (Ia), PEG 300, and water is about 21 w/w % to about 29 w/w %. In some embodiments, the amount of water in the solution comprising a sodium salt of the compound of Formula (Ia), PEG 300, and water is about 23.4 w/w % to about 27.5 w/w %. In some embodiments, the amount of water in the solution comprising a sodium salt of the compound of Formula (Ia), PEG 300, and water is about 23.41 w/w % to about 27.47 w/w %. In some embodiments, the amount of water in the solution comprising a sodium salt of the compound of Formula (Ia), PEG 300, and water is about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, or about 29.0 w/w %. In some embodiments, the amount of water in the solution comprising a sodium salt of the compound of Formula (Ia), PEG 300, and water is about 23.4 w/w %. In some embodiments, the amount of water in the solution comprising a sodium salt of the compound of Formula (Ia), PEG 300, and water is about 23.41 w/w %. In some embodiments, the amount of water in the solution comprising a sodium salt of the compound of Formula (Ia), PEG 300, and water is about 27.47 w/w %. In some embodiments, the amount of water in the solution comprising a sodium salt of the compound of Formula (Ia), PEG 300, and water is about 27.5 w/w %.

In some embodiments, the amount of water in the solution comprising a sodium salt of the compound of Formula (Ia), PEG 300, and water is about 21.1 w/w % to about 27.5 w/w %. In some embodiments, the amount of water in the solution comprising a sodium salt of the compound of Formula (Ia), PEG 300, and water is about 21.13 w/w % to about 27.47 w/w %.

In some embodiments, the amount of water in the solution comprising a sodium salt of the compound of Formula (Ia), PEG 300, and water is about 21.1 w/w %. In some embodiments, the amount of water in the solution comprising a sodium salt of the compound of Formula (Ia), PEG 300, and water is about 21.13 w/w %.

In some embodiments, the amount of PEG 300 in the solution comprising a sodium salt of the compound of Formula (Ia), PEG 300, and water is about 35 w/w % to about 75 w/w %. In some embodiments, the amount of PEG 300 in the solution comprising a sodium salt of the compound of Formula (Ia), PEG 300, and water is about 45 w/w % to about 65 w/w %. In some embodiments, the amount of PEG 300 in the solution comprising a sodium salt of the compound of Formula (Ia), PEG 300, and water is about 48 w/w % to about 60 w/w %. In some embodiments, the amount of PEG 300 in the solution comprising a sodium salt of the compound of Formula (Ia), PEG 300, and water is about 50 w/w % to about 59 w/w %. In some embodiments, the amount of PEG 300 in the solution comprising a sodium salt of the compound of Formula (Ia), PEG 300, and water is about 50.1 w/w % to about 58.8 w/w %. In some embodiments, the amount of PEG 300 in the solution comprising a sodium salt of the compound of Formula (Ia), PEG 300, and water is about 50.13 w/w % to about 58.84 w/w %. In some embodiments, the amount of PEG 300 in the solution comprising a sodium salt of the compound of Formula (Ia), PEG 300, and water is about 45 w/w %, about 46 w/w %, about 47 w/w %, about 48 w/w %, about 49 w/w %, about 50 w/w %, about 51 w/w %, about 52 w/w %, about 53 w/w %, about 54 w/w %, about 55 w/w %, about 56 w/w %, about 57 w/w %, about 58 w/w %, about 59 w/w %, about 60 w/w %, about 61 w/w %, about 62 w/w %, about 63 w/w %, about 64 w/w %, or about 65 w/w %. In some embodiments, the amount of PEG 300 in the solution comprising a sodium salt of the compound of Formula (Ia), PEG 300, and water is about 50.1 w/w %. In some embodiments, the amount of PEG 300 in the solution comprising a sodium salt of the compound of Formula (Ia), PEG 300, and water is about 50.13 w/w %. In some embodiments, the amount of PEG 300 in the solution comprising a sodium salt of the compound of Formula (Ia), PEG 300, and water is about 58.8 w/w %. In some embodiments, the amount of PEG 300 in the solution comprising a sodium salt of the compound of Formula (Ia), PEG 300, and water is about 58.84 w/w %.

In some embodiments, the amount of PEG 300 in the solution comprising a sodium salt of the compound of Formula (Ia), PEG 300, and water is about 45.3 w/w % to about 58.8 w/w %. In some embodiments, the amount of PEG 300 in the solution comprising a sodium salt of the compound of Formula (Ia), PEG 300, and water is about 45.25 w/w % to about 58.84 w/w %.

In some embodiments, the amount of PEG 300 in the solution comprising a sodium salt of the compound of Formula (Ia), PEG 300, and water is about 45.25 w/w %. In some embodiments, the amount of PEG 300 in the solution comprising a sodium salt of the compound of Formula (Ia), PEG 300, and water is about 45.3 w/w %.

In some embodiments, the amount of the sodium salt of the compound of Formula (Ia) in the solution comprising a sodium salt of the compound of Formula (Ia), PEG 300, and water is about 5 w/w % to about 35 w/w %. In some embodiments, the amount of the sodium salt of the compound of Formula (Ia) in the solution comprising a sodium salt of the compound of Formula (Ia), PEG 300, and water is about 10 w/w % to about 30 w/w %. In some embodiments, the amount of the sodium salt of the compound of Formula (Ia) in the solution comprising a sodium salt of the compound of Formula (Ia), PEG 300, and water is about 11 w/w % to about 28 w/w %. In some embodiments, the amount of the sodium salt of the compound of Formula (Ia) in the solution comprising a sodium salt of the compound of Formula (Ia), PEG 300, and water is about 13 w/w % to about 27 w/w %. In some embodiments, the amount of the sodium salt of the compound of Formula (Ia) in the solution comprising a sodium salt of the compound of Formula (Ia), PEG 300, and water is about 13.69 w/w % to about 26.46 w/w %. In some embodiments, the amount of the sodium salt of the compound of Formula (Ia) in the solution comprising a sodium salt of the compound of Formula (Ia), PEG 300, and water is about 13.7 w/w % to about 26.5 w/w %. In some embodiments, the amount of the sodium salt of the compound of Formula (Ia) in the solution comprising a sodium salt of the compound of Formula (Ia), PEG 300, and water is about 13.0 w/w %, about 13.1 w/w %, about 13.2 w/w %, about 13.3 w/w %, about 13.4 w/w %, about 13.5 w/w %, about 13.6 w/w %, about 13.7 w/w %, about 13.8 w/w %, about 13.9 w/w %, about 14.0 w/w %, about 14.1 w/w %, about 14.2 w/w %, about 14.3 w/w %, about 14.4 w/w %, about 14.5 w/w %, about 14.6 w/w %, about 14.7 w/w %, about 14.8 w/w %, about 14.9 w/w %, about 15.0 w/w %, about 15.1 w/w %, about 15.2 w/w %, about 15.3 w/w %, about 15.4 w/w %, about 15.5 w/w %, about 15.6 w/w %, about 15.7 w/w %, about 15.8 w/w %, about 15.9 w/w %, about 16.0 w/w %, about 16.1 w/w %, about 16.2 w/w %, about 16.3 w/w %, about 16.4 w/w %, about 16.5 w/w %, about 16.6 w/w %, about 16.7 w/w %, about 16.8 w/w %, about 16.9 w/w %, about 17.0 w/w %, about 17.1 w/w %, about 17.2 w/w %, about 17.3 w/w %, about 17.4 w/w %, about 17.5 w/w %, about 17.6 w/w %, about 17.7 w/w %, about 17.8 w/w %, about 17.9 w/w %, about 18.0 w/w %, about 18.1 w/w %, about 18.2 w/w %, about 18.3 w/w %, about 18.4 w/w %, about 18.5 w/w %, about 18.6 w/w %, about 18.7 w/w %, about 18.8 w/w %, about 18.9 w/w %, about 19.0 w/w %, about 19.1 w/w %, about 19.2 w/w %, about 19.3 w/w %, about 19.4 w/w %, about 19.5 w/w %, about 19.6 w/w %, about 19.7 w/w %, about 19.8 w/w %, about 19.9 w/w %, about 20.0 w/w %, about 21.1 w/w %, about 21.2 w/w %, about 21.3 w/w %, about 21.4 w/w %, about 21.5 w/w %, about 21.6 w/w %, about 21.7 w/w %, about 21.8 w/w %, about 21.9 w/w %, about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, or about 29.0 w/w %. In some embodiments, the amount of the sodium salt of the compound of Formula (Ia) in the solution comprising a sodium salt of the compound of Formula (Ia), PEG 300, and water is about 13.69 w/w %. In some embodiments, the amount of the sodium salt of the compound of Formula (Ia) in the solution comprising a sodium salt of the compound of Formula (Ia), PEG 300, and water is about 13.7 w/w %. In some embodiments, the amount of the sodium salt of the compound of Formula (Ia) in the solution comprising a sodium salt of the compound of Formula (Ia), PEG 300, and water is about 26.46 w/w %. In some embodiments, the amount of the sodium salt of the compound of Formula (Ia) in the solution comprising a sodium salt of the compound of Formula (Ia), PEG 300, and water is about 26.5 w/w %.

In some embodiments, the amount of the sodium salt of the compound of Formula (Ia) in the solution comprising a sodium salt of the compound of Formula (Ia), PEG 300, and water is about 13.69 w/w % to about 33.61 w/w %. In some embodiments, the amount of the sodium salt of the compound of Formula (Ia) in the solution comprising a sodium salt of the compound of Formula (Ia), PEG 300, and water is about 13.7 w/w % to about 33.6 w/w %.

In some embodiments, the amount of the sodium salt of the compound of Formula (Ia) in the solution comprising a sodium salt of the compound of Formula (Ia), PEG 300, and water is about 33.61 w/w %. In some embodiments, the amount of the sodium salt of the compound of Formula (Ia) in the solution comprising a sodium salt of the compound of Formula (Ia), PEG 300, and water is about 33.6 w/w %.

In some embodiments, the solution comprises about 10 w/w % to about 40 w/w % water, about 35 w/w % to about 75 w/w % PEG 300, and about 5 w/w % to about 35 w/w % of a sodium salt of the compound of Formula (Ia). In some embodiments, the solution comprises about 15 w/w % to about 35 w/w % water, about 45 w/w % to about 65 w/w % PEG 300, and about 10 w/w % to about 30 w/w % of a sodium salt of the compound of Formula (Ia). In some embodiments, the solution comprises about 20 w/w % to about 30 w/w % water, about 48 w/w % to about 60 w/w % PEG 300, and about 11 w/w % to about 28 w/w % of a sodium salt of the compound of Formula (Ia). In some embodiments, the solution comprises about 21 w/w % to about 29 w/w % water, about 50 w/w % to about 59 w/w % PEG 300, and about 13 w/w % to about 27 w/w % of a sodium salt of the compound of Formula (Ia). In some embodiments, the solution comprises about 23.4 w/w % to about 27.5 w/w % water, about 50.1 w/w % to about 58.8 w/w % PEG 300, and about 13.7 w/w % to about 26.5 w/w % of a sodium salt of the compound of Formula (Ia). In some embodiments, the solution comprises about 23.41 w/w % to about 27.47 w/w % water, about 50.13 w/w % to about 58.84 w/w % PEG 300, and about 13.69 w/w % to about 26.46 w/w % of a sodium salt of the compound of Formula (Ia). In some embodiments, the solution comprises about 27.5 w/w % water, about 58.8 w/w % PEG 300, and about 13.7 w/w % of a sodium salt of the compound of Formula (Ia). In some embodiments, the solution comprises about 27.47 w/w % water, about 58.84 w/w % PEG 300, and about 13.69 w/w % of a sodium salt of the compound of Formula (Ia). In some embodiments, the solution comprises about 23.4 w/w % water, about 50.1 w/w % PEG 300, and about 26.5 w/w % of a sodium salt of the compound of Formula (Ia). In some embodiments, the solution comprises about 23.41 w/w % water, about 50.13 w/w % PEG 300, and about 26.46 w/w % of a sodium salt of the compound of Formula (Ia).

In some embodiments, the solution comprises about 10 w/w % to about 40 w/w % water, about 35 w/w % to about 75 w/w % PEG 300, and about 5 w/w % to about 45 w/w % of a sodium salt of the compound of Formula (Ia). In some embodiments, the solution comprises about 10 w/w % to about 30 w/w % water, about 35 w/w % to about 65 w/w % PEG 300, and about 5 w/w % to about 45 w/w % of a sodium salt of the compound of Formula (Ia).

In some embodiments, the solution comprises about 21.1 w/w % to about 27.5 w/w % water, about 45.3 w/w % to about 58.8 w/w % PEG 300, and about 13.7 w/w % to about 33.6 w/w % of a sodium salt of the compound of Formula (Ia). In some embodiments, the solution comprises about 21.13 w/w % to about 27.47 w/w % water, about 45.25 w/w % to about 58.84 w/w % PEG 300, and about 13.69 w/w % to about 33.61 w/w % of a sodium salt of the compound of Formula (Ia).

In some embodiments, the solution comprises about 21.1 w/w % water, about 45.3 w/w % PEG 300, and about 33.6 w/w % of a sodium salt of a compound of Formula (Ia). In some embodiments, the solution comprises about 21.13 w/w % water, about 45.25 w/w % PEG 300, and about 33.61 w/w % of a sodium salt of a compound of Formula (Ia).

In some embodiments, the solution comprises a compound of Formula (Ia) or Formula (Ib), or a pharmaceutically acceptable salt thereof, PEG 300, water, and ethanol. In some embodiments, the solution comprises a compound of Formula (Ia), or a pharmaceutically acceptable salt thereof, PEG 300, water, and ethanol. In some embodiments, the solution comprises a sodium salt of the compound of Formula (Ia), PEG 300, water, and ethanol. In some embodiments, the solution comprises a compound of Formula (Ib), or a pharmaceutically acceptable salt thereof, PEG 300, water, and ethanol.

In some embodiments, the amount of water in the solution comprising a sodium salt of the compound of Formula (Ia), PEG 300, water, and ethanol is about 10 w/w % to about 20 w/w %. In some embodiments, the amount of water in the solution comprising a sodium salt of the compound of Formula (Ia), PEG 300, water, and ethanol is about 12 w/w % to about 20 w/w %. In some embodiments, the amount of water in the solution comprising a sodium salt of the compound of Formula (Ia), PEG 300, water, and ethanol is about 16.93 w/w %. In some embodiments, the amount of water in the solution comprising a sodium salt of the compound of Formula (Ia), PEG 300, water, and ethanol is about 16.9 w/w %.

In some embodiments, the amount of PEG 300 in the solution comprising a sodium salt of the compound of Formula (Ia), PEG 300, water, and ethanol is about 30 w/w % to about 40 w/w %. In some embodiments, the amount of PEG 300 in the solution comprising a sodium salt of the compound of Formula (Ia), PEG 300, water, and ethanol is about 32 w/w % to about 40 w/w %. In some embodiments, the amount of PEG 300 in the solution comprising a sodium salt of the compound of Formula (Ia), PEG 300, water, and ethanol is about 36.22 w/w %. In some embodiments, the amount of PEG 300 in the solution comprising a sodium salt of the compound of Formula (Ia), PEG 300, water, and ethanol is about 36.2 w/w %.

In some embodiments, the amount of the sodium salt of the compound of Formula (Ia) in the solution comprising a sodium salt of the compound of Formula (Ia), PEG 300, water, and ethanol is about 35 w/w % to about 45 w/w %. In some embodiments, the amount of the sodium salt of the compound of Formula (Ia) in the solution comprising a sodium salt of the compound of Formula (Ia), PEG 300, water, and ethanol is about 37 w/w % to about 45 w/w %. In some embodiments, the amount of the sodium salt of the compound of Formula (Ia) in the solution comprising a sodium salt of the compound of Formula (Ia), PEG 300, water, and ethanol is about 41.85 w/w %. In some embodiments, the amount of the sodium salt of the compound of Formula (Ia) in the solution comprising a sodium salt of the compound of Formula (Ia), PEG 300, water, and ethanol is about 41.9 w/w %.

In some embodiments, the amount of ethanol in the solution comprising a sodium salt of the compound of Formula (Ia), PEG 300, water, and ethanol is about 0.1 w/w % to about 10 w/w %. In some embodiments, the amount of ethanol in the solution comprising a sodium salt of the compound of Formula (Ia), PEG 300, water, and ethanol is about 1 w/w % to about 9 w/w %. In some embodiments, the amount of ethanol in the solution comprising a sodium salt of the compound of Formula (Ia), PEG 300, water, and ethanol is about 3 w/w % to about 8 w/w %. In some embodiments, the amount of ethanol in the solution comprising a sodium salt of the compound of Formula (Ia), PEG 300, water, and ethanol is about 5.00 w/w %. In some embodiments, the amount of ethanol in the solution comprising a sodium salt of the compound of Formula (Ia), PEG 300, water, and ethanol is about 5.0 w/w %.

In some embodiments, the solution comprises about 10 w/w % to about 40 w/w % water, about 20 w/w % to about 75 w/w % PEG 300, about 10 w/w % to about 70 w/w % of a sodium salt of the compound of Formula (Ia), and about 1 w/w % to about 9 w/w % of ethanol. In some embodiments, the solution comprises about 10 w/w % to about 20 w/w % water, about 30 w/w % to about 40 w/w % PEG 300, about 37 w/w % to about 45 w/w % of a sodium salt of the compound of Formula (Ia), and about 3 w/w % to about 8 w/w % of ethanol.

In some embodiments, the solution comprises about 16.93 w/w % water, about 36.22 w/w % PEG 300, about 41.85 w/w % of a sodium salt of the compound of Formula (Ia), and about 5.00 w/w % ethanol. In some embodiments, the solution comprises about 16.9 w/w % water, about 36.2 w/w % PEG 300, about 41.9 w/w % of a sodium salt of the compound of Formula (Ia), and about 5.0 w/w % ethanol.

In some embodiments, the solution comprises a compound of Formula (Ia) or Formula (Ib), or a pharmaceutically acceptable salt thereof, PEG 300, poloxamer 188, and water. In some embodiments, the solution comprises a compound of Formula (Ia) or a pharmaceutically acceptable salt thereof, PEG 300, poloxamer 188, and water. In some embodiments, the solution comprises a compound of Formula (Ib), or a pharmaceutically acceptable salt thereof, PEG 300, poloxamer 188, and water. In some embodiments, the solution comprises a compound of Formula (Ia), PEG 300, poloxamer 188, and water. In some embodiments, the solution comprises a compound of Formula (Ib), PEG 300, poloxamer 188, and water.

In some embodiments, the solution comprises a sodium salt of the compound of Formula (Ia), PEG 300, poloxamer 188, and water. In some embodiments, the concentration of the compound of Formula (Ia) in the solution comprising a sodium salt of the compound of Formula (Ia), PEG 300, poloxamer 188, and water is about 50 mg/ml to about 500 mg/ml. In some embodiments, the concentration of the compound of Formula (Ia) in the solution comprising a sodium salt of the compound of Formula (Ia), PEG 300, poloxamer 188, and water is about 50 mg/ml to about 400 mg/ml. In some embodiments, the concentration of the compound of Formula (Ia) in the solution comprising a sodium salt of the compound of Formula (Ia), PEG 300, poloxamer 188, and water is about 50 mg/ml to about 300 mg/ml. In some embodiments, the concentration of the compound of Formula (Ia) in the solution comprising a sodium salt of the compound of Formula (Ia), PEG 300, poloxamer 188, and water is about 75 mg/ml to about 300 mg/ml. In some embodiments, the concentration of the compound of Formula (Ia) in the solution comprising a sodium salt of the compound of Formula (Ia), PEG 300, poloxamer 188, and water is about 50 mg/ml. In some embodiments, the concentration of the compound of Formula (Ia) in the solution comprising a sodium salt of the compound of Formula (Ia), PEG 300, poloxamer 188, and water is about 75 mg/ml. In some embodiments, the concentration of the compound of Formula (Ia) in the solution comprising a sodium salt of the compound of Formula (Ia), PEG 300, poloxamer 188, and water is about 100 mg/ml. In some embodiments, the concentration of the compound of Formula (Ia) in the solution comprising a sodium salt of the compound of Formula (Ia), PEG 300, poloxamer 188, and water is about 125 mg/ml. In some embodiments, the concentration of the compound of Formula (Ia) in the solution comprising a sodium salt of the compound of Formula (Ia), PEG 300, poloxamer 188, and water is about 150 mg/ml. In some embodiments, the concentration of the compound of Formula (Ia) in the solution comprising a sodium salt of the compound of Formula (Ia), PEG 300, poloxamer 188, and water is about 175 mg/ml. In some embodiments, the concentration of the compound of Formula (Ia) in the solution comprising a sodium salt of the compound of Formula (Ia), PEG 300, poloxamer 188, and water is about 200 mg/ml. In some embodiments, the concentration of the compound of Formula (Ia) in the solution comprising a sodium salt of the compound of Formula (Ia), PEG 300, poloxamer 188, and water is about 225 mg/ml. In some embodiments, the concentration of the compound of Formula (Ia) in the solution comprising a sodium salt of the compound of Formula (Ia), PEG 300, poloxamer 188, and water is about 250 mg/ml. In some embodiments, the concentration of the compound of Formula (Ia) in the solution comprising a sodium salt of the compound of Formula (Ia), PEG 300, poloxamer 188, and water is about 275 mg/ml. In some embodiments, the concentration of the compound of Formula (Ia) in the solution comprising a sodium salt of the compound of Formula (Ia), PEG 300, poloxamer 188, and water is about 300 mg/ml. In some embodiments, the concentration of the compound of Formula (Ia) in the solution comprising a sodium salt of the compound of Formula (Ia), PEG 300, poloxamer 188, and water is about 325 mg/ml. In some embodiments, the concentration of the compound of Formula (Ia) in the solution comprising a sodium salt of the compound of Formula (Ia), PEG 300, poloxamer 188, and water is about 350 mg/ml. In some embodiments, the concentration of the compound of Formula (Ia) in the solution comprising a sodium salt of the compound of Formula (Ia), PEG 300, poloxamer 188, and water is about 375 mg/ml. In some embodiments, the concentration of the compound of Formula (Ia) in the solution comprising a sodium salt of the compound of Formula (Ia), PEG 300, poloxamer 188, and water is about 400 mg/ml. In some embodiments, the concentration of the compound of Formula (Ia) in the solution comprising a sodium salt of the compound of Formula (Ia), PEG 300, poloxamer 188, and water is about 425 mg/ml. In some embodiments, the concentration of the compound of Formula (Ia) in the solution comprising a sodium salt of the compound of Formula (Ia), PEG 300, poloxamer 188, and water is about 450 mg/ml. In some embodiments, the concentration of the compound of Formula (Ia) in the solution comprising a sodium salt of the compound of Formula (Ia), PEG 300, poloxamer 188, and water is about 475 mg/ml. In some embodiments, the concentration of the compound of Formula (Ia) in the solution comprising a sodium salt of the compound of Formula (Ia), PEG 300, poloxamer 188, and water is about 500 mg/ml.

In some embodiments, the amount of water in the solution comprising a sodium salt of the compound of Formula (Ia), PEG 300, poloxamer 188, and water is about 10 w/w % to about 45 w/w %. In some embodiments, the amount of water in the solution comprising a sodium salt of the compound of Formula (Ia), PEG 300, poloxamer 188, and water is about 15 w/w % to about 35 w/w %. In some embodiments, the amount of water in the solution comprising a sodium salt of the compound of Formula (Ia), PEG 300, poloxamer 188, and water is about 20 w/w % to about 35 w/w %. In some embodiments, the amount of water in the solution comprising a sodium salt of the compound of Formula (Ia), PEG 300, poloxamer 188, and water is about 20 w/w % to about 31 w/w %. In some embodiments, the amount of water in the solution comprising a sodium salt of the compound of Formula (Ia), PEG 300, poloxamer 188, and water is about 21.9 w/w % to about 30.1 w/w %. In some embodiments, the amount of water in the solution comprising a sodium salt of the compound of Formula (Ia), PEG 300, poloxamer 188, and water is about 21.87 w/w % to about 30.07 w/w %. In some embodiments, the amount of water in the solution comprising a sodium salt of the compound of Formula (Ia), PEG 300, poloxamer 188, and water is about 19.0 w/w %, about 19.1 w/w %, about 19.2 w/w %, about 19.3 w/w %, about 19.4 w/w %, about 19.5 w/w %, about 19.6 w/w %, about 19.7 w/w %, about 19.8 w/w %, about 19.9 w/w %, about 20.0 w/w %, about 20.1 w/w %, about 20.2 w/w %, about 20.3 w/w %, about 20.4 w/w %, about 20.5 w/w %, about 20.6 w/w %, about 20.7 w/w %, about 20.8 w/w %, about 20.9 w/w %, about 21.0 w/w %, about 21.1 w/w %, about 21.2 w/w %, about 21.3 w/w %, about 21.4 w/w %, about 21.5 w/w %, about 21.6 w/w %, about 21.7 w/w %, about 21.8 w/w %, about 21.9 w/w %, about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, about 29.0 w/w %, about 29.1 w/w %, about 29.2 w/w %, about 29.3 w/w %, about 29.4 w/w %, about 29.5 w/w %, about 29.6 w/w %, about 29.7 w/w %, about 29.8 w/w %, about 29.9 w/w %, about 30.0 w/w %, about 30.1 w/w %, about 30.2 w/w %, about 30.3 w/w %, about 30.4 w/w %, about 30.5 w/w %, about 30.6 w/w %, about 30.7 w/w %, about 30.8 w/w %, about 30.9 w/w %, about 31.0 w/w %, about 31.1 w/w %, about 31.2 w/w %, about 31.3 w/w %, about 31.4 w/w %, about 31.5 w/w %, about 31.6 w/w %, about 31.7 w/w %, about 31.8 w/w %, about 31.9 w/w %, about 32.0 w/w %, about 32.1 w/w %, about 32.2 w/w %, about 32.3 w/w %, about 32.4 w/w %, about 32.5 w/w %, about 32.6 w/w %, about 32.7 w/w %, about 32.8 w/w %, about 32.9 w/w %, or about 33.0 w/w %. In some embodiments, the amount of water in the solution comprising a sodium salt of the compound of Formula (Ia), PEG 300, poloxamer 188, and water is about 21.87 w/w %. In some embodiments, the amount of water in the solution comprising a sodium salt of the compound of Formula (Ia), PEG 300, poloxamer 188, and water is about 21.9 w/w %. In some embodiments, the amount of water in the solution comprising a sodium salt of the compound of Formula (Ia), PEG 300, poloxamer 188, and water is about 26.68 w/w %. In some embodiments, the amount of water in the solution comprising a sodium salt of the compound of Formula (Ia), PEG 300, poloxamer 188, and water is about 26.7 w/w %. In some embodiments, the amount of water in the solution comprising a sodium salt of the compound of Formula (Ia), PEG 300, and poloxamer 188, and water is about 27.5 w/w %. In some embodiments, the amount of water in the solution comprising a sodium salt of the compound of Formula (Ia), PEG 300, poloxamer 188, and water is about 27.51 w/w %. In some embodiments, the amount of water in the solution comprising a sodium salt of the compound of Formula (Ia), PEG 300, poloxamer 188, and water is about 28.36 w/w %. In some embodiments, the amount of water in the solution comprising a sodium salt of the compound of Formula (Ia), PEG 300, poloxamer 188, and water is about 28.4 w/w %. In some embodiments, the amount of water in the solution comprising a sodium salt of the compound of Formula (Ia), PEG 300, poloxamer 188, and water is about 29.2 w/w %. In some embodiments, the amount of water in the solution comprising a sodium salt of the compound of Formula (Ia), PEG 300, poloxamer 188, and water is about 29.21 w/w %. In some embodiments, the amount of water in the solution comprising a sodium salt of the compound of Formula (Ia), PEG 300, poloxamer 188, and water is about 30.07 w/w %. In some embodiments, the amount of water in the solution comprising a sodium salt of the compound of Formula (Ia), PEG 300, poloxamer 188, and water is about 30.1 w/w %.

In some embodiments, the amount of water in the solution comprising a sodium salt of the compound of Formula (Ia), PEG 300, poloxamer 188, and water is about 19.18 w/w % to about 30.07 w/w %. In some embodiments, the amount of water in the solution comprising a sodium salt of the compound of Formula (Ia), PEG 300, poloxamer 188, and water is about 19.2 w/w % to about 30.1 w/w %.

In some embodiments, the amount of water in the solution comprising a sodium salt of the compound of Formula (Ia), PEG 300, poloxamer 188, and water is about 19.18 w/w %. In some embodiments, the amount of water in the solution comprising a sodium salt of the compound of Formula (Ia), PEG 300, poloxamer 188, and water is about 19.2 w/w %. In some embodiments, the amount of water in the solution comprising a sodium salt of the compound of Formula (Ia), PEG 300, poloxamer 188, and water is about 20.16 w/w %. In some embodiments, the amount of water in the solution comprising a sodium salt of the compound of Formula (Ia), PEG 300, poloxamer 188, and water is about 20.2 w/w %. In some embodiments, the amount of water in the solution comprising a sodium salt of the compound of Formula (Ia), PEG 300, poloxamer 188, and water is about 22.10 w/w %. In some embodiments, the amount of water in the solution comprising a sodium salt of the compound of Formula (Ia), PEG 300, poloxamer 188, and water is about 22.1 w/w %. In some embodiments, the amount of water in the solution comprising a sodium salt of the compound of Formula (Ia), PEG 300, poloxamer 188, and water is about 22.48 w/w %. In some embodiments, the amount of water in the solution comprising a sodium salt of the compound of Formula (Ia), PEG 300, poloxamer 188, and water is about 22.5 w/w %. In some embodiments, the amount of water in the solution comprising a sodium salt of the compound of Formula (Ia), PEG 300, poloxamer 188, and water is about 22.85 w/w %. In some embodiments, the amount of water in the solution comprising a sodium salt of the compound of Formula (Ia), PEG 300, poloxamer 188, and water is about 22.9 w/w %. In some embodiments, the amount of water in the solution comprising a sodium salt of the compound of Formula (Ia), PEG 300, poloxamer 188, and water is about 23.22 w/w %. In some embodiments, the amount of water in the solution comprising a sodium salt of the compound of Formula (Ia), PEG 300, poloxamer 188, and water is about 23.2 w/w %. In some embodiments, the amount of water in the solution comprising a sodium salt of the compound of Formula (Ia), PEG 300, poloxamer 188, and water is about 26.79 w/w %. In some embodiments, the amount of water in the solution comprising a sodium salt of the compound of Formula (Ia), PEG 300, poloxamer 188, and water is about 26.8 w/w %.

In some embodiments, the amount of water in the solution comprising a sodium salt of the compound of Formula (Ia), PEG 300, poloxamer 188, and water is about 27.61 w/w %. In some embodiments, the amount of water in the solution comprising a sodium salt of the compound of Formula (Ia), PEG 300, poloxamer 188, and water is about 27.6 w/w %. In some embodiments, the amount of water in the solution comprising a sodium salt of the compound of Formula (Ia), PEG 300, poloxamer 188, and water is about 28.43 w/w %. In some embodiments, the amount of water in the solution comprising a sodium salt of the compound of Formula (Ia), PEG 300, poloxamer 188, and water is about 28.4 w/w %.

In some embodiments, the amount of PEG 300 in the solution comprising a sodium salt of the compound of Formula (Ia), PEG 300, poloxamer 188, and water is about 30 w/w % to about 85 w/w %. In some embodiments, the amount of PEG 300 in the solution comprising a sodium salt of the compound of Formula (Ia), PEG 300, poloxamer 188, and water is about 35 w/w % to about 75 w/w %. In some embodiments, the amount of PEG 300 in the solution comprising a sodium salt of the compound of Formula (Ia), PEG 300, poloxamer 188, and water is about 40 w/w % to about 70 w/w %. In some embodiments, the amount of PEG 300 in the solution comprising a sodium salt of the compound of Formula (Ia), PEG 300, poloxamer 188, and water is about 45 w/w % to about 68 w/w %. In some embodiments, the amount of PEG 300 in the solution comprising a sodium salt of the compound of Formula (Ia), PEG 300, poloxamer 188, and water is about 46.8 w/w % to about 64.4 w/w %. In some embodiments, the amount of PEG 300 in the solution comprising a sodium salt of the compound of Formula (Ia), PEG 300, poloxamer 188, and water is about 46.84 w/w % to about 64.40 w/w %. In some embodiments, the amount of PEG 300 in the solution comprising a sodium salt of the compound of Formula (Ia), PEG 300, poloxamer 188, and water is about 40 w/w %, about 41 w/w %, about 42 w/w %, about 43 w/w %, about 44 w/w %, about 45 w/w %, about 46 w/w %, about 47 w/w %, about 48 w/w %, about 49 w/w %, about 50 w/w %, about 51 w/w %, about 52 w/w %, about 53 w/w %, about 54 w/w %, about 55 w/w %, about 56 w/w %, about 57 w/w %, about 58 w/w %, about 59 w/w %, about 60 w/w %, about 61 w/w %, about 62 w/w %, about 63 w/w %, about 64 w/w %, about 65 w/w %, about 66 w/w %, about 67 w/w %, about 68 w/w %, about 69 w/w %, or about 70 w/w %. In some embodiments, the amount of PEG 300 in the solution comprising a sodium salt of the compound of Formula (Ia), PEG 300, poloxamer 188, and water is about 46.8 w/w %. In some embodiments, the amount of PEG 300 in the solution comprising a sodium salt of the compound of Formula (Ia), PEG 300, poloxamer 188, and water is about 46.84 w/w %. In some embodiments, the amount of PEG 300 in the solution comprising a sodium salt of the compound of Formula (Ia), PEG 300, poloxamer 188, and water is about 57.1 w/w %. In some embodiments, the amount of PEG 300 in the solution comprising a sodium salt of the compound of Formula (Ia), PEG 300, poloxamer 188, and water is about 57.13 w/w %. In some embodiments, the amount of PEG 300 in the solution comprising a sodium salt of the compound of Formula (Ia), PEG 300, poloxamer 188, and water is about 58.9 w/w %. In some embodiments, the amount of PEG 300 in the solution comprising a sodium salt of the compound of Formula (Ia), PEG 300, poloxamer 188, and water is about 58.92 w/w %. In some embodiments, the amount of PEG 300 in the solution comprising a sodium salt of the compound of Formula (Ia), PEG 300, poloxamer 188, and water is about 60.7 w/w %. In some embodiments, the amount of PEG 300 in the solution comprising a sodium salt of the compound of Formula (Ia), PEG 300, poloxamer 188, and water is about 60.73 w/w %. In some embodiments, the amount of PEG 300 in the solution comprising a sodium salt of the compound of Formula (Ia), PEG 300, poloxamer 188, and water is about 62.55 w/w %. In some embodiments, the amount of PEG 300 in the solution comprising a sodium salt of the compound of Formula (Ia), PEG 300, poloxamer 188, and water is about 62.6 w/w %. In some embodiments, the amount of PEG 300 in the solution comprising a sodium salt of the compound of Formula (Ia), PEG 300, poloxamer 188, and water is about 64.4 w/w %. In some embodiments, the amount of PEG 300 in the solution comprising a sodium salt of the compound of Formula (Ia), PEG 300, poloxamer 188, and water is about 64.40 w/w %.

In some embodiments, the amount of PEG 300 in the solution comprising a sodium salt of the compound of Formula (Ia), PEG 300, poloxamer 188, and water is about 41.09 w/w % to about 64.40 w/w %. In some embodiments, the amount of PEG 300 in the solution comprising a sodium salt of the compound of Formula (Ia), PEG 300, poloxamer 188, and water is about 41.1 w/w % to about 64.4 w/w %.

In some embodiments, the amount of PEG 300 in the solution comprising a sodium salt of the compound of Formula (Ia), PEG 300, poloxamer 188, and water is about 41.09 w/w %. In some embodiments, the amount of PEG 300 in the solution comprising a sodium salt of the compound of Formula (Ia), PEG 300, poloxamer 188, and water is about 41.1 w/w %. In some embodiments, the amount of PEG 300 in the solution comprising a sodium salt of the compound of Formula (Ia), PEG 300, poloxamer 188, and water is about 43.17 w/w %. In some embodiments, the amount of PEG 300 in the solution comprising a sodium salt of the compound of Formula (Ia), PEG 300, poloxamer 188, and water is about 43.2 w/w %. In some embodiments, the amount of PEG 300 in the solution comprising a sodium salt of the compound of Formula (Ia), PEG 300, poloxamer 188, and water is about 47.33 w/w %. In some embodiments, the amount of PEG 300 in the solution comprising a sodium salt of the compound of Formula (Ia), PEG 300, poloxamer 188, and water is about 47.3 w/w %. In some embodiments, the amount of PEG 300 in the solution comprising a sodium salt of the compound of Formula (Ia), PEG 300, poloxamer 188, and water is about 48.13 w/w %. In some embodiments, the amount of PEG 300 in the solution comprising a sodium salt of the compound of Formula (Ia), PEG 300, poloxamer 188, and water is about 48.1 w/w %. In some embodiments, the amount of PEG 300 in the solution comprising a sodium salt of the compound of Formula (Ia), PEG 300, poloxamer 188, and water is about 48.94 w/w %. In some embodiments, the amount of PEG 300 in the solution comprising a sodium salt of the compound of Formula (Ia), PEG 300, poloxamer 188, and water is about 48.9 w/w %. In some embodiments, the amount of PEG 300 in the solution comprising a sodium salt of the compound of Formula (Ia), PEG 300, poloxamer 188, and water is about 49.73 w/w %. In some embodiments, the amount of PEG 300 in the solution comprising a sodium salt of the compound of Formula (Ia), PEG 300, poloxamer 188, and water is about 49.7 w/w %. In some embodiments, the amount of PEG 300 in the solution comprising a sodium salt of the compound of Formula (Ia), PEG 300, poloxamer 188, and water is about 57.38 w/w %. In some embodiments, the amount of PEG 300 in the solution comprising a sodium salt of the compound of Formula (Ia), PEG 300, poloxamer 188, and water is about 57.4 w/w %. In some embodiments, the amount of PEG 300 in the solution comprising a sodium salt of the compound of Formula (Ia), PEG 300, poloxamer 188, and water is about 59.13 w/w %. In some embodiments, the amount of PEG 300 in the solution comprising a sodium salt of the compound of Formula (Ia), PEG 300, poloxamer 188, and water is about 59.1 w/w %. In some embodiments, the amount of PEG 300 in the solution comprising a sodium salt of the compound of Formula (Ia), PEG 300, poloxamer 188, and water is about 60.90 w/w %. In some embodiments, the amount of PEG 300 in the solution comprising a sodium salt of the compound of Formula (Ia), PEG 300, poloxamer 188, and water is about 60.9 w/w %.

In some embodiments, the amount of the sodium salt of the compound of Formula (Ia) in the solution comprising a sodium salt of the compound of Formula (Ia), PEG 300, poloxamer 188, and water is about 0.5 w/w % to about 40 w/w %. In some embodiments, the amount of the sodium salt of the compound of Formula (Ia) in the solution comprising a sodium salt of the compound of Formula (Ia), PEG 300, poloxamer 188, and water is about 1 w/w % to about 35 w/w %. In some embodiments, the amount of the sodium salt of the compound of Formula (Ia) in the solution comprising a sodium salt of the compound of Formula (Ia), PEG 300, poloxamer 188, and water is about 1 w/w % to about 30 w/w %. In some embodiments, the amount of the sodium salt of the compound of Formula (Ia) in the solution comprising a sodium salt of the compound of Formula (Ia), PEG 300, poloxamer 188, and water is about 3 w/w % to about 28 w/w %. In some embodiments, the amount of the sodium salt of the compound of Formula (Ia) in the solution comprising a sodium salt of the compound of Formula (Ia), PEG 300, poloxamer 188, and water is about 4 w/w % to about 27 w/w %. In some embodiments, the amount of the sodium salt of the compound of Formula (Ia) in the solution comprising a sodium salt of the compound of Formula (Ia), PEG 300, poloxamer 188, and water is about 4.68 w/w % to about 26.47 w/w %. In some embodiments, the amount of the sodium salt of the compound of Formula (Ia) in the solution comprising a sodium salt of the compound of Formula (Ia), PEG 300, poloxamer 188, and water is about 4.7 w/w % to about 26.5 w/w %. In some embodiments, the amount of the sodium salt of the compound of Formula (Ia) in the solution comprising a sodium salt of the compound of Formula (Ia), PEG 300, poloxamer 188, and water is about 3.0 w/w %, about 3.1 w/w %, about 3.2 w/w %, about 3.3 w/w %, about 3.4 w/w %, about 3.5 w/w %, about 3.6 w/w %, about 3.7 w/w %, about 3.8 w/w %, about 3.9 w/w %, about 4.0 w/w %, about 4.1 w/w %, about 4.2 w/w %, about 4.3 w/w %, about 4.4 w/w %, about 4.5 w/w %, about 4.6 w/w %, about 4.7 w/w %, about 4.8 w/w %, about 4.9 w/w %, about 5.0 w/w %, about 5.1 w/w %, about 5.2 w/w %, about 5.3 w/w %, about 5.4 w/w %, about 5.5 w/w %, about 5.6 w/w %, about 5.7 w/w %, about 5.8 w/w %, about 5.9 w/w %, about 6.0 w/w %, about 6.1 w/w %, about 6.2 w/w %, about 6.3 w/w %, about 6.4 w/w %, about 6.5 w/w %, about 6.6 w/w %, about 6.7 w/w %, about 6.8 w/w %, about 6.9 w/w %, about 7.0 w/w %, about 7.1 w/w %, about 7.2 w/w %, about 7.3 w/w %, about 7.4 w/w %, about 7.5 w/w %, about 7.6 w/w %, about 7.7 w/w %, about 7.8 w/w %, about 7.9 w/w %, about 8.0 w/w %, about 8.1 w/w %, about 8.2 w/w %, about 8.3 w/w %, about 8.4 w/w %, about 8.5 w/w %, about 8.6 w/w %, about 8.7 w/w %, about 8.8 w/w %, about 8.9 w/w %, about 9.0 w/w %, about 9.1 w/w %, about 9.2 w/w %, about 9.3 w/w %, about 9.4 w/w %, about 9.5 w/w %, about 9.6 w/w %, about 9.7 w/w %, about 9.8 w/w %, about 9.9 w/w %, about 10.0 w/w %, about 10.1 w/w %, about 10.2 w/w %, about 10.3 w/w %, about 10.4 w/w %, about 10.5 w/w %, about 10.6 w/w %, about 10.7 w/w %, about 10.8 w/w %, about 10.9 w/w %, about 11.0 w/w %, about 11.1 w/w %, about 11.2 w/w %, about 11.3 w/w %, about 11.4 w/w %, about 11.5 w/w %, about 11.6 w/w %, about 11.7 w/w %, about 11.8 w/w %, about 11.9 w/w %, about 12.0 w/w %, about 12.1 w/w %, about 12.2 w/w %, about 12.3 w/w %, about 12.4 w/w %, about 12.5 w/w %, about 12.6 w/w %, about 12.7 w/w %, about 12.8 w/w %, about 12.9 w/w %, about 13.0 w/w %, about 13.1 w/w %, about 13.2 w/w %, about 13.3 w/w %, about 13.4 w/w %, about 13.5 w/w %, about 13.6 w/w %, about 13.7 w/w %, about 13.8 w/w %, about 13.9 w/w %, about 14.0 w/w %, about 14.1 w/w %, about 14.2 w/w %, about 14.3 w/w %, about 14.4 w/w %, about 14.5 w/w %, about 14.6 w/w %, about 14.7 w/w %, about 14.8 w/w %, about 14.9 w/w %, about 15.0 w/w %, about 15.1 w/w %, about 15.2 w/w %, about 15.3 w/w %, about 15.4 w/w %, about 15.5 w/w %, about 15.6 w/w %, about 15.7 w/w %, about 15.8 w/w %, about 15.9 w/w %, about 16.0 w/w %, about 16.1 w/w %, about 16.2 w/w %, about 16.3 w/w %, about 16.4 w/w %, about 16.5 w/w %, about 16.6 w/w %, about 16.7 w/w %, about 16.8 w/w %, about 16.9 w/w %, about 17.0 w/w %, about 17.1 w/w %, about 17.2 w/w %, about 17.3 w/w %, about 17.4 w/w %, about 17.5 w/w %, about 17.6 w/w %, about 17.7 w/w %, about 17.8 w/w %, about 17.9 w/w %, about 18.0 w/w %, about 18.1 w/w %, about 18.2 w/w %, about 18.3 w/w %, about 18.4 w/w %, about 18.5 w/w %, about 18.6 w/w %, about 18.7 w/w %, about 18.8 w/w %, about 18.9 w/w %, about 19.0 w/w %, about 19.1 w/w %, about 19.2 w/w %, about 19.3 w/w %, about 19.4 w/w %, about 19.5 w/w %, about 19.6 w/w %, about 19.7 w/w %, about 19.8 w/w %, about 19.9 w/w %, about 20.0 w/w %, about 20.1 w/w %, about 20.2 w/w %, about 20.3 w/w %, about 20.4 w/w %, about 20.5 w/w %, about 20.6 w/w %, about 20.7 w/w %, about 20.8 w/w %, about 20.9 w/w %, about 21.0 w/w %, about 21.1 w/w %, about 21.2 w/w %, about 21.3 w/w %, about 21.4 w/w %, about 21.5 w/w %, about 21.6 w/w %, about 21.7 w/w %, about 21.8 w/w %, about 21.9 w/w %, about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, or about 29.0 w/w %. In some embodiments, the amount of the sodium salt of the compound of Formula (Ia) in the solution comprising a sodium salt of the compound of Formula (Ia), PEG 300, poloxamer 188, and water is about 4.68 w/w %. In some embodiments, the amount of the sodium salt of the compound of Formula (Ia) in the solution comprising a sodium salt of the compound of Formula (Ia), PEG 300, poloxamer 188, and water is about 4.7 w/w %. In some embodiments, the amount of the sodium salt of the compound of Formula (Ia) in the solution comprising a sodium salt of the compound of Formula (Ia), PEG 300, poloxamer 188, and water is about 6.97 w/w %. In some embodiments, the amount of the sodium salt of the compound of Formula (Ia) in the solution comprising a sodium salt of the compound of Formula (Ia), PEG 300, poloxamer 188, and water is about 7 w/w %. In some embodiments, the amount of the sodium salt of the compound of Formula (Ia) in the solution comprising a sodium salt of the compound of Formula (Ia), PEG 300, poloxamer 188, and water is about 9.2 w/w %. In some embodiments, the amount of the sodium salt of the compound of Formula (Ia) in the solution comprising a sodium salt of the compound of Formula (Ia), PEG 300, poloxamer 188, and water is about 9.23 w/w %. In some embodiments, the amount of the sodium salt of the compound of Formula (Ia) in the solution comprising a sodium salt of the compound of Formula (Ia), PEG 300, poloxamer 188, and water is about 11.48 w/w %. In some embodiments, the amount of the sodium salt of the compound of Formula (Ia) in the solution comprising a sodium salt of the compound of Formula (Ia), PEG 300, poloxamer 188, and water is about 11.5 w/w %. In some embodiments, the amount of the sodium salt of the compound of Formula (Ia) in the solution comprising a sodium salt of the compound of Formula (Ia), PEG 300, poloxamer 188, and water is about 13.7 w/w %. In some embodiments, the amount of the sodium salt of the compound of Formula (Ia) in the solution comprising a sodium salt of the compound of Formula (Ia), PEG 300, poloxamer 188, and water is about 13.70 w/w %. In some embodiments, the amount of the sodium salt of the compound of Formula (Ia) in the solution comprising a sodium salt of the compound of Formula (Ia), PEG 300, poloxamer 188, and water is about 26.47 w/w %. In some embodiments, the amount of the sodium salt of the compound of Formula (Ia) in the solution comprising a sodium salt of the compound of Formula (Ia), PEG 300, poloxamer 188, and water is about 26.5 w/w %.

In some embodiments, the amount of the sodium salt of the compound of Formula (Ia) in the solution comprising a sodium salt of the compound of Formula (Ia), PEG 300, poloxamer 188, and water is about 4.68 w/w % to about 33.61 w/w %. In some embodiments, the amount of the sodium salt of the compound of Formula (Ia) in the solution comprising a sodium salt of the compound of Formula (Ia), PEG 300, poloxamer 188, and water is about 4.7 w/w % to about 33.6 w/w %.

In some embodiments, the amount of the sodium salt of the compound of Formula (Ia) in the solution comprising a sodium salt of the compound of Formula (Ia), PEG 300, poloxamer 188, and water is about 9.03 w/w %. In some embodiments, the amount of the sodium salt of the compound of Formula (Ia) in the solution comprising a sodium salt of the compound of Formula (Ia), PEG 300, poloxamer 188, and water is about 9.0 w/w %. In some embodiments, the amount of the sodium salt of the compound of Formula (Ia) in the solution comprising a sodium salt of the compound of Formula (Ia), PEG 300, poloxamer 188, and water is about 11.22 w/w %. In some embodiments, the amount of the sodium salt of the compound of Formula (Ia) in the solution comprising a sodium salt of the compound of Formula (Ia), PEG 300, poloxamer 188, and water is about 11.2 w/w %. In some embodiments, the amount of the sodium salt of the compound of Formula (Ia) in the solution comprising a sodium salt of the compound of Formula (Ia), PEG 300, poloxamer 188, and water is about 13.39 w/w %. In some embodiments, the amount of the sodium salt of the compound of Formula (Ia) in the solution comprising a sodium salt of the compound of Formula (Ia), PEG 300, poloxamer 188, and water is about 13.4 w/w %. In some embodiments, the amount of the sodium salt of the compound of Formula (Ia) in the solution comprising a sodium salt of the compound of Formula (Ia), PEG 300, poloxamer 188, and water is about 25.85 w/w %. In some embodiments, the amount of the sodium salt of the compound of Formula (Ia) in the solution comprising a sodium salt of the compound of Formula (Ia), PEG 300, poloxamer 188, and water is about 25.87 w/w %. In some embodiments, the amount of the sodium salt of the compound of Formula (Ia) in the solution comprising a sodium salt of the compound of Formula (Ia), PEG 300, poloxamer 188, and water is about 25.9 w/w %. In some embodiments, the amount of the sodium salt of the compound of Formula (Ia) in the solution comprising a sodium salt of the compound of Formula (Ia), PEG 300, poloxamer 188, and water is about 33.61 w/w %. In some embodiments, the amount of the sodium salt of the compound of Formula (Ia) in the solution comprising a sodium salt of the compound of Formula (Ia), PEG 300, poloxamer 188, and water is about 33.6 w/w %.

In some embodiments, the amount of poloxamer 188 in the solution comprising a sodium salt of the compound of Formula (Ia), PEG 300, poloxamer 188, and water is about 0.1 w/w % to about 10 w/w %. In some embodiments, the amount of poloxamer 188 in the solution comprising a sodium salt of the compound of Formula (Ia), PEG 300, poloxamer 188, and water is about 0.3 w/w % to about 8 w/w %. In some embodiments, the amount of poloxamer 188 in the solution comprising a sodium salt of the compound of Formula (Ia), PEG 300, poloxamer 188, and water is about 0.5 w/w % to about 7 w/w %. In some embodiments, the amount of poloxamer 188 in the solution comprising a sodium salt of the compound of Formula (Ia), PEG 300, poloxamer 188, and water is about 0.6 w/w % to about 7 w/w %. In some embodiments, the amount of poloxamer 188 in the solution comprising a sodium salt of the compound of Formula (Ia), PEG 300, poloxamer 188, and water is about 0.85 w/w % to about 4.82 w/w %. In some embodiments, the amount of poloxamer 188 in the solution comprising a sodium salt of the compound of Formula (Ia), PEG 300, poloxamer 188, and water is about 0.9 w/w % to about 4.8 w/w %. In some embodiments, the amount of poloxamer 188 in the solution comprising a sodium salt of the compound of Formula (Ia), PEG 300, poloxamer 188, and water is about 0.5 w/w %, about 0.6 w/w %, about 0.7 w/w %, about 0.8 w/w %, about 0.9 w/w %, about 1.0 w/w %, about 1.1 w/w %, about 1.2 w/w %, about 1.3 w/w %, about 1.4 w/w %, about 1.5 w/w %, about 1.6 w/w %, about 1.7 w/w %, about 1.8 w/w %, about 1.9 w/w %, about 2.0 w/w %, about 2.1 w/w %, about 2.2 w/w %, about 2.3 w/w %, about 2.4 w/w %, about 2.5 w/w %, about 2.6 w/w %, about 2.7 w/w %, about 2.8 w/w %, about 2.9 w/w %, about 3.0 w/w %, about 3.1 w/w %, about 3.2 w/w %, about 3.3 w/w %, about 3.4 w/w %, about 3.5 w/w %, about 3.6 w/w %, about 3.7 w/w %, about 3.8 w/w %, about 3.9 w/w %, about 4.0 w/w %, about 4.1 w/w %, about 4.2 w/w %, about 4.3 w/w %, about 4.4 w/w %, about 4.5 w/w %, about 4.6 w/w %, about 4.7 w/w %, about 4.8 w/w %, about 4.9 w/w %, about 5.0 w/w %, about 5.1 w/w %, about 5.2 w/w %, about 5.3 w/w %, about 5.4 w/w %, about 5.5 w/w %, about 5.6 w/w %, about 5.7 w/w %, about 5.8 w/w %, about 5.9 w/w %, about 6.0 w/w %, about 6.1 w/w %, about 6.2 w/w %, about 6.3 w/w %, about 6.4 w/w %, about 6.5 w/w %, about 6.6 w/w %, about 6.7 w/w %, about 6.8 w/w %, about 6.9 w/w %, or about 7.0 w/w %. In some embodiments, the amount of poloxamer 188 in the solution comprising a sodium salt of the compound of Formula (Ia), PEG 300, poloxamer 188, and water is about 0.85 w/w %. In some embodiments, the amount of poloxamer 188 in the solution comprising a sodium salt of the compound of Formula (Ia), PEG 300, poloxamer 188, and water is about 0.9 w/w %. In some embodiments, the amount of poloxamer 188 in the solution comprising a sodium salt of the compound of Formula (Ia), PEG 300, poloxamer 188, and water is about 1.27 w/w %. In some embodiments, the amount of poloxamer 188 in the solution comprising a sodium salt of the compound of Formula (Ia), PEG 300, poloxamer 188, and water is about 1.3 w/w %. In some embodiments, the amount of poloxamer 188 in the solution comprising a sodium salt of the compound of Formula (Ia), PEG 300, poloxamer 188, and water is about 1.68 w/w %. In some embodiments, the amount of poloxamer 188 in the solution comprising a sodium salt of the compound of Formula (Ia), PEG 300, poloxamer 188, and water is about 1.7 w/w %. In some embodiments, the amount of poloxamer 188 in the solution comprising a sodium salt of the compound of Formula (Ia), PEG 300, poloxamer 188, and water is about 2.09 w/w %. In some embodiments, the amount of poloxamer 188 in the solution comprising a sodium salt of the compound of Formula (Ia), PEG 300, poloxamer 188, and water is about 2.1 w/w %. In some embodiments, the amount of poloxamer 188 in the solution comprising a sodium salt of the compound of Formula (Ia), PEG 300, poloxamer 188, and water is about 2.49 w/w %. In some embodiments, the amount of poloxamer 188 in the solution comprising a sodium salt of the compound of Formula (Ia), PEG 300, poloxamer 188, and water is about 2.5 w/w %. In some embodiments, the amount of poloxamer 188 in the solution comprising a sodium salt of the compound of Formula (Ia), PEG 300, poloxamer 188, and water is about 4.8 w/w %. In some embodiments, the amount of poloxamer 188 in the solution comprising a sodium salt of the compound of Formula (Ia), PEG 300, poloxamer 188, and water is about 4.82 w/w %.

In some embodiments, the amount of poloxamer 188 in the solution comprising a sodium salt of the compound of Formula (Ia), PEG 300, poloxamer 188, and water is about 0.85 w/w % to about 6.12 w/w %. In some embodiments, the amount of poloxamer 188 in the solution comprising a sodium salt of the compound of Formula (Ia), PEG 300, poloxamer 188, and water is about 0.9 w/w % to about 6.1 w/w %.

In some embodiments, the amount of poloxamer 188 in the solution comprising a sodium salt of the compound of Formula (Ia), PEG 300, poloxamer 188, and water is about 1.18 w/w %. In some embodiments, the amount of poloxamer 188 in the solution comprising a sodium salt of the compound of Formula (Ia), PEG 300, poloxamer 188, and water is about 1.2 w/w %. In some embodiments, the amount of poloxamer 188 in the solution comprising a sodium salt of the compound of Formula (Ia), PEG 300, poloxamer 188, and water is about 1.64 w/w %. In some embodiments, the amount of poloxamer 188 in the solution comprising a sodium salt of the compound of Formula (Ia), PEG 300, poloxamer 188, and water is about 1.6 w/w %. In some embodiments, the amount of poloxamer 188 in the solution comprising a sodium salt of the compound of Formula (Ia), PEG 300, poloxamer 188, and water is about 2.04 w/w %. In some embodiments, the amount of poloxamer 188 in the solution comprising a sodium salt of the compound of Formula (Ia), PEG 300, poloxamer 188, and water is about 2.0 w/w %. In some embodiments, the amount of poloxamer 188 in the solution comprising a sodium salt of the compound of Formula (Ia), PEG 300, poloxamer 188, and water is about 2.36 w/w %. In some embodiments, the amount of poloxamer 188 in the solution comprising a sodium salt of the compound of Formula (Ia), PEG 300, poloxamer 188, and water is about 2.44 w/w %. In some embodiments, the amount of poloxamer 188 in the solution comprising a sodium salt of the compound of Formula (Ia), PEG 300, poloxamer 188, and water is about 2.4 w/w %. In some embodiments, the amount of poloxamer 188 in the solution comprising a sodium salt of the compound of Formula (Ia), PEG 300, poloxamer 188, and water is about 3.06 w/w %. In some embodiments, the amount of poloxamer 188 in the solution comprising a sodium salt of the compound of Formula (Ia), PEG 300, poloxamer 188, and water is about 3.1 w/w %. In some embodiments, the amount of poloxamer 188 in the solution comprising a sodium salt of the compound of Formula (Ia), PEG 300, poloxamer 188, and water is about 3.54 w/w %. In some embodiments, the amount of poloxamer 188 in the solution comprising a sodium salt of the compound of Formula (Ia), PEG 300, poloxamer 188, and water is about 3.5 w/w %. In some embodiments, the amount of poloxamer 188 in the solution comprising a sodium salt of the compound of Formula (Ia), PEG 300, poloxamer 188, and water is about 4.72 w/w %. In some embodiments, the amount of poloxamer 188 in the solution comprising a sodium salt of the compound of Formula (Ia), PEG 300, poloxamer 188, and water is about 4.7 w/w %. In some embodiments, the amount of poloxamer 188 in the solution comprising a sodium salt of the compound of Formula (Ia), PEG 300, poloxamer 188, and water is about 6.12 w/w %. In some embodiments, the amount of poloxamer 188 in the solution comprising a sodium salt of the compound of Formula (Ia), PEG 300, poloxamer 188, and water is about 6.1 w/w %.

In some embodiments, the solution comprises about 10 w/w % to about 45 w/w % water, about 30 w/w % to about 85 w/w % PEG 300, about 0.5 w/w % to about 40 w/w % of a sodium salt of a compound of Formula (Ia), and about 0.1 w/w % to about 10 w/w % of poloxamer 188. In some embodiments, the solution comprises about 15 w/w % to about 35 w/w % water, about 35 w/w % to about 75 w/w % PEG 300, about 1 w/w % to about 35 w/w % of a sodium salt of a compound of Formula (Ia), and about 0.3 w/w % to about 8 w/w % of poloxamer 188. In some embodiments, the solution comprises about 20 w/w % to about 35 w/w % water, about 40 w/w % to about 70 w/w % PEG 300, about 1 w/w % to about 30 w/w % of a sodium salt of a compound of Formula (Ia), and about 0.5 w/w % to about 7 w/w % of poloxamer 188. In some embodiments, the solution comprises about 20 w/w % to about 31 w/w % water, about 45 w/w % to about 68 w/w % PEG 300, about 3 w/w % to about 28 w/w % of a sodium salt of a compound of Formula (Ia), and about 0.6 w/w % to about 7 w/w % of poloxamer 188. In some embodiments, the solution comprises about 21.9 w/w % to about 30.1 w/w % water, about 46.8 w/w % to about 64.4 w/w % PEG 300, about 4.7 w/w % to about 26.5 w/w % of a sodium salt of a compound of Formula (Ia), and about 0.9 w/w % to about 4.8 w/w % of poloxamer 188. In some embodiments, the solution comprises about 21.87 w/w % to about 30.07 w/w % water, about 46.84 w/w % to about 64.40 w/w % PEG 300, about 4.68 w/w % to about 26.47 w/w % of a sodium salt of a compound of Formula (Ia), and about 0.85 w/w % to about 4.82 w/w % of poloxamer 188. In some embodiments, the solution comprises about 30.1 w/w % water, about 64.4 w/w % PEG 300, about 4.7 w/w % of a sodium salt of a compound of Formula (Ia), and about 0.9 w/w % of poloxamer 188. In some embodiments, the solution comprises about 30.07 w/w % water, about 64.40 w/w % PEG 300, about 4.68 w/w % of a sodium salt of a compound of Formula (Ia), and about 0.85 w/w % of poloxamer 188. In some embodiments, the solution comprises about 29.2 w/w % water, about 62.6 w/w % PEG 300, about 7 w/w % of a sodium salt of a compound of Formula (Ia), and about 1.3 w/w % of poloxamer 188. In some embodiments, the solution comprises about 29.21 w/w % water, about 62.55 w/w % PEG 300, about 6.97 w/w % of a sodium salt of a compound of Formula (Ia), and about 1.27 w/w % of poloxamer 188. In some embodiments, the solution comprises about 28.4 w/w % water, about 60.7 w/w % PEG 300, about 9.2 w/w % of a sodium salt of a compound of Formula (Ia), and about 1.7 w/w % of poloxamer 188. In some embodiments, the solution comprises about 28.36 w/w % water, about 60.73 w/w % PEG 300, about 9.23 w/w % of a sodium salt of a compound of Formula (Ia), and about 1.68 w/w % of poloxamer 188. In some embodiments, the solution comprises about 27.5 w/w % water, about 58.9 w/w % PEG 300, about 11.5 w/w % of a sodium salt of a compound of Formula (Ia), and about 2.1 w/w % of poloxamer 188. In some embodiments, the solution comprises about 27.51 w/w % water, about 58.92 w/w % PEG 300, about 11.48 w/w % of a sodium salt of a compound of Formula (Ia), and about 2.09 w/w % of poloxamer 188. In some embodiments, the solution comprises about 26.7 w/w % water, about 57.1 w/w % PEG 300, about 13.7 w/w % of a sodium salt of a compound of Formula (Ia), and about 2.5 w/w % of poloxamer 188. In some embodiments, the solution comprises about 26.68 w/w % water, about 57.13 w/w % PEG 300, about 13.70 w/w % of a sodium salt of a compound of Formula (Ia), and about 2.49 w/w % of poloxamer 188. In some embodiments, the solution comprises about 21.9 w/w % water, about 46.8 w/w % PEG 300, about 26.5 w/w % of a sodium salt of a compound of Formula (Ia), and about 4.8 w/w % of poloxamer 188. In some embodiments, the solution comprises about 21.87 w/w % water, about 46.84 w/w % PEG 300, about 26.47 w/w % of a sodium salt of a compound of Formula (Ia), and about 4.82 w/w % of poloxamer 188.

In some embodiments, the solution comprises about 19.2 w/w % to about 30.1 w/w % water, about 41.1 w/w % to about 64.4 w/w % PEG 300, about 4.7 w/w % to about 33.6 w/w % of a sodium salt of a compound of Formula (Ia), and about 0.9 w/w % to about 6.1 w/w % of poloxamer 188. In some embodiments, the solution comprises about 19.18 w/w % to about 30.07 w/w % water, about 41.09 w/w % to about 64.40 w/w % PEG 300, about 4.68 w/w % to about 33.61 w/w % of a sodium salt of a compound of Formula (Ia), and about 0.85 w/w % to about 6.12 w/w % of poloxamer 188.

In some embodiments, the solution comprises about 28.4 w/w % water, about 60.9 w/w % PEG 300, about 9.0 w/w % of a sodium salt of a compound of Formula (Ia), and about 1.6 w/w % of poloxamer 188. In some embodiments, the solution comprises about 28.43 w/w % water, about 60.90 w/w % PEG 300, about 9.03 w/w % of a sodium salt of a compound of Formula (Ia), and about 1.64 w/w % of poloxamer 188.

In some embodiments, the solution comprises about 27.6 w/w % water, about 59.1 w/w % PEG 300, about 11.2 w/w % of a sodium salt of a compound of Formula (Ia), and about 2.0 w/w % of poloxamer 188. In some embodiments, the solution comprises about 27.61 w/w % water, about 59.13 w/w % PEG 300, about 11.22 w/w % of a sodium salt of a compound of Formula (Ia), and about 2.04 w/w % of poloxamer 188.

In some embodiments, the solution comprises about 26.8 w/w % water, about 57.4 w/w % PEG 300, about 13.4 w/w % of a sodium salt of a compound of Formula (Ia), and about 2.4 w/w % of poloxamer 188. In some embodiments, the solution comprises about 26.79 w/w % water, about 57.38 w/w % PEG 300, about 13.39 w/w % of a sodium salt of a compound of Formula (Ia), and about 2.44 w/w % of poloxamer 188.

In some embodiments, the solution comprises about 23.2 w/w % water, about 49.7 w/w % PEG 300, about 25.9 w/w % of a sodium salt of a compound of Formula (Ia), and about 1.2 w/w % of poloxamer 188. In some embodiments, the solution comprises about 23.22 w/w % water, about 49.73 w/w % PEG 300, about 25.87 w/w % of a sodium salt of a compound of Formula (Ia), and about 1.18 w/w % of poloxamer 188.

In some embodiments, the solution comprises about 22.9 w/w % water, about 48.9 w/w % PEG 300, about 25.9 w/w % of a sodium salt of a compound of Formula (Ia), and about 2.4 w/w % of poloxamer 188. In some embodiments, the solution comprises about 22.85 w/w % water, about 48.94 w/w % PEG 300, about 25.85 w/w % of a sodium salt of a compound of Formula (Ia), and about 2.36 w/w % of poloxamer 188.

In some embodiments, the solution comprises about 22.5 w/w % water, about 48.1 w/w % PEG 300, about 25.9 w/w % of a sodium salt of a compound of Formula (Ia), and about 3.5 w/w % of poloxamer 188. In some embodiments, the solution comprises about 22.48 w/w % water, about 48.13 w/w % PEG 300, about 25.85 w/w % of a sodium salt of a compound of Formula (Ia), and about 3.54 w/w % of poloxamer 188.

In some embodiments, the solution comprises about 22.1 w/w % water, about 47.3 w/w % PEG 300, about 25.9 w/w % of a sodium salt of a compound of Formula (Ia), and about 4.7 w/w % of poloxamer 188. In some embodiments, the solution comprises about 22.10 w/w % water, about 47.33 w/w % PEG 300, about 25.85 w/w % of a sodium salt of a compound of Formula (Ia), and about 4.72 w/w % of poloxamer 188.

In some embodiments, the solution comprises about 20.2 w/w % water, about 43.2 w/w % PEG 300, about 33.6 w/w % of a sodium salt of a compound of Formula (Ia), and about 3.1 w/w % of poloxamer 188. In some embodiments, the solution comprises about 20.16 w/w % water, about 43.17 w/w % PEG 300, about 33.61 w/w % of a sodium salt of a compound of Formula (Ia), and about 3.06 w/w % of poloxamer 188.

In some embodiments, the solution comprises about 19.2 w/w % water, about 41.1 w/w % PEG 300, about 33.6 w/w % of a sodium salt of a compound of Formula (Ia), and about 6.1 w/w % of poloxamer 188. In some embodiments, the solution comprises about 19.18 w/w % water, about 41.09 w/w % PEG 300, about 33.61 w/w % of a sodium salt of a compound of Formula (Ia), and about 6.12 w/w % of poloxamer 188.

In some embodiments, the solution comprises a compound of Formula (Ia) or Formula (Ib), or a pharmaceutically acceptable salt thereof, PEG 300, water, poloxamer 188, and ethanol. In some embodiments, the solution comprises a compound of Formula (Ia), or a pharmaceutically acceptable salt thereof, PEG 300, water, poloxamer 188, and ethanol. In some embodiments, the solution comprises a sodium salt of the compound of Formula (Ia), PEG 300, water, poloxamer 188, and ethanol. In some embodiments, the solution comprises a compound of Formula (Ib), or a pharmaceutically acceptable salt thereof, PEG 300, water, poloxamer 188, and ethanol.

In some embodiments, the amount of water in the solution comprising a sodium salt of the compound of Formula (Ia), PEG 300, water, poloxamer 188, and ethanol is about 10 w/w % to about 20 w/w %. In some embodiments, the amount of water in the solution comprising a sodium salt of the compound of Formula (Ia), PEG 300, water, poloxamer 188, and ethanol is about 10 w/w % to about 19 w/w %. In some embodiments, the amount of water in the solution comprising a sodium salt of the compound of Formula (Ia), PEG 300, water, poloxamer 188, and ethanol is about 14.50 w/w % to about 15.71 w/w %. In some embodiments, the amount of water in the solution comprising a sodium salt of the compound of Formula (Ia), PEG 300, water, poloxamer 188, and ethanol is about 14.5 w/w % to about 15.7 w/w %. In some embodiments, the amount of water in the solution comprising a sodium salt of the compound of Formula (Ia), PEG 300, water, poloxamer 188, and ethanol is about 14.50 w/w %. In some embodiments, the amount of water in the solution comprising a sodium salt of the compound of Formula (Ia), PEG 300, water, poloxamer 188, and ethanol is about 14.5 w/w %. In some embodiments, the amount of water in the solution comprising a sodium salt of the compound of Formula (Ia), PEG 300, water, poloxamer 188, and ethanol is about 14.57 w/w %. In some embodiments, the amount of water in the solution comprising a sodium salt of the compound of Formula (Ia), PEG 300, water, poloxamer 188, and ethanol is about 14.6 w/w %. In some embodiments, the amount of water in the solution comprising a sodium salt of the compound of Formula (Ia), PEG 300, water, poloxamer 188, and ethanol is about 15.71 w/w %. In some embodiments, the amount of water in the solution comprising a sodium salt of the compound of Formula (Ia), PEG 300, water, poloxamer 188, and ethanol is about 15.7 w/w %.

In some embodiments, the amount of PEG 300 in the solution comprising a sodium salt of the compound of Formula (Ia), PEG 300, water, poloxamer 188, and ethanol is about 25 w/w % to about 40 w/w %. In some embodiments, the amount of PEG 300 in the solution comprising a sodium salt of the compound of Formula (Ia), PEG 300, water, poloxamer 188, and ethanol is about 27 w/w % to about 37 w/w %. In some embodiments, the amount of PEG 300 in the solution comprising a sodium salt of the compound of Formula (Ia), PEG 300, water, poloxamer 188, and ethanol is about 31.04 w/w % to about 33.63 w/w %. In some embodiments, the amount of PEG 300 in the solution comprising a sodium salt of the compound of Formula (Ia), PEG 300, water, poloxamer 188, and ethanol is about 31.0 w/w % to about 33.6 w/w %. In some embodiments, the amount of PEG 300 in the solution comprising a sodium salt of the compound of Formula (Ia), PEG 300, water, poloxamer 188, and ethanol is about 31.04 w/w %. In some embodiments, the amount of PEG 300 in the solution comprising a sodium salt of the compound of Formula (Ia), PEG 300, water, poloxamer 188, and ethanol is about 31.0 w/w %. In some embodiments, the amount of PEG 300 in the solution comprising a sodium salt of the compound of Formula (Ia), PEG 300, water, poloxamer 188, and ethanol is about 31.21 w/w %. In some embodiments, the amount of PEG 300 in the solution comprising a sodium salt of the compound of Formula (Ia), PEG 300, water, poloxamer 188, and ethanol is about 31.2 w/w %. In some embodiments, the amount of PEG 300 in the solution comprising a sodium salt of the compound of Formula (Ia), PEG 300, water, poloxamer 188, and ethanol is about 33.63 w/w %. In some embodiments, the amount of PEG 300 in the solution comprising a sodium salt of the compound of Formula (Ia), PEG 300, water, poloxamer 188, and ethanol is about 33.6 w/w %.

In some embodiments, the amount of the sodium salt of the compound of Formula (Ia) in the solution comprising a sodium salt of the compound of Formula (Ia), PEG 300, water, poloxamer 188, and ethanol is about 35 w/w % to about 45 w/w %. In some embodiments, the amount of the sodium salt of the compound of Formula (Ia) in the solution comprising a sodium salt of the compound of Formula (Ia), PEG 300, water, poloxamer 188, and ethanol is about 37 w/w % to about 45 w/w %. In some embodiments, the amount of the sodium salt of the compound of Formula (Ia) in the solution comprising a sodium salt of the compound of Formula (Ia), PEG 300, water, poloxamer 188, and ethanol is about 41.64 w/w %. In some embodiments, the amount of the sodium salt of the compound of Formula (Ia) in the solution comprising a sodium salt of the compound of Formula (Ia), PEG 300, water, poloxamer 188, and ethanol is about 41.6 w/w %. In some embodiments, the amount of the sodium salt of the compound of Formula (Ia) in the solution comprising a sodium salt of the compound of Formula (Ia), PEG 300, water, poloxamer 188, and ethanol is about 41.85 w/w %. In some embodiments, the amount of the sodium salt of the compound of Formula (Ia) in the solution comprising a sodium salt of the compound of Formula (Ia), PEG 300, water, poloxamer 188, and ethanol is about 41.9 w/w %.

In some embodiments, the amount of poloxamer 188 in the solution comprising a sodium salt of the compound of Formula (Ia), PEG 300, water, poloxamer 188, and ethanol is about 0.5 w/w % to about 12 w/w %. In some embodiments, the amount of poloxamer 188 in the solution comprising a sodium salt of the compound of Formula (Ia), PEG 300, water, poloxamer 188, and ethanol is about 1 w/w % to about 11 w/w %. In some embodiments, the amount of poloxamer 188 in the solution comprising a sodium salt of the compound of Formula (Ia), PEG 300, water, poloxamer 188, and ethanol is about 3.81 w/w % to about 7.61 w/w %. In some embodiments, the amount of poloxamer 188 in the solution comprising a sodium salt of the compound of Formula (Ia), PEG 300, water, poloxamer 188, and ethanol is about 3.8 w/w % to about 7.6 w/w %. In some embodiments, the amount of poloxamer 188 in the solution comprising a sodium salt of the compound of Formula (Ia), PEG 300, water, poloxamer 188, and ethanol is about 3.81 w/w %. In some embodiments, the amount of poloxamer 188 in the solution comprising a sodium salt of the compound of Formula (Ia), PEG 300, water, poloxamer 188, and ethanol is about 3.8 w/w %. In some embodiments, the amount of poloxamer 188 in the solution comprising a sodium salt of the compound of Formula (Ia), PEG 300, water, poloxamer 188, and ethanol is about 7.58 w/w %. In some embodiments, the amount of poloxamer 188 in the solution comprising a sodium salt of the compound of Formula (Ia), PEG 300, water, poloxamer 188, and ethanol is about 7.61 w/w %. In some embodiments, the amount of poloxamer 188 in the solution comprising a sodium salt of the compound of Formula (Ia), PEG 300, water, poloxamer 188, and ethanol is about 7.6 w/w %.

In some embodiments, the amount of ethanol in the solution comprising a sodium salt of the compound of Formula (Ia), PEG 300, water, poloxamer 188, and ethanol is about 0.1 w/w % to about 10 w/w %. In some embodiments, the amount of ethanol in the solution comprising a sodium salt of the compound of Formula (Ia), PEG 300, water, poloxamer 188, and ethanol is about 1 w/w % to about 9 w/w %. In some embodiments, the amount of ethanol in the solution comprising a sodium salt of the compound of Formula (Ia), PEG 300, water, poloxamer 188, and ethanol is about 3 w/w % to about 8 w/w %. In some embodiments, the amount of ethanol in the solution comprising a sodium salt of the compound of Formula (Ia), PEG 300, water, poloxamer 188, and ethanol is about 5.00 w/w %. In some embodiments, the amount of ethanol in the solution comprising a sodium salt of the compound of Formula (Ia), PEG 300, water, poloxamer 188, and ethanol is about 5.0 w/w %.

In some embodiments, the solution comprises about 10 w/w % to about 40 w/w % water, about 20 w/w % to about 75 w/w % PEG 300, about 10 w/w % to about 70 w/w % of a sodium salt of the compound of Formula (Ia), about 1 w/w % to about 20 w/w % poloxamer 188, and about 1 w/w % to about 10 w/w % of ethanol. In some embodiments, the solution comprises about 10 w/w % to about 20 w/w % water, about 25 w/w % to about 35 w/w % PEG 300, about 37 w/w % to about 45 w/w % of a sodium salt of the compound of Formula (Ia), and about 3 w/w % to about 8 w/w % of ethanol.

In some embodiments, the solution comprises about 15.71 w/w % water, about 33.63 w/w % PEG 300, about 41.85 w/w % of a sodium salt of the compound of Formula (Ia), about 3.81 w/w % poloxamer 188, and about 5.00 w/w % ethanol. In some embodiments, the solution comprises about 15.7 w/w % water, about 33.6 w/w % PEG 300, about 41.9 w/w % of a sodium salt of the compound of Formula (Ia), about 3.8 w/w % poloxamer 188, and about 5.0 w/w % ethanol.

In some embodiments, the solution comprises about 14.57 w/w % water, about 31.21 w/w % PEG 300, about 41.64 w/w % of a sodium salt of the compound of Formula (Ia), about 7.58 w/w % poloxamer 188, and about 5.00 w/w % ethanol. In some embodiments, the solution comprises about 14.6 w/w % water, about 31.2 w/w % PEG 300, about 41.6 w/w % of a sodium salt of the compound of Formula (Ia), about 7.6 w/w % poloxamer 188, and about 5.0 w/w % ethanol.

In some embodiments, the solution comprises about 14.50 w/w % water, about 31.04 w/w % PEG 300, about 41.85 w/w % of a sodium salt of the compound of Formula (Ia), about 7.61 w/w % poloxamer 188, and about 5.00 w/w % ethanol. In some embodiments, the solution comprises about 14.5 w/w % water, about 31.0 w/w % PEG 300, about 41.9 w/w % of a sodium salt of the compound of Formula (Ia), about 7.6 w/w % poloxamer 188, and about 5.0 w/w % ethanol.

In some embodiments of the methods herein, the compound of Formula (Ia) or Formula (Ib), or a pharmaceutically acceptable salt thereof are administered as a parenteral formulation (for example, for SC or IM administration), which is an aqueous suspension. In some embodiments, the parenteral formulation (for example, an SC or IM formulation is an aqueous suspension that includes a compound of Formula (Ia) or Formula (Ib), or a pharmaceutically acceptable salt thereof, and saline. In some embodiments, the parenteral formulation (for example, an SC or IM formulation) is an aqueous suspension that comprises a compound of Formula (Ia) or Formula (Ib), or a pharmaceutically acceptable salt thereof, saline, and a suspending agent. In some embodiments, the parenteral formulation (for example, an SC or IM formulation) is an aqueous suspension that comprises a compound of Formula (Ia) or Formula (Ib), or a pharmaceutically acceptable salt thereof, saline, and a poloxamer (such as poloxamer 338, 188, or 207).

In some embodiments, a suspension comprising a compound of Formula (Ia) or Formula (Ib), or a pharmaceutically acceptable salt thereof, in a poloxamer and saline is provided. In some embodiments, the concentration of poloxamer in saline is from about 0.1% to about 20%. In some embodiments, the concentration of poloxamer in saline is from about 0.1% to about 10%. In some embodiments, the concentration of poloxamer in saline is about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10%. In certain embodiments, the concentration of poloxamer in saline is about 2%. In certain embodiments, the poloxamer is poloxamer 188. In certain embodiments, the compound is a compound of Formula (Ia), or a pharmaceutically acceptable salt thereof. In certain embodiments, the compound is a compound of Formula (Ia). In certain embodiments, the compound is a sodium salt of the compound of Formula (Ia). In certain embodiments, the compound is a compound of Formula (Ib), or a pharmaceutically acceptable salt thereof. In certain embodiments, the compound is a compound of Formula (Ib).

In some embodiments, a suspension comprising a compound of Formula (Ia) or Formula (Ib), or a pharmaceutically acceptable salt thereof, in a poloxamer and mannitol is provided. In some embodiments, the concentration of poloxamer in mannitol is from about 0.1% to about 20%. In some embodiments, the concentration of poloxamer in mannitol is from about 0.1% to about 10%. In some in embodiments, the concentration of poloxamer in mannitol is about 0.1%, about 0.2%, about 0.3%, about 0.4%, about 0.5%, about 0.6%, about 0.7%, about 0.8%, about 0.9%, about 1%, about 2,%, about 3%, about 4%, about 5%, about 6%, about 7%, about 8%, about 9%, or about 10%. In certain embodiments, the concentration of poloxamer in mannitol is about 2%. In certain embodiments, the poloxamer is poloxamer 188. In certain embodiments, the compound is a compound of Formula (Ia), or a pharmaceutically acceptable salt thereof. In certain embodiments, the compound is a compound of Formula (Ia). In certain embodiments, the compound is a sodium salt of the compound of Formula (Ia). In certain embodiments, the compound is a compound of Formula (Ib), or a pharmaceutically acceptable salt thereof. In certain embodiments, the compound is a compound of Formula (Ib).

In certain embodiments, the composition is formulated as a solid dosage form. In some embodiments, the solid dosage form is a solid injectable dosage form, such as a solid depot form.

In certain embodiments, the active ingredient (for example, a compound of Formula (Ia) or Formula (Ib)) is present as a free acid. In certain embodiments, the active ingredient (for example, a compound of Formula (Ia) or Formula (Ib)) is present as a sodium salt. In some embodiments, the active ingredient is a compound of Formula (Ia). In some embodiments, the active ingredient is a compound of Formula (Ib).

In certain embodiments, the pharmaceutical composition is a parenteral formulation. In certain embodiments, the formulation is administered subcutaneously to a subject (e.g., a human patient) in need thereof. In certain embodiments, the formulation is administered intramuscularly to a subject in need thereof.

In certain embodiments, the parenteral formulation comprises N-methyl-2-pyrrolidone (NMP). In certain embodiments, the parenteral formulation consists essentially of N-methyl-2-pyrrolidone. In certain embodiments, the parenteral formulation comprises dimethyl sulfoxide (DMSO). In some embodiments, the parenteral formulation comprises polyethylene glycol (PEG) or glycofurol. In some embodiments, the solution comprises PEG 200, ethanol, and water. In some embodiments, the solution comprises PEG 300 and water. In some embodiments, the solution comprises poloxamer in saline. In some embodiments, the solution comprises 2% poloxamer 188 in normal saline.

In certain embodiments, the parenteral formulation comprises a compound of Formula (Ia) or Formula (Ib), or a pharmaceutically acceptable salt thereof, and water. In certain embodiments, the parenteral formulation comprises a compound of Formula (Ia), or a pharmaceutically acceptable salt thereof, and water. In certain embodiments, the parenteral formulation comprises a compound of Formula (Ib), or a pharmaceutically acceptable salt thereof, and water. In certain embodiments, the parenteral formulation further contains an alcohol. In certain embodiments, the alcohol is ethanol. In certain embodiments, the parenteral formulation further contains polyethylene glycol. In certain embodiments, the polyethylene glycol has an average molecular weight of about 200 g/mol (for example, polyethylene glycol 200). In certain embodiments, the parenteral formulation further contains an inorganic base. In certain embodiments, the inorganic base is sodium hydroxide (NaOH). In certain embodiments, the inorganic base is sodium ethoxide (NaOEt). In certain embodiments, the formulation comprises from about 0.1 molar equivalents to about 1.5 molar equivalents of the inorganic base. In certain embodiments, the formulation comprises from about 0.5 molar equivalents to about 1.5 molar equivalents of the inorganic base. In certain embodiments, the formulation comprises from about 0.75 molar equivalents to about 1.2 molar equivalents of the inorganic base. In certain embodiments, the formulation comprises about 1.0 molar equivalents inorganic base. In certain embodiments, the formulation comprises about 1.2 molar equivalents inorganic base. In some embodiments, the inorganic base is NaOH or NaOEt.

In certain embodiments, the parenteral formulation comprises a compound of Formula (Ia), or a pharmaceutically acceptable salt thereof, water and polyethylene glycol PEG 300. In certain embodiments, the parenteral formulation comprises a compound of Formula (Ib), or a pharmaceutically acceptable salt thereof, water, and polyethylene glycol PEG 300.

In certain embodiments, the parenteral formulation comprises a compound of Formula (Ia), or a pharmaceutically acceptable salt thereof, water, and polyethylene glycol PEG 300 (polyethylene glycol with an average molecular weight of 300 g/mol), and NaOH. In certain embodiments, the parenteral formulation comprises a compound of Formula (Ia), or a pharmaceutically acceptable salt thereof, water, and polyethylene glycol (PEG) 300, and NaOEt. In certain embodiments, the formulation includes from about 0.1 molar equivalents to about 1.5 molar equivalents of NaOH or NaOEt. In certain embodiments, the formulation includes from about 0.5 molar equivalents to about 1.5 molar equivalents of NaOH or NaOEt. In certain embodiments, the formulation includes from about 0.75 molar equivalents to about 1.2 molar equivalents of NaOH or NaOEt. In certain embodiments, the formulation comprises about 1.0 molar equivalents of NaOH or NaOEt. In certain embodiments, the formulation includes about 1.2 molar equivalents of NaOH or NaOEt.

In certain embodiments, the parenteral formulation is a solution formulation that includes a mixture of ethanol, water, and polyethylene glycol. In certain embodiments, the parenteral formulation is a solution formulation that includes a mixture of ethanol, water, and PEG 200. In certain embodiments, the solution formulation includes about 5% to about 20% ethanol, about 5% to about 20% water, and about 60% to about 90% PEG 200. In certain embodiments, the solution formulation comprises about 10% to about 15% ethanol, about 10% to about 15% water, and about 70% to about 80% PEG 200. In certain embodiments, the solution formulation includes about 10% ethanol, about 12% water, and about 78% PEG 200. In certain embodiments, the solution formulation further includes an inorganic base. In certain embodiments, the solution formulation includes about 10% ethanol, about 13% water, and about 77% PEG 200. In certain embodiments, the solution formulation further includes an inorganic base. In certain embodiments, the formulation includes from about 0.1 molar equivalents to about 1.5 molar equivalents of the inorganic base. In certain embodiments, the formulation comprises from about 0.5 molar equivalents to about 1.5 molar equivalents of the inorganic base. In certain embodiments, the formulation comprises from about 1.0 molar equivalents to about 1.2 molar equivalents of the inorganic base. In certain embodiments, the formulation comprises about 1.2 molar equivalents inorganic base. In certain embodiments, the inorganic base is sodium hydroxide or sodium ethoxide. In certain embodiments, the inorganic base is sodium hydroxide.

In certain embodiments, the parenteral formulation is a solution formulation that includes a mixture of water and polyethylene glycol. In certain embodiments, the parenteral formulation is a solution formulation that includes a mixture of water and PEG 300. In certain embodiments, the solution formulation includes about 5% w/w to about 25% w/w water, and about 75% w/w to about 95% w/w PEG 300. In some embodiments, the solution formulation further includes an inorganic base. In certain embodiments, the formulation includes from about 0.1 molar equivalents to about 1.5 molar equivalents of the inorganic base. In certain embodiments, the formulation comprises from about 0.5 molar equivalents to about 1.5 molar equivalents of the inorganic base. In certain embodiments, the formulation comprises from about 0.75 molar equivalents to about 1.2 molar equivalents of the inorganic base. In certain embodiments, the formulation comprises about 1.0 molar equivalents inorganic base. In certain embodiments, the formulation comprises about 1.2 molar equivalents inorganic base. In certain embodiments, the inorganic base is sodium hydroxide or sodium ethoxide. In certain embodiments, the inorganic base is sodium hydroxide.

In some embodiments, the solution comprises a compound of Formula (Ia) or Formula (Ib), or a pharmaceutically acceptable salt thereof, PEG 300, sodium hydroxide, and water. In some embodiments, the solution comprises a compound of Formula (Ia) or a pharmaceutically acceptable salt thereof, PEG 300, sodium hydroxide, and water. In some embodiments, the solution comprises a compound of Formula (Ib), or a pharmaceutically acceptable salt thereof, PEG 300, sodium hydroxide, and water. In some embodiments, the solution comprises a sodium salt of the compound of Formula (Ia), PEG 300, sodium hydroxide, and water. In some embodiments, the solution comprises a compound of Formula (Ib), PEG 300, sodium hydroxide, and water.

In some embodiments, the solution comprises a compound of Formula (Ia), PEG 300, sodium hydroxide, and water. In some embodiments, the concentration of the compound of Formula (Ia) in the solution comprising a compound of Formula (Ia), PEG 300, sodium hydroxide, and water is about 50 mg/ml to about 500 mg/ml. In some embodiments, the concentration of the compound of Formula (Ia) in the solution comprising a compound of Formula (Ia), PEG 300, sodium hydroxide, and water is about 50 mg/ml to about 400 mg/ml. In some embodiments, the concentration of the compound of Formula (Ia) in the solution comprising a compound of Formula (Ia), PEG 300, sodium hydroxide, and water is about 50 mg/ml to about 300 mg/ml. In some embodiments, the concentration of the compound of Formula (Ia) in the solution comprising a compound of Formula (Ia), PEG 300, sodium hydroxide, and water is about 75 mg/ml to about 300 mg/ml. In some embodiments, the concentration of the compound of Formula (Ia) in the solution comprising a compound of Formula (Ia), PEG 300, sodium hydroxide, and water is about 50 mg/ml. In some embodiments, the concentration of the compound of Formula (Ia) in the solution comprising a compound of Formula (Ia), PEG 300, sodium hydroxide, and water is about 75 mg/ml. In some embodiments, the concentration of the compound of Formula (Ia) in the solution comprising a compound of Formula (Ia), PEG 300, sodium hydroxide, and water is about 100 mg/ml. In some embodiments, the concentration of the compound of Formula (Ia) in the solution comprising a compound of Formula (Ia), PEG 300, sodium hydroxide, and water is about 125 mg/ml. In some embodiments, the concentration of the compound of Formula (Ia) in the solution comprising a compound of Formula (Ia), PEG 300, sodium hydroxide, and water is about 150 mg/ml. In some embodiments, the concentration of the compound of Formula (Ia) in the solution comprising a compound of Formula (Ia), PEG 300, sodium hydroxide, and water is about 175 mg/ml. In some embodiments, the concentration of the compound of Formula (Ia) in the solution comprising a compound of Formula (Ia), PEG 300, sodium hydroxide, and water is about 200 mg/ml. In some embodiments, the concentration of the compound of Formula (Ia) in the solution comprising a compound of Formula (Ia), PEG 300, sodium hydroxide, and water is about 225 mg/ml. In some embodiments, the concentration of the compound of Formula (Ia) in the solution comprising a compound of Formula (Ia), PEG 300, sodium hydroxide, and water is about 250 mg/ml. In some embodiments, the concentration of the compound of Formula (Ia) in the solution comprising a compound of Formula (Ia), PEG 300, sodium hydroxide, and water is about 275 mg/ml. In some embodiments, the concentration of the compound of Formula (Ia) in the solution comprising a compound of Formula (Ia), PEG 300, sodium hydroxide, and water is about 300 mg/ml. In some embodiments, the concentration of the compound of Formula (Ia) in the solution comprising a compound of Formula (Ia), PEG 300, sodium hydroxide, and water is about 325 mg/ml. In some embodiments, the concentration of the compound of Formula (Ia) in the solution comprising a compound of Formula (Ia), PEG 300, sodium hydroxide, and water is about 350 mg/ml. In some embodiments, the concentration of the compound of Formula (Ia) in the solution comprising a compound of Formula (Ia), PEG 300, sodium hydroxide, and water is about 375 mg/ml. In some embodiments, the concentration of the compound of Formula (Ia) in the solution comprising a compound of Formula (Ia), PEG 300, sodium hydroxide, and water is about 400 mg/ml. In some embodiments, the concentration of the compound of Formula (Ia) in the solution comprising a compound of Formula (Ia), PEG 300, sodium hydroxide, and water is about 425 mg/ml. In some embodiments, the concentration of the compound of Formula (Ia) in the solution comprising a compound of Formula (Ia), PEG 300, sodium hydroxide, and water is about 450 mg/ml. In some embodiments, the concentration of the compound of Formula (Ia) in the solution comprising a compound of Formula (Ia), PEG 300, sodium hydroxide, and water is about 475 mg/ml. In some embodiments, the concentration of the compound of Formula (Ia) in the solution comprising a compound of Formula (Ia), PEG 300, sodium hydroxide, and water is about 500 mg/ml.

In some embodiments, the amount of water in the solution comprising a compound of Formula (Ia), PEG 300, sodium hydroxide, and water is about 10 w/w % to about 40 w/w %. In some embodiments, the amount of water in the solution comprising a compound of Formula (Ia), PEG 300, sodium hydroxide, and water is about 15 w/w % to about 35 w/w %. In some embodiments, the amount of water in the solution comprising a compound of Formula (Ia), PEG 300, sodium hydroxide, and water is about 20 w/w % to about 30 w/w %. In some embodiments, the amount of water in the solution comprising a compound of Formula (Ia), PEG 300, sodium hydroxide, and water is about 21 w/w % to about 29 w/w %. In some embodiments, the amount of water in the solution comprising a compound of Formula (Ia), PEG 300, sodium hydroxide, and water is about 23.2 w/w % to about 27.9 w/w %. In some embodiments, the amount of water in the solution comprising a compound of Formula (Ia), PEG 300, sodium hydroxide, and water is about 23.2 w/w % to about 27.92 w/w %. In some embodiments, the amount of water in the solution comprising a compound of Formula (Ia), PEG 300, sodium hydroxide, and water is about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, or about 29.0 w/w %. In some embodiments, the amount of water in the solution comprising a compound of Formula (Ia), PEG 300, sodium hydroxide, and water is about 23.2 w/w %. In some embodiments, the amount of water in the solution comprising a compound of Formula (Ia), PEG 300, sodium hydroxide, and water is about 27.9 w/w %. In some embodiments, the amount of water in the solution comprising a compound of Formula (Ia), PEG 300, sodium hydroxide, and water is about 27.92 w/w %.

In some embodiments, the amount of PEG 300 in the solution comprising compound of Formula (Ia), PEG 300, sodium hydroxide, and water is about 35 w/w % to about 75 w/w %. In some embodiments, the amount of PEG 300 in the solution comprising a compound of Formula (Ia), PEG 300, sodium hydroxide, and water is about 45 w/w % to about 65 w/w %. In some embodiments, the amount of PEG 300 in the solution comprising a compound of Formula (Ia), PEG 300, sodium hydroxide, and water is about 48 w/w % to about 60 w/w %. In some embodiments, the amount of PEG 300 in the solution comprising a compound of Formula (Ia), PEG 300, sodium hydroxide, and water is about 49 w/w % to about 59 w/w %. In some embodiments, the amount of PEG 300 in the solution comprising a compound of Formula (Ia), PEG 300, sodium hydroxide, and water is about 50.0 w/w % to about 58.0 w/w %. In some embodiments, the amount of PEG 300 in the solution comprising a compound of Formula (Ia), PEG 300, sodium hydroxide, and water is about 50.0 w/w % to about 58.04 w/w %. In some embodiments, the amount of PEG 300 in the solution comprising a compound of Formula (Ia), PEG 300, sodium hydroxide, and water is about 45 w/w %, about 46 w/w %, about 47 w/w %, about 48 w/w %, about 49 w/w %, about 50 w/w %, about 51 w/w %, about 52 w/w %, about 53 w/w %, about 54 w/w %, about 55 w/w %, about 56 w/w %, about 57 w/w %, about 58 w/w %, about 59 w/w %, about 60 w/w %, about 61 w/w %, about 62 w/w %, about 63 w/w %, about 64 w/w %, or about 65 w/w %. In some embodiments, the amount of PEG 300 in the solution comprising a compound of Formula (Ia), PEG 300, sodium hydroxide, and water is about 50.0 w/w %. In some embodiments, the amount of PEG 300 in the solution comprising a compound of Formula (Ia), PEG 300, sodium hydroxide, and water is about 58.0 w/w %. In some embodiments, the amount of PEG 300 in the solution comprising a compound of Formula (Ia), PEG 300, sodium hydroxide, and water is about 58.04 w/w %.

In some embodiments, the amount of the compound of Formula (Ia) in the solution comprising a compound of Formula (Ia), PEG 300, sodium hydroxide, and water is about 5 w/w % to about 35 w/w %. In some embodiments, the amount of the compound of Formula (Ia) in the solution comprising a compound of Formula (Ia), PEG 300, sodium hydroxide, and water is about 10 w/w % to about 30 w/w %. In some embodiments, the amount of the compound of Formula (Ia) in the solution comprising a compound of Formula (Ia), PEG 300, sodium hydroxide, and water is about 11 w/w % to about 28 w/w %. In some embodiments, the amount of the compound of Formula (Ia) in the solution comprising a compound of Formula (Ia), PEG 300, sodium hydroxide, and water is about 13 w/w % to about 27 w/w %. In some embodiments, the amount of the compound of Formula (Ia) in the solution comprising a compound of Formula (Ia), PEG 300, sodium hydroxide, and water is about 13.5 w/w % to about 25.7 w/w %. In some embodiments, the amount of the compound of Formula (Ia) in the solution comprising a compound of Formula (Ia), PEG 300, sodium hydroxide, and water is about 13.47 w/w % to about 25.7 w/w %. In some embodiments, the amount of the compound of Formula (Ia) in the solution comprising a compound of Formula (Ia), PEG 300, sodium hydroxide, and water is about 13.0 w/w %, about 13.1 w/w %, about 13.2 w/w %, about 13.3 w/w %, about 13.4 w/w %, about 13.5 w/w %, about 13.6 w/w %, about 13.7 w/w %, about 13.8 w/w %, about 13.9 w/w %, about 14.0 w/w %, about 14.1 w/w %, about 14.2 w/w %, about 14.3 w/w %, about 14.4 w/w %, about 14.5 w/w %, about 14.6 w/w %, about 14.7 w/w %, about 14.8 w/w %, about 14.9 w/w %, about 15.0 w/w %, about 15.1 w/w %, about 15.2 w/w %, about 15.3 w/w %, about 15.4 w/w %, about 15.5 w/w %, about 15.6 w/w %, about 15.7 w/w %, about 15.8 w/w %, about 15.9 w/w %, about 16.0 w/w %, about 16.1 w/w %, about 16.2 w/w %, about 16.3 w/w %, about 16.4 w/w %, about 16.5 w/w %, about 16.6 w/w %, about 16.7 w/w %, about 16.8 w/w %, about 16.9 w/w %, about 17.0 w/w %, about 17.1 w/w %, about 17.2 w/w %, about 17.3 w/w %, about 17.4 w/w %, about 17.5 w/w %, about 17.6 w/w %, about 17.7 w/w %, about 17.8 w/w %, about 17.9 w/w %, about 18.0 w/w %, about 18.1 w/w %, about 18.2 w/w %, about 18.3 w/w %, about 18.4 w/w %, about 18.5 w/w %, about 18.6 w/w %, about 18.7 w/w %, about 18.8 w/w %, about 18.9 w/w %, about 19.0 w/w %, about 19.1 w/w %, about 19.2 w/w %, about 19.3 w/w %, about 19.4 w/w %, about 19.5 w/w %, about 19.6 w/w %, about 19.7 w/w %, about 19.8 w/w %, about 19.9 w/w %, about 20.0 w/w %, about 21.1 w/w %, about 21.2 w/w %, about 21.3 w/w %, about 21.4 w/w %, about 21.5 w/w %, about 21.6 w/w %, about 21.7 w/w %, about 21.8 w/w %, about 21.9 w/w %, about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, or about 29.0 w/w %. In some embodiments, the amount of the compound of Formula (Ia) in the solution comprising a compound of Formula (Ia), PEG 300, sodium hydroxide, and water is about 13.47 w/w %. In some embodiments, the amount of the compound of Formula (Ia) in the solution comprising a compound of Formula (Ia), PEG 300, sodium hydroxide, and water is about 13.5 w/w %. In some embodiments, the amount of the compound of Formula (Ia) in the solution comprising a compound of Formula (Ia), PEG 300, sodium hydroxide, and water is about 25.7 w/w %.

In some embodiments, the amount of sodium hydroxide in the solution comprising a compound of Formula (Ia), PEG 300, sodium hydroxide, and water is about 0.05 w/w % to about 2 w/w %. In some embodiments, the amount of sodium hydroxide in the solution comprising a compound of Formula (Ia), PEG 300, sodium hydroxide, and water is about 0.1 w/w % to about 1.5 w/w %. In some embodiments, the amount of sodium hydroxide in the solution comprising a compound of Formula (Ia), PEG 300, sodium hydroxide, and water is about 0.3 w/w % to about 1.3 w/w %. In some embodiments, the amount of sodium hydroxide in the solution comprising a compound of Formula (Ia), PEG 300, sodium hydroxide, and water is about 0.5 w/w % to about 1.2 w/w %. In some embodiments, the amount of sodium hydroxide in the solution comprising a compound of Formula (Ia), PEG 300, sodium hydroxide, and water is about 0.6 w/w % to about 1.1 w/w %. In some embodiments, the amount of sodium hydroxide in the solution comprising a compound of Formula (Ia), PEG 300, sodium hydroxide, and water is about 0.58 w/w % to about 1.1 w/w %. In some embodiments, the amount of sodium hydroxide in the solution comprising a compound of Formula (Ia), PEG 300, sodium hydroxide, and water is about 0.1 w/w %, about 0.2 w/w %, about 0.3 w/w %, about 0.4 w/w %, about 0.5 w/w %, about 0.6 w/w %, about 0.7 w/w %, about 0.8 w/w %, about 0.9 w/w %, about 1.0 w/w %, about 1.1 w/w %, about 1.2 w/w %, about 1.3 w/w %, about 1.4 w/w %, about 1.5 w/w %, about 1.6 w/w %, about 1.7 w/w %, about 1.8 w/w %, about 1.9 w/w %, or about 2.0 w/w %. In some embodiments, the amount of sodium hydroxide in the solution comprising a compound of Formula (Ia), PEG 300, sodium hydroxide, and water is about 0.58 w/w %. In some embodiments, the amount of sodium hydroxide in the solution comprising a compound of Formula (Ia), PEG 300, sodium hydroxide, and water is about 0.6 w/w %. In some embodiments, the amount of sodium hydroxide in the solution comprising a compound of Formula (Ia), PEG 300, sodium hydroxide, and water is about 1.1 w/w %. In some embodiments, the solution comprises about 10 w/w % to about 40 w/w % water, about 35 w/w % to about 75 w/w % PEG 300, about 5 w/w % to about 35 w/w % of a compound of Formula (Ia), and about 0.05 w/w % to about 2 w/w % of sodium hydroxide. In some embodiments, the solution comprises about 15 w/w % to about 35 w/w % water, about 45 w/w % to about 65 w/w % PEG 300, about 10 w/w % to about 30 w/w % of a compound of Formula (Ia), and about 0.1 w/w % to about 1.5 w/w % of sodium hydroxide. In some embodiments, the solution comprises about 20 w/w % to about 30 w/w % water, about 48 w/w % to about 60 w/w % PEG 300, about 11 w/w % to about 28 w/w % of a compound of Formula (Ia), and about 0.3 w/w % to about 1.3 w/w % of sodium hydroxide. In some embodiments, the solution comprises about 21 w/w % to about 29 w/w % water, about 49 w/w % to about 59 w/w % PEG 300, about 13 w/w % to about 27 w/w % of a compound of Formula (Ia), and about 0.5 w/w % to about 1.2 w/w % of sodium hydroxide. In some embodiments, the solution comprises about 23.2 w/w % to about 27.9 w/w % water, about 50 w/w % to about 58 w/w % PEG 300, about 13.5 w/w % to about 25.7 w/w % of a compound of Formula (Ia), and about 0.6 w/w % to about 1.1 w/w % of sodium hydroxide. In some embodiments, the solution comprises about 23.2 w/w % to about 27.92 w/w % water, about 50.0 w/w % to about 58.04 w/w % PEG 300, about 13.47 w/w % to about 25.7 w/w % of a compound of Formula (Ia), and about 0.58 w/w % to about 1.1 w/w % of sodium hydroxide. In some embodiments, the solution comprises about 27.9 w/w % water, about 58 w/w % PEG 300, about 13.5 w/w % of a compound of Formula (Ia), and about 0.6 w/w % of sodium hydroxide. In some embodiments, the solution comprises about 27.92 w/w % water, about 58.04 w/w % PEG 300, about 13.47 w/w % of a compound of Formula (Ia), and about 0.58 w/w % of sodium hydroxide. In some embodiments, the solution comprises about 23.2 w/w % water, about 50.0 w/w % PEG 300, about 25.7 w/w % of a compound of Formula (Ia), and about 1.1 w/w % of sodium hydroxide.

In some embodiments, the compound of Formula (Ia) becomes ionized in situ to a sodium salt of the compound of Formula (Ia) in the presence of sodium hydroxide in the solution comprising a compound of Formula (Ia), PEG 300, sodium hydroxide, and water. Thus, in some embodiments, the compound of Formula (Ia) is present as a sodium salt of the compound of Formula (Ia) in the solution comprising a compound of Formula (Ia), PEG 300, sodium hydroxide, and water.

In some embodiments, the pharmaceutical compositions comprise a compound of Formula (Ia) or Formula (Ib), or a pharmaceutically acceptable salt thereof, a poloxamer, and a pharmaceutically acceptable excipient. In some embodiments, the pharmaceutical compositions comprise a compound of Formula (Ia) or Formula (Ib), or a pharmaceutically acceptable salt thereof, poloxamer 188, and a pharmaceutically acceptable excipient. In some embodiments, the pharmaceutical compositions are solutions that comprise a compound of Formula (Ia) or Formula (Ib), or a pharmaceutically acceptable salt thereof, a poloxamer, and a pharmaceutically acceptable excipient. In some embodiments, the pharmaceutical compositions are solutions that comprise a compound of Formula (Ia) or Formula (Ib), or a pharmaceutically acceptable salt thereof, poloxamer 188, and a pharmaceutically acceptable excipient.

In some embodiments, the solution comprises a compound of Formula (Ia) or Formula (Ib), or a pharmaceutically acceptable salt thereof, PEG 300, sodium hydroxide, poloxamer 188, and water. In some embodiments, the solution comprises a compound of Formula (Ia) or a pharmaceutically acceptable salt thereof, PEG 300, sodium hydroxide, poloxamer 188, and water. In some embodiments, the solution comprises a compound of Formula (Ib), or a pharmaceutically acceptable salt thereof, PEG 300, sodium hydroxide, poloxamer 188, and water. In some embodiments, the solution comprises a sodium salt of the compound of Formula (Ia), PEG 300, sodium hydroxide, poloxamer 188, and water.

In some embodiments, the solution comprises a compound of Formula (Ia), PEG 300, sodium hydroxide, poloxamer 188, and water. In some embodiments, the concentration of the compound of Formula (Ia) in the solution comprising a compound of Formula (Ia), PEG 300, sodium hydroxide, poloxamer 188, and water is about 50 mg/ml to about 500 mg/ml. In some embodiments, the concentration of the compound of Formula (Ia) in the solution comprising a compound of Formula (Ia), PEG 300, sodium hydroxide, poloxamer 188, and water is about 50 mg/ml to about 400 mg/ml. In some embodiments, the concentration of the compound of Formula (Ia) in the solution comprising a compound of Formula (Ia), PEG 300, sodium hydroxide, poloxamer 188, and water is about 50 mg/ml to about 300 mg/ml. In some embodiments, the concentration of the compound of Formula (Ia) in the solution comprising a compound of Formula (Ia), PEG 300, sodium hydroxide, poloxamer 188, and water is about 75 mg/ml to about 300 mg/ml. In some embodiments, the concentration of the compound of Formula (Ia) in the solution comprising a compound of Formula (Ia), PEG 300, sodium hydroxide, poloxamer 188, and water is about 50 mg/ml. In some embodiments, the concentration of the compound of Formula (Ia) in the solution comprising a compound of Formula (Ia), PEG 300, sodium hydroxide, poloxamer 188, and water is about 75 mg/ml. In some embodiments, the concentration of the compound of Formula (Ia) in the solution comprising a compound of Formula (Ia), PEG 300, sodium hydroxide, poloxamer 188, and water is about 100 mg/ml. In some embodiments, the concentration of the compound of Formula (Ia) in the solution comprising a compound of Formula (Ia), PEG 300, sodium hydroxide, poloxamer 188, and water is about 125 mg/ml. In some embodiments, the concentration of the compound of Formula (Ia) in the solution comprising a compound of Formula (Ia), PEG 300, sodium hydroxide, poloxamer 188, and water is about 150 mg/ml. In some embodiments, the concentration of the compound of Formula (Ia) in the solution comprising a compound of Formula (Ia), PEG 300, sodium hydroxide, poloxamer 188, and water is about 175 mg/ml. In some embodiments, the concentration of the compound of Formula (Ia) in the solution comprising a compound of Formula (Ia), PEG 300, sodium hydroxide, poloxamer 188, and water is about 200 mg/ml. In some embodiments, the concentration of the compound of Formula (Ia) in the solution comprising a compound of Formula (Ia), PEG 300, sodium hydroxide, poloxamer 188, and water is about 225 mg/ml. In some embodiments, the concentration of the compound of Formula (Ia) in the solution comprising a compound of Formula (Ia), PEG 300, sodium hydroxide, poloxamer 188, and water is about 250 mg/ml. In some embodiments, the concentration of the compound of Formula (Ia) in the solution comprising a compound of Formula (Ia), PEG 300, sodium hydroxide, poloxamer 188, and water is about 275 mg/ml. In some embodiments, the concentration of the compound of Formula (Ia) in the solution comprising a compound of Formula (Ia), PEG 300, sodium hydroxide, poloxamer 188, and water is about 300 mg/ml. In some embodiments, the concentration of the compound of Formula (Ia) in the solution comprising a compound of Formula (Ia), PEG 300, sodium hydroxide, poloxamer 188, and water is about 325 mg/ml. In some embodiments, the concentration of the compound of Formula (Ia) in the solution comprising a compound of Formula (Ia), PEG 300, sodium hydroxide, poloxamer 188, and water is about 350 mg/ml. In some embodiments, the concentration of the compound of Formula (Ia) in the solution comprising a compound of Formula (Ia), PEG 300, sodium hydroxide, poloxamer 188, and water is about 375 mg/ml. In some embodiments, the concentration of the compound of Formula (Ia) in the solution comprising a compound of Formula (Ia), PEG 300, sodium hydroxide, poloxamer 188, and water is about 400 mg/ml. In some embodiments, the concentration of the compound of Formula (Ia) in the solution comprising a compound of Formula (Ia), PEG 300, sodium hydroxide, poloxamer 188, and water is about 425 mg/ml. In some embodiments, the concentration of the compound of Formula (Ia) in the solution comprising a compound of Formula (Ia), PEG 300, sodium hydroxide, poloxamer 188, and water is about 450 mg/ml. In some embodiments, the concentration of the compound of Formula (Ia) in the solution comprising a compound of Formula (Ia), PEG 300, sodium hydroxide, poloxamer 188, and water is about 475 mg/ml. In some embodiments, the concentration of the compound of Formula (Ia) in the solution comprising a compound of Formula (Ia), PEG 300, sodium hydroxide, poloxamer 188, and water is about 500 mg/ml.

In some embodiments, the amount of water in the solution comprising a compound of Formula (Ia), PEG 300, sodium hydroxide, poloxamer 188, and water is about 10 w/w % to about 45 w/w %. In some embodiments, the amount of water in the solution comprising a of Formula (Ia), PEG 300, sodium hydroxide, poloxamer 188, and water is about 15 w/w % to about 35 w/w %. In some embodiments, the amount of water in the solution comprising a compound of Formula (Ia), PEG 300, sodium hydroxide, poloxamer 188, and water is about 20 w/w % to about 35 w/w %. In some embodiments, the amount of water in the solution comprising a compound of Formula (Ia), PEG 300, sodium hydroxide, poloxamer 188, and water is about 20 w/w % to about 31 w/w %. In some embodiments, the amount of water in the solution comprising a compound of Formula (Ia), PEG 300, sodium hydroxide, poloxamer 188, and water is about 22 w/w % to about 30.1 w/w %. In some embodiments, the amount of water in the solution comprising a compound of Formula (Ia), PEG 300, sodium hydroxide, poloxamer 188, and water is about 21.97 w/w % to about 30.07 w/w %. In some embodiments, the amount of water in the solution comprising a compound of Formula (Ia), PEG 300, sodium hydroxide, poloxamer 188, and water is about 19.0 w/w %, about 19.1 w/w %, about 19.2 w/w %, about 19.3 w/w %, about 19.4 w/w %, about 19.5 w/w %, about 19.6 w/w %, about 19.7 w/w %, about 19.8 w/w %, about 19.9 w/w %, about 20.0 w/w %, about 20.1 w/w %, about 20.2 w/w %, about 20.3 w/w %, about 20.4 w/w %, about 20.5 w/w %, about 20.6 w/w %, about 20.7 w/w %, about 20.8 w/w %, about 20.9 w/w %, about 21.0 w/w %, about 21.1 w/w %, about 21.2 w/w %, about 21.3 w/w %, about 21.4 w/w %, about 21.5 w/w %, about 21.6 w/w %, about 21.7 w/w %, about 21.8 w/w %, about 21.9 w/w %, about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, about 29.0 w/w %, about 29.1 w/w %, about 29.2 w/w %, about 29.3 w/w %, about 29.4 w/w %, about 29.5 w/w %, about 29.6 w/w %, about 29.7 w/w %, about 29.8 w/w %, about 29.9 w/w %, about 30.0 w/w %, about 30.1 w/w %, about 30.2 w/w %, about 30.3 w/w %, about 30.4 w/w %, about 30.5 w/w %, about 30.6 w/w %, about 30.7 w/w %, about 30.8 w/w %, about 30.9 w/w %, about 31.0 w/w %, about 31.1 w/w %, about 31.2 w/w %, about 31.3 w/w %, about 31.4 w/w %, about 31.5 w/w %, about 31.6 w/w %, about 31.7 w/w %, about 31.8 w/w %, about 31.9 w/w %, about 32.0 w/w %, about 32.1 w/w %, about 32.2 w/w %, about 32.3 w/w %, about 32.4 w/w %, about 32.5 w/w %, about 32.6 w/w %, about 32.7 w/w %, about 32.8 w/w %, about 32.9 w/w %, or about 33.0 w/w %. In some embodiments, the amount of water in the solution comprising a compound of Formula (Ia), PEG 300, sodium hydroxide, poloxamer 188, and water is about 21.97 w/w %. In some embodiments, the amount of water in the solution comprising a compound of Formula (Ia), PEG 300, sodium hydroxide, poloxamer 188, and water is about 22 w/w %. In some embodiments, the amount of water in the solution comprising a compound of Formula (Ia), PEG 300, sodium hydroxide, poloxamer 188, and water is about 30.07 w/w %. In some embodiments, the amount of water in the solution comprising a compound of Formula (Ia), PEG 300, sodium hydroxide, poloxamer 188, and water is about 30.1 w/w %.

In some embodiments, the amount of PEG 300 in the solution comprising a compound of Formula (Ia), PEG 300, sodium hydroxide, poloxamer 188, and water is about 30 w/w % to about 85 w/w %. In some embodiments, the amount of PEG 300 in the solution comprising a compound of Formula (Ia), PEG 300, sodium hydroxide, poloxamer 188, and water is about 35 w/w % to about 75 w/w %. In some embodiments, the amount of PEG 300 in the solution comprising a compound of Formula (Ia), PEG 300, sodium hydroxide, poloxamer 188, and water is about 40 w/w % to about 70 w/w %. In some embodiments, the amount of PEG 300 in the solution comprising a compound of Formula (Ia), PEG 300, sodium hydroxide, poloxamer 188, and water is about 45 w/w % to about 68 w/w %. In some embodiments, the amount of PEG 300 in the solution comprising a compound of Formula (Ia), PEG 300, sodium hydroxide, poloxamer 188, and water is about 47.1 w/w % to about 64.4 w/w %. In some embodiments, the amount of PEG 300 in the solution comprising a compound of Formula (Ia), PEG 300, sodium hydroxide, poloxamer 188, and water is about 47.05 w/w % to about 64.41 w/w %. In some embodiments, the amount of PEG 300 in the solution comprising a compound of Formula (Ia), PEG 300, sodium hydroxide, poloxamer 188, and water is about 40 w/w %, about 41 w/w %, about 42 w/w %, about 43 w/w %, about 44 w/w %, about 45 w/w %, about 46 w/w %, about 47 w/w %, about 48 w/w %, about 49 w/w %, about 50 w/w %, about 51 w/w %, about 52 w/w %, about 53 w/w %, about 54 w/w %, about 55 w/w %, about 56 w/w %, about 57 w/w %, about 58 w/w %, about 59 w/w %, about 60 w/w %, about 61 w/w %, about 62 w/w %, about 63 w/w %, about 64 w/w %, about 65 w/w %, about 66 w/w %, about 67 w/w %, about 68 w/w %, about 69 w/w %, or about 70 w/w %. In some embodiments, the amount of PEG 300 in the solution comprising a compound of Formula (Ia), PEG 300, sodium hydroxide, poloxamer 188, and water is about 47.05 w/w %. In some embodiments, the amount of PEG 300 in the solution comprising a compound of Formula (Ia), PEG 300, sodium hydroxide, poloxamer 188, and water is about 47.1 w/w %. In some embodiments, the amount of PEG 300 in the solution comprising a compound of Formula (Ia), PEG 300, sodium hydroxide, poloxamer 188, and water is about 64.4 w/w %. In some embodiments, the amount of PEG 300 in the solution comprising a compound of Formula (Ia), PEG 300, sodium hydroxide, poloxamer 188, and water is about 64.41 w/w %.

In some embodiments, the amount of the compound of Formula (Ia) in the solution comprising a compound of Formula (Ia), PEG 300, sodium hydroxide, poloxamer 188, and water is about 0.5 w/w % to about 40 w/w %. In some embodiments, the amount of the compound of Formula (Ia) in the solution comprising a compound of Formula (Ia), PEG 300, sodium hydroxide, poloxamer 188, and water is about 1 w/w % to about 35 w/w %. In some embodiments, the amount of the compound of Formula (Ia) in the solution comprising a compound of Formula (Ia), PEG 300, sodium hydroxide, poloxamer 188, and water is about 1 w/w % to about 30 w/w %. In some embodiments, the amount of the compound of Formula (Ia) in the solution comprising a compound of Formula (Ia), PEG 300, sodium hydroxide, poloxamer 188, and water is about 3 w/w % to about 28 w/w %. In some embodiments, the amount of the compound of Formula (Ia) in the solution comprising a compound of Formula (Ia), PEG 300, sodium hydroxide, poloxamer 188, and water is about 4 w/w % to about 26 w/w %. In some embodiments, the amount of the compound of Formula (Ia) in the solution comprising a compound of Formula (Ia), PEG 300, sodium hydroxide, poloxamer 188, and water is about 4.6 w/w % to about 25.2 w/w %. In some embodiments, the amount of the compound of Formula (Ia) in the solution comprising a compound of Formula (Ia), PEG 300, sodium hydroxide, poloxamer 188, and water is about 4.57 w/w % to about 25.21 w/w %. In some embodiments, the amount of the compound of Formula (Ia) in the solution comprising a compound of Formula (Ia), PEG 300, sodium hydroxide, poloxamer 188, and water is about 3.0 w/w %, about 3.1 w/w %, about 3.2 w/w %, about 3.3 w/w %, about 3.4 w/w %, about 3.5 w/w %, about 3.6 w/w %, about 3.7 w/w %, about 3.8 w/w %, about 3.9 w/w %, about 4.0 w/w %, about 4.1 w/w %, about 4.2 w/w %, about 4.3 w/w %, about 4.4 w/w %, about 4.5 w/w %, about 4.6 w/w %, about 4.7 w/w %, about 4.8 w/w %, about 4.9 w/w %, about 5.0 w/w %, about 5.1 w/w %, about 5.2 w/w %, about 5.3 w/w %, about 5.4 w/w %, about 5.5 w/w %, about 5.6 w/w %, about 5.7 w/w %, about 5.8 w/w %, about 5.9 w/w %, about 6.0 w/w %, about 6.1 w/w %, about 6.2 w/w %, about 6.3 w/w %, about 6.4 w/w %, about 6.5 w/w %, about 6.6 w/w %, about 6.7 w/w %, about 6.8 w/w %, about 6.9 w/w %, about 7.0 w/w %, about 7.1 w/w %, about 7.2 w/w %, about 7.3 w/w %, about 7.4 w/w %, about 7.5 w/w %, about 7.6 w/w %, about 7.7 w/w %, about 7.8 w/w %, about 7.9 w/w %, about 8.0 w/w %, about 8.1 w/w %, about 8.2 w/w %, about 8.3 w/w %, about 8.4 w/w %, about 8.5 w/w %, about 8.6 w/w %, about 8.7 w/w %, about 8.8 w/w %, about 8.9 w/w %, about 9.0 w/w %, about 9.1 w/w %, about 9.2 w/w %, about 9.3 w/w %, about 9.4 w/w %, about 9.5 w/w %, about 9.6 w/w %, about 9.7 w/w %, about 9.8 w/w %, about 9.9 w/w %, about 10.0 w/w %, about 10.1 w/w %, about 10.2 w/w %, about 10.3 w/w %, about 10.4 w/w %, about 10.5 w/w %, about 10.6 w/w %, about 10.7 w/w %, about 10.8 w/w %, about 10.9 w/w %, about 11.0 w/w %, about 11.1 w/w %, about 11.2 w/w %, about 11.3 w/w %, about 11.4 w/w %, about 11.5 w/w %, about 11.6 w/w %, about 11.7 w/w %, about 11.8 w/w %, about 11.9 w/w %, about 12.0 w/w %, about 12.1 w/w %, about 12.2 w/w %, about 12.3 w/w %, about 12.4 w/w %, about 12.5 w/w %, about 12.6 w/w %, about 12.7 w/w %, about 12.8 w/w %, about 12.9 w/w %, about 13.0 w/w %, about 13.1 w/w %, about 13.2 w/w %, about 13.3 w/w %, about 13.4 w/w %, about 13.5 w/w %, about 13.6 w/w %, about 13.7 w/w %, about 13.8 w/w %, about 13.9 w/w %, about 14.0 w/w %, about 14.1 w/w %, about 14.2 w/w %, about 14.3 w/w %, about 14.4 w/w %, about 14.5 w/w %, about 14.6 w/w %, about 14.7 w/w %, about 14.8 w/w %, about 14.9 w/w %, about 15.0 w/w %, about 15.1 w/w %, about 15.2 w/w %, about 15.3 w/w %, about 15.4 w/w %, about 15.5 w/w %, about 15.6 w/w %, about 15.7 w/w %, about 15.8 w/w %, about 15.9 w/w %, about 16.0 w/w %, about 16.1 w/w %, about 16.2 w/w %, about 16.3 w/w %, about 16.4 w/w %, about 16.5 w/w %, about 16.6 w/w %, about 16.7 w/w %, about 16.8 w/w %, about 16.9 w/w %, about 17.0 w/w %, about 17.1 w/w %, about 17.2 w/w %, about 17.3 w/w %, about 17.4 w/w %, about 17.5 w/w %, about 17.6 w/w %, about 17.7 w/w %, about 17.8 w/w %, about 17.9 w/w %, about 18.0 w/w %, about 18.1 w/w %, about 18.2 w/w %, about 18.3 w/w %, about 18.4 w/w %, about 18.5 w/w %, about 18.6 w/w %, about 18.7 w/w %, about 18.8 w/w %, about 18.9 w/w %, about 19.0 w/w %, about 19.1 w/w %, about 19.2 w/w %, about 19.3 w/w %, about 19.4 w/w %, about 19.5 w/w %, about 19.6 w/w %, about 19.7 w/w %, about 19.8 w/w %, about 19.9 w/w %, about 20.0 w/w %, about 21.1 w/w %, about 21.2 w/w %, about 21.3 w/w %, about 21.4 w/w %, about 21.5 w/w %, about 21.6 w/w %, about 21.7 w/w %, about 21.8 w/w %, about 21.9 w/w %, about 22.0 w/w %, about 22.1 w/w %, about 22.2 w/w %, about 22.3 w/w %, about 22.4 w/w %, about 22.5 w/w %, about 22.6 w/w %, about 22.7 w/w %, about 22.8 w/w %, about 22.9 w/w %, about 23.0 w/w %, about 23.1 w/w %, about 23.2 w/w %, about 23.3 w/w %, about 23.4 w/w %, about 23.5 w/w %, about 23.6 w/w %, about 23.7 w/w %, about 23.8 w/w %, about 23.9 w/w %, about 24.0 w/w %, about 24.1 w/w %, about 24.2 w/w %, about 24.3 w/w %, about 24.4 w/w %, about 24.5 w/w %, about 24.6 w/w %, about 24.7 w/w %, about 24.8 w/w %, about 24.9 w/w %, about 25.0 w/w %, about 25.1 w/w %, about 25.2 w/w %, about 25.3 w/w %, about 25.4 w/w %, about 25.5 w/w %, about 25.6 w/w %, about 25.7 w/w %, about 25.8 w/w %, about 25.9 w/w %, about 26.0 w/w %, about 26.1 w/w %, about 26.2 w/w %, about 26.3 w/w %, about 26.4 w/w %, about 26.5 w/w %, about 26.6 w/w %, about 26.7 w/w %, about 26.8 w/w %, about 26.9 w/w %, about 27.0 w/w %, about 27.1 w/w %, about 27.2 w/w %, about 27.3 w/w %, about 27.4 w/w %, about 27.5 w/w %, about 27.6 w/w %, about 27.7 w/w %, about 27.8 w/w %, about 27.9 w/w %, about 28.0 w/w %, about 28.1 w/w %, about 28.2 w/w %, about 28.3 w/w %, about 28.4 w/w %, about 28.5 w/w %, about 28.6 w/w %, about 28.7 w/w %, about 28.8 w/w %, about 28.9 w/w %, or about 29.0 w/w %. In some embodiments, the amount of the compound of Formula (Ia) in the solution comprising a compound of Formula (Ia), PEG 300, sodium hydroxide, poloxamer 188, and water is about 4.57 w/w %. In some embodiments, the amount of the compound of Formula (Ia) in the solution comprising a compound of Formula (Ia), PEG 300, sodium hydroxide, poloxamer 188, and water is about 4.6 w/w %. In some embodiments, the amount of the compound of Formula (Ia) in the solution comprising a compound of Formula (Ia), PEG 300, sodium hydroxide, poloxamer 188, and water is about 25.2 w/w %. In some embodiments, the amount of the compound of Formula (Ia) in the solution comprising a compound of Formula (Ia), PEG 300, sodium hydroxide, poloxamer 188, and water is about 25.21 w/w %.

In some embodiments, the amount of sodium hydroxide in the solution comprising a compound of Formula (Ia), PEG 300, sodium hydroxide, poloxamer 188, and water is about 0.01 w/w % to about 3.0 w/w %. In some embodiments, the amount of sodium hydroxide in the solution comprising a compound of Formula (Ia), PEG 300, sodium hydroxide, poloxamer 188, and water is about 0.01 w/w % to about 2.0 w/w %. In some embodiments, the amount of sodium hydroxide in the solution comprising a compound of Formula (Ia), PEG 300, sodium hydroxide, poloxamer 188, and water is about 0.05 w/w % to about 1.5 w/w %. In some embodiments, the amount of sodium hydroxide in the solution comprising a compound of Formula (Ia), PEG 300, sodium hydroxide, poloxamer 188, and water is about 0.05 w/w % to about 1.2 w/w %. In some embodiments, the amount of sodium hydroxide in the solution comprising a compound of Formula (Ia), PEG 300, sodium hydroxide, poloxamer 188, and water is about 0.1 w/w % to about 1.1 w/w %. In some embodiments, the amount of sodium hydroxide in the solution comprising a compound of Formula (Ia), PEG 300, sodium hydroxide, poloxamer 188, and water is about 0.10 w/w % to about 1.08 w/w %. In some embodiments, the amount of sodium hydroxide in the solution comprising a compound of Formula (Ia), PEG 300, sodium hydroxide, poloxamer 188, and water is about 0.01 w/w %, about 0.02 w/w %, about 0.03 w/w %, about 0.04 w/w %, about 0.05 w/w %, about 0.06 w/w %, about 0.07 w/w %, about 0.08 w/w %, about 0.09 w/w %, about 0.1 w/w %, about 0.2 w/w %, about 0.3 w/w %, about 0.4 w/w %, about 0.5 w/w %, about 0.6 w/w %, about 0.7 w/w %, about 0.8 w/w %, about 0.9 w/w %, about 1.0 w/w %, about 1.1 w/w %, about 1.2 w/w %, about 1.3 w/w %, about 1.4 w/w %, about 1.5 w/w %, about 1.6 w/w %, about 1.7 w/w %, about 1.8 w/w %, about 1.9 w/w %, or about 2.0 w/w %. In some embodiments, the amount of sodium hydroxide in the solution comprising a compound of Formula (Ia), PEG 300, sodium hydroxide, poloxamer 188, and water is about 0.1 w/w %. In some embodiments, the amount of sodium hydroxide in the solution comprising a compound of Formula (Ia), PEG 300, sodium hydroxide, poloxamer 188, and water is about 0.10 w/w %. In some embodiments, the amount of sodium hydroxide in the solution comprising a compound of Formula (Ia), PEG 300, sodium hydroxide, poloxamer 188, and water is about 1.08 w/w %. In some embodiments, the amount of sodium hydroxide in the solution comprising a compound of Formula (Ia), PEG 300, sodium hydroxide, poloxamer 188, and water is about 1.1 w/w %.

In some embodiments, the amount of poloxamer 188 in the solution comprising a compound of Formula (Ia), PEG 300, sodium hydroxide, poloxamer 188, and water is about 0.1 w/w % to about 10 w/w %. In some embodiments, the amount of poloxamer 188 in the solution comprising a compound of Formula (Ia), PEG 300, sodium hydroxide, poloxamer 188, and water is about 0.3 w/w % to about 8 w/w %. In some embodiments, the amount of poloxamer 188 in the solution comprising a compound of Formula (Ia), PEG 300, sodium hydroxide, poloxamer 188, and water is about 0.5 w/w % to about 7 w/w %. In some embodiments, the amount of poloxamer 188 in the solution comprising a compound of Formula (Ia), PEG 300, sodium hydroxide, poloxamer 188, and water is about 0.6 w/w % to about 7 w/w %. In some embodiments, the amount of poloxamer 188 in the solution comprising a compound of Formula (Ia), PEG 300, sodium hydroxide, poloxamer 188, and water is about 0.85 w/w % to about 4.69 w/w %. In some embodiments, the amount of poloxamer 188 in the solution comprising a compound of Formula (Ia), PEG 300, sodium hydroxide, poloxamer 188, and water is about 0.9 w/w % to about 4.7 w/w %. In some embodiments, the amount of poloxamer 188 in the solution comprising a compound of Formula (Ia), PEG 300, sodium hydroxide, poloxamer 188, and water is about 0.5 w/w %, about 0.6 w/w %, about 0.7 w/w %, about 0.8 w/w %, about 0.9 w/w %, about 1.0 w/w %, about 1.1 w/w %, about 1.2 w/w %, about 1.3 w/w %, about 1.4 w/w %, about 1.5 w/w %, about 1.6 w/w %, about 1.7 w/w %, about 1.8 w/w %, about 1.9 w/w %, about 2.0 w/w %, about 2.1 w/w %, about 2.2 w/w %, about 2.3 w/w %, about 2.4 w/w %, about 2.5 w/w %, about 2.6 w/w %, about 2.7 w/w %, about 2.8 w/w %, about 2.9 w/w %, about 3.0 w/w %, about 3.1 w/w %, about 3.2 w/w %, about 3.3 w/w %, about 3.4 w/w %, about 3.5 w/w %, about 3.6 w/w %, about 3.7 w/w %, about 3.8 w/w %, about 3.9 w/w %, about 4.0 w/w %, about 4.1 w/w %, about 4.2 w/w %, about 4.3 w/w %, about 4.4 w/w %, about 4.5 w/w %, about 4.6 w/w %, about 4.7 w/w %, about 4.8 w/w %, about 4.9 w/w %, about 5.0 w/w %, about 5.1 w/w %, about 5.2 w/w %, about 5.3 w/w %, about 5.4 w/w %, about 5.5 w/w %, about 5.6 w/w %, about 5.7 w/w %, about 5.8 w/w %, about 5.9 w/w %, about 6.0 w/w %, about 6.1 w/w %, about 6.2 w/w %, about 6.3 w/w %, about 6.4 w/w %, about 6.5 w/w %, about 6.6 w/w %, about 6.7 w/w %, about 6.8 w/w %, about 6.9 w/w %, or about 7.0 w/w %. In some embodiments, the amount of poloxamer 188 in the solution comprising a compound of Formula (Ia), PEG 300, sodium hydroxide, poloxamer 188, and water is about 0.85 w/w %. In some embodiments, the amount of poloxamer 188 in the solution comprising a compound of Formula (Ia), PEG 300, sodium hydroxide, poloxamer 188, and water is about 0.9 w/w %. In some embodiments, the amount of poloxamer 188 in the solution comprising a compound of Formula (Ia), PEG 300, sodium hydroxide, poloxamer 188, and water is about 4.69 w/w %. In some embodiments, the amount of poloxamer 188 in the solution comprising a compound of Formula (Ia), PEG 300, sodium hydroxide, poloxamer 188, and water is about 4.7 w/w %.

In some embodiments, the solution comprises about 10 w/w % to about 45 w/w % water, about 30 w/w % to about 85 w/w % PEG 300, about 0.5 w/w % to about 40 w/w % of a compound of Formula (Ia), about 0.01 w/w % to about 3.0 w/w % of sodium hydroxide, and about 0.1 w/w % to about 10 w/w % of poloxamer 188. In some embodiments, the solution comprises about 15 w/w % to about 35 w/w % water, about 35 w/w % to about 75 w/w % PEG 300, about 1 w/w % to about 35 w/w % of a compound of Formula (Ia), about 0.01 w/w % to about 2.0 w/w % of sodium hydroxide, and about 0.3 w/w % to about 8 w/w % of poloxamer 188. In some embodiments, the solution comprises about 20 w/w % to about 35 w/w % water, about 40 w/w % to about 70 w/w % PEG 300, about 1 w/w % to about 30 w/w % of a compound of Formula (Ia), about 0.05 w/w % to about 1.5 w/w % of sodium hydroxide, and about 0.5 w/w % to about 7 w/w % of poloxamer 188. In some embodiments, the solution comprises about 20 w/w % to about 31 w/w % water, about 45 w/w % to about 68 w/w % PEG 300, about 3 w/w % to about 28 w/w % of a compound of Formula (Ia), about 0.05 w/w % to about 1.2 w/w % of sodium hydroxide, and about 0.6 w/w % to about 7 w/w % of poloxamer 188.

In some embodiments, the solution comprises about 22 w/w % to about 30.1 w/w % water, about 47.1 w/w % to about 64.4 w/w % PEG 300, about 4.6 w/w % to about 25.2 w/w % of a compound of Formula (Ia), about 0.1 w/w % to about 1.1 w/w % of sodium hydroxide, and about 0.9 w/w % to about 4.7 w/w % of poloxamer 188. In some embodiments, the solution comprises about 21.97 w/w % to about 30.07 w/w % water, about 47.05 w/w % to about 64.41 w/w % PEG 300, about 4.57 w/w % to about 25.21 w/w % of a compound of Formula (Ia), about 0.10 w/w % to about 1.08 w/w % of sodium hydroxide, and about 0.85 w/w % to about 4.69 w/w % of poloxamer 188. In some embodiments, the solution comprises about 30.1 w/w % water, about 64.4 w/w % PEG 300, about 4.6 w/w % of a compound of Formula (Ia), about 0.1 w/w % of sodium hydroxide, and about 0.9 w/w % of poloxamer 188. In some embodiments, the solution comprises about 30.07 w/w % water, about 64.41 w/w % PEG 300, about 4.57 w/w % of a compound of Formula (Ia), about 0.10 w/w % of sodium hydroxide, and about 0.85 w/w % of poloxamer 188. In some embodiments, the solution comprises about 22 w/w % water, about 47.1 w/w % PEG 300, about 25.2 w/w % of a compound of Formula (Ia), about 1.1 w/w % of sodium hydroxide, and about 4.7 w/w % of poloxamer 188. In some embodiments, the solution comprises about 21.97 w/w % water, about 47.05 w/w % PEG 300, about 25.21 w/w % of a compound of Formula (Ia), about 1.08 w/w % of sodium hydroxide, and about 4.69 w/w % of poloxamer 188.

In some embodiments, the compound of Formula (Ia) becomes ionized in situ to a sodium salt of the compound of Formula (Ia) in the presence of sodium hydroxide in the solution comprising a compound of Formula (Ia), PEG 300, sodium hydroxide, poloxamer 188, and water. Thus, in some embodiments, the compound of Formula (Ia) is present as a sodium salt of the compound of Formula (Ia) in the solution comprising a compound of Formula (Ia), PEG 300, sodium hydroxide, poloxamer 188, and water.

In some embodiments, the solution formulation comprises about 50 mg/mL of the compound of Formula (Ia) or Formula (Ib), or a pharmaceutically acceptable salt thereof. In some embodiments, the solution formulation comprises about 75 mg/mL of the compound of Formula (Ia) or Formula (Ib), or a pharmaceutically acceptable salt thereof. In some embodiments, the solution formulation comprises about 125 mg/mL of the compound of Formula (Ia) or Formula (Ib), or a pharmaceutically acceptable salt thereof. In some embodiments, the solution formulation comprises about 175 mg/mL of the compound of Formula (Ia) or Formula (Ib), or a pharmaceutically acceptable salt thereof. In some embodiments, the solution formulation comprises about 225 mg/mL of the compound of Formula (Ia) or Formula (Ib), or a pharmaceutically acceptable salt thereof. In some embodiments, the solution formulation comprises about 250 mg/mL of the compound of Formula (Ia) or Formula (Ib), or a pharmaceutically acceptable salt thereof. In some embodiments, the solution formulation comprises about 275 mg/mL of the compound of Formula (Ia) or Formula (Ib), or a pharmaceutically acceptable salt thereof. In some embodiments, the solution formulation comprises about 325 mg/mL of the compound of Formula (Ia) or Formula (Ib), or a pharmaceutically acceptable salt thereof. In some embodiments, the solution formulation comprises about 350 mg/mL of the compound of Formula (Ia) or Formula (Ib), or a pharmaceutically acceptable salt thereof. In some embodiments, the solution formulation comprises about 375 mg/mL of the compound of Formula (Ia) or Formula (Ib), or a pharmaceutically acceptable salt thereof.

In some embodiments, the solution formulation comprises about 100 mg/mL of the compound of Formula (Ia) or Formula (Ib), or a pharmaceutically acceptable salt thereof. In some embodiments, the solution formulation comprises about 150 mg/mL of the compound of Formula (Ia) or Formula (Ib), or a pharmaceutically acceptable salt thereof. In some embodiments, the solution formulation comprises about 200 mg/mL of the compound of Formula (Ia) or Formula (Ib), or a pharmaceutically acceptable salt thereof. In some embodiments, the solution formulation comprises about 300 mg/mL of the compound of Formula (Ia) or Formula (Ib), or a pharmaceutically acceptable salt thereof. In some embodiments, the solution formulation comprises about 400 mg/mL of the compound of Formula (Ia) or Formula (Ib), or a pharmaceutically acceptable salt thereof.

In some embodiments, the solution formulation comprises about 425 mg/mL of the compound of Formula (Ia) or Formula (Ib), or a pharmaceutically acceptable salt thereof. In some embodiments, the solution formulation comprises about 450 mg/mL of the compound of Formula (Ia) or Formula (Ib), or a pharmaceutically acceptable salt thereof. In some embodiments, the solution formulation comprises about 475 mg/mL of the compound of Formula (Ia) or Formula (Ib), or a pharmaceutically acceptable salt thereof. In some embodiments, the solution formulation comprises about 500 mg/mL of the compound of Formula (Ia) or Formula (Ib), or a pharmaceutically acceptable salt thereof.

In some embodiments, the PEG 300 of the solutions disclosed herein can be replaced with PEG 400 or PEG 600 in the same amount as the PEG 300. In some embodiments, the PEG 300 of the solutions disclosed herein can be replaced with PEG 400 in the same amount as the PEG 300. In some embodiments, the PEG 300 of the solutions disclosed herein can be replaced with PEG 600 in the same amount as the PEG 300.

In some embodiments, the molar ratio of sodium to a compound of Formula (Ia) or Formula (Ib) is about 0:1 to about 1.5:1. In some embodiments, the molar ratio of sodium to a compound of Formula (Ia) is about 0:1 to about 1.5:1. In some embodiments, the molar ratio of sodium to a compound of Formula (Ia) is about 0:1 to about 1.2:1. In some embodiments, the molar ratio of sodium to a compound of Formula (Ia) is about 0:1. In some embodiments, the molar ratio of sodium to a compound of Formula (Ia) is about 0.5:1. In some embodiments, the molar ratio of sodium to a compound of Formula (Ia) is about 1:1. In some embodiments, the molar ratio of sodium to a compound of Formula (Ia) is about 1.2:1.

In some embodiments, the solutions are administered through subcutaneous injection. In some embodiments, the solutions are administered through intramuscular injection.

In some embodiments of the methods disclosed herein, the compound of Formula (Ia) or Formula (Ib), or a pharmaceutically acceptable salt thereof, is administered subcutaneously at a concentration of about 309 mg/mL.

In some embodiments of the methods disclosed herein, a solution of the sodium salt of the compound of Formula (Ia) is administered subcutaneously, wherein the solution comprises about 20 w/w % to about 30 w/w % water, about 48 w/w % to about 60 w/w % PEG 300, and about 11 w/w % to about 28 w/w % of a sodium salt of the compound of Formula (Ia)

In some embodiments of the methods disclosed herein, a solution of the sodium salt of the compound of Formula (Ia) is administered subcutaneously, wherein the solution comprises about 23.41 w/w % water, about 50.13 w/w % PEG 300, and about 26.46 w/w % of the sodium salt of the compound of Formula (Ia).

In some embodiments of the methods disclosed herein, the compound of Formula (Ia) or Formula (Ib), or a pharmaceutically acceptable salt thereof, is administered intramuscularly.

In some embodiments of the methods disclosed herein, the compound of Formula (Ia) or Formula (Ib), or a pharmaceutically acceptable salt thereof, is administered intramuscularly at a concentration of about 400 mg/mL to about 500 mg/mL.

In certain embodiments, an oral formulation of a compound of Formula (Ia) or Formula (Ib), or a pharmaceutically acceptable salt thereof, and at least one excipient is provided. Excipients can include ethanol, medium chain triglycerides, vitamin E d-α-tocopheryl polyethylene glycol 1000 succinate (TPGS), glycerol monocaprylocaprate, glycerin, and/or pharmaceutically acceptable oils. Examples of suitable medium chain triglycerides include, but are not limited to, MIGLYOL 810, MIGLYOL 821, and MIGLYOL 840. Examples of suitable pharmaceutically acceptable oils include, but are not limited to, sesame oil, castor oil, safflower oil, vegetable oil, and soybean oil. Oral formulations can include any combination of one or more suitable excipients. Excipients taken together can be present in greater than about 65% by weight of the total oral formulation, greater than about 70% by weight of the total oral formulation, greater than about 80% by weight of the total oral formulation, greater than about 90% by weight of the total oral formulation, or greater than about 95% by weight of the total oral formulation.

In some embodiments, the oral formulation of a compound of Formula (Ia) or Formula (Ib), or a pharmaceutically acceptable salt thereof, and at least one excipient as is prepared in hard or soft capsules. In some embodiments, the hard or soft capsules comprise a compound of Formula (Ia) or Formula (Ib), or a pharmaceutically acceptable salt thereof, and one or more excipients selected from the group consisting of ethanol, propylene glycol, glycerine, d-α-tocopheryl polyethylene glycol 1000 succinate (TPGS), polyoxyl 35 castor oil (e.g., Kolliphor® EL), glycerol monocapryolocaprate (e.g., Capmul® MCM), PEG 400 caprylic/capric glycerides (e.g., Labrasol®), PEG 400, diethylene glycol monoethyl ether (e.g., Transcutol®), propylene glycol monocaprylate, Type II (e.g., Capryol® 90), glyceryl monooleate, Type 40 (e.g., Peceol™), medium chain triglycerides (e.g., Miglyol® 812N), glyceryl monolinoleate (e.g., Maisine®), and polysorbate 80. In some embodiments, the hard or soft capsules comprise a compound of Formula (Ia) or Formula (Ib), or a pharmaceutically acceptable salt thereof, and one or more excipients selected from the group consisting of ethanol, medium chain triglycerides (e.g., Miglyol® 812N), d-α-tocopheryl polyethylene glycol 1000 succinate (TPGS), glycerol monocapryolocaprate (e.g., Capmul® MCM), PEG 400 caprylic/capric glycerides (e.g., Labrasol®), and PEG 400.

In some embodiments, the hard or soft capsules further comprise a capsule shell. In some embodiments, the capsule shell comprises one or more pharmaceutically acceptable excipients. In some embodiments, the one or more pharmaceutically acceptable excipients of the capsule shell is selected from the group consisting of a gelatin shell, a plasticizer, an opacifier, and a colorant. Plasticizers, opacifiers, and colorants are well-known in the art. In some embodiments, the capsule shell comprises one or more pharmaceutically acceptable excipients selected from the group consisting of gelatin, glycerin, titanium dioxide, and iron oxide. In some embodiments, the iron oxide comprises iron oxide (yellow).

In some embodiments, an oral formulation of a compound of Formula (Ia) or Formula (Ib), or a pharmaceutically acceptable salt thereof, is provided. In certain embodiments, the oral formulation comprises a compound of Formula (Ia) or Formula (Ib), or a pharmaceutically acceptable salt thereof, and glycerol monocaprylocaprate. In certain embodiments, the oral formulation includes a compound of Formula (Ia) or Formula (Ib), or a pharmaceutically acceptable salt thereof, about 5% to about 20% ethanol, about 10% to about 30% vitamin E TPGS, and about 50% to about 85% MIGLYOL 812. In some embodiments, the oral formulation includes a compound of Formula (Ia) or Formula (Ib), or a pharmaceutically acceptable salt thereof, about 8% to about 15% ethanol, about 15% to about 25% vitamin E TPGS, and about 60% to about 77% MIGLYOL 812. In certain embodiments, the oral formulation includes a compound of Formula (Ia) or Formula (Ib), or a pharmaceutically acceptable salt thereof, in about 10% ethanol, about 20% vitamin E TPGS, and about 70% MIGLYOL 812. In certain embodiments, the oral formulation is prepared in hard gelatin capsules. In certain embodiments, the oral formulation is prepared in soft gelatin capsules.

In some embodiments, the hard gelatin or soft gelatin capsule comprises a compound of Formula (Ia) or Formula (Ib), or a pharmaceutically acceptable salt thereof, and a pharmaceutically acceptable excipient. In some embodiments, the hard gelatin or soft gelatin capsule comprises a compound of Formula (Ia) or Formula (Ib), or a pharmaceutically acceptable salt thereof, and glycerol monocaprylocaprate. In some embodiments, the concentration of a compound of Formula (Ia) or Formula (Ib), or a pharmaceutically acceptable salt thereof, in the hard gelatin or soft gelatin capsule is about 10 mg/ml to about 500 mg/ml. In some embodiments, the concentration of a compound of Formula (Ia) or Formula (Ib), or a pharmaceutically acceptable salt thereof, in the hard gelatin or soft gelatin capsule is about 10 mg/ml to about 400 mg/ml. In some embodiments, the concentration of a compound of Formula (Ia) or Formula (Ib), or a pharmaceutically acceptable salt thereof, in the hard gelatin or soft gelatin capsule is about 50 mg/ml to about 300 mg/ml. In some embodiments, the concentration of a compound of Formula (Ia) or Formula (Ib), or a pharmaceutically acceptable salt thereof, in the hard gelatin or soft gelatin capsule is about 50 mg/ml to about 200 mg/ml. In some embodiments, the concentration of a compound of Formula (Ia) or Formula (Ib), or a pharmaceutically acceptable salt thereof, in the hard gelatin or soft gelatin capsule is about 50 mg/ml to about 100 mg/ml. In some embodiments, the concentration of a compound of Formula (Ia) or Formula (Ib), or a pharmaceutically acceptable salt thereof, in the hard gelatin or soft gelatin capsule is about 10 mg/ml, about 15 mg/ml, about 20 mg/ml, about 25 mg/ml, about 30 mg/ml, about 30 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, about 150 mg/ml, about 155 mg/ml, about 160 mg/ml, about 165 mg/ml, about 170 mg/ml, about 175 mg/ml, about 180 mg/ml, about 185 mg/ml, about 190 mg/ml, about 195 mg/ml, about 200 mg/ml, 205 mg/ml, about 210 mg/ml, about 215 mg/ml, about 220 mg/ml, about 225 mg/ml, about 230 mg/ml, about 235 mg/ml, about 240 mg/ml, about 245 mg/ml, about 250 mg/ml, about 255 mg/ml, about 260 mg/ml, about 265 mg/ml, about 270 mg/ml, about 275 mg/ml, about 280 mg/ml, about 285 mg/ml, about 290 mg/ml, about 295 mg/ml, about 300 mg/ml, about 305 mg/ml, about 310 mg/ml, about 315 mg/ml, about 320 mg/ml, about 325 mg/ml, about 330 mg/ml, about 335 mg/ml, about 340 mg/ml, about 345 mg/ml, about 350 mg/ml, about 355 mg/ml, about 360 mg/ml, about 365 mg/ml, about 370 mg/ml, about 375 mg/ml, about 380 mg/ml, about 385 mg/ml, about 390 mg/ml, about 395 mg/ml, about 400 mg/ml, about 405 mg/ml, about 410 mg/ml, about 415 mg/ml, about 420 mg/ml, about 425 mg/ml, about 430 mg/ml, about 435 mg/ml, about 440 mg/ml, about 445 mg/ml, about 450 mg/ml, about 455 mg/ml, about 460 mg/ml, about 465 mg/ml, about 470 mg/ml, about 475 mg/ml, about 480 mg/ml, about 485 mg/ml, about 490 mg/ml, about 495 mg/ml, or about 500 mg/ml. In some embodiments, the concentration of a compound of Formula (Ia) or Formula (Ib), or a pharmaceutically acceptable salt thereof, in the hard gelatin or soft gelatin capsule is about 10 mg/ml. In some embodiments, the concentration of a compound of Formula (Ia) or Formula (Ib), or a pharmaceutically acceptable salt thereof, in the hard gelatin or soft gelatin capsule is about 20 mg/ml. In some embodiments, the concentration of a compound of Formula (Ia) or Formula (Ib), or a pharmaceutically acceptable salt thereof, in the hard gelatin or soft gelatin capsule is about 30 mg/ml. In some embodiments, the concentration of a compound of Formula (Ia) or Formula (Ib), or a pharmaceutically acceptable salt thereof, in the hard gelatin or soft gelatin capsule is about 40 mg/ml. In some embodiments, the concentration of a compound of Formula (Ia) or Formula (Ib), or a pharmaceutically acceptable salt thereof, in the hard gelatin or soft gelatin capsule is about 50 mg/ml. In some embodiments, the concentration of a compound of Formula (Ia) or Formula (Ib), or a pharmaceutically acceptable salt thereof, in the hard gelatin or soft gelatin capsule is about 75 mg/ml. In some embodiments, the concentration of a compound of Formula (Ia) or Formula (Ib), or a pharmaceutically acceptable salt thereof, in the hard gelatin or soft gelatin capsule is about 100 mg/ml. In some embodiments, the concentration of a compound of Formula (Ia) or Formula (Ib), or a pharmaceutically acceptable salt thereof, in the hard gelatin or soft gelatin capsule is about 125 mg/ml. In some embodiments, the concentration of a compound of Formula (Ia) or Formula (Ib), or a pharmaceutically acceptable salt thereof, in the hard gelatin or soft gelatin capsule is about 150 mg/ml. In some embodiments, the concentration of a compound of Formula (Ia) or Formula (Ib), or a pharmaceutically acceptable salt thereof, in the hard gelatin or soft gelatin capsule is about 175 mg/ml. In some embodiments, the concentration of a compound of Formula (Ia) or Formula (Ib), or a pharmaceutically acceptable salt thereof, in the hard gelatin or soft gelatin capsule is about 200 mg/ml. In some embodiments, the concentration of a compound of Formula (Ia) or Formula (Ib), or a pharmaceutically acceptable salt thereof, in the hard gelatin or soft gelatin capsule is about 225 mg/ml. In some embodiments, the concentration of a compound of Formula (Ia) or Formula (Ib), or a pharmaceutically acceptable salt thereof, in the hard gelatin or soft gelatin capsule is about 250 mg/ml. In some embodiments, the concentration of a compound of Formula (Ia) or Formula (Ib), or a pharmaceutically acceptable salt thereof, in the hard gelatin or soft gelatin capsule is about 275 mg/ml. In some embodiments, the concentration of a compound of Formula (Ia) or Formula (Ib), or a pharmaceutically acceptable salt thereof, in the hard gelatin or soft gelatin capsule is about 300 mg/ml. In some embodiments, the concentration of a compound of Formula (Ia) or Formula (Ib), or a pharmaceutically acceptable salt thereof, in the hard gelatin or soft gelatin capsule is about 325 mg/ml. In some embodiments, the concentration of a compound of Formula (Ia) or Formula (Ib), or a pharmaceutically acceptable salt thereof, in the hard gelatin or soft gelatin capsule is about 350 mg/ml. In some embodiments, the concentration of a compound of Formula (Ia) or Formula (Ib), or a pharmaceutically acceptable salt thereof, in the hard gelatin or soft gelatin capsule is about 375 mg/ml. In some embodiments, the concentration of a compound of Formula (Ia) or Formula (Ib), or a pharmaceutically acceptable salt thereof, in the hard gelatin or soft gelatin capsule is about 400 mg/ml. In some embodiments, the concentration of a compound of Formula (Ia) or Formula (Ib), or a pharmaceutically acceptable salt thereof, in the hard gelatin or soft gelatin capsule is about 425 mg/ml. In some embodiments, the concentration of a compound of Formula (Ia) or Formula (Ib), or a pharmaceutically acceptable salt thereof, in the hard gelatin or soft gelatin capsule is about 450 mg/ml. In some embodiments, the concentration of a compound of Formula (Ia) or Formula (Ib), or a pharmaceutically acceptable salt thereof, in the hard gelatin or soft gelatin capsule is about 475 mg/ml. In some embodiments, the concentration of a compound of Formula (Ia) or Formula (Ib), or a pharmaceutically acceptable salt thereof, in the hard gelatin or soft gelatin capsule is about 500 mg/ml.

In some embodiments, the hard gelatin or soft gelatin capsule comprises a compound of Formula (Ib), or a pharmaceutically acceptable salt thereof, and glycerol monocaprylocaprate.

In some embodiments, the hard gelatin or soft gelatin capsule comprises a compound of Formula (Ia) and glycerol monocaprylocaprate. In some embodiments, the concentration of the compound of Formula (Ia) in the hard gelatin or soft gelatin capsule comprising a compound of Formula (Ia) and glycerol monocaprylocaprate is about 10 mg/ml to about 500 mg/ml. In some embodiments, the concentration of the compound of Formula (Ia) in the hard gelatin or soft gelatin capsule comprising a compound of Formula (Ia) and glycerol monocaprylocaprate is about 10 mg/ml to about 400 mg/ml. In some embodiments, the concentration of the compound of Formula (Ia) in the hard gelatin or soft gelatin capsule comprising a compound of Formula (Ia) and glycerol monocaprylocaprate is about 50 mg/ml to about 300 mg/ml. In some embodiments, the concentration of the compound of Formula (Ia) in the hard gelatin or soft gelatin capsule comprising a compound of Formula (Ia) and glycerol monocaprylocaprate is about 75 mg/ml to about 300 mg/ml. In some embodiments, the concentration of the compound of Formula (Ia) in the hard gelatin or soft gelatin capsule comprising a compound of Formula (Ia) and glycerol monocaprylocaprate is about 50 mg/ml to about 200 mg/ml. In some embodiments, the concentration of the compound of Formula (Ia) in the hard gelatin or soft gelatin capsule comprising a compound of Formula (Ia) and glycerol monocaprylocaprate is about 50 mg/ml to about 100 mg/ml. In some embodiments, the concentration of the compound of Formula (Ia) in the hard gelatin or soft gelatin capsule comprising a compound of Formula (Ia) and glycerol monocaprylocaprate is about 10 mg/ml. In some embodiments, the concentration of the compound of Formula (Ia) in the hard gelatin or soft gelatin capsule comprising a compound of Formula (Ia) and glycerol monocaprylocaprate is about 20 mg/ml. In some embodiments, the concentration of the compound of Formula (Ia) in the hard gelatin or soft gelatin capsule comprising a compound of Formula (Ia) and glycerol monocaprylocaprate is about 30 mg/ml. In some embodiments, the concentration of the compound of Formula (Ia) in the hard gelatin or soft gelatin capsule comprising a compound of Formula (Ia) and glycerol monocaprylocaprate is about 40 mg/ml. In some embodiments, the concentration of the compound of Formula (Ia) in the hard gelatin or soft gelatin capsule comprising a compound of Formula (Ia) and glycerol monocaprylocaprate is about 50 mg/ml. In some embodiments, the concentration of the compound of Formula (Ia) in the hard gelatin or soft gelatin capsule comprising a compound of Formula (Ia) and glycerol monocaprylocaprate is about 75 mg/ml. In some embodiments, the concentration of the compound of Formula (Ia) in the hard gelatin or soft gelatin capsule comprising a compound of Formula (Ia) and glycerol monocaprylocaprate is about 100 mg/ml. In some embodiments, the concentration of a compound of Formula (Ia) in the hard gelatin or soft gelatin capsule comprising a compound of Formula (Ia) and glycerol monocaprylocaprate is about 125 mg/ml. In some embodiments, the concentration of a compound of Formula (Ia) in the hard gelatin or soft gelatin capsule comprising a compound of Formula (Ia) and glycerol monocaprylocaprate is about 150 mg/ml. In some embodiments, the concentration of a compound of Formula (Ia) in the hard gelatin or soft gelatin capsule comprising a compound of Formula (Ia) and glycerol monocaprylocaprate is about 175 mg/ml. In some embodiments, the concentration of a compound of Formula (Ia) in the hard gelatin or soft gelatin capsule comprising a compound of Formula (Ia) and glycerol monocaprylocaprate is about 200 mg/ml. In some embodiments, the concentration of a compound of Formula (Ia) in the hard gelatin or soft gelatin capsule comprising a compound of Formula (Ia) and glycerol monocaprylocaprate is about 225 mg/ml. In some embodiments, the concentration of a compound of Formula (Ia) in the hard gelatin or soft gelatin capsule comprising a compound of Formula (Ia) and glycerol monocaprylocaprate is about 250 mg/ml. In some embodiments, the concentration of a compound of Formula (Ia) in the hard gelatin or soft gelatin capsule comprising a compound of Formula (Ia) and glycerol monocaprylocaprate is about 275 mg/ml. In some embodiments, the concentration of a compound of Formula (Ia) in the hard gelatin or soft gelatin capsule comprising a compound of Formula (Ia) and glycerol monocaprylocaprate is about 300 mg/ml. In some embodiments, the concentration of a compound of Formula (Ia) in the hard gelatin or soft gelatin capsule comprising a compound of Formula (Ia) and glycerol monocaprylocaprate is about 325 mg/ml. In some embodiments, the concentration of a compound of Formula (Ia) in the hard gelatin or soft gelatin capsule comprising a compound of Formula (Ia) and glycerol monocaprylocaprate is about 350 mg/ml. In some embodiments, the concentration of a compound of Formula (Ia) in the hard gelatin or soft gelatin capsule comprising a compound of Formula (Ia) and glycerol monocaprylocaprate is about 375 mg/ml. In some embodiments, the concentration of a compound of Formula (Ia) in the hard gelatin or soft gelatin capsule comprising a compound of Formula (Ia) and glycerol monocaprylocaprate is about 400 mg/ml. In some embodiments, the concentration of a compound of Formula (Ia) in the hard gelatin or soft gelatin capsule comprising a compound of Formula (Ia) and glycerol monocaprylocaprate is about 425 mg/ml. In some embodiments, the concentration of a compound of Formula (Ia) in the hard gelatin or soft gelatin capsule comprising a compound of Formula (Ia) and glycerol monocaprylocaprate is about 450 mg/ml. In some embodiments, the concentration of a compound of Formula (Ia) in the hard gelatin or soft gelatin capsule comprising a compound of Formula (Ia) and glycerol monocaprylocaprate is about 475 mg/ml. In some embodiments, the concentration of a compound of Formula (Ia) in the hard gelatin or soft gelatin capsule comprising a compound of Formula (Ia) and glycerol monocaprylocaprate is about 500 mg/ml.

In some embodiments, the amount of glycerol monocaprylocaprate in the hard gelatin or soft gelatin capsule comprising a compound of Formula (Ia) and glycerol monocaprylocaprate is about 30 w/w % to about 85 w/w %. In some embodiments, the amount of glycerol monocaprylocaprate in the hard gelatin or soft gelatin capsule comprising a compound of Formula (Ia) and glycerol monocaprylocaprate is about 40 w/w % to about 80 w/w %. In some embodiments, the amount of glycerol monocaprylocaprate in the hard gelatin or soft gelatin capsule comprising a compound of Formula (Ia) and glycerol monocaprylocaprate is about 50 w/w % to about 80 w/w %. In some embodiments, the amount of glycerol monocaprylocaprate in the hard gelatin or soft gelatin capsule comprising a compound of Formula (Ia) and glycerol monocaprylocaprate is about 60 w/w % to about 70 w/w %. In some embodiments, the amount of glycerol monocaprylocaprate in the hard gelatin or soft gelatin capsule comprising a compound of Formula (Ia) and glycerol monocaprylocaprate is about 65.9 w/w %. In some embodiments, the amount of glycerol monocaprylocaprate in the hard gelatin or soft gelatin capsule comprising a compound of Formula (Ia) and glycerol monocaprylocaprate is about 65.94 w/w %.

In some embodiments, the amount of the compound of Formula (Ia) in the hard gelatin or soft gelatin capsule comprising a compound of Formula (Ia) and glycerol monocaprylocaprate is about 1 w/w % to about 40 w/w %. In some embodiments, the amount of the compound of Formula (Ia) in the hard gelatin or soft gelatin capsule comprising a compound of Formula (Ia) and glycerol monocaprylocaprate is about 1 w/w % to about 35 w/w %. In some embodiments, the amount of the compound of Formula (Ia) in the hard gelatin or soft gelatin capsule comprising a compound of Formula (Ia) and glycerol monocaprylocaprate is about 2 w/w % to about 30 w/w %. In some embodiments, the amount of the compound of Formula (Ia) in the hard gelatin or soft gelatin capsule comprising a compound of Formula (Ia) and glycerol monocaprylocaprate is about 3 w/w % to about 28 w/w %. In some embodiments, the amount of the compound of Formula (Ia) in the hard gelatin or soft gelatin capsule comprising a compound of Formula (Ia) and glycerol monocaprylocaprate is about 3.4 w/w %. In some embodiments, the amount of the compound of Formula (Ia) in the hard gelatin or soft gelatin capsule comprising a compound of Formula (Ia) and glycerol monocaprylocaprate is about 3.42 w/w %.

In some embodiments, the hard gelatin or soft gelatin capsule comprising a compound of Formula (Ia) and glycerol monocaprylocaprate further comprises a capsule shell. In some embodiments, the capsule shell comprises one or more pharmaceutically acceptable excipients. In some embodiments, the one or more pharmaceutically acceptable excipients of the capsule shell is selected from the group consisting of a gelatin shell, a plasticizer, an opacifier, and a colorant. In some embodiments, the hard gelatin or soft gelatin capsule comprising a compound of Formula (Ia) and glycerol monocaprylocaprate further comprises one or more of a pharmaceutically acceptable excipient selected from the group consisting of gelatin, glycerin, titanium dioxide, and iron oxide. In some embodiments, the hard gelatin or soft gelatin capsule comprising a compound of Formula (Ia) and glycerol monocaprylocaprate further comprises gelatin. In some embodiments, the hard gelatin or soft gelatin capsule comprising a compound of Formula (Ia) and glycerol monocaprylocaprate further comprises glycerin. In some embodiments, the hard gelatin or soft gelatin capsule comprising a compound of Formula (Ia) and glycerol monocaprylocaprate further comprises titanium dioxide. In some embodiments, the hard gelatin or soft gelatin capsule comprising a compound of Formula (Ia) and glycerol monocaprylocaprate further comprises iron oxide. In some embodiments, the hard gelatin or soft gelatin capsule comprising a compound of Formula (Ia) and glycerol monocaprylocaprate further comprises gelatin and glycerin. In some embodiments, the hard gelatin or soft gelatin capsule comprising a compound of Formula (Ia) and glycerol monocaprylocaprate further comprises gelatin, glycerin, and titanium dioxide. In some embodiments, the hard gelatin or soft gelatin capsule comprising a compound of Formula (Ia) and glycerol monocaprylocaprate further comprises gelatin, glycerin, titanium dioxide, and iron oxide. In some embodiments, the iron oxide of the hard gelatin or soft gelatin capsule comprising a compound of Formula (Ia), glycerol monocaprylocaprate, gelatin, glycerin, titanium dioxide, and iron oxide comprises iron oxide (yellow).

In some embodiments, the amount of gelatin in the hard gelatin or soft gelatin capsule comprising a compound of Formula (Ia), glycerol monocaprylocaprate, gelatin, glycerin, titanium dioxide, and iron oxide is about 10 w/w % to about 40 w/w %. In some embodiments, the amount of gelatin in the hard gelatin or soft gelatin capsule comprising a compound of Formula (Ia), glycerol monocaprylocaprate, gelatin, glycerin, titanium dioxide, and iron oxide is about 10 w/w % to about 30 w/w %. In some embodiments, the amount of gelatin in the hard gelatin or soft gelatin capsule comprising a compound of Formula (Ia), glycerol monocaprylocaprate, gelatin, glycerin, titanium dioxide, and iron oxide is about 15 w/w % to about 25 w/w %. In some embodiments, the amount of gelatin in the hard gelatin or soft gelatin capsule comprising a compound of Formula (Ia), glycerol monocaprylocaprate, gelatin, glycerin, titanium dioxide, and iron oxide is about 18 w/w % to about 22 w/w %. In some embodiments, the amount of gelatin in the hard gelatin or soft gelatin capsule comprising a compound of Formula (Ia), glycerol monocaprylocaprate, gelatin, glycerin, titanium dioxide, and iron oxide is about 19.6 w/w %. In some embodiments, the amount of gelatin in the hard gelatin or soft gelatin capsule comprising a compound of Formula (Ia), glycerol monocaprylocaprate, gelatin, glycerin, titanium dioxide, and iron oxide is about 19.60 w/w %.

In some embodiments, the amount of glycerin in the hard gelatin or soft gelatin capsule comprising a compound of Formula (Ia), glycerol monocaprylocaprate, gelatin, glycerin, titanium dioxide, and iron oxide is about 3 w/w % to about 25 w/w %. In some embodiments, the amount of glycerin in the hard gelatin or soft gelatin capsule comprising a compound of Formula (Ia), glycerol monocaprylocaprate, gelatin, glycerin, titanium dioxide, and iron oxide is about 5 w/w % to about 20 w/w %. In some embodiments, the amount of glycerin in the hard gelatin or soft gelatin capsule comprising a compound of Formula (Ia), glycerol monocaprylocaprate, gelatin, glycerin, titanium dioxide, and iron oxide is about 5 w/w % to about 15 w/w %. In some embodiments, the amount of glycerin in the hard gelatin or soft gelatin capsule comprising a compound of Formula (Ia), glycerol monocaprylocaprate, gelatin, glycerin, titanium dioxide, and iron oxide is about 8 w/w % to about 12 w/w %. In some embodiments, the amount of glycerin in the hard gelatin or soft gelatin capsule comprising a compound of Formula (Ia), glycerol monocaprylocaprate, gelatin, glycerin, titanium dioxide, and iron oxide is about 10.8 w/w %. In some embodiments, the amount of glycerin in the hard gelatin or soft gelatin capsule comprising a compound of Formula (Ia), glycerol monocaprylocaprate, gelatin, glycerin, titanium dioxide, and iron oxide is about 10.80 w/w %.

In some embodiments, the amount of titanium dioxide in the hard gelatin or soft gelatin capsule comprising a compound of Formula (Ia), glycerol monocaprylocaprate, gelatin, glycerin, titanium dioxide, and iron oxide is about 0.01 w/w % to about 2 w/w %. In some embodiments, the amount of titanium dioxide in the hard gelatin or soft gelatin capsule comprising a compound of Formula (Ia), glycerol monocaprylocaprate, gelatin, glycerin, titanium dioxide, and iron oxide is about 0.05 w/w % to about 1.5 w/w %. In some embodiments, the amount of titanium dioxide in the hard gelatin or soft gelatin capsule comprising a compound of Formula (Ia), glycerol monocaprylocaprate, gelatin, glycerin, titanium dioxide, and iron oxide is about 0.1 w/w % to about 1.0 w/w %. In some embodiments, the amount of titanium dioxide in the hard gelatin or soft gelatin capsule comprising a compound of Formula (Ia), glycerol monocaprylocaprate, gelatin, glycerin, titanium dioxide, and iron oxide is about 0.1 w/w % to about 0.5 w/w %. In some embodiments, the amount of titanium dioxide in the hard gelatin or soft gelatin capsule comprising a compound of Formula (Ia), glycerol monocaprylocaprate, gelatin, glycerin, titanium dioxide, and iron oxide is about 0.2 w/w %. In some embodiments, the amount of titanium dioxide in the hard gelatin or soft gelatin capsule comprising a compound of Formula (Ia), glycerol monocaprylocaprate, gelatin, glycerin, titanium dioxide, and iron oxide is about 0.22 w/w %.

In some embodiments, the amount of iron oxide in the hard gelatin or soft gelatin capsule comprising a compound of Formula (Ia), glycerol monocaprylocaprate, gelatin, glycerin, titanium dioxide, and iron oxide is about 0.01 w/w % to about 1 w/w %. In some embodiments, the amount of iron oxide in the hard gelatin or soft gelatin capsule comprising a compound of Formula (Ia), glycerol monocaprylocaprate, gelatin, glycerin, titanium dioxide, and iron oxide is about 0.01 w/w % to about 0.5 w/w %. In some embodiments, the amount of iron oxide in the hard gelatin or soft gelatin capsule comprising a compound of Formula (Ia), glycerol monocaprylocaprate, gelatin, glycerin, titanium dioxide, and iron oxide is about 0.01 w/w % to about 0.15 w/w %. In some embodiments, the amount of iron oxide in the hard gelatin or soft gelatin capsule comprising a compound of Formula (Ia), glycerol monocaprylocaprate, gelatin, glycerin, titanium dioxide, and iron oxide is about 0.01 w/w % to about 0.1 w/w %. In some embodiments, the amount of iron oxide in the hard gelatin or soft gelatin capsule comprising a compound of Formula (Ia), glycerol monocaprylocaprate, gelatin, glycerin, titanium dioxide, and iron oxide is about 0.02 w/w %.

In some embodiments, the hard gelatin or soft capsule comprises about 30 w/w % to about 85 w/w % of glycerol monocaprylocaprate and about 1 w/w % to about 40 w/w % of a compound of Formula (Ia). In some embodiments, the hard gelatin or soft capsule comprises about 40 w/w % to about 80 w/w % of glycerol monocaprylocaprate and about 1 w/w % to about 35 w/w % of a compound of Formula (Ia). In some embodiments, the hard gelatin or soft capsule comprises about 50 w/w % to about 80 w/w % of glycerol monocaprylocaprate and about 2 w/w % to about 30 w/w % of a compound of Formula (Ia). In some embodiments, the hard gelatin or soft capsule comprises about 60 w/w % to about 70 w/w % of glycerol monocaprylocaprate and about 3 w/w % to about 28 w/w % of a compound of Formula (Ia). In some embodiments, the hard gelatin or soft capsule comprises about 65.9 w/w % of glycerol monocaprylocaprate and about 3.4 w/w % of a compound of Formula (Ia). In some embodiments, the hard gelatin or soft capsule comprises about 65.94 w/w % of glycerol monocaprylocaprate and about 3.42 w/w % of a compound of Formula (Ia).

In some embodiments, the hard gelatin or soft capsule comprises about 30 w/w % to about 85 w/w % of glycerol monocaprylocaprate, about 1 w/w % to about 40 w/w % of a compound of Formula (Ia), about 10 w/w % to about 40 w/w % of gelatin, about 3 w/w % to about 25 w/w % of glycerin, about 0.01 w/w % to about 2 w/w % of titanium dioxide, and about 0.01 w/w % to about 1 w/w % of iron oxide. In some embodiments, the hard gelatin or soft capsule comprises about 40 w/w % to about 80 w/w % of glycerol monocaprylocaprate, about 1 w/w % to about 35 w/w % of a compound of Formula (Ia), about 10 w/w % to about 30 w/w % of gelatin, about 5 w/w % to about 20 w/w % of glycerin, about 0.05 w/w % to about 1.5 w/w % of titanium dioxide, and about 0.01 w/w % to about 0.5 w/w % of iron oxide. In some embodiments, the hard gelatin or soft capsule comprises about 50 w/w % to about 80 w/w % of glycerol monocaprylocaprate, about 2 w/w % to about 30 w/w % of a compound of Formula (Ia), about 15 w/w % to about 25 w/w % of gelatin, about 5 w/w % to about 15 w/w % of glycerin, about 0.1 w/w % to about 1.0 w/w % of titanium dioxide, and about 0.01 w/w % to about 0.15 w/w % of iron oxide. In some embodiments, the hard gelatin or soft capsule comprises about 60 w/w % to about 70 w/w % of glycerol monocaprylocaprate, about 3 w/w % to about 28 w/w % of a compound of Formula (Ia), about 18 w/w % to about 22 w/w % of gelatin, about 8 w/w % to about 12 w/w % of glycerin, about 0.1 w/w % to about 0.5 w/w % of titanium dioxide, and about 0.01 w/w % to about 0.1 w/w % of iron oxide. In some embodiments, the hard gelatin or soft capsule comprises about 65.9 w/w % of glycerol monocaprylocaprate, about 3.4 w/w % of a compound of Formula (Ia), about 19.6 w/w % of gelatin, about 10.8 w/w % of glycerin, about 0.2 w/w % of titanium dioxide, and about 0.02 w/w % of iron oxide. In some embodiments, the hard gelatin or soft capsule comprises about 65.94 w/w % of glycerol monocaprylocaprate, about 3.42 w/w % of a compound of Formula (Ia), about 19.60 w/w % of gelatin, about 10.80 w/w % of glycerin, about 0.22 w/w % of titanium dioxide, and about 0.02 w/w % of iron oxide.

In some embodiments, the iron oxide in the hard gelatin or soft gelatin capsule comprising a compound of Formula (Ia), glycerol monocaprylocaprate, gelatin, glycerin, titanium dioxide, and iron oxide comprises iron oxide (yellow). In some embodiments, the hard gelatin or soft capsule comprises about 65.9 w/w % of glycerol monocaprylocaprate, about 3.4 w/w % of a compound of Formula (Ia), about 19.6 w/w % of gelatin, about 10.8 w/w % of glycerin, about 0.2 w/w % of titanium dioxide, and about 0.02 w/w % of iron oxide (yellow). In some embodiments, the hard gelatin or soft capsule comprises about 65.94 w/w % of glycerol monocaprylocaprate, about 3.42 w/w % of a compound of Formula (Ia), about 19.60 w/w % of gelatin, about 10.80 w/w % of glycerin, about 0.22 w/w % of titanium dioxide, and about 0.02 w/w % of iron oxide (yellow).

In some embodiments, the hard gelatin or soft gelatin capsule comprises a sodium salt of the compound of Formula (Ia) and glycerol monocaprylocaprate. In some embodiments, the concentration of the compound of Formula (Ia) in the hard gelatin or soft gelatin capsule comprising a sodium salt of the compound of Formula (Ia) and glycerol monocaprylocaprate is about 10 mg/ml to about 500 mg/ml. In some embodiments, the concentration of the compound of Formula (Ia) in the hard gelatin or soft gelatin capsule comprising a sodium salt of the compound of Formula (Ia) and glycerol monocaprylocaprate is about 10 mg/ml to about 400 mg/ml. In some embodiments, the concentration of the compound of Formula (Ia) in the hard gelatin or soft gelatin capsule comprising a sodium salt of the compound of Formula (Ia) and glycerol monocaprylocaprate is about 50 mg/ml to about 300 mg/ml. In some embodiments, the concentration of the compound of Formula (Ia) in the hard gelatin or soft gelatin capsule comprising a sodium salt of the compound of Formula (Ia) and glycerol monocaprylocaprate is about 75 mg/ml to about 300 mg/ml. In some embodiments, the concentration of the compound of Formula (Ia) in the hard gelatin or soft gelatin capsule comprising a sodium salt of the compound of Formula (Ia) and glycerol monocaprylocaprate is about 10 mg/ml. In some embodiments, the concentration of the compound of Formula (Ia) in the hard gelatin or soft gelatin capsule comprising a sodium salt of the compound of Formula (Ia) and glycerol monocaprylocaprate is about 20 mg/ml. In some embodiments, the concentration of the compound of Formula (Ia) in the hard gelatin or soft gelatin capsule comprising a sodium salt of the compound of Formula (Ia) and glycerol monocaprylocaprate is about 30 mg/ml. In some embodiments, the concentration of the compound of Formula (Ia) in the hard gelatin or soft gelatin capsule comprising a sodium salt of the compound of Formula (Ia) and glycerol monocaprylocaprate is about 40 mg/ml. In some embodiments, the concentration of the compound of Formula (Ia) in the hard gelatin or soft gelatin capsule comprising a sodium salt of the compound of Formula (Ia) and glycerol monocaprylocaprate is about 50 mg/ml. In some embodiments, the concentration of the compound of Formula (Ia) in the hard gelatin or soft gelatin capsule comprising a sodium salt of the compound of Formula (Ia) and glycerol monocaprylocaprate is about 75 mg/ml. In some embodiments, the concentration of the compound of Formula (Ia) in the hard gelatin or soft gelatin capsule comprising a sodium salt of the compound of Formula (Ia) and glycerol monocaprylocaprate is about 100 mg/ml. In some embodiments, the concentration of the compound of Formula (Ia) in the hard gelatin or soft gelatin capsule comprising a sodium salt of the compound of Formula (Ia) and glycerol monocaprylocaprate is about 125 mg/ml. In some embodiments, the concentration of the compound of Formula (Ia) in the hard gelatin or soft gelatin capsule comprising a sodium salt of the compound of Formula (Ia) and glycerol monocaprylocaprate is about 150 mg/ml. In some embodiments, the concentration of the compound of Formula (Ia) in the hard gelatin or soft gelatin capsule comprising a sodium salt of the compound of Formula (Ia) and glycerol monocaprylocaprate is about 175 mg/ml. In some embodiments, the concentration of the compound of Formula (Ia) in the hard gelatin or soft gelatin capsule comprising a sodium salt of the compound of Formula (Ia) and glycerol monocaprylocaprate is about 200 mg/ml. In some embodiments, the concentration of the compound of Formula (Ia) in the hard gelatin or soft gelatin capsule comprising a sodium salt of the compound of Formula (Ia) and glycerol monocaprylocaprate is about 225 mg/ml. In some embodiments, the concentration of the compound of Formula (Ia) in the hard gelatin or soft gelatin capsule comprising a sodium salt of the compound of Formula (Ia) and glycerol monocaprylocaprate is about 250 mg/ml. In some embodiments, the concentration of the compound of Formula (Ia) in the hard gelatin or soft gelatin capsule comprising a sodium salt of the compound of Formula (Ia) and glycerol monocaprylocaprate is about 275 mg/ml. In some embodiments, the concentration of the compound of Formula (Ia) in the hard gelatin or soft gelatin capsule comprising a sodium salt of the compound of Formula (Ia) and glycerol monocaprylocaprate is about 300 mg/ml. In some embodiments, the concentration of the compound of Formula (Ia) in the hard gelatin or soft gelatin capsule comprising a sodium salt of the compound of Formula (Ia) and glycerol monocaprylocaprate is about 325 mg/ml. In some embodiments, the concentration of the compound of Formula (Ia) in the hard gelatin or soft gelatin capsule comprising a sodium salt of the compound of Formula (Ia) and glycerol monocaprylocaprate is about 350 mg/ml. In some embodiments, the concentration of the compound of Formula (Ia) in the hard gelatin or soft gelatin capsule comprising a sodium salt of the compound of Formula (Ia) and glycerol monocaprylocaprate is about 375 mg/ml. In some embodiments, the concentration of the compound of Formula (Ia) in the hard gelatin or soft gelatin capsule comprising a sodium salt of the compound of Formula (Ia) and glycerol monocaprylocaprate is about 400 mg/ml. In some embodiments, the concentration of the compound of Formula (Ia) in the hard gelatin or soft gelatin capsule comprising a sodium salt of the compound of Formula (Ia) and glycerol monocaprylocaprate is about 425 mg/ml. In some embodiments, the concentration of the compound of Formula (Ia) in the hard gelatin or soft gelatin capsule comprising a sodium salt of the compound of Formula (Ia) and glycerol monocaprylocaprate is about 450 mg/ml. In some embodiments, the concentration of the compound of Formula (Ia) in the hard gelatin or soft gelatin capsule comprising a sodium salt of the compound of Formula (Ia) and glycerol monocaprylocaprate is about 475 mg/ml. In some embodiments, the concentration of the compound of Formula (Ia) in the hard gelatin or soft gelatin capsule comprising a sodium salt of the compound of Formula (Ia) and glycerol monocaprylocaprate is about 500 mg/ml.

In some embodiments, the amount of glycerol monocaprylocaprate in the hard gelatin or soft gelatin capsule comprising a sodium salt of the compound of Formula (Ia) and glycerol monocaprylocaprate is about 30 w/w % to about 99 w/w %. In some embodiments, the amount of glycerol monocaprylocaprate in the hard gelatin or soft gelatin capsule comprising a sodium salt of the compound of Formula (Ia) and glycerol monocaprylocaprate is about 50 w/w % to about 99 w/w %. In some embodiments, the amount of glycerol monocaprylocaprate in the hard gelatin or soft gelatin capsule comprising a sodium salt of the compound of Formula (Ia) and glycerol monocaprylocaprate is about 60 w/w % to about 99 w/w %. In some embodiments, the amount of glycerol monocaprylocaprate in the hard gelatin or soft gelatin capsule comprising a sodium salt of the compound of Formula (Ia) and glycerol monocaprylocaprate is about 75 w/w % to about 98 w/w %. In some embodiments, the amount of glycerol monocaprylocaprate in the hard gelatin or soft gelatin capsule comprising a sodium salt of the compound of Formula (Ia) and glycerol monocaprylocaprate is about 80.09 w/w % to about 94.85 w/w %. In some embodiments, the amount of glycerol monocaprylocaprate in the hard gelatin or soft gelatin capsule comprising a sodium salt of the compound of Formula (Ia) and glycerol monocaprylocaprate is about 80.1 w/w % to about 94.9 w/w %. In some embodiments, the amount of glycerol monocaprylocaprate in the hard gelatin or soft gelatin capsule comprising a sodium salt of the compound of Formula (Ia) and glycerol monocaprylocaprate is about 80.09 w/w %. In some embodiments, the amount of glycerol monocaprylocaprate in the hard gelatin or soft gelatin capsule comprising a sodium salt of the compound of Formula (Ia) and glycerol monocaprylocaprate is about 80.1 w/w %. In some embodiments, the amount of glycerol monocaprylocaprate in the hard gelatin or soft gelatin capsule comprising a sodium salt of the compound of Formula (Ia) and glycerol monocaprylocaprate is about 94.85 w/w %. In some embodiments, the amount of glycerol monocaprylocaprate in the hard gelatin or soft gelatin capsule comprising a sodium salt of the compound of Formula (Ia) and glycerol monocaprylocaprate is about 94.9 w/w %.

In some embodiments, the amount of the sodium salt of the compound of Formula (Ia) in the hard gelatin or soft gelatin capsule comprising a sodium salt of the compound of Formula (Ia) and glycerol monocaprylocaprate is about 1 w/w % to about 40 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 1 w/w % to about 35 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 2 w/w % to about 30 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 3 w/w % to about 28 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 5.15 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 5.2 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 19.9 w/w %. In some embodiments, the amount of the sodium salt of the compound of Formula (Ia) in the hard gelatin or soft gelatin capsule comprising a sodium salt of the compound of Formula (Ia) and glycerol monocaprylocaprate is about 19.91 w/w %.

In some embodiments, the hard gelatin or soft gelatin capsule comprising a sodium salt of the compound of Formula (Ia) and glycerol monocaprylocaprate further comprises a capsule shell. In some embodiments, the capsule shell comprises one or more pharmaceutically acceptable excipients. In some embodiments, the one or more pharmaceutically acceptable excipients of the capsule shell is selected from the group consisting of a gelatin shell, a plasticizer, an opacifier, and a colorant. In some embodiments, the hard gelatin or soft gelatin capsule comprising a sodium salt of the compound of Formula (Ia) and glycerol monocaprylocaprate further comprises one or more of a pharmaceutically acceptable excipient selected from the group consisting of gelatin, glycerin, titanium dioxide, and iron oxide. In some embodiments, the hard gelatin or soft gelatin capsule comprising a sodium salt of the compound of Formula (Ia) and glycerol monocaprylocaprate further comprises gelatin. In some embodiments, the hard gelatin or soft gelatin capsule comprising a sodium salt of the compound of Formula (Ia) and glycerol monocaprylocaprate further comprises glycerin. In some embodiments, the hard gelatin or soft gelatin capsule comprising a sodium salt of the compound of Formula (Ia) and glycerol monocaprylocaprate further comprises titanium dioxide. In some embodiments, the hard gelatin or soft gelatin capsule comprising a sodium salt of the compound of Formula (Ia) and glycerol monocaprylocaprate further comprises iron oxide. In some embodiments, the hard gelatin or soft gelatin capsule comprising a sodium salt of the compound of Formula (Ia) and glycerol monocaprylocaprate further comprises gelatin and glycerin. In some embodiments, the hard gelatin or soft gelatin capsule comprising a sodium salt of the compound of Formula (Ia) and glycerol monocaprylocaprate further comprises gelatin, glycerin, and titanium dioxide. In some embodiments, the hard gelatin or soft gelatin capsule comprising a sodium salt of the compound of Formula (Ia) and glycerol monocaprylocaprate further comprises gelatin, glycerin, titanium dioxide, and iron oxide. In some embodiments, the iron oxide of the hard gelatin or soft gelatin capsule comprising a sodium salt of the compound of Formula (Ia), glycerol monocaprylocaprate, gelatin, glycerin, titanium dioxide, and iron oxide comprises iron oxide (yellow).

In some embodiments, the amount of gelatin in the hard gelatin or soft gelatin capsule comprising a sodium salt of the compound of Formula (Ia), glycerol monocaprylocaprate, gelatin, glycerin, titanium dioxide, and iron oxide is about 10 w/w % to about 40 w/w %. In some embodiments, the amount of gelatin in the hard gelatin or soft gelatin capsule comprising a sodium salt of the compound of Formula (Ia), glycerol monocaprylocaprate, gelatin, glycerin, titanium dioxide, and iron oxide is about 10 w/w % to about 30 w/w %. In some embodiments, the amount of gelatin in the hard gelatin or soft gelatin capsule comprising a sodium salt of the compound of Formula (Ia), glycerol monocaprylocaprate, gelatin, glycerin, titanium dioxide, and iron oxide is about 15 w/w % to about 25 w/w %. In some embodiments, the amount of gelatin in the hard gelatin or soft gelatin capsule comprising a sodium salt of the compound of Formula (Ia), glycerol monocaprylocaprate, gelatin, glycerin, titanium dioxide, and iron oxide is about 18 w/w % to about 22 w/w %. In some embodiments, the amount of gelatin in the hard gelatin or soft gelatin capsule comprising a sodium salt of the compound of Formula (Ia), glycerol monocaprylocaprate, gelatin, glycerin, titanium dioxide, and iron oxide is about 19.6 w/w %. In some embodiments, the amount of gelatin in the hard gelatin or soft gelatin capsule comprising a sodium salt of the compound of Formula (Ia), glycerol monocaprylocaprate, gelatin, glycerin, titanium dioxide, and iron oxide is about 19.60 w/w %.

In some embodiments, the amount of glycerin in the hard gelatin or soft gelatin capsule comprising a sodium salt of the compound of Formula (Ia), glycerol monocaprylocaprate, gelatin, glycerin, titanium dioxide, and iron oxide is about 3 w/w % to about 25 w/w %. In some embodiments, the amount of glycerin in the hard gelatin or soft gelatin capsule comprising a sodium salt of the compound of Formula (Ia), glycerol monocaprylocaprate, gelatin, glycerin, titanium dioxide, and iron oxide is about 5 w/w % to about 20 w/w %. In some embodiments, the amount of glycerin in the hard gelatin or soft gelatin capsule comprising a sodium salt of the compound of Formula (Ia), glycerol monocaprylocaprate, gelatin, glycerin, titanium dioxide, and iron oxide is about 5 w/w % to about 15 w/w %. In some embodiments, the amount of glycerin in the hard gelatin or soft gelatin capsule comprising a sodium salt of the compound of Formula (Ia), glycerol monocaprylocaprate, gelatin, glycerin, titanium dioxide, and iron oxide is about 8 w/w % to about 12 w/w %. In some embodiments, the amount of glycerin in the hard gelatin or soft gelatin capsule comprising a sodium salt of the compound of Formula (Ia), glycerol monocaprylocaprate, gelatin, glycerin, titanium dioxide, and iron oxide is about 10.8 w/w %. In some embodiments, the amount of glycerin in the hard gelatin or soft gelatin capsule comprising a sodium salt of the compound of Formula (Ia), glycerol monocaprylocaprate, gelatin, glycerin, titanium dioxide, and iron oxide is about 10.80 w/w %.

In some embodiments, the amount of titanium dioxide in the hard gelatin or soft gelatin capsule comprising a sodium salt of the compound of Formula (Ia), glycerol monocaprylocaprate, gelatin, glycerin, titanium dioxide, and iron oxide is about 0.01 w/w % to about 2 w/w %. In some embodiments, the amount of titanium dioxide in the hard gelatin or soft gelatin capsule comprising a sodium salt of the compound of Formula (Ia), glycerol monocaprylocaprate, gelatin, glycerin, titanium dioxide, and iron oxide is about 0.05 w/w % to about 1.5 w/w %. In some embodiments, the amount of titanium dioxide in the hard gelatin or soft gelatin capsule comprising a sodium salt of the compound of Formula (Ia), glycerol monocaprylocaprate, gelatin, glycerin, titanium dioxide, and iron oxide is about 0.1 w/w % to about 1.0 w/w %. In some embodiments, the amount of titanium dioxide in the hard gelatin or soft gelatin capsule comprising a sodium salt of the compound of Formula (Ia), glycerol monocaprylocaprate, gelatin, glycerin, titanium dioxide, and iron oxide is about 0.1 w/w % to about 0.5 w/w %. In some embodiments, the amount of titanium dioxide in the hard gelatin or soft gelatin capsule comprising a sodium salt of the compound of Formula (Ia), glycerol monocaprylocaprate, gelatin, glycerin, titanium dioxide, and iron oxide is about 0.2 w/w %. In some embodiments, the amount of titanium dioxide in the hard gelatin or soft gelatin capsule comprising a sodium salt of the compound of Formula (Ia), glycerol monocaprylocaprate, gelatin, glycerin, titanium dioxide, and iron oxide is about 0.22 w/w %.

In some embodiments, the amount of iron oxide in the hard gelatin or soft gelatin capsule comprising a sodium salt of the compound of Formula (Ia), glycerol monocaprylocaprate, gelatin, glycerin, titanium dioxide, and iron oxide is about 0.01 w/w % to about 1 w/w %. In some embodiments, the amount of iron oxide in the hard gelatin or soft gelatin capsule comprising a sodium salt of the compound of Formula (Ia), glycerol monocaprylocaprate, gelatin, glycerin, titanium dioxide, and iron oxide is about 0.01 w/w % to about 0.5 w/w %. In some embodiments, the amount of iron oxide in the hard gelatin or soft gelatin capsule comprising a sodium salt of the compound of Formula (Ia), glycerol monocaprylocaprate, gelatin, glycerin, titanium dioxide, and iron oxide is about 0.01 w/w % to about 0.15 w/w %. In some embodiments, the amount of iron oxide in the hard gelatin or soft gelatin capsule comprising a sodium salt of the compound of Formula (Ia), glycerol monocaprylocaprate, gelatin, glycerin, titanium dioxide, and iron oxide is about 0.01 w/w % to about 0.1 w/w %. In some embodiments, the amount of iron oxide in the hard gelatin or soft gelatin capsule comprising a sodium salt of the compound of Formula (Ia), glycerol monocaprylocaprate, gelatin, glycerin, titanium dioxide, and iron oxide is about 0.02 w/w %.

In some embodiments, the hard gelatin or soft capsule disclosed herein comprises about 30 w/w % to about 99 w/w % of glycerol monocaprylocaprate and about 1 w/w % to about 40 w/w % of a sodium salt of the compound of Formula (Ia). In some embodiments, the hard gelatin or soft capsule comprises about 50 w/w % to about 99 w/w % of glycerol monocaprylocaprate and about 1 w/w % to about 35 w/w % of a sodium salt of the compound of Formula (Ia). In some embodiments, the hard gelatin or soft capsule comprises about 60 w/w % to about 99 w/w % of glycerol monocaprylocaprate and about 2 w/w % to about 30 w/w % of a sodium salt of the compound of Formula (Ia). In some embodiments, the hard gelatin or soft capsule comprises about 75 w/w % to about 98 w/w % of glycerol monocaprylocaprate and about 3 w/w % to about 28 w/w % of a sodium salt of the compound of Formula (Ia). In some embodiments, the hard gelatin or soft capsule comprises about 80.09 w/w % to about 94.85 w/w % of glycerol monocaprylocaprate and about 5.15 w/w % to about 19.91 w/w % of a sodium salt of the compound of Formula (Ia). In some embodiments, the hard gelatin or soft capsule comprises about 80.1 w/w % to about 94.9 w/w % of glycerol monocaprylocaprate and about 5.2 w/w % to about 19.9 w/w % of a sodium salt of the compound of Formula (Ia). In some embodiments, the hard gelatin or soft capsule comprises about 94.85 w/w % of glycerol monocaprylocaprate and about 5.15 w/w % of a sodium salt of the compound of Formula (Ia). In some embodiments, the hard gelatin or soft capsule comprises about 94.9 w/w % of glycerol monocaprylocaprate and about 5.2 w/w % of a sodium salt of the compound of Formula (Ia).

In some embodiments, the hard gelatin or soft capsule comprises about 80.09 w/w % of glycerol monocaprylocaprate and about 19.91 w/w % of a sodium salt of the compound of Formula (Ia). In some embodiments, the hard gelatin or soft capsule comprises about 80.1 w/w % of glycerol monocaprylocaprate and about 19.9 w/w % of a sodium salt of the compound of Formula (Ia).

In some embodiments, the iron oxide in the hard gelatin or soft gelatin capsule comprising a sodium salt of the compound of Formula (Ia), glycerol monocaprylocaprate, gelatin, glycerin, titanium dioxide, and iron oxide comprises iron oxide (yellow).

In some embodiments, the oral formulation of a compound of Formula (Ia) or Formula (Ib), or a pharmaceutically acceptable salt thereof, is a tablet. In some embodiments, the tablet is prepared from a spray-dried dispersion of a compound of Formula (Ia) or Formula (Ib), or a pharmaceutically acceptable salt thereof. In some embodiments, the amount of a compound of Formula (Ia) or Formula (Ib), or a pharmaceutically acceptable salt thereof, in the tablet is about 5 mg to about 500 mg. In some embodiments, the amount of a compound of Formula (Ia) or Formula (Ib), or a pharmaceutically acceptable salt thereof, in the tablet is about 25 mg to about 500 mg. In some embodiments, the amount of a compound of Formula (Ia) or Formula (Ib), or a pharmaceutically acceptable salt thereof, in the tablet is about 25 mg to about 400 mg. In some embodiments, the amount of a compound of Formula (Ia) or Formula (Ib), or a pharmaceutically acceptable salt thereof, in the tablet is about 25 mg to about 300 mg. In some embodiments, the amount of a compound of Formula (Ia) or Formula (Ib), or a pharmaceutically acceptable salt thereof, in the tablet is about 50 mg to about 500 mg. In some embodiments, the amount of a compound of Formula (Ia) or Formula (Ib), or a pharmaceutically acceptable salt thereof, in the tablet is about 75 mg to about 500 mg. In some embodiments, the amount of a compound of Formula (Ia) or Formula (Ib), or a pharmaceutically acceptable salt thereof, in the tablet is about 50 mg to about 400 mg. In some embodiments, the amount of a compound of Formula (Ia) or Formula (Ib), or a pharmaceutically acceptable salt thereof, in the tablet is about 50 mg to about 300 mg. In some embodiments, the amount of a compound of Formula (Ia) or Formula (Ib), or a pharmaceutically acceptable salt thereof, in the tablet is about 75 mg to about 400 mg. In some embodiments, the amount of a compound of Formula (Ia) or Formula (Ib), or a pharmaceutically acceptable salt thereof, in the tablet is about 75 mg to about 300 mg. In some embodiments, the amount of a compound of Formula (Ia) or Formula (Ib), or a pharmaceutically acceptable salt thereof, in the tablet is about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, or about 500 mg. In some embodiments, the amount of a compound of Formula (Ia) or Formula (Ib), or a pharmaceutically acceptable salt thereof, in the tablet is about 5 mg. In some embodiments, the amount of a compound of Formula (Ia) or Formula (Ib), or a pharmaceutically acceptable salt thereof, in the tablet is about 10 mg. In some embodiments, the amount of a compound of Formula (Ia) or Formula (Ib), or a pharmaceutically acceptable salt thereof, in the tablet is about 20 mg. In some embodiments, the amount of a compound of Formula (Ia) or Formula (Ib), or a pharmaceutically acceptable salt thereof, in the tablet is about 25 mg. In some embodiments, the amount of a compound of Formula (Ia) or Formula (Ib), or a pharmaceutically acceptable salt thereof, in the tablet is about 30 mg. In some embodiments, the amount of a compound of Formula (Ia) or Formula (Ib), or a pharmaceutically acceptable salt thereof, in the tablet is about 40 mg. In some embodiments, the amount of a compound of Formula (Ia) or Formula (Ib), or a pharmaceutically acceptable salt thereof, in the tablet is about 50 mg. In some embodiments, the amount of a compound of Formula (Ia) or Formula (Ib), or a pharmaceutically acceptable salt thereof, in the tablet is about 75 mg. In some embodiments, the amount of a compound of Formula (Ia) or Formula (Ib), or a pharmaceutically acceptable salt thereof, in the tablet is about 100 mg. In some embodiments, the amount of a compound of Formula (Ia) or Formula (Ib), or a pharmaceutically acceptable salt thereof, in the tablet is about 125 mg. In some embodiments, the amount of a compound of Formula (Ia) or Formula (Ib), or a pharmaceutically acceptable salt thereof, in the tablet is about 150 mg. In some embodiments, the amount of a compound of Formula (Ia) or Formula (Ib), or a pharmaceutically acceptable salt thereof, in the tablet is about 175 mg. In some embodiments, the amount of a compound of Formula (Ia) or Formula (Ib), or a pharmaceutically acceptable salt thereof, in the tablet is about 200 mg. In some embodiments, the amount of a compound of Formula (Ia) or Formula (Ib), or a pharmaceutically acceptable salt thereof, in the tablet is about 225 mg. In some embodiments, the amount of a compound of Formula (Ia) or Formula (Ib), or a pharmaceutically acceptable salt thereof, in the tablet is about 250 mg. In some embodiments, the amount of a compound of Formula (Ia) or Formula (Ib), or a pharmaceutically acceptable salt thereof, in the tablet is about 275 mg. In some embodiments, the amount of a compound of Formula (Ia) or Formula (Ib), or a pharmaceutically acceptable salt thereof, in the tablet is about 300 mg.

In some embodiments, the amount of a compound of Formula (Ia) or Formula (Ib), or a pharmaceutically acceptable salt thereof, in the tablet is about 325 mg. In some embodiments, the amount of a compound of Formula (Ia) or Formula (Ib), or a pharmaceutically acceptable salt thereof, in the tablet is about 350 mg. In some embodiments, the amount of a compound of Formula (Ia) or Formula (Ib), or a pharmaceutically acceptable salt thereof, in the tablet is about 375 mg. In some embodiments, the amount of a compound of Formula (Ia) or Formula (Ib), or a pharmaceutically acceptable salt thereof, in the tablet is about 400 mg. In some embodiments, the amount of a compound of Formula (Ia) or Formula (Ib), or a pharmaceutically acceptable salt thereof, in the tablet is about 425 mg. In some embodiments, the amount of a compound of Formula (Ia) or Formula (Ib), or a pharmaceutically acceptable salt thereof, in the tablet is about 450 mg. In some embodiments, the amount of a compound of Formula (Ia) or Formula (Ib), or a pharmaceutically acceptable salt thereof, in the tablet is about 475 mg. In some embodiments, the amount of a compound of Formula (Ia) or Formula (Ib), or a pharmaceutically acceptable salt thereof, in the tablet is about 500 mg.

In some embodiments, the tablet herein comprises a compound of Formula (Ia) or Formula (Ib), or a pharmaceutically acceptable salt thereof, and one or more pharmaceutically acceptable excipients. In some embodiments, the tablet comprises a compound of Formula (Ia) or a pharmaceutically acceptable salt thereof, and one or more pharmaceutically acceptable excipients. In some embodiments, the tablet comprises a compound of Formula (Ia) and one or more pharmaceutically acceptable excipients. In some embodiments, the tablet comprises a sodium salt of the compound of Formula (Ia) and one or more pharmaceutically acceptable excipients. In some embodiments, the tablet comprises a compound of Formula (Ib) and one or more pharmaceutically acceptable excipients.

The pharmaceutically acceptable excipients of the tablets disclosed herein should be compatible with the other ingredients of the formulation and physiologically innocuous to the recipient thereof. Examples of suitable excipients are well known to the person skilled in the art of tablet formulation and may be found e.g. in Handbook of Pharmaceutical Excipients (eds. Rowe, Sheskey & Quinn), 6th edition 2009. As used herein the term "excipients" is intended to refer to inter alia basifying agents, solubilisers, glidants, fillers, binders, lubricant, diluents, preservatives, surface active agents, dispersing agents and the like. The term also includes agents such as sweetening agents, flavoring agents, coloring agents and preserving agents. Such components will generally be present in admixture within the tablet.

Examples of solubilisers include, but are not limited to, surfactants (including both ionic and non-ionic surfactants) such as sodium lauryl sulphate, cetyltrimethylammonium bromide, polysorbates (such as polysorbate 20 or 80), poloxamers (such as poloxamer 188 or 207), and macrogols. Examples of lubricants, glidants and flow aids include, but are not limited to, magnesium stearate, calcium stearate, stearic acid, hydrogenated vegetable oil, glyceryl palmitostearate, glyceryl behenate, sodium stearyl fumarate, colloidal silicon dioxide, and talc.

Examples of disintegrants include, but are not limited to, starches, celluloses, cross-linked PVP, sodium starch glycolate, croscarmellose sodium, and the like. Examples of fillers (also known as bulking agents or diluents) include, but are not limited to, starches, maltodextrins, polyols (such as lactose), and celluloses. Examples of binders include, but are not limited to, cross-linked PVP, HPMC, microcrystalline cellulose, sucrose, starches, and the like.

In some embodiments, the tablets disclosed herein comprise a compound of Formula (Ia) or Formula (Ib), or a pharmaceutically acceptable salt thereof, and one or more pharmaceutically acceptable excipients selected from the group consisting of a matrix former, a surfactant, a filler, a disintegrant, and a lubricant. In some embodiments, the tablet comprises about 1 w/w % to about 10 w/w % of a matrix former. In some embodiments, the matrix former comprises copovidone. In some embodiments, the tablet comprises about 0.01 w/w % to about 10 w/w % of a surfactant. In some embodiments, the surfactant comprises poloxamer 407. In some embodiments, the tablet comprises about 25-85 w/w % of one or more fillers. In some embodiments, the one or more fillers comprises microcrystalline cellulose and/or mannitol. In some embodiments, the tablet comprises about 1 w/w % to about 30 w/w % of a disintegrant. In some embodiments, the disintegrant comprises croscarmellose sodium. In some embodiments, the tablet comprises about 0.01 w/w % to about 10 w/w % of a lubricant. In some embodiments, the lubricant comprises magnesium stearate.

The tablets disclosed herein may be uncoated or coated (in which case they include an outer film coat). Although uncoated tablets may be used, it is more usual to provide a coated tablet, in which case a conventional non-enteric coating may be used. Film coatings are known in the art and can be composed of hydrophilic polymer materials, but are not limited to, polysaccharide materials, such as hydroxypropylmethyl cellulose (HPMC), methylcellulose, hydroxyethyl cellulose (HEC), hydroxypropyl cellulose (HPC), poly(vinylalcohol-co-ethylene glycol) and other water soluble polymers. Though the water-soluble material included in the film coating of the tablets may include a single polymer material, it may also be formed using a mixture of more than one polymer. The coating may be white or colored. Suitable coatings include, but are not limited to, polymeric film coatings such as those comprising polyvinyl alcohol e.g. 'Opadry® II' (which includes part-hydrolysed PVA, titanium dioxide, macrogol 3350 and talc, with optional colouring such as iron oxide or indigo carmine or iron oxide yellow or FD&C yellow #6). The amount of coating will generally be between about 1-8% of the uncoated tablet's weight.

In some embodiments, the tablet disclosed herein comprises a compound of Formula (Ia) or a pharmaceutically acceptable salt thereof, and one or more pharmaceutically acceptable excipients. In some embodiments, the one or more pharmaceutically acceptable excipients is selected from the group consisting of copovidone, poloxamer 407, microcrystalline cellulose, mannitol, croscarmellose sodium, and magnesium stearate. In some embodiments, the one or more pharmaceutically acceptable excipient comprises copovidone. In some embodiments, the one or more pharmaceutically acceptable excipient comprises poloxamer 407. In some embodiments, the one or more pharmaceutically acceptable excipient comprises microcrystalline cellulose. In some embodiments, the one or more pharmaceutically acceptable excipient comprises mannitol. In some embodiments, the one or more pharmaceutically acceptable excipient comprises croscarmellose sodium. In some embodiments, the one or more pharmaceutically acceptable excipient comprises magnesium stearate. In some embodiments, the one or more pharmaceutically acceptable excipient comprises copovidone and poloxamer 407. In some embodiments, the one or more pharmaceutically acceptable excipient comprises copovidone, poloxamer 407, and microcrystalline cellulose. In some embodiments, the one or more pharmaceutically acceptable excipient comprises copovidone, poloxamer 407, microcrystalline cellulose, and mannitol. In some embodiments, the one or more pharmaceutically acceptable excipient comprises copovidone, poloxamer 407, microcrystalline cellulose, mannitol, and croscarmellose sodium. In some embodiments, the one or more pharmaceutically acceptable excipient comprises copovidone, poloxamer 407, microcrystalline cellulose, mannitol, croscarmellose sodium, and magnesium stearate.

In some embodiments, the tablet disclosed herein comprises a compound of Formula (Ia) or a pharmaceutically acceptable salt thereof, copovidone, poloxamer 407, microcrystalline cellulose, mannitol, croscarmellose sodium, and magnesium stearate. In some embodiments, the tablet comprises a compound of Formula (Ib), or a pharmaceutically acceptable salt thereof, copovidone, poloxamer 407, microcrystalline cellulose, mannitol, croscarmellose sodium, and magnesium stearate. In some embodiments, the tablet comprises a compound of Formula (Ia), copovidone, poloxamer 407, microcrystalline cellulose, mannitol, croscarmellose sodium, and magnesium stearate. In some embodiments, the tablet comprises a compound of Formula (Ib), copovidone, poloxamer 407, microcrystalline cellulose, mannitol, croscarmellose sodium, and magnesium stearate.

In some embodiments, the tablet disclosed herein comprises a sodium salt of the compound of Formula (Ia), copovidone, poloxamer 407, microcrystalline cellulose, mannitol, croscarmellose sodium, and magnesium stearate. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 5 mg to about 500 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 25 mg to about 500 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 25 mg to about 400 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 25 mg to about 300 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 50 mg to about 300 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 5 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 10 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 20 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 25 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 30 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 40 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 50 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 75 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 100 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 125 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 150 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 175 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 200 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 225 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 250 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 275 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 300 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 325 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 350 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 375 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 400 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 425 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 450 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 475 mg. In some embodiments, the amount of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 500 mg.

In some embodiments, the amount of the sodium salt of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 5 w/w % to about 45 w/w %. In some embodiments, the amount of the sodium salt of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 10 w/w % to about 40 w/w %. In some embodiments, the amount of the sodium salt of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 15 w/w % to about 35 w/w %. In some embodiments, the amount of the sodium salt of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 15 w/w % to about 25 w/w %. In some embodiments, the amount of the sodium salt of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 20.46 w/w %. In some embodiments, the amount of the sodium salt of the compound of Formula (Ia) in the tablet comprising a sodium salt of the compound of Formula (Ia), copovidone, poloxamer 407, microcrystalline cellulose, mannitol, croscarmellose sodium, and magnesium stearate is about 20.5 w/w %.

In some embodiments, the amount of copovidone in the tablet comprising a sodium salt of the compound of Formula (Ia), copovidone, poloxamer 407, microcrystalline cellulose, mannitol, croscarmellose sodium, and magnesium stearate is about 1 w/w % to about 10 w/w %. In some embodiments, the amount of copovidone in the tablet comprising a sodium salt of the compound of Formula (Ia), copovidone, poloxamer 407, microcrystalline cellulose, mannitol, croscarmellose sodium, and magnesium stearate is about 2 w/w % to about 10 w/w %. In some embodiments, the amount of copovidone in the tablet comprising a sodium salt of the compound of Formula (Ia), copovidone, poloxamer 407, microcrystalline cellulose, mannitol, croscarmellose sodium, and magnesium stearate is about 3 w/w % to about 8 w/w %. In some embodiments, the amount of copovidone in the tablet comprising a sodium salt of the compound of Formula (Ia), copovidone, poloxamer 407, microcrystalline cellulose, mannitol, croscarmellose sodium, and magnesium stearate is about 3 w/w % to about 6 w/w %. In some embodiments, the amount of copovidone in the tablet comprising a sodium salt of the compound of Formula (Ia), copovidone, poloxamer 407, microcrystalline cellulose, mannitol, croscarmellose sodium, and magnesium stearate is about 4.88 w/w %. In some embodiments, the amount of copovidone in the tablet comprising a sodium salt of the compound of Formula (Ia), copovidone, poloxamer 407, microcrystalline cellulose, mannitol, croscarmellose sodium, and magnesium stearate is about 4.9 w/w %.

In some embodiments, the amount of poloxamer 407 in the tablet comprising a sodium salt of the compound of Formula (Ia), copovidone, poloxamer 407, microcrystalline cellulose, mannitol, croscarmellose sodium, and magnesium stearate is about 0.01 w/w % to about 10 w/w %. In some embodiments, the amount of poloxamer 407 in the tablet comprising a sodium salt of the compound of Formula (Ia), copovidone, poloxamer 407, microcrystalline cellulose, mannitol, croscarmellose sodium, and magnesium stearate is about 0.05 w/w % to about 8 w/w %. In some embodiments, the amount of poloxamer 407 in the tablet comprising a sodium salt of the compound of Formula (Ia), copovidone, poloxamer 407, microcrystalline cellulose, mannitol, croscarmellose sodium, and magnesium stearate is about 0.5 w/w % to about 4 w/w %. In some embodiments, the amount of poloxamer 407 in the tablet comprising a sodium salt of the compound of Formula (Ia), copovidone, poloxamer 407, microcrystalline cellulose, mannitol, croscarmellose sodium, and magnesium stearate is about 0.5 w/w % to about 3.0 w/w %. In some embodiments, the amount of poloxamer 407 in the tablet comprising a sodium salt of the compound of Formula (Ia), copovidone, poloxamer 407, microcrystalline cellulose, mannitol, croscarmellose sodium, and magnesium stearate is about 1.3 w/w %. In some embodiments, the amount of poloxamer 407 in the tablet comprising a sodium salt of the compound of Formula (Ia), copovidone, poloxamer 407, microcrystalline cellulose, mannitol, croscarmellose sodium, and magnesium stearate is about 1.33 w/w %.

In some embodiments, the amount of microcrystalline cellulose in the tablet comprising a sodium salt of the compound of Formula (Ia), copovidone, poloxamer 407, microcrystalline cellulose, mannitol, croscarmellose sodium, and magnesium stearate is about 5 w/w % to about 45 w/w %. In some embodiments, the amount of microcrystalline cellulose in the tablet comprising a sodium salt of the compound of Formula (Ia), copovidone, poloxamer 407, microcrystalline cellulose, mannitol, croscarmellose sodium, and magnesium stearate is about 10 w/w % to about 40 w/w %. In some embodiments, the amount of microcrystalline cellulose in the tablet comprising a sodium salt of the compound of Formula (Ia), copovidone, poloxamer 407, microcrystalline cellulose, mannitol, croscarmellose sodium, and magnesium stearate is about 15 w/w % to about 35 w/w %. In some embodiments, the amount of microcrystalline cellulose in the tablet comprising a sodium salt of the compound of Formula (Ia), copovidone, poloxamer 407, microcrystalline cellulose, mannitol, croscarmellose sodium, and magnesium stearate is about 18 w/w % to about 30 w/w %. In some embodiments, the amount of microcrystalline cellulose in the tablet comprising a sodium salt of the compound of Formula (Ia), copovidone, poloxamer 407, microcrystalline cellulose, mannitol, croscarmellose sodium, and magnesium stearate is about 21.28 w/w %. In some embodiments, the amount of microcrystalline cellulose in the tablet comprising a sodium salt of the compound of Formula (Ia), copovidone, poloxamer 407, microcrystalline cellulose, mannitol, croscarmellose sodium, and magnesium stearate is about 21.3 w/w %.

In some embodiments, the amount of mannitol in the tablet comprising a sodium salt of the compound of Formula (Ia), copovidone, poloxamer 407, microcrystalline cellulose, mannitol, croscarmellose sodium, and magnesium stearate is about 15 w/w % to about 70 w/w %. In some embodiments, the amount of mannitol in the tablet comprising a sodium salt of the compound of Formula (Ia), copovidone, poloxamer 407, microcrystalline cellulose, mannitol, croscarmellose sodium, and magnesium stearate is about 20 w/w % to about 60 w/w %. In some embodiments, the amount of mannitol in the tablet comprising a sodium salt of the compound of Formula (Ia), copovidone, poloxamer 407, microcrystalline cellulose, mannitol, croscarmellose sodium, and magnesium stearate is about 30 w/w % to about 55 w/w %. In some embodiments, the amount of mannitol in the tablet comprising a sodium salt of the compound of Formula (Ia), copovidone, poloxamer 407, microcrystalline cellulose, mannitol, croscarmellose sodium, and magnesium stearate is about 40 w/w % to about 50 w/w %. In some embodiments, the amount of mannitol in the tablet comprising a sodium salt of the compound of Formula (Ia), copovidone, poloxamer 407, microcrystalline cellulose, mannitol, croscarmellose sodium, and magnesium stearate is about 42.55 w/w %. In some embodiments, the amount of mannitol in the tablet comprising a sodium salt of the compound of Formula (Ia), copovidone, poloxamer 407, microcrystalline cellulose, mannitol, croscarmellose sodium, and magnesium stearate is about 42.6 w/w %.

In some embodiments, the amount of croscarmellose sodium in the tablet comprising a sodium salt of the compound of Formula (Ia), copovidone, poloxamer 407, microcrystalline cellulose, mannitol, croscarmellose sodium, and magnesium stearate is about 1 w/w % to about 30 w/w %. In some embodiments, the amount of croscarmellose sodium in the tablet comprising a sodium salt of the compound of Formula (Ia), copovidone, poloxamer 407, microcrystalline cellulose, mannitol, croscarmellose sodium, and magnesium stearate is about 1 w/w % to about 20 w/w %. In some embodiments, the amount of croscarmellose sodium in the tablet comprising a sodium salt of the compound of Formula (Ia), copovidone, poloxamer 407, microcrystalline cellulose, mannitol, croscarmellose sodium, and magnesium stearate is about 4 w/w % to about 16 w/w %. In some embodiments, the amount of croscarmellose sodium in the tablet comprising a sodium salt of the compound of Formula (Ia), copovidone, poloxamer 407, microcrystalline cellulose, mannitol, croscarmellose sodium, and magnesium stearate is about 6 w/w % to about 10 w/w %. In some embodiments, the amount of croscarmellose sodium in the tablet comprising a sodium salt of the compound of Formula (Ia), copovidone, poloxamer 407, microcrystalline cellulose, mannitol, croscarmellose sodium, and magnesium stearate is about 8.0 w/w %. In some embodiments, the amount of croscarmellose sodium in the tablet comprising a sodium salt of the compound of Formula (Ia), copovidone, poloxamer 407, microcrystalline cellulose, mannitol, croscarmellose sodium, and magnesium stearate is about 8.00 w/w %.

In some embodiments, the amount of magnesium stearate in the tablet comprising a sodium salt of the compound of Formula (Ia), copovidone, poloxamer 407, microcrystalline cellulose, mannitol, croscarmellose sodium, and magnesium stearate is about 0.01 w/w % to about 10 w/w %. In some embodiments, the amount of magnesium stearate in the tablet comprising a sodium salt of the compound of Formula (Ia), copovidone, poloxamer 407, microcrystalline cellulose, mannitol, croscarmellose sodium, and magnesium stearate is about 0.05 w/w % to about 8 w/w %. In some embodiments, the amount of magnesium stearate in the tablet comprising a sodium salt of the compound of Formula (Ia), copovidone, poloxamer 407, microcrystalline cellulose, mannitol, croscarmellose sodium, and magnesium stearate is about 0.5 w/w % to about 4 w/w %. In some embodiments, the amount of magnesium stearate in the tablet comprising a sodium salt of the compound of Formula (Ia), copovidone, poloxamer 407, microcrystalline cellulose, mannitol, croscarmellose sodium, and magnesium stearate is about 1.0 w/w % to about 3.0 w/w %. In some embodiments, the amount of magnesium stearate in the tablet comprising a sodium salt of the compound of Formula (Ia), copovidone, poloxamer 407, microcrystalline cellulose, mannitol, croscarmellose sodium, and magnesium stearate is about 1.5 w/w %. In some embodiments, the amount of magnesium stearate in the tablet comprising a sodium salt of the compound of Formula (Ia), copovidone, poloxamer 407, microcrystalline cellulose, mannitol, croscarmellose sodium, and magnesium stearate is about 1.50 w/w %.

In some embodiments, the tablet disclosed herein comprises about 5 w/w % to about 45 w/w % of a sodium salt of the compound of Formula (Ia), about 1 w/w % to about 10 w/w % of copovidone, about 0.01 w/w % to about 10 w/w % of poloxamer 407, about 5 w/w % to about 45 w/w % of microcrystalline cellulose, about 15 w/w % to about 70 w/w % of mannitol, about 1 w/w % to about 30 w/w % of croscarmellose sodium, and about 0.01 w/w % to about 10 w/w % of magnesium stearate. In some embodiments, the tablet comprises about 10 w/w % to about 40 w/w % of a sodium salt of the compound of Formula (Ia), about 2 w/w % to about 10 w/w % of copovidone, about 0.05 w/w % to about 8 w/w % of poloxamer 407, about 10 w/w % to about 40 w/w % of microcrystalline cellulose, about 20 w/w % to about 60 w/w % of mannitol, about 1 w/w % to about 20 w/w % of croscarmellose sodium, and about 0.05 w/w % to about 8 w/w % of magnesium stearate. In some embodiments, the tablet comprises about 15 w/w % to about 35 w/w % of a sodium salt of the compound of Formula (Ia), about 3 w/w % to about 8 w/w % of copovidone, about 0.5 w/w % to about 4 w/w % of poloxamer 407, about 15 w/w % to about 35 w/w % of microcrystalline cellulose, about 30 w/w % to about 55 w/w % of mannitol, about 4 w/w % to about 16 w/w % of croscarmellose sodium, and about 0.5 w/w % to about 4 w/w % of magnesium stearate. In some embodiments, the tablet comprises about 15 w/w % to about 25 w/w % of a sodium salt of the compound of Formula (Ia), about 3 w/w % to about 6 w/w % of copovidone, about 0.5 w/w % to about 3.0 w/w % of poloxamer 407, about 18 w/w % to about 30 w/w % of microcrystalline cellulose, about 40 w/w % to about 50 w/w % of mannitol, about 6 w/w % to about 10 w/w % of croscarmellose sodium, and about 1.0 w/w % to about 3.0 w/w % of magnesium stearate. In some embodiments, the tablet comprises about 20.5 w/w % of a sodium salt of the compound of Formula (Ia), about 4.9 w/w % of copovidone, about 1.3 w/w % of poloxamer 407, about 21.3 w/w % of microcrystalline cellulose, about 42.6 w/w % of mannitol, about 8.0 w/w % of croscarmellose sodium, and about 1.5 w/w % of magnesium stearate. In some embodiments, the tablet comprises about 20.46 w/w % of a sodium salt of the compound of Formula (Ia), about 4.88 w/w % of copovidone, about 1.33 w/w % of poloxamer 407, about 21.28 w/w % of microcrystalline cellulose, about 42.55 w/w % of mannitol, about 8.00 w/w % of croscarmellose sodium, and about 1.50 w/w % of magnesium stearate.

In some embodiments, the tablet disclosed herein further comprises an outer film coat. In some embodiments, the tablet comprising a sodium salt of the compound of Formula (Ia), copovidone, poloxamer 407, microcrystalline cellulose, mannitol, croscarmellose sodium, and magnesium stearate further comprises an outer film coat. In some embodiments, the outer film coat provides from about 1% to about 8% weight gain based on the uncoated tablet. In some embodiments, the outer film coat provides from about 2% to about 6% weight gain based on the uncoated tablet. In some embodiments, the outer film coat provides from about 2% to about 4% weight gain based on the uncoated tablet. In some embodiments, the outer film coat provides from about 4% to about 6% weight gain based on the uncoated tablet. In some embodiments, the outer film coat provides about 1%, about 2%, about 3%, about 4%, about 5%, about 6%, about 7%, or about 8% weight gain based on the uncoated tablet. In some embodiments, the outer film coat provides about 1% weight gain based on the uncoated tablet. In some embodiments, the outer film coat provides about 2% weight gain based on the uncoated tablet. In some embodiments, the outer film coat provides about 3% weight gain based on the uncoated tablet. In some embodiments, the outer film coat provides about 4% weight gain based on the uncoated tablet. In some embodiments, the outer film coat provides about 5% weight gain based on the uncoated tablet. In some embodiments, the outer film coat provides about 6% weight gain based on the uncoated tablet. In some embodiments, the outer film coat provides about 7% weight gain based on the uncoated tablet. In some embodiments, the outer film coat provides about 8% weight gain based on the uncoated tablet. In some embodiments, the outer film coat comprises Opadry® II. In some embodiments, the outer film coat comprises Opadry® II White. In some embodiments, the outer film coat comprises Opadry® II White 85F18422.

In some embodiments, the outer film coat comprises Opadry® II Green. In some embodiments, the outer film coat comprises Opadry® II Green 85F110187. In some embodiments, the outer film coat comprises Opadry® II Green 85F110186.

In some embodiments, the tablet comprises about 20.5 w/w % of a sodium salt of a compound of Formula (Ia), about 4.9 w/w % copovidone, about 1.3 w/w % poloxamer 407, about 21.3 w/w % of microcrystalline cellulose, about 42.6 w/w % of mannitol, about 8.0 w/w % of croscarmellose sodium, about 1.5 w/w % of magnesium stearate, and about 3% weight gain from Opadry® II White 85F18422, wherein the weight gain is based on the uncoated tablet. In some embodiments, the tablet comprises about 20.46 w/w % of a sodium salt of a compound of Formula (Ia), about 4.88 w/w % copovidone, about 1.33 w/w % poloxamer 407, about 21.28 w/w % of microcrystalline cellulose, about 42.55 w/w % of mannitol, about 8.00 w/w % of croscarmellose sodium, about 1.50 w/w % of magnesium stearate, and about 3.0% weight gain from Opadry® II White 85F18422, wherein the weight gain is based on the uncoated tablet.

In some embodiments, the tablet comprises about 20.5 w/w % of a sodium salt of a compound of Formula (Ia), about 4.9 w/w % copovidone, about 1.3 w/w % poloxamer 407, about 21.3 w/w % of microcrystalline cellulose, about 42.6 w/w % of mannitol, about 8.0 w/w % of croscarmellose sodium, about 1.5 w/w % of magnesium stearate, and about 4% weight gain from Opadry® II Green 85F110187, wherein the weight gain is based on the uncoated tablet. In some embodiments, the tablet comprises about 20.46 w/w % of a sodium salt of a compound of Formula (Ia), about 4.88 w/w % copovidone, about 1.33 w/w % poloxamer 407, about 21.28 w/w % of microcrystalline cellulose, about 42.55 w/w % of mannitol, about 8.00 w/w % of croscarmellose sodium, about 1.50 w/w % of magnesium stearate, and about 4.0% weight gain from Opadry® II Green 85F110187, wherein the weight gain is based on the uncoated tablet.

In some embodiments, the tablet comprises about 20.5 w/w % of a sodium salt of a compound of Formula (Ia), about 4.9 w/w % copovidone, about 1.3 w/w % poloxamer 407, about 21.3 w/w % of microcrystalline cellulose, about 42.6 w/w % of mannitol, about 8.0 w/w % of croscarmellose sodium, about 1.5 w/w % of magnesium stearate, and about 4% weight gain from Opadry® II Green 85F110186, wherein the weight gain is based on the uncoated tablet. In some embodiments, the tablet comprises about 20.46 w/w % of a sodium salt of a compound of Formula (Ia), about 4.88 w/w % copovidone, about 1.33 w/w % poloxamer 407, about 21.28 w/w % of microcrystalline cellulose, about 42.55 w/w % of mannitol, about 8.00 w/w % of croscarmellose sodium, about 1.50 w/w % of magnesium stearate, and about 4.0% weight gain from Opadry® II Green 85F110186, wherein the weight gain is based on the uncoated tablet.

The pharmaceutical compositions disclosed herein can be also prepared by other methodologies known in the pharmaceutical art. For example, in certain embodiments, a pharmaceutical composition intended to be administered by injection can prepared by combining the compound of Formula (Ia) or Formula (Ib), or a pharmaceutically acceptable salt thereof, with sterile, distilled water so as to form a solution. In some embodiments, a surfactant is added to facilitate the formation of a homogeneous solution or suspension. Surfactants are compounds that non-covalently interact with the compound of Formula (Ia) or Formula (Ib), or a pharmaceutically acceptable salt thereof, so as to facilitate dissolution or homogeneous suspension of the compound in the aqueous delivery system.

The terms "effective amount" or "therapeutically effective amount" refer to an amount of the compound of Formula (Ia) or Formula (Ib), or other anti-HIV agent, or a pharmaceutically acceptable salt thereof, which when administered to a subject in need thereof, is sufficient to effect preventing an HIV infection or reducing the risk of contracting HIV infection, as described herein. Such an amount would be sufficient to elicit the biological or medical response of a tissue system, or subject that is sought by a researcher or clinician. The amount of the compound of Formula (Ia) or Formula (Ib) or other anti-HIV agent which constitutes a therapeutically effective amount will vary depending on such factors as the compound, salt, or composition used for administration, the time of administration, the route of administration, the rate of excretion of the compound, the duration of the treatment, the type of disease-state or disorder being treated and its severity, drugs used in combination with or coincidentally with the compound of Formula (Ia) or Formula (Ib), and the age, body weight, general health, sex and diet of the subject. Such a therapeutically effective amount can be determined routinely by one of ordinary skill in the art having regard to their own knowledge, the state of the art, and this disclosure.

The term "subject" is meant to refer to a human or other mammals such as laboratory animals and household pets (e.g., cats, dogs, swine, cattle, sheep, goats, horses, rabbits), and non-domestic animals such as non-human primates, mammalian wildlife, and the like, that are in need of therapeutic or preventative treatment for a viral infection, such as HIV infection. In some embodiments of the methods provided herein, the subject is a human.

Combination Therapies

One or more additional therapeutic agents can be used in combination with the compounds, salts, and compositions of the present disclosure for preventing an HIV infection in a subject (e.g., in a human subject). In some embodiments, the composition of the disclosure comprises the compound of Formula (Ia) or Formula (Ib), or a pharmaceutically acceptable salt thereof, and one or more additional therapeutic agents.

In some embodiments, the composition of the disclosure comprises a compound of Formula (Ia) or Formula (Ib), or a pharmaceutically acceptable salt thereof, and one to three additional therapeutic agents (e.g., one to three anti-HIV agents). In some embodiments, the methods provided herein further comprise administering one to three additional therapeutic agents to the subject. In some embodiments, the compound of Formula (Ia) or Formula (Ib), or a pharmaceutically acceptable salt thereof, and the one to three additional therapeutic agents are administered simultaneously. In some embodiments, the compound of Formula (Ia) or Formula (Ib), or a pharmaceutically acceptable salt thereof, and the one to three additional therapeutic agents are administered as a unitary dosage form. In some embodiments, the compound of Formula (Ia) or Formula (Ib), or a pharmaceutically acceptable salt thereof, and the one to three additional therapeutic agents are administered as a fixed dose combination tablet. In some embodiments, the compound of Formula (Ia) or Formula (Ib), or a pharmaceutically acceptable salt thereof, and the one to three additional therapeutic agents are administered sequentially.

In the above embodiments, the one to three additional therapeutic agents may be anti-HIV agents. For example, in some embodiments, each of the additional therapeutic agents is independently selected from the group consisting of HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, compounds that target the HIV capsid ("capsid inhibitors"; e.g., capsid polymerization inhibitors or capsid disrupting compounds such as those disclosed in WO 2013/006738 (Gilead Sciences), US 2013/0165489 (University of Pennsylvania), and WO 2013/006792 (Pharma Resources), pharmacokinetic enhancers, and other drugs for treating HIV, and combinations thereof. In some embodiments, each of the additional therapeutic agents is independently selected from an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a broadly neutralizing antibody (e.g., against HIV), a bispecific antibody (e.g., against HIV), an HIV vaccine, and an HIV capsid inhibitor, or any combination thereof. In some embodiments, the anti-HIV agent is an HIV protease inhibitor, an HIV non-nucleoside inhibitor of reverse transcriptase, an HIV nucleoside inhibitor of reverse transcriptase, an HIV nucleotide inhibitor of reverse transcriptase, a pharmacokinetic enhancer, broadly neutralizing antibodies against HIV, bispecific antibodies against HIV, an HIV vaccine, or combination thereof. In some embodiments, the anti-HIV agent is an HIV nucleoside inhibitor of reverse transcriptase, an HIV nucleotide inhibitor of reverse transcriptase, or combination thereof. In some embodiments, each of the one or more additional therapeutic agents is an anti-HIV agent.

In further embodiments, the additional therapeutic agent is selected from one or more of:

(1) HIV protease inhibitors selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, AG 1859, and the compounds disclosed in U.S. Patent Application Publication No. US20180258097;

(2) HIV non-nucleoside or non-nucleotide inhibitors of reverse transcriptase selected from the group consisting of rilpivirine, doravirine, capravirine, emivirine, delaviridine, efavirenz, nevirapine, (+) calanolide A, etravirine, GW5634, DPC-083, DPC-961, DPC-963, MIV-150, TMC-120, rilpivirene, BILR 355 BS, VRX 840773, lersivirine (UK-453061), RDEA806, KM023 and MK-1439;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, phosphazide, fozivudine tidoxil, apricitibine (AVX754), KP-1461, GS-9131 (Gilead Sciences), MK-8591, and fosalvudine tidoxil (formerly HDP 99.0003);

(4) HIV nucleotide inhibitors of reverse transcriptase selected from the group consisting of tenofovir, tenofovir disoproxil fumarate, tenofovir alafenamide (Gilead Sciences), GS-7340 (Gilead Sciences), GS-9148 (Gilead Sciences), adefovir, adefovir dipivoxil, CMX-001 (Chimerix) or CMX-157 (Chimerix);

(5) HIV integrase inhibitors selected from the group consisting of raltegravir, elvitegravir, dolutegravir, bictegravir, cabotegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, BMS-538158, GSK364735C, BMS-707035, MK-2048, BA 011, and GSK-744;

(6) HIV non-catalytic site, or allosteric, integrase inhibitors (NCINI) including, but not limited to, BI-224436, CX0516, CX05045, CX14442, compounds disclosed in WO 2009/062285 (Boehringer Ingelheim), WO 2010/130034 (Boehringer Ingelheim), WO 2013/159064 (Gilead Sciences), WO 2012/145728 (Gilead Sciences), WO 2012/003497 (Gilead Sciences), WO 2012/003498 (Gilead Sciences) each of which is incorporated by references in its entirety herein;

(7) gp41 inhibitors selected from the group consisting of enfuvirtide, sifuvirtide, albuvirtide, FB006M, and TRI-1144;

(8) the CXCR4 inhibitor AMD-070;

(9) the entry inhibitor SP01A;

(10) gp120 inhibitors, including BMS-488043;

(11) the G6PD and NADH-oxidase inhibitor immunitin;

(12) CCR5 inhibitors selected from the group consisting of aplaviroc, vicriviroc, maraviroc, cenicriviroc, PRO-140, INCB15050, PF-232798 (Pfizer), and CCR5mAb004;

(13) CD4 attachment inhibitors, including ibalizumab (TMB-355) and BMS-068 (BMS-663068);

(14) pharmacokinetic enhancers selected from the group consisting of ritonavir, cobicistat and SPI-452;

(15) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040);

(16) pharmaceutically acceptable salts of the compounds disclosed in U.S. Patent Application Publication No. US20180258097;

(17) compounds disclosed in U.S. Pat. No. 9,730,936, or a pharmaceutically acceptable salt thereof;

and combinations thereof.

As used herein, "bictegravir" or "BIC" each refer to the integrase inhibitor drug compound (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (IUPAC name) represented by the structure shown below:

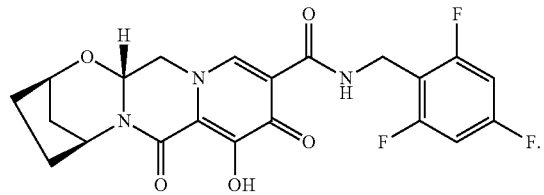 [SMILES: O=C(NCc1c(F)cc(F)cc1F)c1cn2c(c(O)c1=O)C(=O)N1[C@H]3CC[C@H](C3)O[C@@H]1C2]

Bictegravir is described in U.S. Pat. No. 9,216,996, the disclosure of which is incorporated herein by reference in its entirety. The term bictegravir further includes its pharmaceutically acceptable salts including, for example, its mono sodium salt.

As used herein, "elvitegravir" or "EVG" each refer to the integrase inhibitor drug compound 6-(3-chloro-2-fluorobenzyl)-1-[(2S)-1-hydroxy-3-methylbutan-2-yl]-7-methoxy-4-oxo-1,4-dihydroquinoline-3-carboxylic acid represented by the structure shown below:

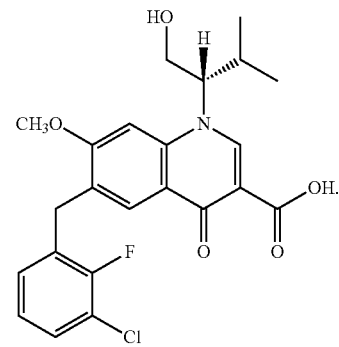

Elvitegravir is described in U.S. Pat. No. 9,216,996, the disclosure of which is incorporated herein by reference in its entirety. The term elvitegravir further includes its pharmaceutically acceptable salts including, for example, its mono sodium salt.

In some embodiments, elvitegravir, or a pharmaceutically acceptable salt thereof, is administered to the subject in a dosage of from about 1 mg to about 200 mg, for example, about 1 mg, about 5 mg, about 10 mg, about 25 mg, about 50 mg, about 75 mg, about 100 mg, about 125 mg, about 150 mg, about 175 mg, or about 200 mg. When administered daily, the dosage can be about 1 mg/day to about 200 mg/day, for example, about 1 mg/day, about 5 mg/day, about 10 mg/day, about 25 mg/day, about 50 mg/day, about 75 mg/day, about 100 mg/day, about 125 mg/day, about 150 mg/day, about 175 mg/day, or about 200 mg/day. In some embodiments, elvitegravir, or a pharmaceutically acceptable salt thereof, is administered to the subject in a dosage of from about 100 mg to about 200 mg. In some embodiments, elvitegravir, or a pharmaceutically acceptable salt thereof, is administered in a dosage of from about 125 mg to about 175 mg. In some embodiments, elvitegravir, or a pharmaceutically acceptable salt thereof, is administered in a dosage of from about 150 mg to about 160 mg. In some embodiments, elvitegravir, or a pharmaceutically acceptable salt thereof, is administered in a dosage of about 150 mg. In some embodiments, the elvitegravir is a pharmaceutically acceptable salt of elvitegravir. In some embodiments, the elvitegravir is elvitegravir sodium salt. In some embodiments, the elvitegravir is administered as the sodium salt in a dosage of about 157 mg.

As used herein, "tenofovir alafenamide" or "TAF" each refer to the nucleoside analog reverse transcriptase inhibitor drug compound {9-[(R)-2-[[(S)—[[(S)-1-(isopropoxycarbonyl)ethyl]amino]phenoxyphosphinyl]-methoxy]propyl]adenine} having the structure shown below.

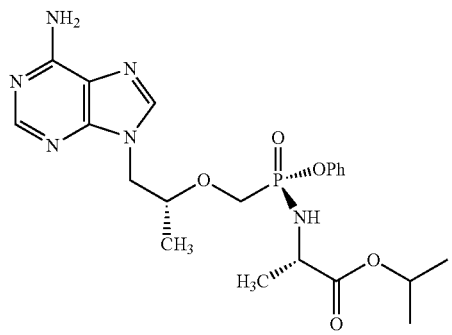 [SMILES: CC(C)OC(=O)[C@H](C)N[P@](=O)(CO[C@H](C)Cn1cnc2c(N)ncnc21)Oc1ccccc1]

TAF may be associated with fumarate, such as monofumarate and hemifumarate salts or co-crystal (co-formers). See, e.g., U.S. Pat. Nos. 7,390,791, 7,803,788, and 8,754,065, each of which is hereby incorporated by reference in its entirety. It is understood that reference to "TAF" may be inclusive of a co-formers, such as fumarate. In some embodiments, the tenofovir alafenamide, or a pharmaceutically acceptable salt thereof, is tenofovir alafenamide hemifumarate. TAF is the active pharmaceutical ingredient in Vemlidy® and is a component of the tablets Bictarvy®, Genvoya®, Descovy®, Odefsey®, and Symtuza®.

In the absence of specific reference to a particular pharmaceutically acceptable salt and/or solvate of tenofovir alafenamide, any dosages, whether expressed in milligrams or as a % by weight, should be understood as referring to the amount of tenofovir alafenamide free base. For example reference to 25 mg of tenofovir alafenamide, or a pharmaceutically acceptable salt and/or solvate thereof, refers to an amount of tenofovir alafenamide, or a pharmaceutically acceptable salt and/or solvate thereof, which provides the same amount of tenofovir alafenamide as 25 mg of tenofovir alafenamide free base. In some embodiments, a dosage referring to 25 mg of tenofovir alafenamide contains about 28 mg of tenofovir alafenamide hemifumarate.

As used herein, "tenofovir disoproxil" or "TD" each refer to the compound 9-[(R) [[bis[[(isopropoxycarbonyl)oxy]methoxy]phosphinyl]methoxy]propyl]adenine. TD, a prodrug of tenofovir, may be associated with fumarate, such as monofumarate. See e.g., U.S. Pat. Nos. 5,922,695, 5,935,946, and 5,977,089, each of which is hereby incorporated by reference in its entirety. Tenofovir disoproxil fumarate is referred to as "TDF" and is the active pharmaceutical ingredient in Viread®.

In the absence of specific reference to a particular pharmaceutically acceptable salt and/or solvate of tenofovir disoproxil, any dosages, whether expressed in milligrams or as a % by weight, should be taken as referring to the amount of tenofovir disoproxil free base. For example, reference to 245 mg tenofovir disoproxil, or a pharmaceutically acceptable salt and/or solvate thereof, refers to an amount of tenofovir disoproxil or a pharmaceutically acceptable salt and/or solvate thereof which provides the same amount of tenofovir disoproxil as 245 mg of tenofovir disoproxil free base. In some embodiments, a dosage referring to 245 mg of tenofovir disoproxil contains about 300 mg of tenofovir disoproxil fumarate.

As used herein, "emtricitabine" or "FTC" each refer to the compound 4-amino-5-fluoro-1-[(2R,5S)-2-(hydroxymethyl)-1,3-oxathiolan-5-yl]-1,2-dihydropyrimidin-2-one having the below structure.

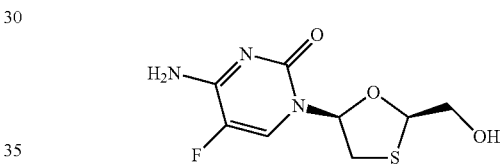

Emtricitabine can be present in dosage forms as a free base or as a pharmaceutically acceptable salt. Additionally, emtricitabine can be present in dosage forms in solvated or unsolvated forms. Typically, emtricitabine is present as a free base.

The present disclosure further provides that for any of the embodiments provided herein, emtricitabine, or a pharmaceutically acceptable salt thereof, can be replaced by lamivudine (i.e., 3TC), or a pharmaceutically acceptable salt thereof, in any appropriate dosage (e.g., 10 mg to 300 mg; 100 mg to 200 mg; 150 mg, and the like), or combination with other additional therapeutic agents, including the compounds of Formula (Ia) and Formula (Ib), or pharmaceutically acceptable salts thereof, as described herein.

In the absence of specific reference to a particular pharmaceutically acceptable salt and/or solvate of emtricitabine, any dosages, whether expressed in milligrams or as a % by weight, should be taken as referring to the amount of emtricitabine free base. For example, reference to 200 mg emtricitabine, or a pharmaceutically acceptable salt and/or solvate thereof, refers to an amount of emtricitabine or a pharmaceutically acceptable salt and/or solvate thereof which provides the same amount of emtricitabine as 200 mg of emtricitabine free base.

As used herein, "cobicistat" or "cobi" each refer to the compound 2,7,10,12-tetraazatridecanoic acid, 12-methyl-13-[2-(1-methylethyl)-4-thiazolyl]-9-[2-(4-morpholinyl)ethyl]-8,11-dioxo-3,6-bis(phenylmethyl)-, 5-thiazolylmethyl ester, (3R,6R,9S)- having the below structure.

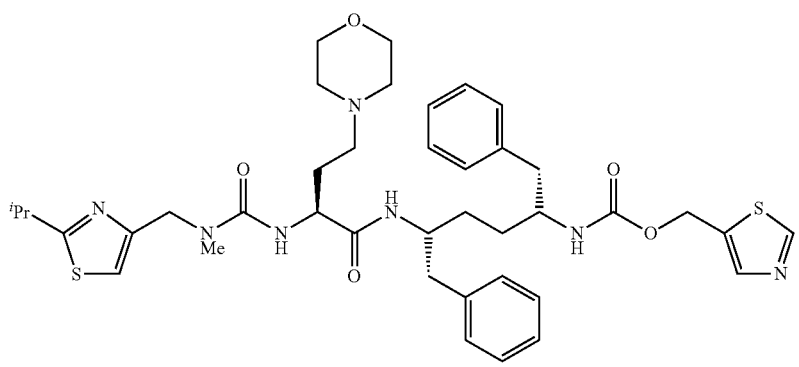

Cobicistat can be present in dosage forms as a free base or as a pharmaceutically acceptable salt. Additionally, cobicistat can be present in dosage forms in solvated or unsolvated forms. Typically, cobicistat is present as a free base. In certain embodiments, cobicistat is present in pharmaceutical compositions in combination with elvitegravir.

In the absence of specific reference to a particular pharmaceutically acceptable salt and/or solvate of cobicistat, any dosages, whether expressed in milligrams or as a % by weight, should be taken as referring to the amount of cobicistat free base. For example, reference to 200 mg cobicistat or a pharmaceutically acceptable salt and/or solvate thereof refers to an amount of cobicistat or a pharmaceutically acceptable salt and/or solvate thereof which provides the same amount of cobicistat as 200 mg of cobicistat free base.

In some embodiments, cobicistat, or a pharmaceutically acceptable salt thereof, is administered to the subject in a dosage of from about 1 mg to about 200 mg, for example, about 1 mg, about 5 mg, about 10 mg, about 25 mg, about 50 mg, about 75 mg, about 100 mg, about 125 mg, about 150 mg, about 175 mg, or about 200 mg. When administered daily, the dosage can be about 1 mg/day to about 200 mg/day, for example, about 1 mg/day, about 5 mg/day, about 10 mg/day, about 25 mg/day, about 50 mg/day, about 75 mg/day, about 100 mg/day, about 125 mg/day, about 150 mg/day, about 175 mg/day, or about 200 mg/day. In some embodiments, cobicistat, or a pharmaceutically acceptable salt thereof, is administered to the subject in a dosage of from about 100 mg to about 200 mg. In some embodiments, cobicistat, or a pharmaceutically acceptable salt thereof, is administered in a dosage of from about 125 mg to about 175 mg. In some embodiments, cobicistat, or a pharmaceutically acceptable salt thereof, is administered in a dosage of from about 150 mg to about 160 mg. In some embodiments, cobicistat, or a pharmaceutically acceptable salt thereof, is administered in a dosage of about 150 mg.

In some embodiments, the compound of Formula (Ia) or Formula (Ib), or a pharmaceutically acceptable salt thereof, is combined with one, two, three, or more additional therapeutic agents. The one, two, three, or more additional therapeutic agents can be different therapeutic agents selected from the same class of therapeutic agents, or they can be selected from different classes of therapeutic agents. In a specific embodiment, the compound of Formula (Ia) or Formula (Ib), or a pharmaceutically acceptable salt thereof, is combined with an HIV nucleotide or nucleoside inhibitor of reverse transcriptase and an HIV non-nucleoside inhibitor of reverse transcriptase. In another specific embodiment, the compound of Formula (Ia) or Formula (Ib), or a pharmaceutically acceptable salt thereof, is combined with an HIV nucleotide or nucleoside inhibitor of reverse transcriptase, and an HIV protease inhibiting compound. In a further embodiment, the compound of Formula (Ia) or Formula (Ib), or a pharmaceutically acceptable salt thereof, is combined with an HIV nucleotide or nucleoside inhibitor of reverse transcriptase, an HIV non-nucleoside inhibitor of reverse transcriptase, and an HIV protease inhibiting compound. In an additional embodiment, the compound of Formula (Ia) or Formula (Ib), or a pharmaceutically acceptable salt thereof, is combined with an HIV nucleotide or nucleoside inhibitor of reverse transcriptase, an HIV non-nucleoside inhibitor of reverse transcriptase, and a pharmacokinetic enhancer.

In some embodiments, the compound of Formula (Ia) or Formula (Ib), or a pharmaceutically acceptable salt thereof, is administered in combination with an additional therapeutic agent which is bictegravir, or a pharmaceutically acceptable salt thereof.

In some embodiments, the additional therapeutic agent is bictegravir sodium (i.e., a bictegravir sodium salt). In some embodiments, the bictegravir, or a pharmaceutically acceptable salt thereof, is administered to the subject in a dosage of from about 1 mg to about 2000 mg, for example, about 1 mg, about 5 mg, about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1900 mg, about 1925 mg, about 1950 mg, about 1975 mg, or about 2000 mg. When administered daily, the dosage can be about 1 mg/day to about 200 mg/day, for example, about 1 mg/day, about 5 mg/day, about 10 mg/day, about 25 mg/day, about 50 mg/day, about 75 mg/day, about 100 mg/day, about 125 mg/day, about 150 mg/day, about 175 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day, or about 500 mg/day. In some embodiments, bictegravir, or a pharmaceutically acceptable salt thereof, is administered to the subject in a dosage of from about 10 mg to about 2000 mg. In some embodiments, bictegravir, or a pharmaceutically acceptable salt thereof, is administered to the subject in a dosage of from about 10 mg to about 200 mg. In some embodiments, bictegravir, or a pharmaceutically acceptable salt thereof, is administered to the subject in a dosage of from about 50 mg to about 2000 mg. In some embodiments, bictegravir, or a pharmaceutically acceptable salt thereof, is administered to the subject in a dosage of from about 50 mg to about 200 mg. In some embodiments, bictegravir, or a pharmaceutically acceptable salt thereof, is administered to the subject in a dosage of from about 10 mg to about 1000 mg. In some embodiments, bictegravir, or a pharmaceutically acceptable salt thereof, is administered to the subject in a dosage of from about 10 mg to about 100 mg. In some embodiments, bictegravir, or a pharmaceutically acceptable salt thereof, is administered in a dosage of from about 50 mg to about 100 mg. In some embodiments, bictegravir, or a pharmaceutically acceptable salt thereof, is administered in a dosage of from about 50 mg to about 600 mg (e.g., at a dosage of about about 50 mg, about 100 mg, about 150 mg, about 200 mg, about 250 mg, about 300 mg, about 350 mg, about 400 mg, about 400 mg, about 450 mg, about 500 mg, about 550 mg, or about 600 mg). In some embodiments, bictegravir, or a pharmaceutically acceptable salt thereof, is administered in a dosage of from about 50 mg to about 150 mg. In some embodiments, bictegravir, or a pharmaceutically acceptable salt thereof, is administered in a dosage of about 100 mg. In some embodiments, bictegravir, or a pharmaceutically acceptable salt thereof, is administered in a dosage of about 75 mg. In some embodiments, bictegravir, or a pharmaceutically acceptable salt thereof, is administered in a dosage of from about 45 mg to about 55 mg. In some embodiments, bictegravir, or a pharmaceutically acceptable salt thereof, is administered in a dosage of about 50 mg. In some embodiments, the bictegravir is a pharmaceutically acceptable salt of bictegravir. In some embodiments, the bictegravir is bictegravir sodium salt. In some embodiments, the bictegravir is administered as the sodium salt in a dosage of about 52 mg (e.g., 52.5 mg). In some embodiments, the bictegravir is administered as the sodium salt in a dosage of about 104 mg (e.g., 105 mg). In some embodiments, the bictegravir is administered subcutaneously (e.g., in a dosage of from about 50 mg to about 2000 mg; a dosage of from about 100 mg to about 600 mg; a dosage of from about 100 mg to about 500 mg; a dosage of about 400 mg; a dosage of about 500 mg; or a dosage of about 600 mg). In some embodiments, the bictegravir is administered orally (e.g., in a dosage of from about 50 mg to about 200 mg; a dosage of about 50 mg; or a dosage of about 100 mg). In some embodiments, the bicetgravir is administered in a long-acting (or sustained release) dosage form.

In some embodiments, the compound of Formula (Ia) or Formula (Ib), or a pharmaceutically acceptable salt thereof, is administered in combination with an additional therapeutic agent which is emtricitabine, or a pharmaceutically acceptable salt thereof. In some embodiments, the additional therapeutic agent is emtricitabine.

In some embodiments, the emtricitabine, or a pharmaceutically acceptable salt thereof, is administered in a dosage of about 10 mg to about 500 mg, for example, about 10 mg, about 50 mg, about 100 mg, about 150 mg, about 200 mg, about 250 mg, about 300 mg, about 350 mg, about 400 mg, about 450 mg, or about 500 mg. When administered daily, the dosage can be about 10 mg/day to about 500 mg/day, for example, about 10 mg/day, about 50 mg/day, about 100 mg/day, about 150 mg/day, about 200 mg/day, about 250 mg/day, about 300 mg/day, about 350 mg/day, about 400 mg/day, about 450 mg/day, or about 500 mg/day. In some embodiments, the emtricitabine, or a pharmaceutically acceptable salt thereof, is administered in a dosage of about 100 mg to about 300 mg. In some embodiments, the emtricitabine, or a pharmaceutically acceptable salt thereof, is administered in a dosage of about 175 mg to about 225 mg. In some embodiments, the emtricitabine, or a pharmaceutically acceptable salt thereof, is administered in a dosage of about 190 mg to about 210 mg. In some embodiments, the emtricitabine, or a pharmaceutically acceptable salt thereof, is administered in a dosage of about 200 mg.

In some embodiments, the compound of Formula (Ia) or Formula (Ib), or a pharmaceutically acceptable salt thereof, is administered in combination with an additional therapeutic agent selected from tenofovir alafenamide, or a pharmaceutically acceptable salt thereof, and tenofovir disoproxil, or a pharmaceutically acceptable salt thereof.

In some embodiments, the additional therapeutic agent is tenofovir alafenamide, or a pharmaceutically acceptable salt thereof. In some embodiments, the tenofovir alafenamide, or a pharmaceutically acceptable salt thereof, is administered in a dosage of 1 mg to about 100 mg, for example, about 1 mg, about 10 mg, about 25 mg, about 50 mg, about 75 mg, or about 100 mg. When administered daily, the dosage can be about 1 mg/day to about 100 mg/day, for example, about 1 mg/day, about 10 mg/day, about 25 mg/day, about 50 mg/day, about 75 mg/day, or about 100 mg/day. In some embodiments, the tenofovir alafenamide, or a pharmaceutically acceptable salt thereof, is administered in a dosage of about 10 mg to about 50 mg. In some embodiments, the tenofovir alafenamide, or a pharmaceutically acceptable salt thereof, is administered in a dosage of about 20 mg to about 30 mg. In some embodiments, the tenofovir alafenamide, or a pharmaceutically acceptable salt thereof, is administered in a dosage of about 25 mg. In some embodiments, the tenofovir alafenamide is tenofovir alafenamide hemifumarate. In some embodiments, the tenofovir alafenamide hemifumarate is administered in a dosage of about 28 mg.

In some embodiments, the additional therapeutic agent is tenofovir disoproxil, or a pharmaceutically acceptable salt thereof. In some embodiments, the tenofovir disoproxil, or a pharmaceutically acceptable salt thereof, is administered in a dosage of about 1 mg to about 500 mg, for example, about 1 mg, about 10 mg, about 25 mg, about 50 mg, about 75 mg, about 100 mg, about 150 mg, about 200 mg, about 250 mg, about 300 mg, about 350 mg, about 400 mg, about 450 mg, or about 500 mg. When administered daily, the dosage can be about 1 mg/day to about 500 mg/day, for example, about 1 mg/day, about 10 mg/day, about 25 mg/day, about 50 mg/day, about 75 mg/day, about 100 mg/day, about 150 mg/day, about 200 mg/day, about 250 mg/day, about 300 mg/day, about 350 mg/day, about 400 mg/day, about 450 mg/day, or about 500 mg/day. In some embodiments, the tenofovir disoproxil, or a pharmaceutically acceptable salt thereof, is administered in a dosage of about 123 mg, about 163 mg, about 204 mg, or about 245 mg. In some embodiments, the tenofovir disoproxil, or a pharmaceutically acceptable salt thereof, is administered in a dosage of about 10 mg to about 500 mg. In some embodiments, the tenofovir disoproxil, or a pharmaceutically acceptable salt thereof, is administered in a dosage of about 20 mg to about 300 mg. In some embodiments, the tenofovir disoproxil, or a pharmaceutically acceptable salt thereof, is administered in a dosage of about 10 mg to about 50 mg. In some embodiments, the tenofovir disoproxil, or a pharmaceutically acceptable salt thereof, is administered in a dosage of about 20 mg to about 30 mg. In some embodiments, the tenofovir disoproxil, or a pharmaceutically acceptable salt thereof, is administered in a dosage of about 25 mg. In some embodiments, the tenofovir disoproxil is tenofovir disoproxil fumarate. In some embodiments, the tenofovir disoproxil fumarate is administered in a dosage of about 150 mg, about 200 mg, about 250 mg, or about 300 mg.

In some embodiments, the methods provided herein comprise administering a first additional therapeutic agent which is bictegravir, or a pharmaceutically acceptable salt thereof, and a second additional therapeutic agent which is tenofovir alafenamide, or a pharmaceutically acceptable salt thereof. In some embodiments, the methods provided herein comprise administering a first additional therapeutic agent which is bictegravir sodium salt and a second additional therapeutic agent which is tenofovir alafenamide hemifumarate.

In some embodiments, the compound of Formula (Ia) or Formula (Ib), or a pharmaceutically acceptable salt thereof, is administered as a monotherapy.

The present disclosure further provides methods for reducing the risk of acquiring HIV (e.g., HIV-1 and/or HIV-2), comprising administering to the subject a compound of Formula (Ia) or Formula (Ib), or a pharmaceutically acceptable salt thereof, in combination with one or more additional therapeutic agents as described herein. For example, methods for reducing the risk of acquiring HIV (e.g., HIV-1 and/or HIV-2) comprise administration of a compound of Formula (Ia) or Formula (Ib), or a pharmaceutically acceptable salt thereof, in combination with one, two, or three additional therapeutic agents as disclosed herein.

In certain embodiments, the reduction in risk of acquiring HIV is at least about 40%, 50%, 60%, 70%, 80%, 90%, or 95%. In certain embodiments, the reduction in risk of acquiring HIV is about 80%, 85%, or 90%. In certain embodiments, the reduction in risk of acquiring HIV is at least about 75%. In certain embodiments, the reduction in risk of acquiring HIV is at least about 80%. In certain embodiments, the reduction in risk of acquiring HIV is at least about 85%. In certain embodiments, the reduction in risk of acquiring HIV is at least about 90%.

In certain embodiments, when the compound of Formula (Ia) or Formula (Ib), or a pharmaceutically acceptable salt thereof, is combined with one or more additional therapeutic agents as described above, the components of the composition are administered as a simultaneous or sequential regimen. When administered sequentially, the combination may be administered in two or more administrations.

In certain embodiments, the compound of Formula (Ia) or Formula (Ib), or a pharmaceutically acceptable salt thereof, is combined with one or more additional therapeutic agents in a unitary dosage form for simultaneous administration to a subject, for example, as a solid dosage form for oral administration (e.g., a fixed dose combination tablet).

Co-administration of the compound of Formula (Ia) or Formula (Ib), or a pharmaceutically acceptable salt thereof, with one or more additional therapeutic agents generally refers to simultaneous or sequential administration of the compound of Formula (Ia) or Formula (Ib), or a pharmaceutically acceptable salt thereof, and one or more additional therapeutic agents, such that therapeutically effective amounts of the compound of Formula (Ia) or Formula (Ib), or a pharmaceutically acceptable salt thereof, and one or more additional therapeutic agents are both present in the body of the subject.

Co-administration includes administration of unit dosages of the compound of Formula (Ia) or Formula (Ib), or a pharmaceutically acceptable salt thereof, before or after administration of unit dosages of one or more additional therapeutic agents. For example, administration of the compound of Formula (Ia) or Formula (Ib), or a pharmaceutically salt thereof, can occur within seconds, minutes, or hours of the administration of one or more additional therapeutic agents. For example, in some embodiments, a unit dose of the compound of Formula (Ia) or Formula (Ib), or a pharmaceutically acceptable salt thereof, is administered first, followed within seconds or minutes by administration of a unit dose of one or more additional therapeutic agents. Alternatively, in other embodiments, a unit dose of one or more additional therapeutic agents is administered first, followed by administration of a unit dose of the compound of Formula (Ia) or Formula (Ib), or a pharmaceutically acceptable salt thereof, within seconds or minutes. In some embodiments, a unit dose of the compound of Formula (Ia) or Formula (Ib), or a pharmaceutically acceptable salt thereof, is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of the compound of Formula (Ia) or Formula (Ib), or a pharmaceutically acceptable salt thereof.

The disclosure will be described in greater detail by way of specific examples. The following examples are offered for illustrative purposes, and are not intended to limit the disclosure in any manner. Those of skill in the art will readily recognize a variety of noncritical parameters which can be changed or modified to yield essentially the same results.

EXAMPLES

Example 1. Evaluation of Capsid Inhibitors (e.g., Compounds of Formula (Ia) or Formula (Ib), or a Pharmaceutically Acceptable Salt Thereof) for PrEP in Non-Human Primate Model This study will be performed to establish a minimal effective dosing regimen of capsid inhibitors of Formula (Ia) and (Ib), or a pharmaceutically acceptable salt thereof, for HIV PrEP using a non-human primate (NHP) animal model.

Rhesus macaques of Indian origin are the best characterized and most utilized non-human primate model for HIV transmission (see e.g., Hatziioannou and Evans. Nature Rev Microbiol, 2012). Infection of these animals with SHIV recapitulates hallmarks of HIV-1 pathogenesis (Del Prete and Lifson. Curr Top Microbiol Immunol, 2017). SHIV is a chimeric virus bearing R5 tropic HIV-1 envelope, which readily infects macaques and resembles naturally transmitted virus in the human population.

The proposed study is summarized in Table 1 and FIG. 1. A compound of Formula (Ib) will be dosed by subcutaneous injection to anesthetized animals as detailed in the study groups schema (FIG. 1). Plasma viral loads will be measured by standard qPCR assay at 1-week or 2-week intervals to confirm infection. The animals will be monitored for a total of at least 60 days following the last challenge. The resulting rates of protection relative to placebo will determine the efficacy of compounds of Formula (Ia) and (Ib), or a pharmaceutically acceptable salt thereof, in PrEP and also serve as a starting point for determining the minimal effective dosing regimen.

TABLE 1

| Species | Indian Rhesus Macaques (males, females, or mixture of males and females) |
|---|---|
| N per group | N = 6 (+/−1) |
| Inoculation route | Rectal (or vaginal if subject is a female) |
| Virus strain | SHIV SF162P3 |
| Total exposures/animal | Q14D × 8 challenges |
| Virus dose | 10-50 $TCID_{50}$ |
| Route of drug administration & dosing schedule | SC F/TDF: Daily SC dosing, starting 1 week prior to $1^{st}$ challenge<br>Compound (Ib)*: SC dose (e.g., solutions of 300 mg/mL or 50 mg/mL), 1 week prior to $1^{st}$ challenge at a dosage of 100 mg/kg (= 1 total SC dose over the course of the study)<br>Compound (Ib) SC administration, 1 week prior to $1^{st}$ challenge and 9 weeks after the first Compound (Ib) administration (=2 total SC doses over the course of study) |
| Alternative dosing schedules | Compound (Ib) SC administration, 1 week prior to 1st challenge and 6 and 12 weeks after the first Compound (Ib) administration (=3 total SC doses over the course of study)<br>Compound (Ib) SC administration, 1 week prior to $1^{st}$ challenge and 4, 8 and 10 weeks after the first Compound (Ib) administration (=4 total SC doses over the course of study)<br>Compound (Ib) SC administration, 1 week prior to $1^{st}$ challenge and 12 weeks after the first Compound (Ib) administration (=2 total SC doses over the course of study) |

*Compound (Ib) refers to a compound of Formula (Ib), or a pharmaceutically acceptable salt thereof.

Example 2. Further Evaluation of Capsid Inhibitors (e.g., Compounds of Formula (Ia) or Formula (Ib), or a Pharmaceutically Acceptable Salt Thereof) for PrEP in Non-Human Primate Model The PrEP efficacy a compound of Formula (Ia) or (Ib), or a pharmaceutically acceptable salt thereof, in rhesus will be evaluated using a repeat low-dose (10 $TCID_{50}$) male intrarectal (IR) challenge model.

This study will also establish a correlation between exposure and protection using a single high-dose administration of a compound of Formula (Ia) or (Ib), or a pharmaceutically acceptable salt thereof, vs. placebo, followed by multiple weekly IR challenges until infection occurs. In this study, multiple challenges will overlap with clinically-relevant drug levels. The supratherapeutic IQs (inhibitory quotients) to maximize protection and achieve proof-of-concept will be assessed in cases where rectal tissue levels are much lower than in plasma. Lower doses of a compound of Formula (Ia) or (Ib), or a pharmaceutically acceptable salt thereof, will be assessed for capturing more challenges at clinically relevant exposures, reducing the number of IR challenges, and facilitating a drug washout phase. The washout phase will last for at least 20, 21, 22, 23, or 25 weeks. In some embodiments, the washout phase will last for 20-25 weeks. The washout phase of these studies is important to enable the administered drug concentrations to decline sufficiently below those that are expected to be clinically suppressive in order to confirm that animals that remain aviremic in the study did so because they were protected from infection as opposed to being infected following one or more of the viral challenges but remaining suppressed by prolonged therapeutic concentrations of the long-acting drug in plasma and/or tissue compartments.

Figure 2:
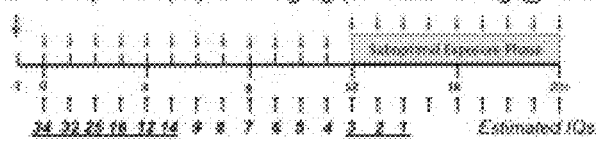
FIG. 2 shows a representative scheme illustrating the PrEP study design of Example 2.
Figure 2:
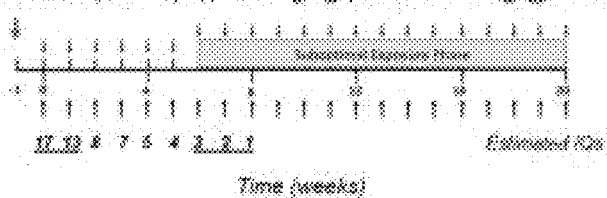

FIG. 2 is a schematic of the proposed study using a compound of Formula (Ib), or a pharmaceutically acceptable salt thereof. FIG. 2, Part A, shows the untreated, control arm of the study for eight subjects (n=8). In this scenario, it is expected that most subjects will be infected within 3 to 4 challenges (or up to 6 to 8 challenges). FIG. 2, Part B, shows the proposed study design to establish an exposure vs. protection correlation (while ensuring proof-of-concept in the event that rectal tissue levels are suboptimal). This study arm will include eight subjects (n=8), each to be administered a single high dose of a compound of Formula (Ib), or a pharmaceutically acceptable salt thereof (e.g., 300 mg/kg via subcutaneous injection). This study arm will require multiple challenges and a longer washout phase. FIG. 2, Part C, shows a third proposed arm of the study wherein subjects (n=8) will receive a single, lower dose of a compound of Formula (Ib), or a pharmaceutically acceptable salt thereof (e.g., 150 mg/kg via subcutaneous injection). This study arm will have fewer challenges prior to infection and a shorter washout period than the arm shown in FIG. 2, Part B. In both Parts B and C, the underlined values are inhibitory quotients (IQs) that are higher or lower than the expected clinical range; the remaining IQs are within the expected clinical range.

Similar studies can be performed with a compound of Formula (Ib), or a pharmaceutically acceptable salt thereof, in female NHPs via intravaginal challenges using a higher dose (10-100 $TCID_{50}$) of SHIV162-P3.

Example 3. Additional Evaluation of Capsid Inhibitors (e.g., Compound of Formula (Ib)) for PrEP in Non-Human Primate Model The PrEP efficacy a compound of Formula (Ib) in rhesus was evaluated using a repeat intrarectal (IR) challenge model.

This study also established a correlation between exposure and protection using a single high-dose administration of a compound of Formula (Ib) vs. placebo, followed by multiple weekly IR challenges until infection occured. In this study, multiple challenges overlapped with clinically-relevant drug levels. The supratherapeutic IQs (inhibitory quotients) were assessed to maximize protection and achieve proof-of-concept in case rectal tissue levels were much lower than in plasma. Lower doses of a compound of Formula (Ib), or a pharmaceutically acceptable salt thereof, were assessed to capture more challenges at clinically relevant exposures, reducing the number of IR challenges, and facilitating a drug washout phase. The washout phase lasted for at least 20 weeks. In some embodiments, the washout phase lasted for 20-25 weeks. The washout phase of these studies was important to enable the administered drug concentrations to decline sufficiently below those that were expected to be clinically suppressive in order to confirm that animals that remained aviremic in the study did so because they were protected from infection as opposed to being infected following one or more of the viral challenges but remaining suppressed by prolonged therapeutic concentrations of the long-acting drug in plasma and/or tissue compartments.

Figure 3:
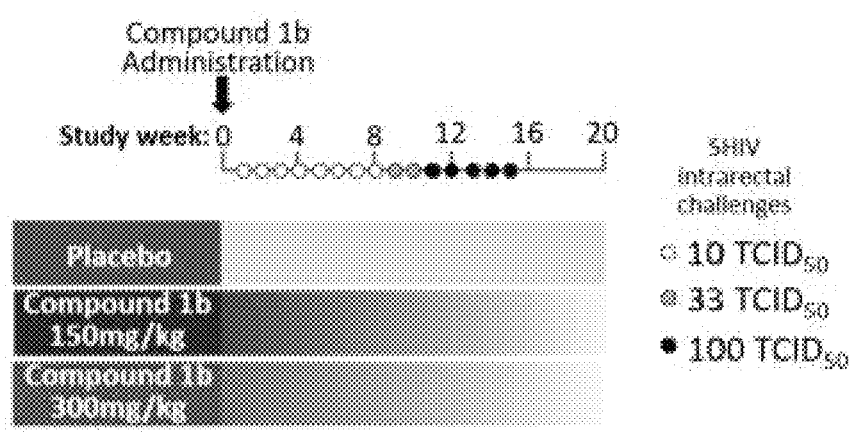
FIG. 3 shows a representative scheme illustrating the PrEP study design of Example 3.

FIG. 3 is a schematic of the study using a compound of Formula (Ib) in adult rhesus macaques (1:1 male/female ratio). Eight animals per group were treated with a single dose of placebo control, 150 mg/kg of a compound of Formula (Ib) ("Compound 1b") or 300 mg/kg of a compound of Formula (Ib) ("Compound 1b") on week 0 and allowed to wash out over time. All animals were challenged intrarectally with SHIV weekly beginning on week 1 until detectable viremia or up to a maximum of 15 challenges. SHIV challenge titer was increased over time from 10 TCID50 to 100 TCID50 through week 15 as depicted. Animal SHIV infection rate was assessed by weekly plasma viral load monitoring by qRT-PCR through study week 20. The protective efficacy of a compound of Formula (Ib) ("Compound 1b") was established by comparing to infection rate observed in the placebo control group using the Cox proportional hazards model analysis.

Similar studies can be performed with a compound of Formula (Ib), or a pharmaceutically acceptable salt thereof, in female NHPs via intravaginal challenges using SHIV162-P3.

Table 2 shows the plasma concentration and calculated inhibitory quotient (IQ, equal to the designated multiple of the rhesus plasma protein binding-adjusted $EC_{95}$ value) vs. time profile for a compound of Formula (Ib) ("Compound Ib") in the male/female rhesus animals (n=8/group) challenged with SHIV starting 1 week after a compound of Formula (Ib) ("Compound Ib") was dosed subcutaneously on Day 0. The first timepoint in which a given animal showed detectable plasma virus (>200 copies/mL), with the corresponding Compound Ib plasma concentrations and IQs in those animals, is bolded. The mean IQ for Compound Ib in animals at either 1 week or the 2 weeks prior to the first detectable plasma virus were 0.78±0.36 and 0.85±0.33, respectively.

TABLE 2

| | | | Plasma Compound Ib Concentrations in nM (Inhibitory Quotient) SHIV Dose (x $TCID_{50}$) | | | | | | | | |
|---|---|---|---|---|---|---|---|---|---|---|---|
| | | | 10 | 10 | 10 | 10 | 10 | 10 | 10 | 10 | 33 |
| | | | | | | | Study Week | | | | |
| Group | NHP ID | Sex | 1 | 2 | 3 | 4 | 5 | 6 | 7 | 8 | 9 |
| Compound Ib 300 mg/kg | 12-041 | Female | 6745 (223) | 5021 (166) | 1254 (42) | 743 (25) | 556 (18) | 396 (13) | 343 (11) | 287 (9.5) | 147 (4.9) |
| | 12-056 | Male | 5528 (183) | 1944 (64) | 942 (31) | 863 (29) | 402 (13) | 370 (12) | 180 (6.0) | 209 (6.9) | 127 (4.2) |
| | DGE2 | Male | 3174 (105) | 2466 (82) | 1003 (33) | 664 (22) | 487 (16) | 282 (9.4) | 261 (8.6) | 240 (7.9) | 131 (4.4) |
| | J928 | Male | 2251 (75) | 1332 (44) | 894 (30) | 530 (18) | 395 (13) | 382 (13) | 339 (11) | 319 (11) | 83 (2.7) |
| | K486 | Female | 1572 (52) | 2066 (68) | 508 (17) | 359 (12) | 266 (8.8) | 161 (5.3) | 180 (6.0) | 140 (4.7) | 88 (2.9) |
| | K488 | Female | 7818 (259) | 3983 (132) | 1654 (55) | 725 (24) | 523 (17) | 242 (8.0) | 132 (4.4) | 378 (13) | 177 (5.9) |
| | K621 | Female | 2215 (73) | 1949 (65) | 632 (21) | 416 (14) | 268 (8.9) | 273 (9.0) | 158 (5.2) | 155 (5.1) | 104 (3.4) |
| | K637 | Male | 1944 (64) | 1830 (61) | 742 (25) | 362 (12) | 377 (13) | 350 (12) | 307 (10) | 226 (7.5) | 122 (4.0) |
| Compound Ib 150 mg/kg | 12-077 | Female | 3112 (103) | 2108 (70) | 750 (25) | 538 (18) | 333 (11) | 164 (5.4) | 139 (4.6) | 118 (3.9) | 54 (1.8) |
| | 12-120 | Male | 2516 (83) | 2027 (67) | 1371 (45) | 448 (15) | 449 (15) | 313 (10) | 250 (8.3) | 160 (5.3) | 140 (4.6) |
| | K212 | Male | 762 (25) | 1059 (35) | 334 (11.1) | 225 (7.5) | 141 (4.7) | 82 (2.7) | 69 (2.3) | 80 (2.7) | 58 (1.9) |
| | K289 | Female | 882 (29) | 1219 (40) | 209 (6.9) | 165 (5.5) | 113 (3.8) | 78 (2.6) | 46 (1.5) | 56 (1.8) | 14 (0.5) |
| | K342 | Male | 688 (23) | 773 (26) | 197 (6.5) | 68 (2.2) | 95 (3.2) | 94 (3.1) | 65 (2.1) | 82 (2.7) | 25 (0.8) |
| | K394 | Male | 900 (30) | 1189 (39) | 498 (16.5) | 153 (5.1) | 181 (6.0) | 239 (7.9) | 104 (3.4) | 126 (4.2) | 66 (2.2) |
| | K653 | Female | 682 (23) | 785 (26) | 269 (8.9) | 237 (7.8) | 87 (2.9) | 84 (2.8) | 58 (1.9) | 152 (5.0) | 41 (1.4) |
| | K734 | Female | 607 (20) | 1097 (36) | 334 (11.1) | 181 (6.0) | 203 (6.7) | 202 (6.7) | 136 (4.5) | 171 (5.6) | 79 (2.6) |

| | | | Plasma Compound Ib Concentrations in nM (Inhibitory Quotient) SHIV Dose (x $TCID_{50}$) | | | | | | | |
|---|---|---|---|---|---|---|---|---|---|---|
| | | | 33 | 100 | 100 | 100 | 100 | 100 | N/A | N/A |
| | | | | | | | Study Week | | | |
| Group | NHP ID | Sex | 10 | 11 | 12 | 13 | 14 | 15 | 16 | 17 |
| Compound Ib 300 mg/kg | 12-041 | Female | 131 (4.3) | 96 (3.2) | 83 (2.8) | 66 (2.2) | 63 (2.1) | 45 (1.5) | 26 (0.9) | 23 (0.8) |
| | 12-056 | Male | 73 (2.4) | 32 (1.0) | 53 (1.7) | 32 (1.1) | 40 (1.3) | 32 (1.1) | 22 (0.7) | 17 (0.5) |
| | DGE2 | Male | 70 (2.3) | 50 (1.7) | 93 (3.1) | 74 (2.4) | 83 (2.7) | 48 (1.6) | 28 (0.9) | 28 (0.9) |

TABLE 2-continued

|  | NHP ID | Sex | | | | | | | | |
|---|---|---|---|---|---|---|---|---|---|---|
|  | J928 | Male | 55 (1.8) | 50 (1.7) | 85 (2.8) | 74 (2.5) | 94 (3.1) | 47 (1.6) | 24 (0.8) | 26 (0.9) |
|  | K486 | Female | 98 (3.2) | 60 (2.0) | 66 (2.2) | 43 (1.4) | 45 (1.5) | 47 (1.6) | 20 (0.7) | 21 (0.7) |
|  | K488 | Female | 117 (3.9) | 94 (3.1) | 84 (2.8) | 66 (2.2) | 85 (2.8) | 46 (1.5) | 34 (1.1) | 24 (0.8) |
|  | K621 | Female | 106 (3.5) | 52 (1.7) | 75 (2.5) | 47 (1.5) | 41 (1.4) | 29 (1.0) | 15 (0.5) | 13 (0.4) |
|  | K637 | Male | 114 (3.8) | 72 (2.4) | 101 (3.4) | 77 (2.5) | 86 (2.9) | 50 (1.7) | 30 (1.0) | 38 (1.3) |
| Compound Ib 150 mg/kg | 12-077 | Female | 51 (1.7) | 345 (1.1) | 44 (1.5) | 37 (1.2) | 33 (1.1) | 26 (0.8) | 11 (0.4) | 12 (0.4) |
|  | 12-120 | Male | 157 (5.2) | 41 (1.4) | 112 (3.7) | 51 (1.7) | 84 (2.8) | 39 (1.3) | 28 (0.9) | 21 (0.7) |
|  | K212 | Male | 35 (1.2) | 18 (0.6) | 35 (1.1) | 41 (1.3) | 22 (0.7) | 19 (0.6) | 13 (0.4) | 14 (0.5) |
|  | K289 | Female | 37 (1.2) | 14 (0.5) | 13 (0.4) | 7.3 (0.2) | 5.2 (0.2) | 3.2 (0.1) | 1.6 (0.1) | 1.2 (0.0) |
|  | K342 | Male | 31 (1.0) | 15 (0.5) | 19 (0.6) | 13 (0.4) | 13 (0.4) | 8.9 (0.3) | 6.1 (0.2) | 5.1 (0.2) |
|  | K394 | Male | 47 (1.5) | 26 (0.9) | 47 (1.6) | 44 (1.5) | 34 (1.1) | 16 (0.5) | 13 (0.4) | 17 (0.5) |
|  | K653 | Female | 61 (2.0) | 16 (0.5) | 59 (2.0) | 61 (2.0) | 31 (1.0) | 32 (1.1) | 18 (0.6) | 21 (0.7) |
|  | K734 | Female | 87 (2.9) | 52 (1.7) | 58 (1.9) | 42 (1.4) | 40 (1.3) | 22 (0.7) | 12 (0.4) | 14 (0.5) |

Table 3 shows the plasma SHIV viral loads values in individual male/female rhesus monkeys after having received a single subcutaneous administration on Day 0 of either vehicle or a compound of Formula (Ib) ("Compound Ib"), followed by weekly intrarectal challenges with escalating SHIV doses (weeks 1-15 of study). Viral infection was scored one week after each SHIV challenge using a quantitative RT-PCR assay. Infected animals were defined as having a viral load >200 copies per mL plasma and the corresponding plasma viral load values are bolded. The first timepoint in which a given animal showed detectable plasma virus is the timepoint with the first bolded plasma viral load value for that given animal.

TABLE 3

| | | | Plasma SHIV (copies/mL) | | | | | | | | | |
|---|---|---|---|---|---|---|---|---|---|---|---|---|
| | | | SHIV Dose (× TCID$_{50}$) | | | | | | | | | |
| | | | 10 | 10 | 10 | 10 | 10 | 10 | 10 | 10 | 33 | 33 |
| | | | Study Week | | | | | | | | | |
| Group | NHP ID | Sex | 1 | 2 | 3 | 4 | 5 | 6 | 7 | 8 | 9 | 10 |
| Vehicle | 12-158 | Male | <200 | <200 | <200 | <200 | <200 | <200 | <200 | <200 | <200 | <200 |
| | 12-172 | Male | <200 | 13873 | 1632119 | 81207 | 26307 | 13188 | 16637 | 3622 | 2883 | 3095 |
| | BC53 | Female | <200 | <200 | <200 | <200 | <200 | <200 | <200 | <200 | <200 | <200 |
| | BD74 | Female | <200 | 29315 | 37364758 | 1783106 | 483765 | 281187 | 16637 | 553396 | 269413 | 178663 |
| | H71A | Male | <200 | <200 | <200 | <200 | <200 | <200 | <200 | <200 | <200 | <200 |
| | K871 | Female | <200 | <200 | <200 | <200 | <200 | <200 | 76022 | 12704729 | 3340841 | 2515944 |
| | K940 | Male | <200 | <200 | <200 | <200 | <200 | <200 | <200 | 229 | 2100477 | 888762 |
| | TM1 | Female | <200 | 670 | 3813187 | 94473 | 150816 | 6408 | 2611 | 208 | <200 | <200 |
| Compound Ib 300 mg/kg | 12-041 | Female | <200 | <200 | <200 | <200 | <200 | <200 | <200 | <200 | <200 | <200 |
| | 12-056 | Male | <200 | <200 | <200 | <200 | <200 | <200 | <200 | <200 | <200 | <200 |
| | DGE2 | Male | <200 | <200 | <200 | <200 | <200 | <200 | <200 | <200 | <200 | <200 |
| | J928 | Male | <200 | <200 | <200 | <200 | <200 | <200 | <200 | <200 | <200 | <200 |
| | K486 | Female | <200 | <200 | <200 | <200 | <200 | <200 | <200 | <200 | <200 | <200 |
| | K488 | Female | <200 | <200 | <200 | <200 | <200 | <200 | <200 | <200 | <200 | <200 |
| | K621 | Female | <200 | <200 | <200 | <200 | <200 | <200 | <200 | <200 | <200 | <200 |
| | K637 | Male | <200 | <200 | <200 | <200 | <200 | <200 | <200 | <200 | <200 | <200 |
| Compound Ib 150 mg/kg | 12-077 | Female | <200 | <200 | <200 | <200 | <200 | <200 | <200 | <200 | <200 | <200 |
| | 12-120 | Male | <200 | <200 | <200 | <200 | <200 | <200 | <200 | <200 | <200 | <200 |
| | K212 | Male | <200 | <200 | <200 | <200 | <200 | <200 | <200 | <200 | <200 | <200 |
| | K289 | Female | <200 | <200 | <200 | <200 | <200 | <200 | <200 | <200 | <200 | <200 |
| | K342 | Male | <200 | <200 | <200 | <200 | <200 | <200 | <200 | <200 | <200 | <200 |
| | K394 | Male | <200 | <200 | <200 | <200 | <200 | <200 | <200 | <200 | <200 | <200 |
| | K653 | Female | <200 | <200 | <200 | <200 | <200 | <200 | <200 | <200 | <200 | <200 |
| | K734 | Female | <200 | <200 | <200 | <200 | <200 | <200 | <200 | <200 | <200 | <200 |

TABLE 3-continued

| | | | Plasma SHIV (copies/mL) SHIV Dose (× TCID$_{50}$) | | | | | | | | |
|---|---|---|---|---|---|---|---|---|---|---|---|
| | | | 100 | 100 | 100 | 100 | 100 | N/A | N/A | N/A | N/A |
| | | | | | | | Study Week | | | | |
| Group | NHP ID | Sex | 11 | 12 | 13 | 14 | 15 | 16 | 17 | 18 | 19 |
| Vehicle | 12-158 | Male | <200 | <200 | 2759968 | 344896 | 48735 | 72239 | 115509 | 29821 | 16927 |
| | 12-172 | Male | 297 | <200 | <200 | 425 | <200 | 283 | <200 | <200 | <200 |
| | BC53 | Female | <200 | <200 | <200 | <200 | 296 | 4069812 | 815223 | 816205 | 213008 |
| | BD74 | Female | 44474 | 66257 | 187210 | 107525 | 24932 | 58464 | 31321 | 56191 | 30838 |
| | H71A | Male | <200 | <200 | <200 | 1170389 | 8666473 | 1053090 | 76010 | 123554 | 44625 |
| | K871 | Female | 1057665 | 2478517 | 5011319 | 3429659 | 1156044 | 2086495 | 2218364 | 2389443 | 1032416 |
| | K940 | Male | 224614 | 108109 | 40333 | 2103 | <200 | 2243 | 18279 | <200 | <200 |
| | TM1 | Female | 339 | <200 | 266 | <200 | 515 | 405 | <200 | <200 | <200 |
| Compound Ib 300 mg/kg | 12-041 | Female | <200 | <200 | <200 | <200 | <200 | <200 | 9063 | <200 | <200 |
| | 12-056 | Male | <200 | <200 | <200 | <200 | <200 | <200 | 13193 | 6116 | <200 |
| | DGE2 | Male | <200 | <200 | <200 | <200 | <200 | <200 | <200 | <200 | 200 |
| | J928 | Male | <200 | <200 | <200 | <200 | <200 | <200 | <200 | <200 | 200 |
| | K486 | Female | <200 | <200 | <200 | <200 | <200 | <200 | <200 | <200 | 200 |
| | K488 | Female | <200 | <200 | <200 | <200 | <200 | <200 | <200 | <200 | 200 |
| | K621 | Female | <200 | <200 | <200 | <200 | <200 | <200 | 13143 | 1633235 | 123639 |
| | K637 | Male | <200 | <200 | <200 | <200 | <200 | <200 | <200 | <200 | <200 |
| Compound Ib 150 mg/kg | 12-077 | Female | <200 | <200 | <200 | <200 | <200 | 43433 | 28104 | 8535 | 2197 |
| | 12-120 | Male | <200 | <200 | <200 | <200 | <200 | <200 | <200 | <200 | <200 |
| | K212 | Male | <200 | <200 | <200 | <200 | <200 | 144532 | 128422 | 144695 | 23783 |
| | K289 | Female | <200 | <200 | 4495324 | 192698 | 1636073 | 37186 | 4020 | 18625 | 733 |
| | K342 | Male | 2317 | 1251253 | 15543 | 302527 | 41252 | 15508 | 5872 | 13017 | 4607 |
| | K394 | Male | <200 | <200 | 200 | 14481 | 436449 | 62513 | 1974 | 2250 | 1586 |
| | K653 | Female | <200 | <200 | <200 | <200 | <200 | <200 | <200 | <200 | <200 |
| | K734 | Female | <200 | <200 | <200 | <200 | <200 | <200 | 76901 | 14905 | 872 |

Figure 4:
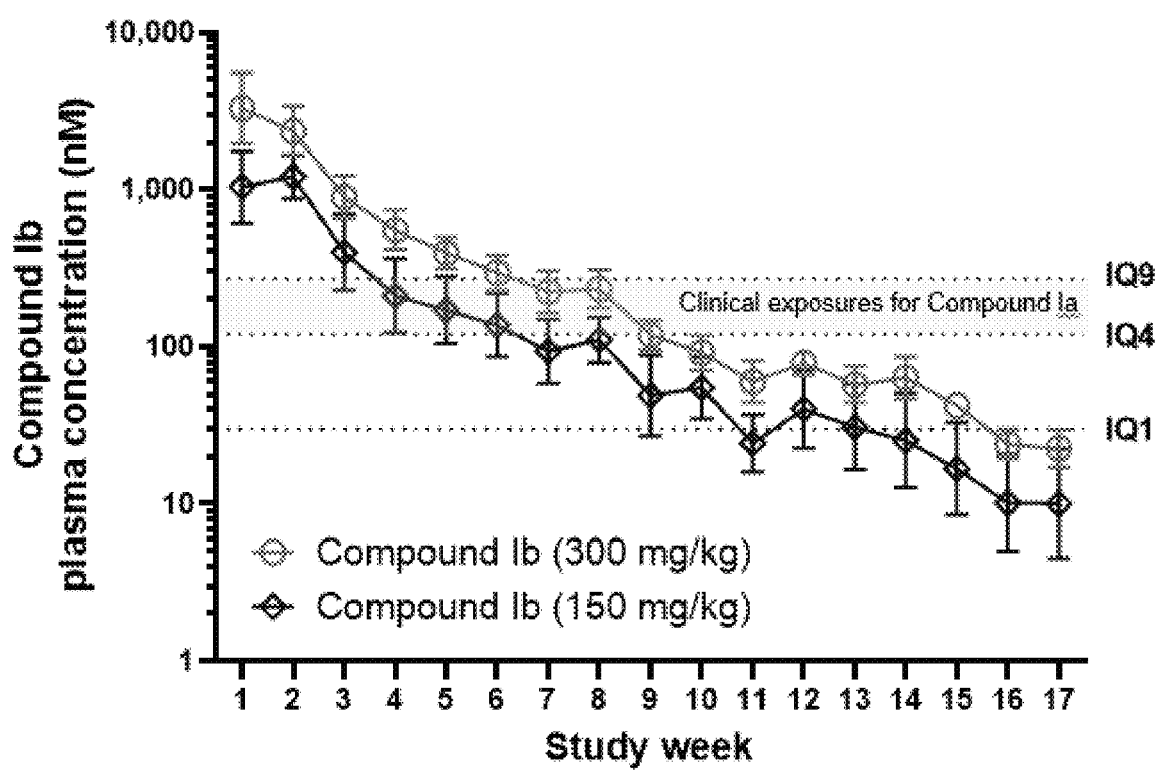
FIG. 4 shows a graph of the pharmacokinetic profile for a compound of Formula (Ib) ("Compound Ib") in the male/female rhesus animals challenged with SHIV, where study week is on the x-axis and plasma concentration (nM) of the compound of Formula (Ib) ("Compound Ib") is on the y-axis.

FIG. 4 shows the pharmacokinetic (plasma concentration vs. time) profile for a compound of Formula (Ib) ("Compound Ib") in the male/female rhesus animals (n=8/group) challenged with SHIV starting 1 week after Compound Ib was dosed subcutaneously on Day 0. Mean±s.d. values are shown. Dashed lines denote the Compound Ib concentrations corresponding to an inhibitory quotient (IQ) of 1 (30 nM), 4 (121 nM) and 9 (272 nM) are shown. The shaded area in the graph represents the clinically relevant inhibitory quotient values for a compound of Formula (Ia) ("Compound Ia").

PK analysis details: Rhesus plasma samples were stored frozen at −80° C. and analyzed using high resolution mass spectrometry (HRMS) with electrospray ionization in the positive mode. Quantification was performed using an accurate mass ([M+H]+) of 958.1853 for a compound of Formula (Ib) ("Compound Ib") and 758.3270 for the internal standard, respectively. The lower and upper limits of quantitation for Compound Ib in this bioanalytical method were 1 nM and 10,000 nM, respectively.

The mean 95% effective concentration (EC$_{95}$) of 1.91±0.16 nM for a compound of Formula (Ib) ("Compound Ib") was determined using a 7-day antiviral assay (p24 ELISA endpoint) in rhesus peripheral blood mononuclear cells (PBMCs) infected with SHIV-162P3. A competitive equilibrium dialysis assay was used to quantify rhesus plasma protein binding to Compound Ib, resulting in an inhibitory quotient (IQ) equal to Compound Ib plasma concentrations divided by a mean rhesus plasma protein-binding-adjusted EC$_{95}$ (paEC$_{95}$) value of 30.2±2.5 nM. Since the mean IQ targeted in the clinic with a compound of Formula (Ia), or a pharmaceutically acceptable salt thereof, is about 4 to about 9, a compound of Formula (Ib) ("Compound Ib") was dosed at levels in rhesus animals to permit repeated SHIV challenges at IQs greater than 1 and, at least for a subset of challenges, within the target clinically relevant range of IQs of 4 (121 nM) to 9 (272 nM) for this capsid inhibitor.

Equilibrium dialysis shift (EQDS) assay details: Rhesus plasma protein binding to a compound of Formula (Ib) ("Compound Ib") was determined by competitive equilibrium dialysis. Rhesus plasma (10%) was spiked with Compound Ib (2 μM) and blank RPMI cell culture medium containing 2% fetal bovine serum (CCM) were placed into opposite sides of assembled dialysis cells, and incubations were performed in triplicate. After a 24-h equilibration period at 37° C., samples were corrected for the matrix effect, quenched, and quantified by liquid chromatography tandem mass spectrometry (LC-MS/MS) with electrospray ionization in positive mode and multiple-reaction monitoring (MRM). The fold change value in 100% rhesus plasma was then calculated using the plasma/CCM ratio after correcting for the sample dilution factor and the percent free fraction in the matrix.

Figure 5:
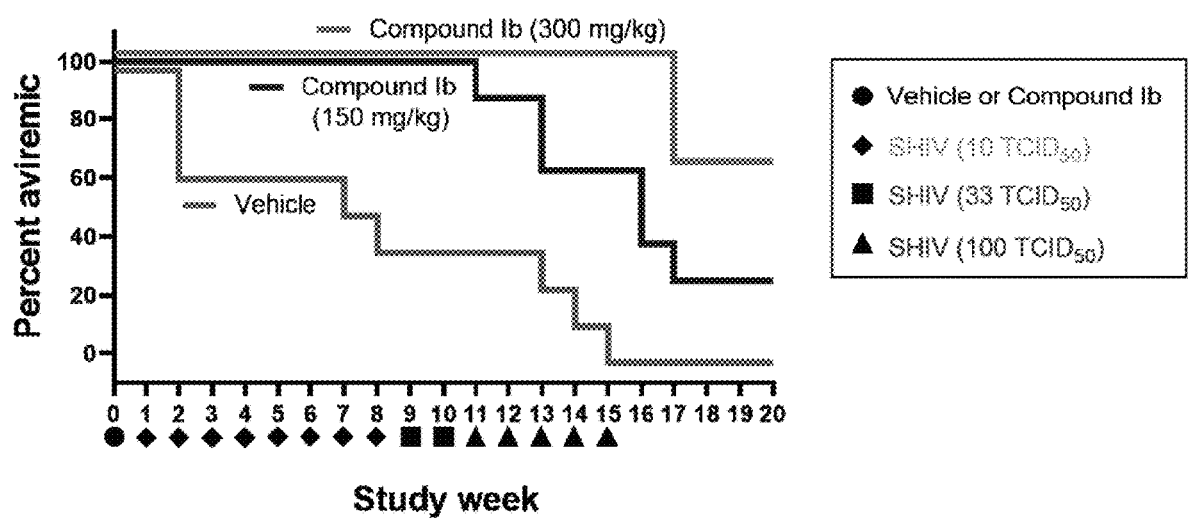
FIG. 5 shows a graph of the infection rate over time in male/female rhesus monkeys after a single subcutaneous administration of vehicle or a compound of Formula (Ib) ("Compound Ib") followed by challenges with SHIV, where study week is on the x-axis and percent aviremic is on the y-axis.

FIG. 5 shows the infection rate over time in male/female rhesus monkeys after a single subcutaneous administration on Day 0 of vehicle or a compound of Formula (Ib) ("Compound Ib") followed by weekly intrarectal challenges with escalating SHIV doses. Numbers indicate the fraction of animals in each rhesus cohort that became infected after 15 weekly SHIV intrarectal challenges.

Figure 6A:
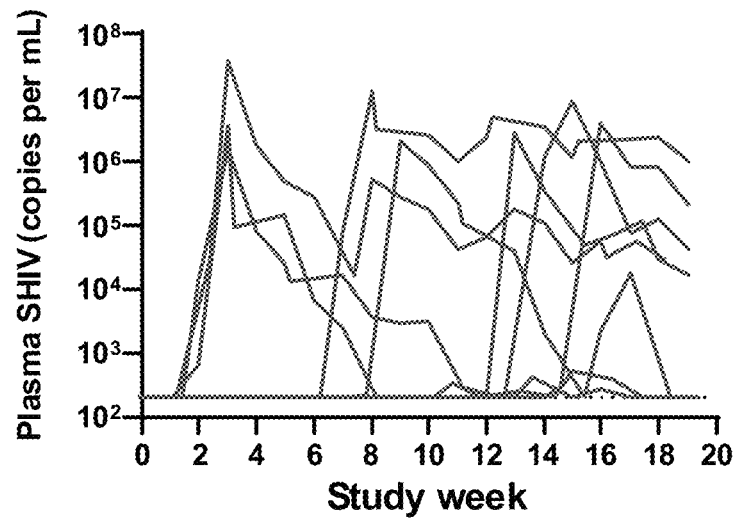
FIG. 6A shows the plasma SHIV viral loads over time in individual male/female rhesus monkeys after having received a single subcutaneous administration of vehicle, followed by repeated weekly intrarectal challenges with escalating SHIV doses, where study week is on the x-axis and plasma SHIV in copies per mL is on the y-axis.
Figure 6B:
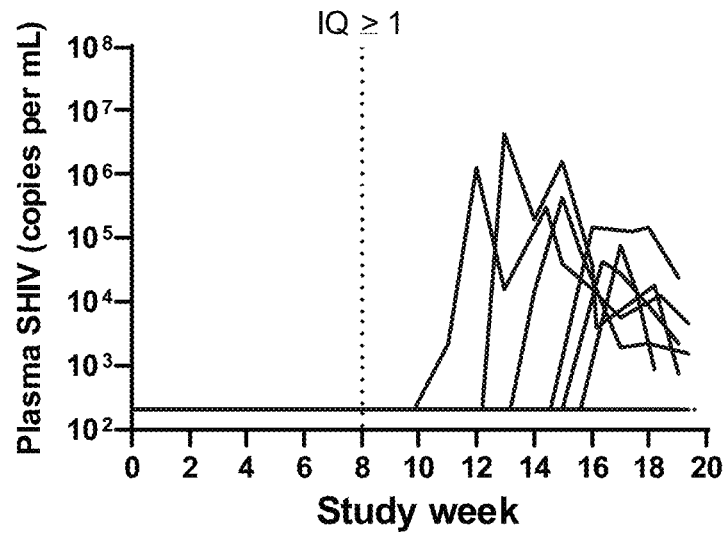
FIG. 6B shows the plasma SHIV viral loads over time in individual male/female rhesus monkeys after having received a single subcutaneous administration of 150 mg/kg of a compound of Formula (Ib) ("Compound Ib"), followed by repeated weekly intrarectal challenges with escalating SHIV doses, where study week is on the x-axis and plasma SHIV in copies per mL is on the y-axis.
Figure 6C:
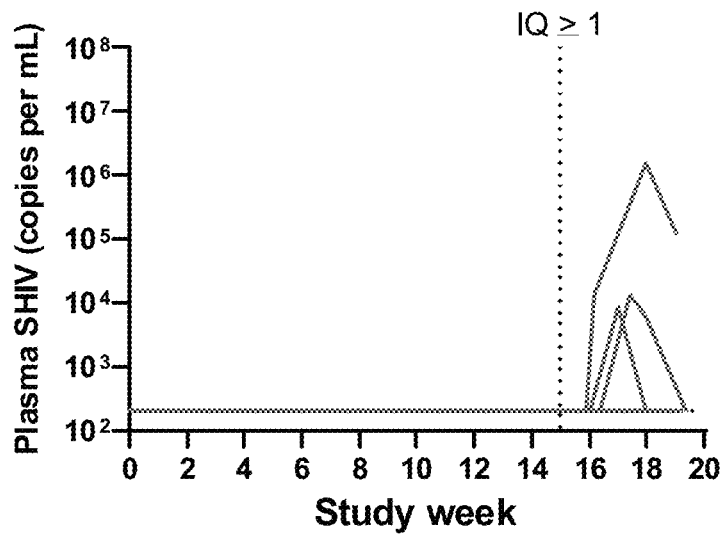
FIG. 6C shows the plasma SHIV viral loads over time in individual male/female rhesus monkeys after having received a single subcutaneous administration of 300 mg/kg of a compound of Formula (Ib) ("Compound Ib"), followed by repeated weekly intrarectal challenges with escalating SHIV doses, where study week is on the x-axis and plasma SHIV in copies per mL is on the y-axis.

FIGS. 6A-C show the plasma SHIV viral loads (copies/mL) over time in individual male/female rhesus monkeys after having received a single subcutaneous administration of either vehicle, 150 mg/kg of a compound of Formula (Ib) ("Compound Ib"), or 300 mg/kg of a compound of Formula (Ib) ("Compound Ib") on Day 0, followed by repeated weekly intrarectal challenges with escalating SHIV doses. The dotted lines in FIGS. 6B and 6C denote the latest study week in which all animals within that group had an IQ >1, demonstrating that the animals became infected only after the viral challenges were administered at Compound Ib plasma exposures well below the clinical IQ exposure range of 4 to 9.

Viral load measurements details: RNA was extracted from plasma using a QIAcube HT and the QIAcube 96 Cador pathogen HT kit (Qiagen). Gag RNA standards were generated using the AmpliCapMax™ T7 High Yield Message Maker Kit (Cell Script) and purified with RNA clean and concentrator kit (Zymo Research). Log dilutions of RNA were included with each assay run. Reverse transcription of both standards and samples was performed using Superscript III VILO (Invitrogen). Quantitative PCR was performed using the Quantstudio 6 Flex system with TaqMan™ Fast Advanced Master Mix (Applied Biosystems). Primer sequences were F-GTCTGCGTCATCTGGTGCATTC (SEQ ID NO. 1) and R-CACTAGGTGTCTCTGCAC-TATCTGTTTTG (SEQ ID NO. 2). The probe sequence was CTTCCTCAGTGTGTTTCACTTTCTCTTCTGCG (SEQ ID NO. 3), and probe was labeled with FAM and BHQ (Biosearch Technologies). Viral loads were calculated as gag copies per mL.

Example 4: Formulations

Formulations containing the compound of Formula (Ia), or a pharmaceutically acceptable salt thereof, were prepared as solutions and optionally administered subcutaneously or intramuscularly to rats, rabbits, and/or dogs.

A. 28.43 w/w % water, 60.90 w/w % PEG 300, 9.03 w/w % of a sodium salt of a compound of Formula (Ia), and 1.64 w/w % poloxamer 188 solution (about 100 mg/mL of compound of Formula (Ia))

A solution of about 100 mg/ml of the compound of Formula (Ia) having 28.43 w/w % water, 60.90 w/w % PEG 300, 9.03 w/w % of a sodium salt of a compound of Formula (Ia), and 1.64 w/w % poloxamer 188 was prepared.

B. 27.61 w/w % water, 59.13 w/w % PEG 300, 11.22 w/w % of a sodium salt of a compound of Formula (Ia), and 2.04 w/w % poloxamer 188 solution (about 125 mg/mL of compound of Formula (Ia))

A solution of about 125 mg/ml of the compound of Formula (Ia) having 27.61 w/w % water, 59.13 w/w % PEG 300, 11.22 w/w % of a sodium salt of a compound of Formula (Ia), and 2.04 w/w % poloxamer 188 was prepared.

C. 26.79 w/w % water, 57.38 w/w % PEG 300, 13.39 w/w % of a sodium salt of a compound of Formula (Ia), and 2.44 w/w % poloxamer 188 solution (about 150 mg/mL of compound of Formula (Ia))

A solution of about 150 mg/ml of the compound of Formula (Ia) having 26.79 w/w % water, 57.38 w/w % PEG 300, 13.39 w/w % of a sodium salt of a compound of Formula (Ia), and 2.44 w/w % poloxamer 188 was prepared.

D. 23.22 w/w % water, 49.73 w/w % PEG 300, 25.87 w/w % of a sodium salt of a compound of Formula (Ia), and 1.18 w/w % poloxamer 188 solution (about 300 mg/mL of compound of Formula (Ia))

A solution of about 300 mg/ml of the compound of Formula (Ia) having 23.22 w/w % water, 49.73 w/w % PEG 300, 25.87 w/w % of a sodium salt of a compound of Formula (Ia), and 1.18 w/w % poloxamer 188 was prepared.

E. 22.85 w/w % water, 48.94 w/w % PEG 300, 25.85 w/w % of a sodium salt of a compound of Formula (Ia), and 2.36 w/w % poloxamer 188 solution (about 300 mg/mL of compound of Formula (Ia))

A solution of about 300 mg/ml of the compound of Formula (Ia) having 22.85 w/w % water, 48.94 w/w % PEG 300, 25.85 w/w % of a sodium salt of a compound of Formula (Ia), and 2.36 w/w % poloxamer 188 was prepared.

F. 22.48 w/w % water, 48.13 w/w % PEG 300, 25.85 w/w % of a sodium salt of a compound of Formula (Ia), and 3.54 w/w % poloxamer 188 solution (300 mg/mL of compound of Formula (Ia))

A solution of about 300 mg/ml of the compound of Formula (Ia) having 22.48 w/w % water, 48.13 w/w % PEG 300, 25.85 w/w % of a sodium salt of a compound of Formula (Ia), and 3.54 w/w % poloxamer 188 was prepared.

G. 22.10 w/w % water, 47.33 w/w % PEG 300, 25.85 w/w % of a sodium salt of a compound of Formula (Ia), and 4.72 w/w % poloxamer 188 solution (about 300 mg/mL of compound of Formula (Ia))

A solution of about 300 mg/ml of the compound of Formula (Ia) having 22.10 w/w % water, 47.33 w/w % PEG 300, 25.85 w/w % of a sodium salt of a compound of Formula (Ia), and 4.72 w/w % poloxamer 188 was prepared.

H. 21.13 w/w % water, 45.25 w/w % PEG 300, and 33.61 w/w % of a sodium salt of a compound of Formula (Ia) solution (about 400 mg/mL of compound of Formula (Ia))

A solution of about 400 mg/ml of the compound of Formula (Ia) having 21.13 w/w % water, 45.25 w/w % PEG 300, and 33.61 w/w % of a sodium salt of a compound of Formula (Ia) was prepared. The solution was administered intramuscularly to Wistar Han rats at a dose of about 100 mg/kg and beagle dogs at a dose of about 30 mg/kg. Pharmacokinetic data for rats is reported in Table and Table below.

TABLE 4

PK parameters of the compound of Formula (Ia) following a single IM dose in male Wistar Han rats (mean ± SD, n = 4)

| | |
|---|---|
| Dosing Concentration (mg/mL) | 400 |
| Dosing Volume (mL/kg) | 0.25 |
| Dose (mg/kg) | 100 |
| Vehicle | 31.85 w/w % water and 68.2 w/w % PEG 300 |
| $AUC_{0-24h}$ (μM · h) | 7.59 ± 2.93 |
| $AUC_{0-168h}$ (μM · h) | 77.7 ± 26.1 |

TABLE 5

Plasma concentration-time data of the compound of Formula (Ia) in Wistar Han rats after intramuscular administration of 100 mg/kg dose (mean ± SD, n = 4)

| | Plasma concentration (nM) | | | | | |
|---|---|---|---|---|---|---|
| Time (h) | #1 | #2 | #3 | #4 | Mean | SD |
| 0 | BLQ | BLQ | BLQ | BLQ | NC | NC |
| 1.00 | 104 | 205 | 76.2 | 213 | 150 | 70 |
| 3.00 | 179 | 314 | 168 | 320 | 245 | 83 |
| 8.00 | 216 | 380 | 164 | 380 | 285 | 112 |
| 24.0 | 340 | 473 | 265 | 677 | 439 | 181 |
| 48.0 | 354 | 586 | 346 | 596 | 471 | 139 |
| 72.0 | 343 | 400 | 281 | 564 | 397 | 121 |
| 96.0 | 415 | 534 | 305 | 655 | 477 | 151 |
| 168 | 599 | 547 | 314 | 892 | 588 | 238 |

I. 20.16 w/w % water, 43.17 w/w % PEG 300, 33.61 w/w % of a sodium salt of a compound of Formula (Ia), and 3.06 w/w % poloxamer 188 solution (about 400 mg/mL of compound of Formula (Ia))

A solution of about 400 mg/ml of the compound of Formula (Ia) having 20.16 w/w % water, 43.17 w/w % PEG 300, 33.61 w/w % of a sodium salt of a compound of Formula (Ia), and 3.06 w/w % poloxamer 188 was prepared.

J. 19.18 w/w % water, 41.09 w/w % PEG 300, 33.61 w/w % of a sodium salt of a compound of Formula (Ia), and 6.12 w/w % poloxamer 188 solution (about 400 mg/mL of compound of Formula (Ia))

A solution of about 400 mg/ml of the compound of Formula (Ia) having 19.18 w/w % water, 41.09 w/w % PEG 300, 33.61 w/w % of a sodium salt of a compound of Formula (Ia), and 6.12 w/w % poloxamer 188 was prepared. The solution was administered intramuscularly to Wistar Han rats at a dose of about 100 mg/kg and beagle dogs at a dose of about 30 mg/kg. Pharmacokinetic data for rats is reported in Table and Table below.

TABLE 6

PK parameters of the compound of Formula (Ia) following a single IM dose in male Wistar Han rats (mean ± SD, n = 4)

| | |
|---|---|
| Dosing Concentration (mg/mL) | 400 |
| Dosing Volume (mL/kg) | 0.25 |
| Dose (mg/kg) | 100 |
| Vehicle | 28.9% w/w water, 61.9% w/w PEG 300, 9.2% poloxamer 188 |
| $AUC_{0-24h}$ (μM · h) | 12.1 ± 1.9 |
| $AUC_{0-168h}$ (μM · h) | 82.5 ± 8.7 |

TABLE 7

Plasma concentration-time data of the compound of Formula (Ia) in Wistar Han rats after intramuscular administration of 100 mg/kg dose (mean ± SD, n = 4)

| | Plasma concentration (nM) | | | | | |
|---|---|---|---|---|---|---|
| Time (h) | #1 | #2 | #3 | #4 | Mean | SD |
| 0 | BLQ | BLQ | BLQ | BLQ | NC | NC |
| 1.00 | 230 | 199 | 149 | 418 | 249 | 118 |
| 3.00 | 463 | 450 | 312 | 554 | 445 | 99.9 |
| 8.00 | 510 | 539 | 426 | 555 | 507 | 57.4 |
| 24.0 | 761 | 514 | 475 | 669 | 605 | 134 |
| 48.0 | 716 | 421 | 535 | 558 | 558 | 121 |
| 72.0 | 526 | 380 | 458 | 442 | 452 | 60.0 |
| 96.0 | 506 | 398 | 474 | 466 | 461 | 45.4 |
| 168 | 481 | 526 | 409 | 450 | 467 | 49.4 |

K. 16.93 w/w % water, 36.22 w/w % PEG 300, 41.85 w/w % of a sodium salt of a compound of Formula (Ia), and 5.00% ethanol solution (about 500 mg/mL of compound of Formula (Ia))

A solution of about 500 mg/ml of the compound of Formula (Ia) having 16.93 w/w % water, 36.22 w/w % PEG 300, 41.85 w/w % of a sodium salt of a compound of Formula (Ia), and 5.00% ethanol was prepared. The solution was administered intramuscularly to Wistar Han rats at a dose of about 100 mg/kg and beagle dogs at a dose of about 30 mg/kg. Pharmacokinetic data for rats is reported in Table and Table below.

TABLE 8

PK parameters of the compound of Formula (Ia) following a single IM dose in male Wistar Han rats (mean ± SD, n = 4)

| | |
|---|---|
| Dosing Concentration (mg/mL) | 500 |
| Dosing Volume (mL/kg) | 0.2 |
| Dose (mg/kg) | 100 |
| Vehicle | 29.1 w/w % water, 8.6 w/w % ethanol, and 62.3 w/w % PEG 300 |

TABLE 8-continued

PK parameters of the compound of Formula (Ia) following a single IM dose in male Wistar Han rats (mean ± SD, n = 4)

| | |
|---|---|
| $AUC_{0-24h}$ (μM · h) | 6.13 ± 1.70 |
| $AUC_{0-168h}$ (μM · h) | 67.4 ± 15.7 |

TABLE 9

Plasma concentration-time data of the compound of Formula (Ia) in Wistar Han rats after intramuscular administration of 100 mg/kg dose (mean ± SD, n = 4)

| | Plasma concentration (nM) | | | | | |
|---|---|---|---|---|---|---|
| Time (h) | #1 | #2 | #3 | #4 | Mean | SD |
| 0 | BLQ | BLQ | BLQ | BLQ | NC | NC |
| 1.00 | 214 | 61.9 | 173 | 135 | 146 | 64.7 |
| 3.00 | 261 | 127 | 207 | 240 | 209 | 58.9 |
| 8.00 | 297 | 126 | 231 | 219 | 218 | 70.4 |
| 24.0 | 438 | 245 | 416 | 345 | 361 | 86.9 |
| 48.0 | 439 | 282 | 436 | 347 | 376 | 75.8 |
| 72.0 | 516 | 403 | 495 | 319 | 433 | 90.6 |
| 96.0 | 537 | 337 | 427 | 301 | 401 | 105 |
| 168 | 640 | 422 | 609 | 359 | 507 | 138 |

L. 15.71 w/w % water, 33.63 w/w % PEG 300, 41.85 w/w % of a sodium salt of a compound of Formula (Ia), 5.00% ethanol, and 3.81 w/w % poloxamer 188 solution (about 500 mg/mL of compound of Formula (Ia))

A solution of about 500 mg/ml of the compound of Formula (Ia) having 15.71 w/w % water, 33.63 w/w % PEG 300, 41.85 w/w % of a sodium salt of a compound of Formula (Ia), 5.00% ethanol, and 3.81 w/w % poloxamer 188 was prepared.

M. 14.50 w/w % water, 31.04 w/w % PEG 300, 41.85 w/w % of a sodium salt of a compound of Formula (Ia), 5.00% ethanol, and 7.61 w/w % poloxamer 188 solution (about 500 mg/mL of compound of Formula (Ia))

A solution of about 500 mg/ml of the compound of Formula (Ia) having 14.50 w/w % water, 31.04 w/w % PEG 300, 41.85 w/w % of a sodium salt of a compound of Formula (Ia), 5.00% ethanol, and 7.61 w/w % poloxamer 188 was prepared. The solution was administered intramuscularly to Wistar Han rats at a dose of about 100 mg/kg and beagle dogs at a dose of about 30 mg/kg. Pharmacokinetic data for rats is reported in Table and Table below.

TABLE 10

PK parameters of the compound of Formula (Ia) following a single IM dose in male Wistar Han rats (mean ± SD, n = 4)

| | |
|---|---|
| Dosing Concentration (mg/mL) | 500 |
| Dosing Volume (mL/kg) | 0.2 |
| Dose (mg/kg) | 100 |
| Vehicle | 24.9 w/w % water, 8.6 w/w % ethanol, 13.1 w/w % poloxamer 188, and 55.4 w/w % PEG 300 |
| $AUC_{0-24h}$ (μM · h) | 13.4 ± 2.4 |
| $AUC_{0-168h}$ (μM · h) | 92.9 ± 9.6 |

TABLE 11

Plasma concentration-time data of the compound of Formula (Ia) in Wistar Han rats after intramuscular administration of 100 mg/kg dose (mean ± SD, n = 4)

| Time (h) | Plasma concentration (nM) | | | | | |
|---|---|---|---|---|---|---|
| | #1 | #2 | #3 | #4 | Mean | SD |
| 0 | BLQ | BLQ | BLQ | BLQ | NC | NC |
| 1.00 | 177 | 166 | 159 | 233 | 184 | 33.7 |
| 3.00 | 304 | 432 | 353 | 530 | 405 | 98.8 |
| 8.00 | 443 | 563 | 478 | 692 | 544 | 111 |
| 24.0 | 737 | 824 | 573 | 865 | 750 | 129 |
| 48.0 | 623 | 599 | 575 | 689 | 622 | 49.1 |
| 72.0 | 179 | 519 | 480 | 527 | 426 | 166 |
| 96.0 | 593 | 485 | 464 | 561 | 526 | 61.2 |
| 168 | 504 | 433 | 626 | 676 | 560 | 111 |

N. 13 w/w % water, 10 w/w % ethanol, and 77 w/w % PEG 200 solution with 1 equivalent of sodium hydroxide (about 200 mg/mL of compound of Formula (Ia))

A solution of about 200 mg/mL of the compound of Formula (Ia) was prepared by dissolving the compound of Formula (Ia) in a vehicle of 13 w/w % water, 10 w/w % ethanol, and 77 w/w % PEG 200 with 1 molar equivalent of sodium hydroxide. The solution was administered subcutaneously to twenty-four male New Zealand white rabbits; each animal received a single injection at a fixed dose of 0.5 mL (about 100 mg) or 1.0 mL (about 200 mg).

O. 13 w/w % water, 10 w/w % ethanol, and 77 w/w % PEG 200 solution (about 200 mg/mL of compound of Formula (Ia))

A solution of about 200 mg/mL of the compound of Formula (Ia) was prepared by dissolving the compound of Formula (Ia) in a vehicle of 10% ethanol, 13% water, and 77% PEG 200. The solution was administered subcutaneously to twenty-four male New Zealand white rabbits; each animal received a single injection at a fixed dose of 0.5 mL (about 100 mg) or 1.0 mL (about 200 mg).

P. 13 w/w % water, 10 w/w % ethanol, and 77 w/w % PEG 200 solution (about 400 mg/mL of compound of Formula (Ia))

A solution of about 400 mg/mL of the compound of Formula (Ia) was prepared by dissolving the compound of Formula (Ia) in a vehicle of 13 w/w % water, 10 w/w % ethanol, and 77 w/w % PEG 200. The solution was administered subcutaneously to twenty-four male New Zealand white rabbits; each animal received a single injection at a fixed dose of 0.5 mL (about 200 mg) or 1.0 mL (about 400 mg).

Q. 14.04 w/w % water, 30.07 w/w % PEG 300, 43.06 w/w % of a sodium salt of a compound of Formula (Ia), 5.00 w/w % ethanol, and 7.83 w/w % poloxamer 188 solution (about 500 mg/mL of compound of Formula (Ia))

A solution of about 500 mg/ml of the compound of Formula (Ia) having 14.04 w/w % water, 30.07 w/w % PEG 300, 43.06 w/w % of a sodium salt of a compound of Formula (Ia), 5.00 w/w % ethanol, and 7.83 w/w % poloxamer 188 was prepared. The solution was administered subcutaneously to six male New Zealand white rabbits; each animal received a single injection at a fixed dose of 0.6 mL (about 300 mg).

R. 19.14 w/w % water, 40.66 w/w % PEG 300, 35.20 w/w % of a sodium salt of a compound of Formula (Ia), and 5.00% ethanol solution (about 400 mg/mL of compound of Formula (Ia))

A solution of about 400 mg/mL of the compound of Formula (Ia) having 19.14 w/w % water, 40.66 w/w % PEG 300, 35.20 w/w % of a sodium salt of a compound of Formula (Ia), and 5.00% ethanol was prepared. The solution was administered subcutaneously to male Wistar Han rats at a dose level of about 50 mg/kg and dose volume of 0.125 mL/kg and the pharmacokinetic (PK) profile was determined. The results are summarized in Table and Table below.

TABLE 12

PK parameters of the compound of Formula (Ia) following a single SC dose in male Wistar Han rats (mean ± SD, n = 3)

| Dosing Concentration (mg/mL) | 400 |
|---|---|
| Dosing Volume (mL/kg) | 0.125 |
| Dose (mg/kg) | 50 |
| Vehicle | 29.53 w/w % water, 62.75 w/w % PEG 300, and 7.72 w/w % ethanol |
| $AUC_{0-24h}$ (µM · h) | 3.02 ± 0.65 |
| $AUC_{0-168h}$ (µM · h) | 25.2 ± 5.3 |
| $AUC_{0-336h}$ (µM · h) | 60.6 ± 8.3 |
| $AUC_{0-672h}$ (µM · h) | 170 ± 5.4 |
| $AUC_{0-1008h}$ (µM · h) | 287 ± 32 |
| $AUC_{0-1344h}$ (µM · h) | 402 ± 58 |
| $AUC_{0-1680h}$ (µM · h) | 504 ± 80 |
| $AUC_{0-2352h}$ (µM · h) | 649 ± 95 |
| $AUC_{0-3024h}$ (µM · h) | 752 ± 92 |
| $AUC_{0-3696h}$ (µM · h) | 825 ± 80 |
| $AUC_{0-4704h}$ (µM · h) | 915 ± 44 |
| $AUC_{0-5376h}$ (µM · h) | 958 ± 21 |
| $AUC_{0-6048h}$ (µM · h) | 988 ± 4 |
| $AUC_{0-6720h}$ (µM · h) | 1007 ± 8 |
| $AUC_{0-7392h}$ (µM · h) | 1021 ± 18 |
| $AUC_{0-8064h}$ (µM · h) | 1031 ± 25 |
| $t_{1/2}$ (days) | NA |
| $C_{max}$ (nM) | 370 ± 65 |
| $T_{max}$ (h) | 616 ± 194 |

TABLE 13

Plasma concentration-time data of the compound of Formula (Ia) in Wistar Han rats after subcutaneous administration of 50 mg/kg dose (mean ± SD, n = 3)

| Time (h) | Plasma concentration (nM) | | | | |
|---|---|---|---|---|---|
| | #1 | #2 | #3 | Mean | SD |
| 0 | BLQ | BLQ | BLQ | NC | NC |
| 1.00 | 67.6 | 59.3 | 42.4 | 56.4 | 12.8 |
| 3.00 | 128 | 164 | 104 | 132 | 30.2 |
| 8.00 | 120 | 131 | 84.1 | 112 | 25 |
| 24.0 | 167 | 194 | 125 | 162 | 35 |
| 48.0 | 184 | 162 | 107 | 151 | 40 |
| 72.0 | 168 | 154 | 123 | 148 | 23 |
| 96.0 | 181 | 162 | 112 | 152 | 36 |
| 168 | 191 | 166 | 124 | 160 | 34 |
| 336 | 251 | 275 | 256 | 261 | 13 |
| 504 | 348 | 319 | 393 | 353 | 37 |
| 672 | 290 | 286 | 442 | 339 | 89 |
| 840 | 295 | 313 | 443 | 350 | 80 |
| 1008 | 303 | 318 | 442 | 354 | 76 |
| 1334 | 296 | 266 | 421 | 328 | 82 |
| 1680 | 271 | 233 | 328 | 277 | 48 |
| 2016 | 199 | 181 | 227 | 202 | 23 |
| 2352 | 183 | 182 | 182 | 182 | 0.6 |
| 2688 | 168 | 146 | 147 | 154 | 12 |
| 3024 | 136 | 118 | 111 | 122 | 13 |
| 3360 | 132 | 116 | 84.7 | 111 | 24.1 |
| 3696 | 117 | 109 | 58.4 | 94.8 | 31.8 |
| 4032 | 109 | 136 | 59.5 | 102 | 38.8 |
| 4704 | 84.4 | 92.7 | 29.9 | 69.0 | 34.1 |
| 5376 | 62.6 | 90.4 | 20.9 | 58.0 | 35.0 |

TABLE 13-continued

Plasma concentration-time data of the compound of Formula (Ia) in Wistar Han rats after subcutaneous administration of 50 mg/kg dose (mean ± SD, n = 3)

|  | Plasma concentration (nM) | | | | |
|---|---|---|---|---|---|
| Time (h) | #1 | #2 | #3 | Mean | SD |
| 6048 | 27.4 | 48.6 | 14.6 | 30.2 | 17.2 |
| 6720 | 22.7 | 45.8 | 10.4 | 26.3 | 18.0 |
| 7392 | 13.5 | 28.6 | 7.43 | 16.5 | 10.9 |
| 8064 | 8.39 | 24.1 | 4.52 | 12.3 | 10.4 |

S. 16.64 w/w % water, 35.36 w/w % PEG 300, 43.00 w/w % of a sodium salt of a compound of Formula (Ia), and 5.00% ethanol solution (about 500 mg/mL of compound of Formula (Ia))

A solution of about 500 mg/mL of the compound of Formula (Ia) having 16.64 w/w % water, 35.36 w/w % PEG 300, 43.00 w/w % of a sodium salt of a compound of Formula (Ia), and 5.00% ethanol was prepared. The solution was administered subcutaneously to male Wistar Han rats at a dose level of about 50 mg/kg and dose volume of 0.1 mL/kg and the pharmacokinetic (PK) profile was determined. The results are summarized in Table and Table below.

TABLE 14

PK parameters of the compound of Formula (Ia) following a single SC dose in male Wistar Han rats (mean ± SD, n = 3)

| Dosing Concentration (mg/mL) | 500 |
|---|---|
| Dosing Volume (mL/kg) | 0.1 |
| Dose (mg/kg) | 50 |
| Vehicle | 29.19 w/w % water, 62.04 w/w % PEG 300, and 8.77 w/w % ethanol |
| $AUC_{0-24\ h}$ (µM · h) | 2.47 ± 0.39 |
| $AUC_{0-168\ h}$ (µM · h) | 19.7 ± 3.1 |
| $AUC_{0-336\ h}$ (µM · h) | 44.2 ± 7.5 |
| $AUC_{0-672\ h}$ (µM · h) | 133 ± 40 |
| $AUC_{0-1008\ h}$ (µM · h) | 233 ± 79 |
| $AUC_{0-1344\ h}$ (µM · h) | 334 ± 120 |
| $AUC_{0-1680\ h}$ (µM · h) | 426 ± 148 |
| $AUC_{0-2352\ h}$ (µM · h) | 554 ± 185 |
| $AUC_{0-3024\ h}$ (µM · h) | 652 ± 203 |
| $AUC_{0-3696\ h}$ (µM · h) | 722 ± 216 |
| $AUC_{0-4704\ h}$ (µM · h) | 817 ± 224 |
| $AUC_{0-5376\ h}$ (µM · h) | 861 ± 226 |
| $AUC_{0-6048\ h}$ (µM · h) | 896 ± 220 |
| $AUC_{0-6720\ h}$ (µM · h) | 923 ± 229 |
| $AUC_{0-7392\ h}$ (µM · h) | 945 ± 229 |
| $AUC_{0-8064\ h}$ (µM · h) | 964 ± 228 |
| $t_{1/2}$ (days) | NA |
| $C_{max}$ (nM) | 328 ± 131 |
| $T_{max}$ (h) | 840 ± 168 |

TABLE 15

Plasma concentration-time data of the compound of Formula (Ia) in Wistar Han rats after subcutaneous administration of 50 mg/kg dose (mean ± SD, n = 3)

|  | Plasma concentration (nM) | | | | |
|---|---|---|---|---|---|
| Time (h) | #1 | #2 | #3 | Mean | SD |
| 0 | BLQ | BLQ | BLQ | NC | NC |
| 1.00 | 37.7 | 33.8 | 76.1 | 49.2 | 23.4 |
| 3.00 | 87.6 | 72.7 | 118 | 92.8 | 23.1 |
| 8.00 | 92.0 | 82.0 | 127 | 100 | 23.6 |
| 24.0 | 111 | 138 | 133 | 127 | 14.4 |

TABLE 15-continued

Plasma concentration-time data of the compound of Formula (Ia) in Wistar Han rats after subcutaneous administration of 50 mg/kg dose (mean ± SD, n = 3)

|  | Plasma concentration (nM) | | | | |
|---|---|---|---|---|---|
| Time (h) | #1 | #2 | #3 | Mean | SD |
| 48.0 | 92.6 | 158 | 119 | 123 | 32.9 |
| 72.0 | 95.8 | 166 | 120 | 127 | 35.7 |
| 96.0 | 105 | 149 | 107 | 120 | 24.8 |
| 168 | 123 | 121 | 82.3 | 109 | 22.9 |
| 336 | 277 | 140 | 131 | 183 | 81.8 |
| 504 | 415 | 211 | 235 | 287 | 111 |
| 672 | 407 | 254 | 227 | 296 | 97 |
| 840 | 429 | 221 | 250 | 300 | 113 |
| 1008 | 479 | 207 | 215 | 300 | 155 |
| 1334 | 398 | 254 | 248 | 300 | 85 |
| 1680 | 342 | 216 | 189 | 249 | 82 |
| 2016 | 221 | 158 | 133 | 171 | 45 |
| 2352 | 231 | 170 | 119 | 173 | 56 |
| 2688 | 171 | 148 | 126 | 148 | 23 |
| 3024 | 125 | 116 | 81.8 | 108 | 23 |
| 3360 | 135 | 118 | 77.5 | 110 | 30 |
| 3696 | 102 | 105 | 69.1 | 92.0 | 19.9 |
| 4032 | 118 | 133 | 78.3 | 110 | 28.3 |
| 4704 | 62.9 | 96.4 | 55.2 | 71.5 | 21.9 |
| 5376 | 59.7 | 78.6 | 38.1 | 58.8 | 20.3 |
| 6048 | 32.6 | 75.5 | 27.0 | 45.0 | 26.5 |
| 6720 | 24.0 | 64.9 | 22.0 | 37.0 | 24.2 |
| 7392 | 13.8 | 56.8 | 17.5 | 29.4 | 23.8 |
| 8064 | 10.4 | 49.5 | 14.5 | 24.8 | 21.5 |

T. 17.00 w/w % water, 36.40 w/w % PEG 300, 35.20 w/w % of a sodium salt of a compound of Formula (Ia), 5.00 w/w % ethanol, and 6.40 w/w % poloxamer 188 solution (about 400 mg/mL of compound of Formula (Ia))

A solution of about 400 mg/mL of the compound of Formula (Ia) having 17.00 w/w % water, 36.40 w/w % PEG 300, 35.20 w/w % of a sodium salt of a compound of Formula (Ia), 5.00 w/w % ethanol, and 6.40 w/w % poloxamer 188 was prepared. The solution was administered subcutaneously to male beagle dogs at a dose level of about 12 mg/kg and male Wistar Han rats at a dose level of about 50 mg/kg. The pharmacokinetic profiles were determined, and the results for dogs are summarized in Table and Table, while the results for rats are summarized in Table and Table below.

TABLE 16

PK parameters of the compound of Formula (Ia) following a single SC dose in male beagle dogs (mean ± SD, n = 3)

| Dosing Concentration (mg/mL) | 400 |
|---|---|
| Dosing Volume (mL/kg) | 0.03 |
| Dose (mg/kg) | 12 |
| Vehicle | 26.2 w/w % water, 56.2 w/w % PEG 300, 7.7 w/w % ethanol, and 9.9 w/w % poloxamer 188 |
| $AUC_{0-24\ h}$ (µM · h) | 2.64 ± 0.50 |
| $AUC_{0-168\ h}$ (µM · h) | 36.0 ± 26.2 |
| $AUC_{0-336\ h}$ (µM · h) | 76.1 ± 46.7 |
| $AUC_{0-672\ h}$ (µM · h) | 148 ± 51 |
| $AUC_{0-1334\ h}$ (µM · h) | 197 ± 48 |
| $AUC_{0-2016\ h}$ (µM · h) | 213 ± 53 |
| $AUC_{0-2352\ h}$ (µM · h) | 216 ± 54 |
| $AUC_{inf}$ (µM · h) | 219 ± 54 |
| $t_{1/2}$ (days) | 14.7 ± 2.6 |
| $C_{max}$ (nM) | 353 ± 148 |
| $T_{max}$ (h) | 312 ± 205 |

TABLE 17

Plasma concentration-time data of the compound of Formula (Ia) in beagle dogs after subcutaneous administration of 12 mg/kg dose (mean ± SD, n = 3)

| Time (h) | Plasma concentration (nM) | | | | |
|---|---|---|---|---|---|
| | #1 | #2 | #3 | Mean | SD |
| 0 | BLQ | BLQ | BLQ | NC | NC |
| 1.00 | 10.5 | 4.75 | 2.96 | 6.07 | 3.94 |
| 3.00 | 26.1 | 18.6 | 9.64 | 18.1 | 8.24 |
| 8.00 | 83.9 | 84.5 | 50.3 | 72.9 | 19.6 |
| 24.0 | 233 | 254 | 187 | 224 | 34.3 |
| 48.0 | 166 | 380 | 179 | 241 | 120 |
| 72.0 | 105 | 452 | 112 | 223 | 198 |
| 96.0 | 89.8 | 523 | 83.8 | 232 | 251 |
| 168 | 105 | 408 | 151 | 221 | 163 |
| 336 | 179 | 353 | 250 | 261 | 87.5 |
| 504 | 286 | 229 | 199 | 238 | 44.2 |
| 672 | 150 | 106 | 90.6 | 116 | 30.8 |
| 840 | 139 | 69.8 | 63.7 | 90.8 | 41.8 |
| 1008 | 75.5 | 71.1 | 74.2 | 73.6 | 2.3 |
| 1344 | 42.5 | 35.6 | 30.6 | 36.2 | 6.0 |
| 1680 | 19.9 | 34.6 | 17.3 | 23.9 | 9.3 |
| 2016 | 7.9 | 19.6 | 7.9 | 11.8 | 6.8 |
| 2352 | 4.8 | 7.6 | 5.7 | 6.0 | 1.4 |

TABLE 18

PK parameters of the compound of Formula (Ia) following a single SC dose in male Wistar Han rats (mean ± SD, n = 5)

| | |
|---|---|
| Dosing Concentration (mg/mL) | 400 |
| Dosing Volume (mL/kg) | 0.125 |
| Dose (mg/kg) | 50 |
| Vehicle | 26.2 w/w % water, 56.2 w/w % PEG 300, 7.7 w/w % ethanol, and 9.9 w/w % poloxamer 188 |
| $AUC_{0-24\,h}$ (μM · h) | 5.49 ± 1.6 |
| $AUC_{0-168\,h}$ (μM · h) | 40.6 ± 15.3 |
| $AUC_{0-336\,h}$ (μM · h) | 76.4 ± 25.3 |
| $AUC_{0-672\,h}$ (μM · h) | 173 ± 75.6 |
| $AUC_{0-1008\,h}$ (μM · h) | 313 ± 157 |
| $AUC_{0-1344\,h}$ (μM · h) | 394 ± 185 |
| $AUC_{0-1680\,h}$ (μM · h) | 485 ± 195 |
| $AUC_{0-2352\,h}$ (μM · h) | 581 ± 146 |
| $AUC_{0-3024\,h}$ (μM · h) | 655 ± 112 |
| $AUC_{0-3696\,h}$ (μM · h) | 679 ± 103 |
| $AUC_{0-4704\,h}$ (μM · h) | 718 ± 88 |
| $AUC_{0-5376\,h}$ (μM · h) | 745 ± 76 |
| $AUC_{0-6048\,h}$ (μM · h) | 766 ± 66 |
| $AUC_{0-6720\,h}$ (μM · h) | 783 ± 59 |
| $t_{1/2}$ (days) | NA |
| $C_{max}$ (nM) | 450 ± 155 |
| $T_{max}$ (h) | 451 ± 420 |

TABLE 19

Plasma concentration-time data of the compound of Formula (Ia) in Wistar Han rats after subcutaneous administration of 50 mg/kg dose (mean ± SD, n = 5)

| Time (h) | Plasma concentration (nM) | | | | | | |
|---|---|---|---|---|---|---|---|
| | #1 | #2 | #3 | #4 | #5 | Mean | SD |
| 0 | BLQ | BLQ | BLQ | BLQ | BLQ | NC | NC |
| 1.00 | 32.9 | 54.4 | 38.0 | 67.5 | 89.1 | 56.4 | 22.8 |
| 3.00 | 128 | 113 | 129 | 156 | 149 | 135 | 17.4 |
| 8.00 | 294 | 173 | 232 | 171 | 185 | 211 | 053 |
| 24.0 | 548 | 250 | 444 | 233 | 221 | 339 | 148 |
| 48.0 | 562 | 212 | 398 | 172 | 190 | 307 | 169 |
| 72.0 | 353 | 204 | 319 | 181 | 178 | 247 | 83 |
| 96.0 | 366 | 228 | 294 | 177 | 134 | 240 | 92 |
| 168 | 214 | 231 | 203 | 125 | 89.9 | 173 | 62 |
| 336 | 205 | 529 | 195 | 241 | 102 | 254 | 161 |
| 504 | 168 | 627 | 178 | 345 | 187 | 301 | 196 |
| 672 | 123 | 603 | 149 | 387 | 229 | 298 | 199 |
| 840 | 101 | 441 | 93.2 | 251 | 189 | 215 | 142 |
| 1008 | 69.5 | 426 | 77.2 | 230 | 231 | 207 | 146 |
| 1344 | 74.9 | 262 | 58.9 | 211 | 189 | 159 | 89 |
| 1680 | NS | 161 | 52.9 | 172 | 193 | 145 | 63 |
| 2016 | NS | 110 | 63.7 | 194 | 194 | 140 | 65 |
| 2352 | NS | 90.5 | 66.8 | 161 | 150 | 117 | 46 |
| 2688 | NS | 49.6 | 372 | 151 | 77.2 | 162 | 146 |
| 3024 | NS | 44.3 | 261 | 138 | 78.8 | 131 | 95 |
| 3360 | NS | 38.5 | 227 | 119 | 85.4 | 117 | 80.1 |
| 3696 | NS | 27.1 | 126 | 72.8 | 68.7 | 73.7 | 40.6 |
| 4032 | NS | 30.4 | 124 | 63.6 | 68.0 | 71.5 | 38.8 |
| 4704 | NS | 15.9 | 71.3 | 31.7 | 58.1 | 44.3 | 25.1 |
| 5376 | NS | 12.7 | 57.9 | 21.5 | 45.6 | 34.4 | 20.9 |
| 6048 | NS | 14.9 | 40.8 | 16.9 | 43.4 | 29.0 | 15.2 |
| 6720 | NS | 10.5 | 33.3 | 8.92 | 33.4 | 21.5 | 13.7 |

U. 14.06 w/w % water, 30.12 w/w % PEG 300, 35.20 w/w % of a sodium salt of a compound of Formula (Ia), 5.00 w/w % ethanol, and 6.40 w/w % poloxamer 188 solution (about 500 mg/mL of compound of Formula (Ia))

A solution of about 500 mg/mL of the compound of Formula (Ia) having 14.06 w/w % water, 30.12 w/w % PEG 300, 35.20 w/w % of a sodium salt of a compound of Formula (Ia), 5.00 w/w % ethanol, and 6.40 w/w % poloxamer 188 was prepared. The solution was administered subcutaneously to male beagle dogs at a dose level of about 12 mg/kg and male Wistar Han rats at a dose level of about 50 mg/kg. The pharmacokinetic profiles were determined, and the results for dogs are summarized in Table and Table, while the results for rats are summarized in Table and Table below.

TABLE 20

PK parameters of the compound of Formula (Ia) following a single SC dose in male beagle dogs (mean ± SD, n = 3)

| | |
|---|---|
| Dosing Concentration (mg/mL) | 500 |
| Dosing Volume (mL/kg) | 0.024 |
| Dose (mg/kg) | 12 |
| Vehicle | 24.6 w/w % water, 52.7 w/w % PEG 300, 8.7 w/w % ethanol, and 14 w/w % poloxamer 188 |
| $AUC_{0-24\,h}$ (μM · h) | 1.80 ± 0.85 |
| $AUC_{0-168\,h}$ (μM · h) | 12.9 ± 5.1 |
| $AUC_{0-336\,h}$ (μM · h) | 33.9 ± 14.2 |
| $AUC_{0-672\,h}$ (μM · h) | 78.5 ± 11.4 |
| $AUC_{0-1334\,h}$ (μM · h) | 118 ± 6 |
| $AUC_{0-2016\,h}$ (μM · h) | 133 ± 11 |
| $AUC_{0-2352\,h}$ (μM · h) | 136 ± 12 |
| $AUC_{inf}$ (μM · h) | 141 ± 14 |
| $t_{1/2}$ (days) | 18.3 ± 1.0 |
| $C_{max}$ (nM) | 175 ± 29 |
| $T_{max}$ (h) | 344 ± 277 |

TABLE 21

Plasma concentration-time data of the compound of Formula (Ia) in beagle dogs after subcutaneous administration of 12 mg/kg dose (mean ± SD, n = 3)

| Time (h) | Plasma concentration (nM) | | | | |
|---|---|---|---|---|---|
| | #1 | #2 | #3 | Mean | SD |
| 0 | BLQ | BLQ | BLQ | NC | NC |
| 1.00 | 4.85 | 2.05 | 9.86 | 5.59 | 3.96 |
| 3.00 | 22.9 | 7.00 | 36.1 | 22.0 | 14.6 |
| 8.00 | 68.7 | 26.4 | 88.4 | 61.2 | 31.7 |
| 24.0 | 101 | 92.7 | 207 | 134 | 63.7 |
| 48.0 | 72.8 | 94.1 | 94.8 | 87.2 | 12.5 |
| 72.0 | 49.4 | 62.3 | 64.0 | 58.6 | 7.98 |
| 96.0 | 49.0 | 45.7 | 62.6 | 52.4 | 8.96 |
| 168 | 55.9 | 49.6 | 187 | 97.5 | 77.6 |
| 336 | 114 | 155 | 187 | 152 | 36.6 |
| 504 | 151 | 166 | 129 | 149 | 18.6 |
| 672 | 106 | 101 | 38.7 | 81.9 | 37.5 |
| 840 | 107 | 69.7 | 41.2 | 72.6 | 33.0 |
| 1008 | 83.5 | 61.1 | 30.4 | 58.3 | 26.7 |
| 1344 | 43.3 | 38.5 | 22.5 | 34.8 | 10.9 |
| 1680 | 25.7 | 27.7 | 10.5 | 21.3 | 9.4 |
| 2016 | 10.7 | 13.8 | 6.40 | 10.3 | 3.7 |
| 2352 | 8.8 | 10.2 | 3.45 | 7.5 | 3.6 |

TABLE 22

PK parameters of the compound of Formula (Ia) following a single SC dose in male Wistar Han rats (mean ± SD, n = 5)

| Dosing Concentration (mg/mL) | 500 |
|---|---|
| Dosing Volume (mL/kg) | 0.1 |
| Dose (mg/kg) | 50 |
| Vehicle | 24.6 w/w % water, 52.7 w/w % PEG 300, 8.7 w/w % ethanol, and 14 w/w % poloxamer 188 |
| $AUC_{0-24\ h}$ (µM · h) | 3.74 ± 0.78 |
| $AUC_{0-168\ h}$ (µM · h) | 29.8 ± 7.5 |
| $AUC_{0-336\ h}$ (µM · h) | 63.2 ± 20.7 |
| $AUC_{0-672\ h}$ (µM · h) | 159 ± 77 |
| $AUC_{0-1008\ h}$ (µM · h) | 338 ± 141 |
| $AUC_{0-1344\ h}$ (µM · h) | 409 ± 159 |
| $AUC_{0-1680\ h}$ (µM · h) | 529 ± 194 |
| $AUC_{0-2352\ h}$ (µM · h) | 610 ± 215 |
| $AUC_{0-3024\ h}$ (µM · h) | 669 ± 233 |
| $AUC_{0-3696\ h}$ (µM · h) | 692 ± 233 |
| $AUC_{0-4704\ h}$ (µM · h) | 728 ± 249 |
| $AUC_{0-5376\ h}$ (µM · h) | 756 ± 256 |
| $AUC_{0-6048\ h}$ (µM · h) | 781 ± 261 |
| $AUC_{0-6720\ h}$ (µM · h) | 802 ± 266 |
| $t_{1/2}$ (days) | NA |
| $C_{max}$ (nM) | 362 ± 147 |
| $T_{max}$ (h) | 710 ± 501 |

TABLE 23

Plasma concentration-time data of the compound of Formula (Ia) in Wistar Han rats after subcutaneous administration of 50 mg/kg dose (mean ± SD, n = 5)

| Time (h) | Plasma concentration (nM) | | | | | | |
|---|---|---|---|---|---|---|---|
| | #1 | #2 | #3 | #4 | #5 | Mean | SD |
| 0 | BLQ | BLQ | BLQ | BLQ | BLQ | NC | NC |
| 1.00 | 42.6 | 53.6 | 48.0 | 66.8 | 41.7 | 50.5 | 10.3 |
| 3.00 | 123 | 74.2 | 81.3 | 164 | 108 | 110 | 36.0 |
| 8.00 | 176 | 106 | 107 | 168 | 154 | 142 | 33.5 |
| 24.0 | 300 | 178 | 196 | 214 | 230 | 224 | 46.9 |
| 48.0 | 279 | 172 | 138 | 218 | 246 | 211 | 56.5 |
| 72.0 | 298 | 157 | 138 | 181 | 210 | 197 | 62.7 |
| 96.0 | 230 | 137 | 130 | 169 | 170 | 167 | 39.5 |
| 168 | 195 | 139 | 75.3 | 187 | 175 | 154 | 49.1 |
| 336 | 185 | 211 | 63.2 | 474 | 285 | 244 | 151 |
| 504 | 231 | 288 | 96.8 | 592 | 307 | 303 | 181 |
| 672 | 203 | 256 | 114 | 614 | 292 | 296 | 190 |
| 840 | 132 | 316 | 171 | 431 | 254 | 261 | 119 |
| 1008 | 118 | 358 | 230 | 419 | 295 | 284 | 117 |
| 1344 | 84.8 | 256 | 231 | 289 | 270 | 226 | 82 |
| 1680 | 69.2 | 293 | 199 | 254 | 177 | 198 | 85 |
| 2016 | 54.7 | 255 | 177 | 212 | 171 | 174 | 75 |
| 2352 | 64.0 | 171 | 207 | 223 | 168 | 167 | 62 |
| 2688 | 42.3 | 142 | 125 | 115 | 118 | 108 | 38 |
| 3024 | 39.5 | 148 | 97.7 | 113 | 113 | 102 | 40 |
| 3360 | 32.2 | 135 | 79.2 | 93.6 | 100 | 88.0 | 37.3 |
| 3696 | 34.7 | 98.8 | 73.3 | 75.1 | 70.7 | 70.5 | 23.0 |
| 4032 | 33.9 | 112 | 58.5 | 61.8 | 62.1 | 65.7 | 28.4 |
| 4704 | 25.7 | 69.8 | 30.2 | 48.8 | 41.2 | 43.1 | 17.5 |
| 5376 | 30.0 | 66.5 | 26.3 | 33.2 | 38.7 | 38.9 | 16.1 |
| 6048 | 30.8 | 60.0 | 18.5 | 30.4 | 41.5 | 36.2 | 15.6 |
| 6720 | 22.7 | 49.9 | 13.5 | 22.8 | 23.8 | 26.5 | 13.7 |

V. 23.33 w/w % water, 48.99 w/w % PEG 300, 26.47 w/w % of a sodium salt of a compound of Formula (Ia), and 1.21 w/w % poloxamer 188 solution (about 300 mg/mL of compound of Formula (Ia))

A solution of about 300 mg/mL of the compound of Formula (Ia) having 23.33 w/w % water, 48.99 w/w % PEG 300, 26.47 w/w % of a sodium salt of a compound of Formula (Ia), and 1.21 w/w % poloxamer 188 was prepared. The solution was administered subcutaneously to male beagle dogs at a dose level of about 6 mg/kg and male Wistar Han rats at a dose level of about 50 mg/kg. The pharmacokinetic profiles were determined, and the results for dogs are summarized in Table and Table, while the results for rats are summarized in Table and Table below.

TABLE 24

PK parameters of the compound of Formula (Ia) following a single SC dose in male beagle dogs (mean ± SD, n = 3)

| Dosing Concentration (mg/mL) | 300 |
|---|---|
| Dosing Volume (mL/kg) | 0.02 |
| Dose (mg/kg) | 6 |
| Vehicle | 31.7 w/w % water, 66.7 w/w % PEG 300, and 1.6 w/w % poloxamer 188 |
| $AUC_{0-24\ h}$ (µM · h) | 0.304 ± 0.028 |
| $AUC_{0-168\ h}$ (µM · h) | 5.07 ± 0.50 |
| $AUC_{0-672\ h}$ (µM · h) | 65.6 ± 9.9 |
| $AUC_{0-1344\ h}$ (µM · h) | 97.4 ± 12.7 |
| $AUC_{0-1680\ h}$ (µM · h) | 103 ± 12 |
| $AUC_{0-2016\ h}$ (µM · h) | 107 ± 12 |
| $AUC_{0-2253\ h}$ (µM · h) | 109 ± 12 |
| $AUC_{0-2688\ h}$ (µM · h) | 110 ± 12 |
| $AUC_{0-3024\ h}$ (µM · h) | 111 ± 13 |
| $AUC_{0-4032\ h}$ (µM · h) | 112 ± 13 |
| $AUC_{0-4368\ h}$ (µM · h) | 112 ± 13 |
| $AUC_{inf}$ (µM · h) | 113 ± 12 |
| $t_{1/2}$ (days) | 25.5 ± 5.5 |
| $C_{max}$ (nM) | 155 ± 30 |
| $T_{max}$ (h) | 448 ± 97 |

TABLE 25

Plasma concentration-time data of the compound of Formula (Ia) in beagle dogs after subcutaneous administration of 6 mg/kg dose (mean ± SD, n = 3)

| Time (h) | Plasma concentration (nM) | | | | |
|---|---|---|---|---|---|
| | #1 | #2 | #3 | Mean | SD |
| 0 | BLQ | BLQ | BLQ | NC | NC |
| 1.00 | BLQ | BLQ | BLQ | NC | NC |
| 3.00 | 2.26 | BLQ | 3.25 | 2.75 | 2.26 |
| 8.00 | 8.26 | 11.6 | 11.4 | 10.4 | 1.9 |
| 24.0 | 22.3 | 25.7 | 22.6 | 23.5 | 1.9 |
| 48.0 | 37.1 | 27.9 | 29.4 | 31.5 | 4.9 |
| 72.0 | 32.8 | 29.6 | 31.5 | 31.3 | 1.6 |
| 96.0 | 39.5 | 28.8 | 29.6 | 32.6 | 6.0 |
| 168 | 41.8 | 34.5 | 41.4 | 39.2 | 4.1 |
| 336 | 99.2 | 125 | 164 | 129 | 32.6 |
| 504 | 122 | 179 | 151 | 151 | 28.5 |
| 672 | 95.3 | 135 | 135 | 122 | 22.9 |
| 840 | 53.3 | 51.7 | 71.6 | 58.9 | 11.1 |
| 1008 | 29.1 | 32.0 | 29.6 | 30.2 | 1.6 |
| 1344 | 26.9 | 22.1 | 22.5 | 23.8 | 2.7 |
| 1680 | 13.7 | 9.9 | 13.4 | 12.3 | 2.1 |
| 2016 | 8.9 | 5.4 | 11.1 | 8.5 | 2.9 |
| 2352 | 4.5 | 4.2 | 5.4 | 4.7 | 0.6 |
| 2688 | 2.1 | 2.0 | 4.0 | 2.7 | 1.1 |
| 3024 | 2.5 | 1.6 | 2.9 | 2.3 | 0.7 |
| 3360 | 1.5 | 1.3 | 1.2 | 1.3 | 0.2 |
| 3696 | BLQ | BLQ | BLQ | NC | NC |
| 4032 | BLQ | BLQ | BLQ | NC | NC |

TABLE 26

PK parameters of the compound of Formula (Ia) following a single SC dose in male Wistar Han rats (mean ± SD, n = 3)

| | |
|---|---|
| Dosing Concentration (mg/mL) | 300 |
| Dosing Volume (mL/kg) | 0.167 |
| Dose (mg/kg) | 50 |
| Vehicle | 31.7 w/w % water, 66.7 w/w % PEG 300, and 1.6 w/w % poloxamer 188 |
| $AUC_{0-24\ h}$ (μM · h) | 3.66 ± 4.29 |
| $AUC_{0-168\ h}$ (μM · h) | 24.5 ± 5.4 |
| $AUC_{0-336\ h}$ (μM · h) | 50.1 ± 9.2 |
| $AUC_{0-672\ h}$ (μM · h) | 137 ± 27 |
| $AUC_{0-1008\ h}$ (μM · h) | 237 ± 52 |
| $AUC_{0-1344\ h}$ (μM · h) | 331 ± 85 |
| $AUC_{0-1680\ h}$ (μM · h) | 423 ± 96 |
| $AUC_{0-2352\ h}$ (μM · h) | 554 ± 113 |
| $AUC_{0-3024\ h}$ (μM · h) | 646 ± 121 |
| $AUC_{0-3696\ h}$ (μM · h) | 700 ± 121 |
| $AUC_{0-4704\ h}$ (μM · h) | 720 ± 120 |

TABLE 27

Plasma concentration-time data of the compound of Formula (Ia) in Wistar Han rats after subcutaneous administration of 50 mg/kg dose (mean ± SD, n = 3)

| Time (h) | Plasma concentration (nM) | | | | |
|---|---|---|---|---|---|
| | #1 | #2 | #3 | Mean | SD |
| 0 | BLQ | BLQ | BLQ | NC | NC |
| 1.00 | 51.4 | 48.4 | 54.4 | 51.4 | 3.0 |
| 3.00 | 141 | 109 | 97.1 | 116 | 23 |
| 8.00 | 170 | 142 | 153 | 155 | 14 |
| 24.0 | 222 | 169 | 189 | 193 | 27 |
| 48.0 | 265 | 138 | 187 | 197 | 64 |
| 72.0 | 187 | 116 | 142 | 148 | 36 |
| 96.0 | 164 | 90.1 | 155 | 136 | 40 |
| 168 | 100 | 80.1 | 132 | 104 | 26 |
| 336 | 194 | 170 | 238 | 201 | 35 |
| 504 | 241 | 210 | 343 | 265 | 70 |
| 672 | 274 | 275 | 375 | 308 | 58 |
| 840 | 285 | 278 | 362 | 308 | 47 |
| 1008 | 221 | 126 | 427 | 258 | 154 |
| 1344 | 272 | 282 | 350 | 301 | 42 |
| 1680 | 221 | 246 | 284 | 250 | 32 |
| 2016 | 138 | 191 | 213 | 181 | 39 |
| 2352 | 122 | 176 | 197 | 165 | 38 |
| 2688 | 113 | 155 | 156 | 141 | 25 |
| 3024 | 81.4 | 121 | 94.9 | 99.1 | 20.1 |
| 3360 | 81.1 | 74.6 | 76.5 | 77.4 | 3.3 |
| 3696 | 72.2 | 62.3 | 70.7 | 68.4 | 5.3 |
| 4032 | 56.6 | 55.8 | 44.5 | 52.3 | 6.8 |
| 4704 | 35.9 | 31.3 | 23.4 | 30.2 | 6.3 |

W. 18.80 w/w % water, 40.25 w/w % PEG 300, 34.38 w/w % of a sodium salt of a compound of Formula (Ia), 5.00 w/w % ethanol, and 1.57 w/w % poloxamer 188 solution (about 400 mg/mL of compound of Formula (Ia))

A solution of about 400 mg/mL of the compound of Formula (Ia) having 18.80 w/w % water, 40.25 w/w % PEG 300, 34.38 w/w % of a sodium salt of a compound of Formula (Ia), 5.00 w/w % ethanol, and 1.57 w/w % poloxamer 188 was prepared. The solution was administered subcutaneously to male beagle dogs at a dose level of about 12 mg/kg and male Wistar Han rats at a dose level of about 50 mg/kg. The pharmacokinetic profiles were determined, and the results for dogs are summarized in Table and Table, while the results for rats are summarized in Table and Table below.

TABLE 28

PK parameters of the compound of Formula (Ia) following a single SC dose in male beagle dogs (mean ± SD, n = 3)

| | |
|---|---|
| Dosing Concentration (mg/mL) | 400 |
| Dosing Volume (mL/kg) | 0.03 |
| Dose (mg/kg) | 12 |
| Vehicle | 28.7 w/w % water, 61.3 w/w % PEG 300, 7.6 w/w % ethanol, and 2.4 w/w % poloxamer 188 |
| $AUC_{0-24\ h}$ (μM · h) | 0.505 ± 0.194 |
| $AUC_{0-168\ h}$ (μM · h) | 6.82 ± 3.38 |
| $AUC_{0-672\ h}$ (μM · h) | 65.1 ± 43.1 |
| $AUC_{0-1344\ h}$ (μM · h) | 123 ± 54 |
| $AUC_{0-1680\ h}$ (μM · h) | 142 ± 50 |
| $AUC_{0-2016\ h}$ (μM · h) | 154 ± 47 |
| $AUC_{0-2253\ h}$ (μM · h) | 164 ± 44 |
| $AUC_{0-2688\ h}$ (μM · h) | 170 ± 42 |
| $AUC_{0-3024\ h}$ (μM · h) | 174 ± 41 |
| $AUC_{0-4032\ h}$ (μM · h) | 181 ± 39 |
| $AUC_{0-4368\ h}$ (μM · h) | 182 ± 38 |
| $AUC_{inf}$ (μM · h) | NA |
| $t_{1/2}$ (days) | NA |
| $C_{max}$ (nM) | 200 ± 90 |
| $T_{max}$ (h) | 784 ± 513 |

TABLE 29

Plasma concentration-time data of the compound of Formula (Ia) in beagle dogs after subcutaneous administration of 12 mg/kg dose (mean ± SD, n = 3)

| Time (h) | Plasma concentration (nM) | | | | |
|---|---|---|---|---|---|
| | #1 | #2 | #3 | Mean | SD |
| 0 | BLQ | BLQ | BLQ | NC | NC |
| 1.00 | BLQ | BLQ | BLQ | NC | NC |
| 3.00 | 3.45 | 2.80 | 5.26 | 3.84 | 1.27 |
| 8.00 | 16.6 | 10.0 | 27.4 | 18.0 | 8.78 |
| 24.0 | 35.4 | 27.0 | 50.9 | 37.8 | 12.1 |
| 48.0 | 40.2 | 31.7 | 72.7 | 48.2 | 21.6 |
| 72.0 | 36.8 | 25.8 | 83.3 | 48.6 | 30.5 |
| 96.0 | 31.8 | 23.1 | 75.7 | 43.5 | 28.2 |
| 168 | 53.2 | 18.5 | 49.3 | 40.3 | 19.0 |
| 336 | 284 | 33.1 | 82.4 | 133 | 133 |
| 504 | 187 | 26.4 | 150 | 121 | 84.1 |
| 672 | 179 | 46.3 | 210 | 145 | 87.0 |
| 840 | 90.9 | 46.3 | 110 | 82.4 | 32.7 |
| 1008 | 80.7 | 55.3 | 79.1 | 71.7 | 14.2 |
| 1344 | 72.3 | 105 | 64.9 | 80.7 | 21.3 |
| 1680 | 28.8 | 42.5 | 33.3 | 34.9 | 7.0 |
| 2016 | 25.8 | 46.8 | 33.3 | 35.3 | 10.6 |
| 2352 | 16.8 | 29.2 | 19.7 | 21.9 | 6.5 |
| 2688 | 9.87 | 18.3 | 11.6 | 13.3 | 4.5 |
| 3024 | 10.5 | 14.8 | 8.8 | 11.4 | 3.1 |
| 3360 | 6.7 | 10.0 | 5.4 | 7.4 | 2.4 |
| 3696 | 4.1 | 6.9 | 3.3 | 4.7 | 1.9 |
| 4032 | 4.3 | 9.0 | 3.6 | 5.6 | 2.9 |
| 4368 | 4.0 | 10.1 | 3.0 | 5.7 | 3.8 |

TABLE 30

PK parameters of the compound of Formula (Ia) following a single SC dose in male Wistar Han rats (mean ± SD, n = 3)

| | |
|---|---|
| Dosing Concentration (mg/mL) | 400 |
| Dosing Volume (mL/kg) | 0.125 |
| Dose (mg/kg) | 50 |
| Vehicle | 28.7 w/w % water, 61.3 w/w % PEG 300, 7.6 w/w % ethanol, and 2.4 w/w % poloxamer 188 |
| $AUC_{0-24\,h}$ (µM · h) | 2.00 ± 0.58 |
| $AUC_{0-168\,h}$ (µM · h) | 21.6 ± 4.5 |
| $AUC_{0-336\,h}$ (µM · h) | 45.9 ± 11.9 |
| $AUC_{0-672\,h}$ (µM · h) | 124 ± 32 |
| $AUC_{0-1008\,h}$ (µM · h) | 215 ± 45 |
| $AUC_{0-1344\,h}$ (µM · h) | 306 ± 65 |
| $AUC_{0-1680\,h}$ (µM · h) | 401 ± 86 |
| $AUC_{0-2352\,h}$ (µM · h) | 540 ± 114 |
| $AUC_{0-3024\,h}$ (µM · h) | 647 ± 126 |
| $AUC_{0-3696\,h}$ (µM · h) | 730 ± 131 |
| $AUC_{0-4704\,h}$ (µM · h) | 765 ± 131 |

TABLE 31

Plasma concentration-time data of the compound of Formula (Ia) in Wistar Han rats after subcutaneous administration of 50 mg/kg dose (mean ± SD, n = 3)

| Time (h) | Plasma concentration (nM) | | | | |
|---|---|---|---|---|---|
| | #1 | #2 | #3 | Mean | SD |
| 0 | BLQ | BLQ | BLQ | NC | NC |
| 1.00 | 46.2 | 18.8 | 26.7 | 30.6 | 14.1 |
| 3.00 | 73.8 | 36.4 | 50.0 | 53.4 | 18.9 |
| 8.00 | 109 | 45.9 | 75.8 | 76.9 | 31.6 |
| 24.0 | 127 | 90.1 | 144 | 120 | 28 |
| 48.0 | 128 | 127 | 201 | 152 | 42 |
| 72.0 | 112 | 169 | 176 | 152 | 35 |
| 96.0 | 98.6 | 150 | 164 | 138 | 34 |
| 168 | 80.0 | 121 | 154 | 118 | 37 |
| 336 | 123 | 166 | 224 | 171 | 51 |
| 504 | 194 | 228 | 321 | 248 | 66 |
| 672 | 217 | 239 | 328 | 261 | 59 |
| 840 | 273 | 283 | 313 | 290 | 21 |
| 1008 | 176 | 239 | 302 | 239 | 63 |
| 1344 | 260 | 284 | 370 | 305 | 58 |
| 1680 | 206 | 242 | 335 | 261 | 67 |
| 2016 | 163 | 193 | 247 | 201 | 43 |
| 2352 | 164 | 144 | 179 | 162 | 18 |
| 2688 | 170 | 135 | 214 | 173 | 40 |
| 3024 | 145 | 106 | 143 | 131 | 22 |
| 3360 | 151 | 90.5 | 144 | 129 | 33 |
| 3696 | 133 | 76.3 | 112 | 107 | 29 |
| 4032 | 147 | 55.5 | 90.0 | 97.5 | 46.2 |
| 4704 | 84.2 | 34.6 | 54.8 | 57.9 | 24.9 |

X. 16.29 w/w % water, 34.88 w/w % PEG 300, 41.92 w/w % of a sodium salt of a compound of Formula (Ia), 5.00 w/w % ethanol, and 1.91 w/w % poloxamer 188 solution (about 500 mg/mL of compound of Formula (Ia))

A solution of about 500 mg/mL of the compound of Formula (Ia) having 16.29 w/w % water, 34.88 w/w % PEG 300, 41.92 w/w % of a sodium salt of a compound of Formula (Ia), 5.00 w/w % ethanol, and 1.91 w/w % poloxamer 188 was prepared. The solution was administered subcutaneously to male beagle dogs at a dose level of about 12 mg/kg and male Wistar Han rats at a dose level of about 50 mg/kg. The pharmacokinetic profiles were determined, and the results for dogs are summarized in Table and Table, while the results for rats are summarized in Table and Table below.

TABLE 32

PK parameters of the compound of Formula (Ia) following a single SC dose in male beagle dogs (mean ± SD, n = 3)

| | |
|---|---|
| Dosing Concentration (mg/mL) | 500 |
| Dosing Volume (mL/kg) | 0.024 |
| Dose (mg/kg) | 12 |
| Vehicle | 28 w/w % water, 60.1 w/w % PEG 300, 8.6 w/w % ethanol, and 3.3 w/w % poloxamer 188 |
| $AUC_{0-24\,h}$ (µM · h) | 0.663 ± 0.157 |
| $AUC_{0-168\,h}$ (µM · h) | 6.01 ± 1.87 |
| $AUC_{0-672\,h}$ (µM · h) | 46.1 ± 32.5 |
| $AUC_{0-1344\,h}$ (µM · h) | 90.8 ± 60 |
| $AUC_{0-1680\,h}$ (µM · h) | 106 ± 68 |
| $AUC_{0-2016\,h}$ (µM · h) | 116 ± 75 |
| $AUC_{0-2253\,h}$ (µM · h) | 124 ± 44 |
| $AUC_{0-2688\,h}$ (µM · h) | 130 ± 83 |
| $AUC_{0-3024\,h}$ (µM · h) | 135 ± 86 |
| $AUC_{0-4032\,h}$ (µM · h) | 145 ± 90 |
| $AUC_{0-4368\,h}$ (µM · h) | 148 ± 91 |
| $AUC_{inf}$ (µM · h) | NA |
| $t_{1/2}$ (days) | NA |
| $C_{max}$ (nM) | 125 ± 95 |
| $T_{max}$ (h) | 560 ± 97 |

TABLE 33

Plasma concentration-time data of the compound of Formula (Ia) in beagle dogs after subcutaneous administration of 12 mg/kg dose (mean ± SD, n = 3)

| | Plasma concentration (nM) | | | | |
|---|---|---|---|---|---|
| Time (h) | #1 | #2 | #3 | Mean | SD |
| 1.00 | 18.3 | 11.9 | 6.00 | 12.1 | 6.15 |
| 3.00 | 19.4 | 16.3 | 9.86 | 15.2 | 4.87 |
| 8.00 | 22.3 | 34.2 | 21.8 | 26.1 | 7.02 |
| 24.0 | 32.8 | 51.1 | 35.2 | 39.7 | 9.95 |
| 48.0 | 39.8 | 59.5 | 34.8 | 44.7 | 13.1 |
| 72.0 | 33.0 | 54.0 | 22.6 | 36.5 | 16.0 |
| 96.0 | 40.3 | 34.6 | 19.2 | 31.4 | 10.9 |
| 168 | 37.9 | 56.3 | 23.5 | 39.2 | 16.4 |
| 336 | 40.1 | 90.4 | 20.5 | 50.3 | 36.1 |
| 504 | 78.8 | 225 | 36.8 | 114 | 98.8 |
| 672 | 114 | 191 | 25.6 | 110 | 82.8 |
| 840 | 89.6 | 82.3 | 12.4 | 61.4 | 42.6 |
| 1008 | 98.7 | 93.8 | 12.5 | 68.3 | 48.4 |
| 1344 | 77.2 | 58.0 | 10.2 | 48.5 | 34.5 |
| 1680 | 56.5 | 48.5 | 8.2 | 37.7 | 25.9 |
| 2016 | 37.2 | 27.9 | 5.1 | 23.4 | 16.5 |
| 2352 | 41.2 | 26.5 | 5.3 | 24.3 | 18.1 |
| 2688 | 19.0 | 19.5 | 5.2 | 14.6 | 8.1 |
| 3024 | 19.9 | 17.3 | 6.7 | 14.6 | 7.0 |
| 3360 | 12.3 | 11.8 | 4.6 | 9.6 | 4.3 |
| 3696 | 8.3 | 13.1 | 4.2 | 8.6 | 4.4 |
| 4032 | 8.5 | 12.3 | 4.0 | 8.3 | 4.2 |
| 4368 | 8.0 | 7.9 | 3.3 | 6.4 | 2.7 |

TABLE 34

PK parameters of the compound of Formula (Ia) following a single SC dose in male Wistar Han rats (mean ± SD, n = 3)

| | |
|---|---|
| Dosing Concentration (mg/mL) | 500 |
| Dosing Volume (mL/kg) | 0.1 |
| Dose (mg/kg) | 50 |
| Vehicle | 28 w/w % water, 60.1 w/w % PEG 300, 8.6 w/w % ethanol, and 3.3 w/w % poloxamer 188 |
| $AUC_{0-24\,h}$ (µM · h) | 2.82 ± 0.53 |
| $AUC_{0-168\,h}$ (µM · h) | 30.1 ± 5.1 |
| $AUC_{0-336\,h}$ (µM · h) | 64.5 ± 11.4 |
| $AUC_{0-672\,h}$ (µM · h) | 152 ± 23 |
| $AUC_{0-1008\,h}$ (µM · h) | 244 ± 29 |
| $AUC_{0-1344\,h}$ (µM · h) | 329 ± 35 |
| $AUC_{0-1680\,h}$ (µM · h) | 416 ± 47 |
| $AUC_{0-2352\,h}$ (µM · h) | 549 ± 64 |
| $AUC_{0-3024\,h}$ (µM · h) | 659 ± 80 |
| $AUC_{0-3696\,h}$ (µM · h) | 761 ± 84 |
| $AUC_{0-4704\,h}$ (µM · h) | 806 ± 83 |

TABLE 35

Plasma concentration-time data of the compound of Formula (Ia) in Wistar Han rats after subcutaneous administration of 50 mg/kg dose (mean ± SD, n = 3)

| | Plasma concentration (nM) | | | | |
|---|---|---|---|---|---|
| Time (h) | #1 | #2 | #3 | Mean | SD |
| 0 | BLQ | BLQ | BLQ | NC | NC |
| 1.00 | 62.6 | 30.6 | 47.1 | 46.8 | 16.0 |
| 3.00 | 89.0 | 57.8 | 86.0 | 77.6 | 17.2 |
| 8.00 | 115 | 75.9 | 97.7 | 96.2 | 19.6 |
| 24.0 | 164 | 151 | 237 | 184 | 46 |
| 48.0 | 209 | 165 | 254 | 209 | 45 |
| 72.0 | 207 | 153 | 237 | 199 | 43 |
| 96.0 | 193 | 166 | 201 | 187 | 18 |
| 168 | 204 | 134 | 189 | 176 | 37 |
| 336 | 269 | 185 | 246 | 233 | 43 |
| 504 | 311 | 239 | 261 | 270 | 37 |
| 672 | 312 | 246 | 252 | 270 | 37 |
| 840 | 361 | 282 | 239 | 294 | 62 |
| 1008 | 209 | 312 | 183 | 235 | 68 |
| 1344 | 314 | 321 | 182 | 272 | 78 |
| 1680 | 206 | 310 | 224 | 247 | 56 |
| 2016 | 161 | 248 | 169 | 193 | 48 |
| 2352 | 111 | 222 | 141 | 158 | 57 |
| 2688 | 141 | 205 | 157 | 168 | 33 |
| 3024 | 127 | 187 | 168 | 161 | 31 |
| 3360 | 122 | 171 | 178 | 157 | 31 |
| 3696 | 121 | 138 | 144 | 134 | 12 |
| 4032 | 97.5 | 132 | 175 | 135 | 39 |
| 4704 | 79.4 | 68.0 | 119 | 88.8 | 26.8 |

Y. 20.90 w/w % water, 44.72 w/w % PEG 300, and 34.38 w/w % of a sodium salt of a compound of Formula (Ia) solution (about 400 mg/mL of compound of Formula (Ia))

A solution of about 400 mg/mL of the compound of Formula (Ia) having 20.90 w/w % water, 44.72 w/w % PEG 300, and 34.38 w/w % of a sodium salt of a compound of Formula (Ia) was prepared. The solution was administered subcutaneously to male beagle dogs at a dose level of about 12 mg/kg and male Wistar Han rats at a dose level of about 50 mg/kg. The pharmacokinetic profiles were determined, and the results for dogs are summarized in Table and Table, while the results for rats are summarized in Table and Table below.

TABLE 36

PK parameters of the compound of Formula (Ia) following a single SC dose in male beagle dogs (mean ± SD, n = 3)

| | |
|---|---|
| Dosing Concentration (mg/mL) | 400 |
| Dosing Volume (mL/kg) | 0.03 |
| Dose (mg/kg) | 12 |
| Vehicle | 31.85 w/w % water, 68.15 w/w % PEG 300 |
| $AUC_{0-24\,h}$ (µM · h) | 0.996 ± 0.513 |
| $AUC_{0-168\,h}$ (µM · h) | 9.61 ± 2.6 |
| $AUC_{0-336\,h}$ (µM · h) | 27.4 ± 1.9 |
| $AUC_{0-672\,h}$ (µM · h) | 100 ± 7.2 |
| $AUC_{0-1008\,h}$ (µM · h) | 146 ± 11 |
| $AUC_{0-1344\,h}$ (µM · h) | 172 ± 16 |
| $AUC_{0-2352\,h}$ (µM · h) | 200 ± 19 |
| $AUC_{0-3024\,h}$ (µM · h) | 207 ± 19 |
| $AUC_{0-3696\,h}$ (µM · h) | 210 ± 18 |

TABLE 37

Plasma concentration-time data of the compound of Formula (Ia) in beagle dogs after subcutaneous administration of 12 mg/kg dose (mean ± SD, n = 3)

| | Plasma concentration (nM) | | | | |
|---|---|---|---|---|---|
| Time (h) | #1 | #2 | #3 | Mean | SD |
| 1.00 | 19.2 | 6.79 | 2.84 | 9.61 | 8.54 |
| 3.00 | 31.9 | 14.3 | 7.45 | 17.9 | 12.6 |
| 8.00 | 52.5 | 30.0 | 19.1 | 33.9 | 17.0 |
| 24.0 | 109 | 56.1 | 44.7 | 69.9 | 34.3 |
| 48.0 | 109 | 72.8 | 49.4 | 77.1 | 30.0 |
| 72.0 | 73.6 | 60.2 | 41.7 | 58.5 | 16.0 |

TABLE 37-continued

Plasma concentration-time data of the compound of Formula (Ia) in beagle dogs after subcutaneous administration of 12 mg/kg dose (mean ± SD, n = 3)

| Time (h) | Plasma concentration (nM) | | | | |
|---|---|---|---|---|---|
| | #1 | #2 | #3 | Mean | SD |
| 96.0 | 73.8 | 61.3 | 40.0 | 58.4 | 17.1 |
| 168 | 41.2 | 49.2 | 53.1 | 47.8 | 6.07 |
| 336 | 163 | 145 | 185 | 164 | 20.0 |
| 504 | 247 | 230 | 267 | 248 | 18.5 |
| 672 | 229 | 182 | 204 | 205 | 23.5 |
| 840 | 136 | 116 | 118 | 123 | 11.0 |
| 1008 | 119 | 83.6 | 84.7 | 95.8 | 20.1 |
| 1334 | 70.5 | 49.0 | 55.0 | 58.2 | 11.1 |
| 1680 | 27.2 | 26.1 | 32.0 | 28.4 | 3.1 |
| 2016 | 17.7 | 16.0 | 22.2 | 18.6 | 3.2 |
| 2352 | 18.1 | 14.0 | 14.0 | 15.4 | 2.4 |
| 2688 | 8.23 | 10.3 | 9.88 | 9.47 | 1.09 |
| 3024 | 5.55 | 6.06 | 6.84 | 6.15 | 0.65 |
| 3360 | 3.54 | 7.18 | 4.62 | 5.11 | 1.87 |
| 3696 | 2.18 | 5.38 | 3.71 | 3.76 | 1.60 |

TABLE 38

PK parameters of the compound of Formula (Ia) following a single SC dose in male Wistar Han rats (mean ± SD, n = 4)

| | |
|---|---|
| Dosing Concentration (mg/mL) | 400 |
| Dosing Volume (mL/kg) | 0.125 |
| Dose (mg/kg) | 50 |
| Vehicle | 31.85 w/w % water, 68.15 w/w % PEG 300 |
| $AUC_{0-24\,h}$ (µM · h) | 1.66 ± 0.32 |
| $AUC_{0-168\,h}$ (µM · h) | 15.7 ± 4.7 |
| $AUC_{0-336\,h}$ (µM · h) | 31.6 ± 10.9 |
| $AUC_{0-672\,h}$ (µM · h) | 74.9 ± 33.7 |
| $AUC_{0-1008\,h}$ (µM · h) | 128 ± 64 |
| $AUC_{0-1344\,h}$ (µM · h) | 182 ± 100 |
| $AUC_{0-1680\,h}$ (µM · h) | 230 ± 132 |
| $AUC_{0-2352\,h}$ (µM · h) | 312 ± 181 |
| $AUC_{0-3024\,h}$ (µM · h) | 389 ± 229 |
| $AUC_{0-3696\,h}$ (µM · h) | 454 ± 255 |

TABLE 39

Plasma concentration-time data of the compound of Formula (Ia) in Wistar Han rats after subcutaneous administration of 50 mg/kg dose (mean ± SD, n = 4)

| Time (h) | Plasma concentration (nM) | | | | | |
|---|---|---|---|---|---|---|
| | #1 | #2 | #3 | #4 | Mean | SD |
| 0 | BLQ | BLQ | BLQ | BLQ | NC | NC |
| 1.00 | 28.7 | 22.1 | 39.4 | 24.1 | 28.6 | 7.73 |
| 3.00 | 51.3 | 39.2 | 68.9 | 49.5 | 52.2 | 12.3 |
| 8.00 | 62.1 | 66.8 | 80.4 | 53.7 | 65.8 | 11.2 |
| 24.0 | 72.1 | 110 | 116 | 74.5 | 93.2 | 23.1 |
| 48.0 | 83.0 | 113 | 154 | 88.9 | 110 | 32.2 |
| 72.0 | 87.1 | 126 | 149 | 75.4 | 109 | 34.1 |
| 96.0 | 81.8 | 109 | 129 | 61.5 | 95.3 | 29.7 |
| 168 | 67.9 | 102 | 120 | 52.8 | 85.7 | 30.8 |
| 336 | 81.5 | 116 | 159 | 56.9 | 103 | 44.3 |
| 504 | 97.0 | 151 | 214 | 60.5 | 131 | 66.9 |
| 672 | 94.7 | 147 | 289 | 73.9 | 151 | 96.9 |
| 840 | 102 | 184 | 266 | 78.0 | 158 | 85.4 |
| 1008 | 88.4 | 185 | 295 | 80.2 | 162 | 101 |
| 1344 | 89.4 | 175 | 314 | 57.7 | 159 | 115 |
| 1680 | 71.7 | 161 | 226 | 68.3 | 132 | 76.1 |
| 2016 | 58.4 | 130 | 217 | 63.8 | 117 | 74.0 |
| 2352 | 57.5 | 130 | 209 | 74.0 | 118 | 68.4 |
| 2688 | 57.2 | 122 | 233 | 62.0 | 119 | 81.8 |
| 3024 | 49.5 | 122 | 178 | 71.9 | 105 | 57.1 |

TABLE 39-continued

Plasma concentration-time data of the compound of Formula (Ia) in Wistar Han rats after subcutaneous administration of 50 mg/kg dose (mean ± SD, n = 4)

| Time (h) | Plasma concentration (nM) | | | | | |
|---|---|---|---|---|---|---|
| | #1 | #2 | #3 | #4 | Mean | SD |
| 3360 | 45.1 | 107 | 146 | 82.8 | 95.2 | 42.4 |
| 3696 | 46.7 | 84.9 | 120 | 110 | 90.4 | 32.7 |

Z. 19.90 w/w % water, 42.59 w/w % PEG 300, 34.38 w/w % of a sodium salt of a compound of Formula (Ia), and 3.13 w/w % poloxamer 188 solution (about 400 mg/mL of compound of Formula (Ia))

A solution of about 400 mg/mL of the compound of Formula (Ia) having 19.90 w/w % water, 42.59 w/w % PEG 300, 34.38 w/w % of a sodium salt of a compound of Formula (Ia), and 3.13 w/w % poloxamer 188 was prepared. The solution was administered subcutaneously to male beagle dogs at a dose level of about 12 mg/kg and male Wistar Han rats at a dose level of about 50 mg/kg. The pharmacokinetic profiles were determined, and the results for dogs are summarized in Table and Table, while the results for rats are summarized in Table and Table below.

TABLE 40

PK parameters of the compound of Formula (Ia) following a single SC dose in male beagle dogs (mean ± SD, n = 3)

| | |
|---|---|
| Dosing Concentration (mg/mL) | 400 |
| Dosing Volume (mL/kg) | 0.03 |
| Dose (mg/kg) | 12 |
| Vehicle | 30.33 w/w % water, 64.91 w/w % PEG 300, 4.76 w/w % poloxamer 188 |
| $AUC_{0-24\,h}$ (µM · h) | 1.02 ± 0.58 |
| $AUC_{0-168\,h}$ (µM · h) | 10.6 ± 4.9 |
| $AUC_{0-336\,h}$ (µM · h) | 30.1 ± 14.8 |
| $AUC_{0-672\,h}$ (µM · h) | 92.7 ± 31.0 |
| $AUC_{0-1008\,h}$ (µM · h) | 125 ± 31 |
| $AUC_{0-1344\,h}$ (µM · h) | 147 ± 32 |
| $AUC_{0-2352\,h}$ (µM · h) | 170 ± 33 |
| $AUC_{0-3024\,h}$ (µM · h) | 175 ± 32 |
| $AUC_{0-3696\,h}$ (µM · h) | 177 ± 31 |

TABLE 41

Plasma concentration-time data of the compound of Formula (Ia) in beagle dogs after subcutaneous administration of 12 mg/kg dose (mean ± SD, n = 3)

| Time (h) | Plasma concentration (nM) | | | | |
|---|---|---|---|---|---|
| | #1 | #2 | #3 | Mean | SD |
| 0 | BLQ | BLQ | BLQ | NC | NC |
| 1.00 | 1.66 | BLQ | 1.50 | 1.58 | NC |
| 3.00 | 8.73 | 2.95 | 5.82 | 5.83 | 2.89 |
| 8.00 | 57.8 | 16.2 | 28.1 | 34.0 | 21.4 |
| 24.0 | 124 | 38.2 | 79.2 | 80.5 | 42.9 |
| 48.0 | 88.2 | 37.9 | 58.7 | 61.6 | 25.3 |
| 72.0 | 89.8 | 46.5 | 59.0 | 65.1 | 22.3 |
| 96.0 | 91.9 | 36.2 | 83.7 | 70.6 | 30.1 |
| 168 | 75.5 | 10.5 | 95.8 | 60.6 | 44.6 |
| 336 | 211 | 84.0 | 220 | 172 | 76.1 |
| 504 | 301 | 162 | 221 | 228 | 69.8 |
| 672 | 144 | 133 | 75.2 | 117 | 37.0 |
| 840 | 107 | 112 | 68.2 | 95.7 | 24.0 |
| 1008 | 93.3 | 83.7 | 62.8 | 79.9 | 15.6 |
| 1334 | 51.6 | 52.8 | 46.1 | 50.2 | 3.57 |
| 1680 | 29.7 | 29.2 | 13.8 | 24.2 | 9.0 |

TABLE 41-continued

Plasma concentration-time data of the compound of Formula (Ia) in beagle dogs after subcutaneous administration of 12 mg/kg dose (mean ± SD, n = 3)

| Time (h) | Plasma concentration (nM) | | | | |
|---|---|---|---|---|---|
| | #1 | #2 | #3 | Mean | SD |
| 2016 | 20.4 | 15.4 | 9.67 | 15.2 | 5.4 |
| 2352 | 7.04 | 14.4 | 5.12 | 8.85 | 4.9 |
| 2688 | 4.59 | 9.89 | 3.70 | 6.06 | 3.35 |
| 3024 | 3.65 | 6.54 | 6.65 | 5.61 | 1.70 |
| 3360 | 2.04 | 5.86 | 2.32 | 3.41 | 2.13 |
| 3696 | 1.20 | 2.94 | 1.12 | 1.75 | 1.03 |

TABLE 42

PK parameters of the compound of Formula (Ia) following a single SC dose in male Wistar Han rats (mean ± SD, n = 4)

| | |
|---|---|
| Dosing Concentration (mg/mL) | 400 |
| Dosing Volume (mL/kg) | 0.125 |
| Dose (mg/kg) | 50 |
| Vehicle | 30.33 w/w % water, 64.91 w/w % PEG 300, 4.76 w/w % poloxamer 188 |
| $AUC_{0-24\,h}$ (µM · h) | 2.37 ± 1.60 |
| $AUC_{0-168\,h}$ (µM · h) | 23.9 ± 12.4 |
| $AUC_{0-336\,h}$ (µM · h) | 49.4 ± 25.4 |
| $AUC_{0-672\,h}$ (µM · h) | 106 ± 49 |
| $AUC_{0-1008\,h}$ (µM · h) | 163 ± 68 |
| $AUC_{0-1344\,h}$ (µM · h) | 214 ± 85 |
| $AUC_{0-1680\,h}$ (µM · h) | 259 ± 99 |
| $AUC_{0-2352\,h}$ (µM · h) | 344 ± 117 |
| $AUC_{0-3024\,h}$ (µM · h) | 435 ± 129 |
| $AUC_{0-3696\,h}$ (µM · h) | 544 ± 156 |

TABLE 43

Plasma concentration-time data of the compound of Formula (Ia) in Wistar Han rats after subcutaneous administration of 50 mg/kg dose (mean ± SD, n = 4)

| Time (h) | Plasma concentration (nM) | | | | | |
|---|---|---|---|---|---|---|
| | #1 | #2 | #3 | #4 | Mean | SD |
| 0 | BLQ | BLQ | BLQ | BLQ | NC | NC |
| 1.00 | 43.8 | 17.5 | 21.7 | 83.6 | 41.7 | 30.3 |
| 3.00 | 70.7 | 41.0 | 36.7 | 133 | 70.3 | 44.4 |
| 8.00 | 71.8 | 45.9 | 48.0 | 178 | 85.9 | 62.5 |
| 24.0 | 130 | 84.5 | 82.4 | 281 | 144 | 93.6 |
| 48.0 | 176 | 127 | 84.5 | 271 | 165 | 80.2 |
| 72.0 | 140 | 127 | 90.0 | 295 | 163 | 90.5 |
| 96.0 | 138 | 123 | 83.1 | 245 | 147 | 69.1 |
| 168 | 130 | 122 | 65.0 | 222 | 135 | 65.0 |
| 336 | 152 | 140 | 86.4 | 299 | 169 | 91.0 |
| 504 | 152 | 140 | 98.2 | 275 | 166 | 076 |
| 672 | 163 | 155 | 136 | 235 | 172 | 43.3 |
| 840 | 156 | 144 | 128 | 267 | 174 | 63.2 |
| 1008 | 137 | 136 | 139 | 244 | 164 | 53.3 |
| 1344 | 113 | 110 | 110 | 220 | 138 | 54.5 |
| 1680 | 108 | 115 | 116 | 169 | 127 | 28.2 |
| 2016 | 111 | 137 | 93.8 | 165 | 127 | 31.1 |
| 2352 | 101 | 117 | 122 | 167 | 127 | 28.3 |
| 2688 | 118 | 117 | 158 | 172 | 141 | 28.0 |
| 3024 | 110 | 115 | 151 | 154 | 133 | 23.2 |
| 3360 | 109 | NS | 158 | 133 | 133 | 24.5 |
| 3696 | 91.2 | NS | 163 | 150 | 135 | 38.3 |

AA. 18.91 w/w % water, 40.46 w/w % PEG 300, 34.38 w/w % of a sodium salt of a compound of Formula (Ia), and 6.25 w/w % poloxamer 188 solution (about 400 mg/mL of compound of Formula (Ia))

A solution of about 400 mg/mL of the compound of Formula (Ia) having 18.91 w/w % water, 40.46 w/w % PEG 300, 34.38 w/w % of a sodium salt of a compound of Formula (Ia), and 6.25 w/w % poloxamer 188 was prepared. The solution was administered subcutaneously to male beagle dogs at a dose level of about 12 mg/kg and male Wistar Han rats at a dose level of about 50 mg/kg. The pharmacokinetic profiles were determined, and the results for dogs are summarized in Table and Table, while the results for rats are summarized in Table and Table below.

TABLE 44

PK parameters of the compound of Formula (Ia) following a single SC dose in male beagle dogs (mean ± SD, n = 3)

| | |
|---|---|
| Dosing Concentration (mg/mL) | 400 |
| Dosing Volume (mL/kg) | 0.03 |
| Dose (mg/kg) | 12 |
| Vehicle | 28.81 w/w % water, 61.66 w/w % PEG 300, 9.53 w/w % poloxamer 188 |
| $AUC_{0-24\,h}$ (µM · h) | 1.57 ± 0.56 |
| $AUC_{0-168\,h}$ (µM · h) | 22.2 ± 7.0 |
| $AUC_{0-336\,h}$ (µM · h) | 46.3 ± 9.4 |
| $AUC_{0-672\,h}$ (µM · h) | 108 ± 26 |
| $AUC_{0-1008\,h}$ (µM · h) | 149 ± 31 |
| $AUC_{0-1344\,h}$ (µM · h) | 171 ± 33 |
| $AUC_{0-2352\,h}$ (µM · h) | 195 ± 35 |
| $AUC_{0-3024\,h}$ (µM · h) | 200 ± 35 |
| $AUC_{0-3696\,h}$ (µM · h) | 208 ± 47 |

TABLE 45

Plasma concentration-time data of the compound of Formula (Ia) in beagle dogs after subcutaneous administration of 12 mg/kg dose (mean ± SD, n = 3)

| Time (h) | Plasma concentration (nM) | | | | |
|---|---|---|---|---|---|
| | #1 | #2 | #3 | Mean | SD |
| 0 | BLQ | BLQ | BLQ | NC | NC |
| 1.00 | 3.54 | 2.52 | 5.95 | 4.00 | 1.76 |
| 3.00 | 12.6 | 7.87 | 21.0 | 13.8 | 6.65 |
| 8.00 | 45.1 | 24.8 | 57.0 | 42.3 | 16.3 |
| 24.0 | 118 | 98.3 | 187 | 134 | 46.6 |
| 48.0 | 102 | 148 | 194 | 148 | 46.0 |
| 72.0 | 97.2 | 102 | 207 | 135 | 62.1 |
| 96.0 | 140 | 141 | 258 | 180 | 67.8 |
| 168 | 106 | 88.7 | 108 | 101 | 10.6 |
| 336 | 204 | 147 | 204 | 185 | 32.9 |
| 504 | 202 | 105 | 239 | 182 | 69.2 |
| 672 | 157 | 161 | 232 | 183 | 42.2 |
| 840 | 103 | 99.7 | 124 | 109 | 13.2 |
| 1008 | 77.6 | 84.5 | 94.2 | 85.4 | 8.34 |
| 1334 | 35.8 | 54.6 | 52.4 | 47.6 | 10.3 |
| 1680 | 24.0 | 26.5 | 33.5 | 28.0 | 4.9 |
| 2016 | 10.2 | 18.6 | 17.4 | 15.4 | 4.5 |
| 2352 | 6.79 | 10.8 | 13.8 | 10.5 | 3.5 |
| 2688 | 3.21 | 7.11 | 6.09 | 5.47 | 2.02 |
| 3024 | 1.90 | 4.39 | 4.33 | 3.54 | 1.42 |
| 3360 | 1.23 | 2.57 | 2.10 | 1.97 | 0.68 |
| 3696 | BLQ | 1.63 | 1.49 | 1.56 | NC |

TABLE 46

PK parameters of the compound of Formula (Ia) following a single SC dose in male Wistar Han rats (mean ± SD, n = 4)

| | |
|---|---|
| Dosing Concentration (mg/mL) | 400 |
| Dosing Volume (mL/kg) | 0.125 |
| Dose (mg/kg) | 50 |
| Vehicle | 28.81 w/w % water, 61.66 w/w % PEG 300, 9.53 w/w % poloxamer 188 |
| $AUC_{0\text{-}24\,h}$ (µM · h) | 3.44 ± 0.69 |
| $AUC_{0\text{-}168\,h}$ (µM · h) | 32.4 ± 7.6 |
| $AUC_{0\text{-}336\,h}$ (µM · h) | 55.2 ± 16.3 |
| $AUC_{0\text{-}672\,h}$ (µM · h) | 98.0 ± 30.4 |
| $AUC_{0\text{-}1008\,h}$ (µM · h) | 136 ± 36 |
| $AUC_{0\text{-}1344\,h}$ (µM · h) | 167 ± 41 |
| $AUC_{0\text{-}2352\,h}$ (µM · h) | 190 ± 45 |
| $AUC_{0\text{-}3024\,h}$ (µM · h) | 240 ± 59 |
| $AUC_{0\text{-}3696\,h}$ (µM · h) | 289 ± 76 |

TABLE 47

Plasma concentration-time data of the compound of Formula (Ia) in Wistar Han rats after subcutaneous administration of 50 mg/kg dose (mean ± SD, n = 4)

| Time (h) | Plasma concentration (nM) | | | | Mean | SD |
|---|---|---|---|---|---|---|
| | #1 | #2 | #3 | #4 | | |
| 0 | BLQ | BLQ | BLQ | BLQ | NC | NC |
| 1.00 | 29.0 | 36.7 | 45.6 | 32.4 | 35.9 | 7.18 |
| 3.00 | 67.9 | 61.1 | 94.5 | 54.3 | 69.5 | 17.6 |
| 8.00 | 109 | 102 | 159 | 119 | 122 | 25.5 |
| 24.0 | 259 | 163 | 281 | 228 | 233 | 51.3 |
| 48.0 | 272 | 174 | 310 | 246 | 251 | 57.4 |
| 72.0 | 231 | 144 | 267 | 265 | 227 | 57.6 |
| 96.0 | 211 | 130 | 238 | 226 | 201 | 48.8 |
| 168 | 131 | 86.2 | 178 | 168 | 141 | 41.6 |
| 336 | 95.2 | 70.2 | 235 | 120 | 130 | 72.8 |
| 504 | 136 | 91.2 | 192 | 105 | 131 | 44.7 |
| 672 | 130 | 93.1 | 141 | 105 | 117 | 22.1 |
| 840 | 170 | 92.9 | 122 | 87.7 | 118 | 37.7 |
| 1008 | 134 | 92.1 | 120 | 67.1 | 103 | 29.8 |
| 1344 | 93.0 | 79.3 | 88.8 | 47.2 | 77.1 | 20.7 |
| 1680 | 77.7 | 61.2 | 78.1 | 38.2 | 63.8 | 18.8 |
| 2016 | 111 | 80.1 | 83.2 | 38.5 | 78.2 | 29.9 |
| 2352 | 96.8 | 65.9 | 103 | 36.0 | 75.4 | 30.9 |
| 2688 | 107 | 63.3 | 89.6 | 38.5 | 74.6 | 30.0 |
| 3024 | 81.7 | 70.5 | 89.5 | 37.6 | 69.8 | 22.9 |
| 3360 | 85.4 | 53.7 | 78.7 | 38.4 | 64.1 | 21.9 |
| 3696 | 81.4 | 52.8 | 92.7 | 35.9 | 65.7 | 26.0 |

It should be appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure.

What is claimed is:

1. A method of preventing an HIV infection in a subject, comprising administering to the subject a compound of Formula (Ia) or Formula (Ib):

(Ia)

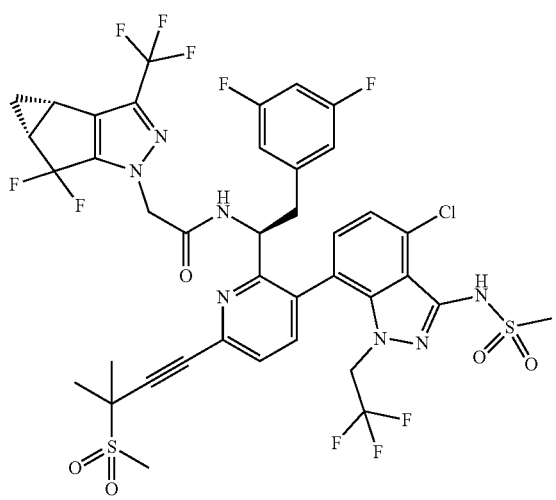

(Ib)

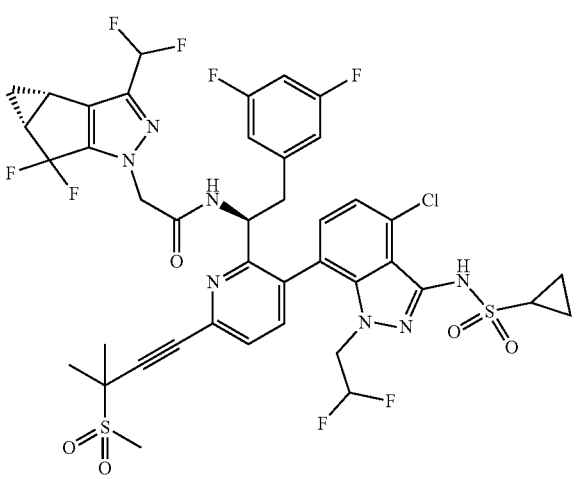

or a pharmaceutically acceptable salt thereof, wherein:
the compound of Formula (Ia) or Formula (Ib), or a pharmaceutically acceptable salt thereof, is administered subcutaneously at a concentration of about 309 mg/mL; or the compound of Formula (Ia) or Formula (Ib), or a pharmaceutically acceptable salt thereof, is administered intramuscularly at a concentration of about 400 mg/mL to about 500 mg/mL; or the compound of Formula (Ia) or Formula (Ib), or a pharmaceutically acceptable salt thereof, is administered subcutaneously at a concentration of about 400 mg/mL; or the compound of Formula (Ia) or Formula (Ib), or a pharmaceutically acceptable salt thereof, is administered subcutaneously at a concentration of about 500 mg/mL.

2. The method of claim 1, wherein the compound of Formula (Ia) or Formula (Ib), or a pharmaceutically acceptable salt thereof, is administered subcutaneously at a concentration of about 309 mg/mL.

3. The method of claim 1, wherein the compound of Formula (Ia) or Formula (Ib), or a pharmaceutically acceptable salt thereof, is administered intramuscularly at a concentration of about 400 mg/mL to about 500 mg/mL.

4. The method of claim 1, wherein the compound of Formula (Ia) or Formula (Ib), or a pharmaceutically acceptable salt thereof, is administered intramuscularly at a concentration of about 400 mg/mL.

5. The method of claim 1, wherein the compound of Formula (Ia) or Formula (Ib), or a pharmaceutically acceptable salt thereof, is administered in a dosage of about 2000 mg or about 2500 mg.

6. The method of claim 1, wherein the compound of Formula (Ia) or Formula (Ib), or a pharmaceutically acceptable salt thereof, is administered intramuscularly at a concentration of about 500 mg/mL.

7. The method of claim 1, wherein the compound of Formula (Ia) or Formula (Ib), or a pharmaceutically acceptable salt thereof, is administered as a monotherapy.

8. The method of claim 1, wherein the method comprises event driven administration of the compound of Formula (Ia) or Formula (Ib), or a pharmaceutically acceptable salt thereof, to the subject.

9. The method of claim 1, wherein the method comprises pre-exposure prophylaxis (PrEP).

10. The method of claim 1, wherein the method comprises post-exposure prophylaxis (PEP).

11. The method of claim 1, wherein the method comprises pre-exposure prophylaxis (PrEP) and post-exposure prophylaxis (PEP).

12. The method of claim 1, wherein the compound of Formula (Ia) or Formula (Ib), or a pharmaceutically acceptable salt thereof, is administered before exposure of the subject to the HIV.

13. The method of claim 1, wherein the compound of Formula (Ia) or Formula (Ib), or a pharmaceutically acceptable salt thereof, is administered once from about 14 days to about one day before exposure of the subject to the HIV.

14. The method of claim 1, wherein the compound of Formula (Ia) or Formula (Ib), or a pharmaceutically acceptable salt thereof, is administered once from about 72 hours to about 1 hour before exposure of the subject to the HIV.

15. The method of claim 9, wherein the pre-exposure prophylaxis (PrEP) comprises continuous PrEP.

16. The method of claim 15, wherein the continuous PrEP comprises daily administration of the compound of Formula (Ia) or Formula (Ib), or a pharmaceutically acceptable salt thereof, from about 14 days to about 1 hour before the exposure of the subject to the HIV.

17. The method of claim 1, comprising administering the compound of Formula (Ia) or Formula (Ib), or a pharmaceutically acceptable salt thereof, during the period of exposure of the subject to the HIV.

18. The method of claim 17, wherein the compound of Formula (Ia) or Formula (Ib), or a pharmaceutically acceptable salt thereof, is administered once about every 7 days, about every 14 days, about every 21 days, about every 28 days, about every 35 days, or about every 42 days during the period of exposure of the subject to the HIV.

19. The method of claim 17, wherein the compound of Formula (Ia) or Formula (Ib), or a pharmaceutically acceptable salt thereof, is administered once about every month, about every 2 months, about every 3 months, about every 6 months, or about every 12 months during the period of exposure of the subject to the HIV.

20. The method of claim 1, comprising administering the compound of Formula (Ia) or Formula (Ib), or a pharmaceutically acceptable salt thereof, after final exposure of the subject to the HIV.

21. The method of claim 20, wherein the compound of Formula (Ia) or Formula (Ib), or a pharmaceutically acceptable salt thereof, is administered once from about 1 hour to about 14 days after final exposure of the subject to the HIV.

22. The method of claim 1, wherein the method comprises:
   (i) administering the compound of Formula (Ia) or Formula (Ib), or a pharmaceutically acceptable salt thereof, at about 7 days prior to exposure of the subject to the HIV; and
   (ii) administering the compound of Formula (Ia) or Formula (Ib), or a pharmaceutically acceptable salt thereof, once every 7 days, once every 14 days, once every 21 days, once every 28 days, once every 35 days, or once every 42 days, during the period of exposure to the HIV.

23. The method of claim 1, wherein the method comprises:
   (i) administering the compound of Formula (Ia) or Formula (Ib), or a pharmaceutically acceptable salt thereof, at about 7 days prior to exposure of the subject to the HIV; and
   (ii) administering the compound of Formula (Ia) or Formula (Ib), or a pharmaceutically salt thereof, once every 1 month, once every 2 months, once every 3 months, once every 6 months, or once every 12 months during the period of exposure to the HIV.

24. A method of reducing the risk of acquiring HIV in a subject, comprising administering to the subject a compound of Formula (Ia) or Formula (Ib):

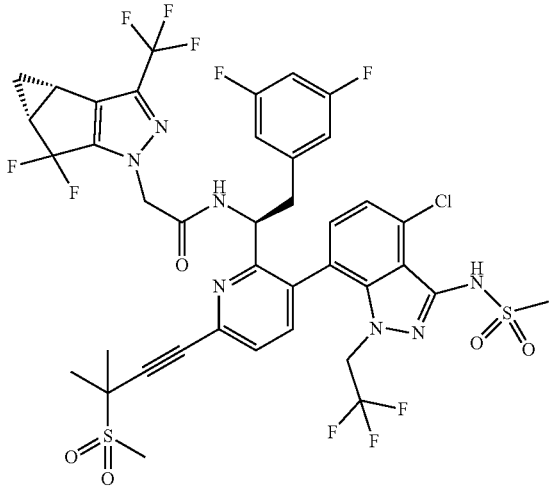

(Ia)

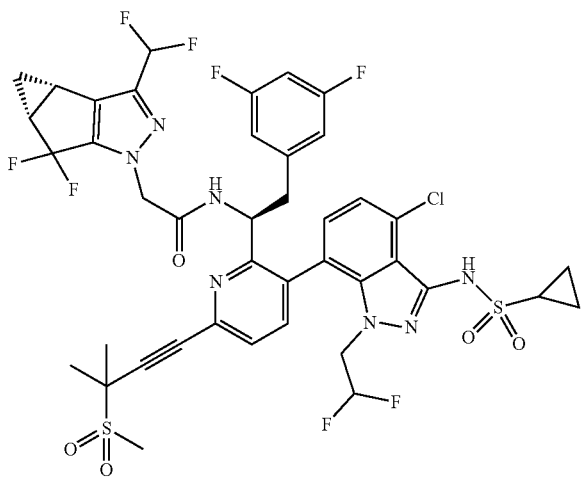

(Ib)

or a pharmaceutically acceptable salt thereof, wherein:
   the compound of Formula (Ia) or Formula (Ib), or a pharmaceutically acceptable salt thereof, is administered subcutaneously at a concentration of about 309 mg/mL, or
   the compound of Formula (Ia) or Formula (Ib), or a pharmaceutically acceptable salt thereof, is administered intramuscularly at a concentration of about 400 mg/mL to about 500 mg/mL; or
   the compound of Formula (Ia) or Formula (Ib), or a pharmaceutically acceptable salt thereof, is administered subcutaneously at a concentration of about 400 mg/mL; or
   the compound of Formula (Ia) or Formula (Ib), or a pharmaceutically acceptable salt thereof, is administered subcutaneously at a concentration of about 500 mg/mL.

25. The method of claim 24, wherein the reduction in risk of acquiring HIV is at least about 75% compared to a subject having not been administered the compound of Formula (Ia) or Formula (Ib), or a pharmaceutically acceptable salt thereof.

26. The method of claim 1, wherein the subject has been identified as an individual who is at risk of sexual transmission of HIV.

27. The method of claim 1, wherein the HIV is HIV-1 or HIV-2.

28. The method of claim 1, wherein the method comprises administering the compound of Formula (Ia), or a pharmaceutically acceptable salt thereof.

29. The method of claim 28, wherein the pharmaceutically acceptable salt of the compound of Formula (Ia) is a sodium salt.

30. The method of claim 1, wherein a solution of the sodium salt of the compound of Formula (Ia) is administered subcutaneously and wherein the solution comprises about 20 w/w % to about 30 w/w % water, about 48 w/w % to about 60 w/w % PEG 300, and about 11 w/w % to about 28 w/w % of a sodium salt of the compound of Formula (Ia).

31. The method of claim 30, wherein a solution of the sodium salt of the compound of Formula (Ia) is administered subcutaneously and wherein the solution comprises about 23.41 w/w % water, about 50.13 w/w % PEG 300, and about 26.46 w/w % of the sodium salt of the compound of Formula (Ia).

32. The method of claim 1, wherein the subject is a human.

33. The method of claim 1, wherein the method comprises administering the compound of Formula (Ia), or a pharmaceutically acceptable salt thereof, once every six months.

34. The method of claim 33, wherein the compound of Formula (Ia), or a pharmaceutically acceptable salt thereof, is administered subcutaneously once every six months as two administrations, each at a concentration of about 309 mg/mL.

35. The method of claim 1, wherein the compound of Formula (Ia), or a pharmaceutically acceptable salt thereof, is administered intramuscularly once every year.

36. The method of claim 35, wherein the compound of Formula (Ia), or a pharmaceutically acceptable salt thereof, is administered intramuscularly once every year as two administrations, each at a concentration of about 400 mg/mL to about 500 mg/mL.

37. The method of claim 24, wherein the method comprises administering the compound of Formula (Ia), or a pharmaceutically acceptable salt thereof, once every six months.

38. The method of claim 37, wherein the compound of Formula (Ia), or a pharmaceutically acceptable salt thereof, is administered subcutaneously once every six months as two administrations, each at a concentration of about 309 mg/mL.

39. The method of claim 24, wherein the compound of Formula (Ia), or a pharmaceutically acceptable salt thereof, is administered intramuscularly once every year.

40. The method of claim 39, wherein the compound of Formula (Ia), or a pharmaceutically acceptable salt thereof, is administered intramuscularly once every year as two administrations, each at a concentration of about 400 mg/mL to about 500 mg/mL.

41. The method of claim 1, wherein the intramuscular administration comprises administering to the patient a pharmaceutical composition comprising about 10 w/w % to about 30 w/w % water, about 35 w/w % to about 65 w/w % PEG 300, and about 5 w/w % to about 45 w/w % of a sodium salt of the compound of Formula (Ia), wherein the pharmaceutical composition is a solution.

42. The method of claim 1, wherein the intramuscular administration comprises administering to the patient a pharmaceutical composition comprising about 21.13 w/w % water, about 45.25 w/w % PEG 300, and about 33.61 w/w % of the sodium salt of the compound of Formula (Ia), wherein the pharmaceutical composition is a solution.

43. The method of claim 1, wherein the intramuscular administration comprises administering to the patient a pharmaceutical composition comprising about 10 w/w % to about 20 w/w % water, about 30 w/w % to about 40 w/w % PEG 300, about 37 w/w % to about 45 w/w % of a sodium salt of the compound of Formula (Ia), and about 3 w/w % to about 8 w/w % of ethanol, wherein the pharmaceutical composition is a solution.

44. The method of claim 1, wherein the intramuscular administration comprises administering to the patient a pharmaceutical composition comprising about 16.93 w/w % water, about 36.22 w/w % PEG 300, about 41.85 w/w % of the sodium salt of the compound of Formula (Ia), and about 5.00% ethanol, wherein the pharmaceutical composition is a solution.

45. The method of claim 1, wherein the intramuscular administration comprises administering to the patient a pharmaceutical composition comprising about 15 w/w % to about 35 w/w % water, about 35 w/w % to about 75 w/w % PEG 300, about 1 w/w % to about 35 w/w % of a sodium salt of a compound of Formula (Ia), and about 0.3 w/w % to about 8 w/w % of poloxamer 188, wherein the pharmaceutical composition is a solution.

46. The method of claim 1, wherein the intramuscular administration comprises administering to the patient a pharmaceutical composition comprising about 20.16 w/w % water, about 43.17 w/w % PEG 300, about 33.61 w/w % of a sodium salt of a compound of Formula (Ia), and about 3.06 w/w % of poloxamer 188, wherein the pharmaceutical composition is a solution.

47. The method of claim 1, wherein the intramuscular administration comprises administering to the patient a pharmaceutical composition comprising about 19.18 w/w % water, about 41.09 w/w % PEG 300, about 33.61 w/w % of a sodium salt of a compound of Formula (Ia), and about 6.12 w/w % of poloxamer 188, wherein the pharmaceutical composition is a solution.

48. The method of claim 1, wherein the intramuscular administration comprises administering to the patient a pharmaceutical composition comprising about 10 w/w % to about 40 w/w % water, about 20 w/w % to about 75 w/w % PEG 300, about 10 w/w % to about 70 w/w % of a sodium salt of the compound of Formula (Ia), about 1 w/w % to about 20 w/w % poloxamer 188, and about 1 w/w % to about 10 w/w % of ethanol, wherein the pharmaceutical composition is a solution.

49. The method of claim 1, wherein the intramuscular administration comprises administering to the patient a pharmaceutical composition comprising about 15.71 w/w % water, about 33.63 w/w % PEG 300, about 41.85 w/w % of the sodium salt of the compound of Formula (Ia), about 5.00% ethanol, about 3.81 w/w % poloxamer 188, wherein the pharmaceutical composition is a solution.

50. The method of claim 1, wherein the intramuscular administration comprises administering to the patient a pharmaceutical composition comprising about 14.57 w/w % water, about 31.21 w/w % PEG 300, about 41.64 w/w % of a sodium salt of the compound of Formula (Ia), about 7.58 w/w % poloxamer 188, and about 5.00 w/w % ethanol, wherein the pharmaceutical composition is a solution.

51. The method of claim 1, wherein the intramuscular administration comprises administering to the patient a pharmaceutical composition comprising about 14.50 w/w % water, about 31.04 w/w % PEG 300, about 41.85 w/w % of the sodium salt of the compound of Formula (Ia), about 5.00% ethanol, about 7.61 w/w % poloxamer 188, wherein the pharmaceutical composition is a solution.

52. The method of claim 24, wherein the intramuscular administration comprises administering to the patient a pharmaceutical composition comprising about 10 w/w % to about 30 w/w % water, about 35 w/w % to about 65 w/w % PEG 300, and about 5 w/w % to about 45 w/w % of a sodium salt of the compound of Formula (Ia), wherein the pharmaceutical composition is a solution.

53. The method of claim 24, wherein the intramuscular administration comprises administering to the patient a pharmaceutical composition comprising about 21.13 w/w % water, about 45.25 w/w % PEG 300, and about 33.61 w/w % of the sodium salt of the compound of Formula (Ia), wherein the pharmaceutical composition is a solution.

54. The method of claim 24, wherein the intramuscular administration comprises administering to the patient a pharmaceutical composition comprising about 10 w/w % to about 20 w/w % water, about 30 w/w % to about 40 w/w % PEG 300, about 37 w/w % to about 45 w/w % of a sodium salt of the compound of Formula (Ia), and about 3 w/w % to about 8 w/w % of ethanol, wherein the pharmaceutical composition is a solution.

55. The method of claim 24, wherein the intramuscular administration comprises administering to the patient a pharmaceutical composition comprising about 16.93 w/w % water, about 36.22 w/w % PEG 300, about 41.85 w/w % of the sodium salt of the compound of Formula (Ia), and about 5.00% ethanol, wherein the pharmaceutical composition is a solution.

56. The method of claim 24, wherein the intramuscular administration comprises administering to the patient a pharmaceutical composition comprising about 15 w/w % to about 35 w/w % water, about 35 w/w % to about 75 w/w % PEG 300, about 1 w/w % to about 35 w/w % of a sodium salt of a compound of Formula (Ia), and about 0.3 w/w % to about 8 w/w % of poloxamer 188, wherein the pharmaceutical composition is a solution.

57. The method of claim 24, wherein the intramuscular administration comprises administering to the patient a pharmaceutical composition comprising about 20.16 w/w % water, about 43.17 w/w % PEG 300, about 33.61 w/w % of a sodium salt of a compound of Formula (Ia), and about 3.06 w/w % of poloxamer 188, wherein the pharmaceutical composition is a solution.

58. The method of claim 24, wherein the intramuscular administration comprises administering to the patient a pharmaceutical composition comprising about 19.18 w/w % water, about 41.09 w/w % PEG 300, about 33.61 w/w % of a sodium salt of a compound of Formula (Ia), and about 6.12 w/w % of poloxamer 188, wherein the pharmaceutical composition is a solution.

59. The method of claim 24, wherein the intramuscular administration comprises administering to the patient a pharmaceutical composition comprising about 10 w/w % to about 40 w/w % water, about 20 w/w % to about 75 w/w % PEG 300, about 10 w/w % to about 70 w/w % of a sodium salt of the compound of Formula (Ia), about 1 w/w % to about 20 w/w % poloxamer 188, and about 1 w/w % to about 10 w/w % of ethanol, wherein the pharmaceutical composition is a solution.

60. The method of claim 24, wherein the intramuscular administration comprises administering to the patient a pharmaceutical composition comprising about 15.71 w/w % water, about 33.63 w/w % PEG 300, about 41.85 w/w % of the sodium salt of the compound of Formula (Ia), about 5.00% ethanol, about 3.81 w/w % poloxamer 188, wherein the pharmaceutical composition is a solution.

61. The method of claim 24, wherein the intramuscular administration comprises administering to the patient a pharmaceutical composition comprising about 14.57 w/w % water, about 31.21 w/w % PEG 300, about 41.64 w/w % of a sodium salt of the compound of Formula (Ia), about 7.58 w/w % poloxamer 188, and about 5.00 w/w % ethanol, wherein the pharmaceutical composition is a solution.

62. The method of claim 24, wherein the intramuscular administration comprises administering to the patient a pharmaceutical composition comprising about 14.50 w/w % water, about 31.04 w/w % PEG 300, about 41.85 w/w % of the sodium salt of the compound of Formula (Ia), about 5.00% ethanol, about 7.61 w/w % poloxamer 188, wherein the pharmaceutical composition is a solution.

63. The method of claim 1, wherein the compound of Formula (Ia), or a pharmaceutically acceptable salt thereof, is administered subcutaneously at a concentration of about 400 mg/mL.

64. The method of claim 1, wherein the compound of Formula (Ia), or a pharmaceutically acceptable salt thereof, is administered subcutaneously at a concentration of about 500 mg/mL.

65. The method of claim 24, wherein the compound of Formula (Ia), or a pharmaceutically acceptable salt thereof, is administered subcutaneously at a concentration of about 400 mg/mL.

66. The method of claim 24, wherein the compound of Formula (Ia), or a pharmaceutically acceptable salt thereof, is administered subcutaneously at a concentration of about 500 mg/mL.

67. The method of claim 24, wherein a solution of the sodium salt of the compound of Formula (Ia) is administered subcutaneously and wherein the solution comprises about 20 w/w% to about 30 w/w% water, about 48 w/w% to about 60 w/w% PEG 300, and about 11 w/w% to about 28 w/w% of a sodium salt of the compound of Formula (Ia).

68. The method of claim 67, wherein a solution of the sodium salt of the compound of Formula (Ia) is administered subcutaneously and wherein the solution comprises about 23.41 w/w% water, about 50.13 w/w% PEG 300, and about 26.46 w/w% of the sodium salt of the compound of Formula (Ia).

69. The method of claim 24, wherein the subject is a human.

* * * * *

SEQUENCE LISTING

<160> NUMBER OF SEQ ID NOS: 3

<210> SEQ ID NO 1
<211> LENGTH: 22
<212> TYPE: DNA
<213> ORGANISM: Artificial
<220> FEATURE:
<223> OTHER INFORMATION: synthetic oligonucleotides

<400> SEQUENCE: 1
gtctgcgtca tctggtgcat tc                                              22

<210> SEQ ID NO 2
<211> LENGTH: 29
<212> TYPE: DNA
<213> ORGANISM: Artificial
<220> FEATURE:
<223> OTHER INFORMATION: synthetic oligonucleotides

<400> SEQUENCE: 2
cactaggtgt ctctgcacta tctgttttg                                       29

<210> SEQ ID NO 3
<211> LENGTH: 32
<212> TYPE: DNA
<213> ORGANISM: Artificial

-continued

```
<220> FEATURE:
<223> OTHER INFORMATION: synthetic oligonucleotides

<400> SEQUENCE: 3
cttcctcagt gtgtttcact ttctcttctg cg                               32
```